US011993793B2

(12) United States Patent
Owens et al.

(10) Patent No.: US 11,993,793 B2
(45) Date of Patent: *May 28, 2024

(54) POLYNUCLEOTIDES ENCODING ENGINEERED MEGANUCLEASES HAVING SPECIFICITY FOR RECOGNITION SEQUENCES IN THE DYSTROPHIN GENE

(71) Applicant: Precision BioSciences, Inc., Durham, NC (US)

(72) Inventors: Gary Owens, Durham, NC (US); Janel Lape, Wake Forest, NC (US); James Jefferson Smith, Morrisville, NC (US); John Morris, Raleigh, NC (US); Caitlin Turner, Durham, NC (US); Whitney Lewis, Oxford, NC (US); Derek Jantz, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/360,517

(22) Filed: Jul. 27, 2023

(65) Prior Publication Data

US 2024/0002823 A1 Jan. 4, 2024

Related U.S. Application Data

(60) Division of application No. 17/931,896, filed on Sep. 13, 2022, now Pat. No. 11,753,630, which is a continuation of application No. PCT/US2021/059146, filed on Nov. 12, 2021.

(60) Provisional application No. 63/233,664, filed on Aug. 16, 2021, provisional application No. 63/113,131, filed on Nov. 12, 2020.

(51) Int. Cl.
*C12N 9/22* (2006.01)
*C12N 15/86* (2006.01)

(52) U.S. Cl.
CPC .............. *C12N 9/22* (2013.01); *C12N 15/86* (2013.01); *C12N 2750/14143* (2013.01)

(58) Field of Classification Search
CPC . C12N 9/22; C12N 15/86; C12N 2750/14143
See application file for complete search history.

(56) References Cited

U.S. PATENT DOCUMENTS

| 2018/0064827 A1 | 3/2018 | Conway et al. |
| 2018/2913791 | 10/2018 | Brown et al. |
| 2022/0090047 A1 | 3/2022 | Davey et al. |

FOREIGN PATENT DOCUMENTS

| WO | WO 2007/047859 A2 | 4/2007 |
| WO | WO 2011/141820 A1 | 11/2011 |
| WO | WO 2015/138739 A2 | 9/2015 |
| WO | WO 2016/057893 A1 | 4/2016 |
| WO | WO 2018/154459 A1 | 8/2018 |
| WO | WO 2020/028327 A1 | 2/2020 |

OTHER PUBLICATIONS

International Search Report and Written Opinion for Application No. PCT/US2019/068186 dated Mar. 25, 2020.
International Preliminary Report on Patentability for PCT/US2019/068186 dated Jul. 1, 2021.
International Search Report and Written Opinion dated Mar. 10, 2022 for Application No. PCT/US2021/059146.
Geneseq Submission; Accession No. BCP61031, Seq 1317, Jun. 2, 2016.
Geneseq Submission; Accession No. BCP62127, Seq 2413, Jun. 2, 2016.
Genseq Submission; Accession No. BFS93579, Seq ID 161, Nov. 29, 2018.
Genseq Submission; Accession No. BFS93577, Seq ID 159, Nov. 29, 2018.
Iyombe-Engembe, et al,. The advances and challenges of Gene Therapy for Duchenne Muscular Dystrophy, Journal of Genetic Medicine and Gene Therapy, Jul. 25, 2017; 1(1): 019-036, doi: 10.29328/journal.jgmgt . . . 1001003.
Recalcati, et al., Peroxisomal targeting of mammalian hydroxyacid oxidase 1 requires the C-terminal tripeptide SK1, J Cell Sci. May 2001; 114(Pt. 9): 1625-9.
Uniprot Submission; Accession No. A0A2J8MSM2. Sequence Version Mar. 1, 28, 2018. Version 5 Oct. 10, 2018, 2 pages.
Waldrop et al., Update in Duchenne and Becker muscular dystrophy. Curr Opin Neurol. Oct. 2019; 23(5): 722-727.
Zabaleta et al., CRISPR/Cas9-mediated glycolate oxidase disruption is an efficacious and safe treatment for primary hyperoxaluria type I. Nat Commun. Dec. 21, 2018; 9(1) : 5454With Supplemental Information.
Zabaleta et al., Development of advanced genetic therapies for primary hyperoxaluria type I. Ph.D. Thesis, University of Navarra. Jan. 19, 2018, pp. 1-180.

*Primary Examiner* — Delia M Ramirez
(74) *Attorney, Agent, or Firm* — Womble Bond Dickinson (US) LLP

(57) ABSTRACT

The present disclosure encompasses engineered meganucleases that bind and cleave recognition sequences within a dystrophin gene. The present disclosure also encompasses methods of using such engineered meganucleases to make genetically modified cells. Further, the disclosure encompasses pharmaceutical compositions comprising engineered meganuclease proteins, or polynucleotides encoding engineered meganucleases of the disclosure, and the use of such compositions for the modification of a dystrophin gene in a subject, or for treatment of Duchenne Muscular Dystrophy.

16 Claims, 63 Drawing Sheets

Specification includes a Sequence Listing.

```
                    DMD 19         DMD 20
                    Half-Site      Half-Site
DMD 19-20           AAGGATTATGTATTACCTCCCG       SEQ ID NO:6
Recognition Sequence TTCCTAATACATAATGGAGGGC      SEQ ID NO:7

DMD 29         DMD 30
                    Half-Site      Half-Site
DMD 29-30           TAAGATTGGGTATGAGGGATAG       SEQ ID NO:8
Recognition Sequence ATTCTAACCCATACTCCCTATC      SEQ ID NO:9

DMD 35         DMD 36
                    Half-Site      Half-Site
DMD 35-36           CTACATGGTGTATCTGACTAAG       SEQ ID NO:10
Recognition Sequence GATGTACCACATAGACTGATTC      SEQ ID NO:11

DMD 37         DMD 38
                    Half-Site      Half-Site
DMD 37-38           CTGGCCGAAGTATAGGAATATG       SEQ ID NO:12
Recognition Sequence GACCGGCTTCATATCCTTATAC      SEQ ID NO:13
```

FIGURE 2

```
DMD 19-20x.13  (SEQ ID NO: 36)    MNTKYNKEFLLYLAGFVDSDGSIYATIRPVQSTKFKHTLRLWFAVTQKTQRRWFLDKLVD    60
DMD 19-20x.87  (SEQ ID NO: 37)    MNTKYNKEFLLYLAGFVDSDGSIFAVIEPVQSAKFKHRLKLSFVVTQKTQRRWFLDKLVD    60
DMD 19-20L.249 (SEQ ID NO: 38)    MNTKYNKEFLLYLAGFVDSDGSIYASIMPIQTAKFKHRLKLQFAVAQKTQRRWFLDKLVD    60
DMD 19-20L.302 (SEQ ID NO: 39)    MNTKYNKEFLLYLAGFVDSDGSIIAFIMPSQTAKFKHRLKLQFAVAQKTQRRWFLDKLVD    60
DMD 19-20L.329 (SEQ ID NO: 40)    MNTKYNKEFLLYLAGFVDSDGSIMAFIMPTQTAKFKHRLKLQFAVAQKTQRRWFLDKLVD    60
DMD 19-20L.374 (SEQ ID NO: 41)    MNTKYNKEFLLYLAGFVDSDGSIMAFILPEQHMKFKHRLRLQFAVAQKTQRRWFLDKLVD    60
DMD 19-20L.375 (SEQ ID NO: 42)    MNTKYNKEFLLYLAGFVDSDGSIMAFILPEQHLKFKHRLRLQFAVAQKTQRRWFLDKLVD    60
DMD 19-20L.431 (SEQ ID NO: 43)    MNTKYNKEFLLYLAGFVDSDGSIMAFILPEQGLKFKHRLRLQFAVAQKTQRRWFLDKLVD    60
DMD 19-20L.458 (SEQ ID NO: 44)    MNTKYNKEFLLYLAGFVDSDGSIMAFIMPDQAPKFKHRLRLQFAVAQKTQRRWFLDKLVD    60
                                  ************************   *    *  *  * *******************

DMD 19-20x.13  (SEQ ID NO: 36)    EIGVGYVYDNGSVSWYYLSEIKPLHNFLTQLQPFLKLKQKQANLVLKIIEQLPSAKESPD    120
DMD 19-20x.87  (SEQ ID NO: 37)    EIGVGYVYDQGSVSFYRLSEIKPLHNFLTQLQPFLKLKQKQANLVLKIIEQLPSAKESPD    120
DMD 19-20L.249 (SEQ ID NO: 38)    EIGVGYVYDFGSVSYYRLSQIKPLHNFLTQLQPFLKLKQKQANLVLKIIEQLPSAKESPD    120
DMD 19-20L.302 (SEQ ID NO: 39)    EIGVGYVYDFGSVSYYRLSQIKPLHNFLTQLQPFLKLKQKQANLVLKIIEQLPSAKESPD    120
DMD 19-20L.329 (SEQ ID NO: 40)    EIGVGYVYDFGSVSYYRLSEIKPLHNFLTQLQPFLKLKQKQANLVLKIIEQLPSAKESPD    120
DMD 19-20L.374 (SEQ ID NO: 41)    EIGVGYVYDFGSVSYYRLSEIKPLHNFLTQLQPFLKLKQKQANLVLKIIEQLPSAKESPD    120
DMD 19-20L.375 (SEQ ID NO: 42)    EIGVGYVYDFGSVSYYRLSQIKPLHNFLTQLQPFLKLKQKQANLVLKIIEQLPSAKESPD    120
DMD 19-20L.431 (SEQ ID NO: 43)    EIGVGYVYDFGSVSYYRLSQIKPLHNFLTQLQPFLKLKQKQANLVLKIIEQLPSAKESPD    120
DMD 19-20L.458 (SEQ ID NO: 44)    EIGVGYVYDFGSVSYYRLSEIKPLHNFLTQLQPFLKLKQKQANLVLKIIEQLPSAKESPD    120
                                  ********** ****  *  ** *************************************

DMD 19-20x.13  (SEQ ID NO: 36)    KFLEVCTWVDQIAALNDSKTRKTTSETVRAVLDSLPGSVGGLSPSQASSAASSASSSPGS    180
DMD 19-20x.87  (SEQ ID NO: 37)    KFLEVCTWVDQIAALNDSKTRKTTSETVRAVLDSLPGSVGGLSPSQASSAASSASSSPGS    180
DMD 19-20L.249 (SEQ ID NO: 38)    KFLEVCTWVDQIAALNDSKTRKTTSETVRAVLDSLPGSVGGLSPSQASSAASSASSSPGS    180
DMD 19-20L.302 (SEQ ID NO: 39)    KFLEVCTWVDQIAALNDSKTRKTTSETVRAVLDSLPGSVGGLSPSQASSAASSASSSPGS    180
DMD 19-20L.329 (SEQ ID NO: 40)    KFLEVCTWVDQIAALNDSKTRKTTSETVRAVLDSLPGSVGGLSPSQASSAASSASSSPGS    180
DMD 19-20L.374 (SEQ ID NO: 41)    KFLEVCTWVDQIAALNDSKTRKTTSETVRAVLDSLPGSVGGLSPSQASSAASSASSSPGS    180
DMD 19-20L.375 (SEQ ID NO: 42)    KFLEVCTWVDQIAALNDSKTRKTTSETVRAVLDSLPGSVGGLSPSQASSAASSASSSPGS    180
DMD 19-20L.431 (SEQ ID NO: 43)    KFLEVCTWVDQIAALNDSKTRKTTSETVRAVLDSLPGSVGGLSPSQASSAASSASSSPGS    180
DMD 19-20L.458 (SEQ ID NO: 44)    KFLEVCTWVDQIAALNDSKTRKTTSETVRAVLDSLPGSVGGLSPSQASSAASSASSSPGS    180
                                  ************************************************************

DMD 19-20x.13  (SEQ ID NO: 36)    GISEALRAGAGSGTGYNKEFLLYLAGFVDGDGSICACIVPRQDRKFKHQLRLFFEVGQKT    240
DMD 19-20x.87  (SEQ ID NO: 37)    GISEALRAGAGSGTGYNKEFLLYLAGFVDGDGSICACIVPRQDRKFKHQLRLFFEVGQTT    240
DMD 19-20L.249 (SEQ ID NO: 38)    GISEALRAGAGSGTGYNKEFLLYLAGFVDGDGSICACIVPRQDRKFKHQLRLFFEVGQKT    240
DMD 19-20L.302 (SEQ ID NO: 39)    GISEALRAGAGSGTGYNKEFLLYLAGFVDGDGSICACIVPRQDRKFKHQLRLFFEIGQKT    240
DMD 19-20L.329 (SEQ ID NO: 40)    GISEALRAGAGSGTGYNKEFLLYLAGFVDGDGSICACIVPRQDRKFKHQLRLFFEVGQKT    240
DMD 19-20L.374 (SEQ ID NO: 41)    GISEALRAGAGSGTGYNKEFLLYLAGFVDGDGSICACIVPRQDRKFKHQLRLFFEVGQKT    240
DMD 19-20L.375 (SEQ ID NO: 42)    GISEALRAGAGSGTGYNKEFLLYLAGFVDGDGSICACIVPRQDRKFKHQLRLFFEVGQKT    240
DMD 19-20L.431 (SEQ ID NO: 43)    GISEALRAGAGSGTGYNKEFLLYLAGFVDGDGSICACIVPRQDRKFKHQLRLFFEVGQKT    240
DMD 19-20L.458 (SEQ ID NO: 44)    GISEALRAGAGSGTGYNKEFLLYLAGFVDGDGSICACIVPRQDRKFKHQLRLFFEVGQKT    240
                                  ********************************************************** *

DMD 19-20x.13  (SEQ ID NO: 36)    KRRWFLDKLVDEIGVGYVEDTGRASRYRLSQIKPLHNFLTQLQPFLKLKQKQANLVLKII    300
DMD 19-20x.87  (SEQ ID NO: 37)    RRRWFLDKLVDEIGVGYVFDKGSASMYRLSEIKPLHNFLTQLQPFLKLKQKQANLVLKII    300
DMD 19-20L.249 (SEQ ID NO: 38)    QRRWFLDKLVDEIGVGYVRDLGSASTYRLSEIKPLHNFLTQLQPFLKLKQKQANLVLKII    300
DMD 19-20L.302 (SEQ ID NO: 39)    QRRWFLDKLVDEIGVGYVRDLGSASTYRLSQIKPLHNFLTQLQPFLKLKQKQANLVLKII    300
DMD 19-20L.329 (SEQ ID NO: 40)    QRRWFLDKLVDEIGVGYVRDLGSASTYRLSQIKPLHNFLTQLQPFLKLKQKQANLVLKII    300
DMD 19-20L.374 (SEQ ID NO: 41)    QRRWFLDKLVDEIGVGYVRDLGSASTYRLSEIKPLHNFLTQLQPFLKLKQKQANLVLKII    300
DMD 19-20L.375 (SEQ ID NO: 42)    QRRWFLDKLVDEIGVGYVRDLGSASTYRLSEIKPLHNFLTQLQPFLKLKQKQANLVLKII    300
DMD 19-20L.431 (SEQ ID NO: 43)    QRRWFLDKLVDEIGVGYVRDLGSASTYRLSQIKPLHNFLTQLQPFLKLKQKQANLVLKII    300
DMD 19-20L.458 (SEQ ID NO: 44)    QRRWFLDKLVDEIGVGYVRDLGSASTYRLSQIKPLHNFLTQLQPFLKLKQKQANLVLKII    300
                                   ************** * * ** **** ********************************

DMD 19-20x.13  (SEQ ID NO: 36)    EQLPSAKESPDKFLEVCTWVDQIAALNDSRTRKTTSETVRAVLDSLSEKKKSSP    354
DMD 19-20x.87  (SEQ ID NO: 37)    EQLPSAKESPDKFLEVCTWVDQIAALNDSRTRKTTSETVRAVLDSLSEKKKSSP    354
DMD 19-20L.249 (SEQ ID NO: 38)    EQLPSAKESPDKFLEVCTWVDQIAALNDSRTRKTTSETVRAVLDSLSEKKKSSP    354
DMD 19-20L.302 (SEQ ID NO: 39)    EQLPSAKESPDKFLEVCTWVDQIAALNDSKTRKTTSETVRAVLDSLSEKKKSSP    354
DMD 19-20L.329 (SEQ ID NO: 40)    EQLPSAKESPDKFLEVCTWVDQIAALNDSRTRKTTSETVRAVLDSLSEKKKSSP    354
DMD 19-20L.374 (SEQ ID NO: 41)    EQLPSAKESPDKFLEVCTWVDQIAALNDSRTRKTTSETVRAVLDSLSEKKKSSP    354
DMD 19-20L.375 (SEQ ID NO: 42)    EQLPSAKESPDKFLEVCTWVDQIAALNDSRTRKTTSETVRAVLDSLSEKKKSSP    354
DMD 19-20L.431 (SEQ ID NO: 43)    EQLPSAKESPDKFLEVCTWVDQIAALNDSRTRKTTSETVRAVLDSLSEKKKSSP    354
DMD 19-20L.458 (SEQ ID NO: 44)    EQLPSAKESPDKFLEVCTWVDQIAALNDSRTRKTTSETVRAVLDSLSEKKKSSP    354
                                  ***************************** ***********************
```

FIGURE 4A

```
DMD 35-36x.63  (SEQ ID NO: 45)   MNTKYNKEFLLYLAGFVDADGSIYACIKPHQQLKFKHQLLLYFEVYQKTQRRWFLDKLVD    60
DMD 35-36x.81  (SEQ ID NO: 46)   MNTKYNKEFLLYLAGFVDADGSIYACIKPHQQLKFKHQLLLYFEVYQKTQRRWFLDKLVD    60
DMD 35-36L.195 (SEQ ID NO: 47)   MNTKYNKEFLLYLAGFVDADGSIYACIKPHQQLKFKHQLLLYFEVYQKTQRRWFLDKLVD    60
DMD 35-36L.282 (SEQ ID NO: 48)   MNTKYNKEFLLYLAGFVDSDGSIYACIKPHQQLKFKHQLLLYFEVYQKTQRRWFLDKLVD    60
DMD 35-36L.349 (SEQ ID NO: 49)   MNTKYNKEFLLYLAGFVDADGSIYACIKPHQQLKFKHQLLLYFEVYQKTQRRWFLDKLVD    60
DMD 35-36L.378 (SEQ ID NO: 50)   MNTKYNKEFLLYLAGFVDADGSIYACIKPHQQLKFKHQLLLYFEVYQKTQRRWFLDKLVD    60
DMD 35-36L.457 (SEQ ID NO: 51)   MNTKYNKEFLLYLAGFVDSDGSIYACIKPHQQLKFKHQLLLYFEVYQKTQRRWFLDKLVD    60
DMD 35-36L.469 (SEQ ID NO: 52)   MNTKYNKEFLLYLAGFVDADGSIYACIKPHQELKFKHQLLLYFEVYQKTQRRWFLDKLVD    60
                                 ****************** ************** *************************

DMD 35-36x.63  (SEQ ID NO: 45)   EIGVGYVADRGSVSEYRLSQIKPLHNFLTQLQPFLKLKQKQANLVLKIIEQLPSAKESPD   120
DMD 35-36x.81  (SEQ ID NO: 46)   EIGVGYVIDSGSVSTYRLSQIKPLHNFLTQLQPFLKLKQKQANLVLKIIEQLPSAKESPD   120
DMD 35-36L.195 (SEQ ID NO: 47)   EIGVGYVADRGSVSEYRLSQIKPLHNFLTQLQPFLKLKQKQANLVLKIIEQLPSAKESPD   120
DMD 35-36L.282 (SEQ ID NO: 48)   EIGVGYVADRGSVSEYRLSQIKPLHNFLTQLQPFLKLKQKQANLVLKIIEQLPSAKESPD   120
DMD 35-36L.349 (SEQ ID NO: 49)   EIGVGYVADRGSVSEYRLSQIKPLHNFLTQLQPFLKLKQKQANLVLKIIEQLPSAKESPD   120
DMD 35-36L.378 (SEQ ID NO: 50)   EIGVGYVADRGSVSEYRLSQIKPLHNFLTQLQPFLKLKQKQANLVLKIIEQLPSAKESPD   120
DMD 35-36L.457 (SEQ ID NO: 51)   EIGVGYVADRGSVSEYRLSQIKPLHNFLTQLQPFLKLKQKQANLVLKIIEQLPSAKESPD   120
DMD 35-36L.469 (SEQ ID NO: 52)   EIGVGYVADRGSVSEYRLSEIKPLHNFLTQLQPFLKLKQKQANLVLKIIEQLPSAKESPD   120
                                 ******* * **** **** ****************************************

DMD 35-36x.63  (SEQ ID NO: 45)   KFLEVCTWVDQIAALNDSKTRKTTSETVRAVLDSLPGSVGGLSPSQASSAASSASSSPGS   180
DMD 35-36x.81  (SEQ ID NO: 46)   KFLEVCTWVDQIAALNDSKTRKTTSETVRAVLDSLPGSVGGLSPSQASSAASSASSSPGS   180
DMD 35-36L.195 (SEQ ID NO: 47)   KFLEVCTWVDQIAALNDSKTRKTTSETVRAVLDSLPGSVGGLSPSQASSAASSASSSPGS   180
DMD 35-36L.282 (SEQ ID NO: 48)   KFLEVCTWVDQIAALNDSKTRKTTSETVRAVLDSLPGSVGGLSPSQASSAASSASSSPGS   180
DMD 35-36L.349 (SEQ ID NO: 49)   KFLEVCTWVDQIAALNDSKTRKTTSETVRAVLDSLPGSVGGLSPSQASSAASSASSSPGS   180
DMD 35-36L.378 (SEQ ID NO: 50)   KFLEVCTWVDQIAALNDSKTRKTTSETVRAVLDSLPGSVGGLSPSQASSAASSASSSPGS   180
DMD 35-36L.457 (SEQ ID NO: 51)   KFLEVCTWVDQIAALNDSKTRKTTSETVRAVLDSLPGSVGGLSPSQASSAASSASSSPGS   180
DMD 35-36L.469 (SEQ ID NO: 52)   KFLEVCTWVDQIAALNDSKTRKTTSETVRAVLDSLPGSVGGLSPSQASSAASSASSSPGS   180
                                 ************************************************************

DMD 35-36x.63  (SEQ ID NO: 45)   GISEALRAGAGSGTGYNKEFLLYLAGFVDGDGSIFASIMPTQWTKFKHSLLLRFRVTQST   240
DMD 35-36x.81  (SEQ ID NO: 46)   GISEALRAGAGSGTGYNKEFLLYLAGFVDGDGSIFASIIPSQLVKFKHTLLLRFRVTQAT   240
DMD 35-36L.195 (SEQ ID NO: 47)   GISEALRAGAGSGTGYNKEFLLYLAGFVDGDGSIFASIIPSQLVKFKHTLLLRFRVCQAT   240
DMD 35-36L.282 (SEQ ID NO: 48)   GISEALRAGAGSGTGYNKEFLLYLAGFVDGDGSIFASIIPSQFVKFKHTLLLRFRVCQAT   240
DMD 35-36L.349 (SEQ ID NO: 49)   GISEALRAGAGSGTGYNKEFLLYLAGFVDGDGSIFASIIPSQEVKFKHTLLLRFRVCQAT   240
DMD 35-36L.378 (SEQ ID NO: 50)   GISEALRAGAGSGTGYNKEFLLYLAGFVDGDGSIFASIIPSQEVKFKHTLLLRFRVTQAT   240
DMD 35-36L.457 (SEQ ID NO: 51)   GISEALRAGAGSGTGYNKEFLLYLAGFVDGDGSIFASIIPSQEVKFKHTLLLRFRVCQAT   240
DMD 35-36L.469 (SEQ ID NO: 52)   GISEALRAGAGSGTGYNKEFLLYLAGFVDGDGSIFASIIPSQEVKFKHTLLLRFRVCQAT   240
                                 ************************************* *   **** *******  * *

DMD 35-36x.63  (SEQ ID NO: 45)   RRRWFLDKLMDEIGVGYVSDQGRASYYTLSEIKPLHNFLTQLQPFLKLKQKQANLVLKII   300
DMD 35-36x.81  (SEQ ID NO: 46)   RRRWFLDKLVDEIGVGYVTDNGRASYYTLSEIKPLHNFLTQLQPFLKLKQKQANLVLKII   300
DMD 35-36L.195 (SEQ ID NO: 47)   KRRWFLDKLVDEIGVGYVSDQGSASYYTLSEIKPLHNFLTQLQPFLKLKQKQANLVLKII   300
DMD 35-36L.282 (SEQ ID NO: 48)   KRRWFLDKLVDEIGVGYVSDQGSASYYTLSEIKPLHNFLTQLQPFLKLKQKQANLVLKII   300
DMD 35-36L.349 (SEQ ID NO: 49)   KRRWFLDKLVDEIGVGYVSDQGSASYYTLSEIKPLHNFLTQLQPFLKLKQKQANLVLKII   300
DMD 35-36L.378 (SEQ ID NO: 50)   KRRWFLDKLVDEIGVGYVSDVGSASYYTLSEIKPLHNFLTQLQPFLKLKQKQANLVLKII   300
DMD 35-36L.457 (SEQ ID NO: 51)   KRRWFLDKLVDEIGVGYVSDRGSASYYTLSEIKPLHNFLTQLQPFLKLKQKQANLVLKII   300
DMD 35-36L.469 (SEQ ID NO: 52)   KRRWFLDKLVDEIGVGYVSDQGSASYYTLSQIKPLHNFLTQLQPFLKLKQKQANLVLKII   300
                                  ********* ******** * * ****** ******************************

DMD 35-36x.63  (SEQ ID NO: 45)   EQLPSAKESPDKFLEVCTWVDQIAALNDSRTRKTTSETVRAVLDSLSEKKKSSP   354
DMD 35-36x.81  (SEQ ID NO: 46)   EQLPSAKESPDKFLEVCTWVDQIAALNDSRTRKTTSETVRAVLDSLSEKKKSSP   354
DMD 35-36L.195 (SEQ ID NO: 47)   EQLPSAKESPDKFLEVCTWVDQIAALNDSRTRKTTSETVRAVLDSLSEKKKSSP   354
DMD 35-36L.282 (SEQ ID NO: 48)   EQLPSAKESPDKFLEVCTWVDQIAALNDSRTRKTTSETVRAVLDSLSEKKKSSP   354
DMD 35-36L.349 (SEQ ID NO: 49)   EQLPSAKESPDKFLEVCTWVDQIAALNDSRTRKTTSETVRAVLDSLSEKKKSSP   354
DMD 35-36L.378 (SEQ ID NO: 50)   EQLPSAKESPDKFLEVCTWVDQIAALNDSRTRKTTSETVRAVLDSLSEKKKSSP   354
DMD 35-36L.457 (SEQ ID NO: 51)   EQLPSAKESPDKFLEVCTWVDQIAALNDSRTRKTTSETVRAVLDSLSEKKKSSP   354
DMD 35-36L.469 (SEQ ID NO: 52)   EQLPSAKESPDKFLEVCTWVDQIAALNDSRTRKTTSETVRAVLDSLSEKKKSSP   354
                                 *****************************************************
```

FIGURE 4B

```
DMD 37-38x.15  (SEQ ID NO: 53)    MNTKYNKEFLLYLAGFVDSDGSIVATIRPGQELKFKHGLRLRFYVCQKTQRRWFLDKLVD    60
DMD 37-38x.66  (SEQ ID NO: 54)    MNTKYNKEFLLYLAGFVDADGSIVATIRPGQELKFKHGLRLRFYVCQKTQRRWFLDKLVD    60
DMD 37-38x.79  (SEQ ID NO: 55)    MNTKYNKEFLLYLAGFVDADGSIVATIRPGQELKFKHGLRLRFYVCQKTQRRWFLDKLVD    60
DMD 37-38L.166 (SEQ ID NO: 56)    MNTKYNKEFLLYLAGFVDSDGSIVASIAPAQDCKFKHRLRLRFFVSQKTQRRWFLDKLVD    60
DMD 37-38L.478 (SEQ ID NO: 57)    MNTKYNKEFLLYLAGFVDSDGSIVARIEPAQDCKFKHRLRLQFFVSQKTQRRWFLDKLVD    60
DMD 37-38L.512 (SEQ ID NO: 58)    MNTKYNKEFLLYLAGFVDSDGSIVARIEPAQDCKFKHRLRLQFFVSQKTQRRWFLDKLVD    60
DMD 37-38L.528 (SEQ ID NO: 59)    MNTKYNKEFLLYLAGFVDADGSIVARIEPAQDCKFKHRLRLQFFVSQKTQRRWFLDKLVD    60
                                  ********************  ******  *  *    ****  ***  *  * *********************

DMD 37-38x.15  (SEQ ID NO: 53)    EIGVGYVTDSGSVSRYELSQIKPLHNFLTQLQPFLKLKQKQANLVLKIIEQLPSAKESPD   120
DMD 37-38x.66  (SEQ ID NO: 54)    EIGAGYVTDSGSVSRYELSQIKPLHNFLTQLQPFLKLKQKQANLVLKIIEQLPSAKESPD   120
DMD 37-38x.79  (SEQ ID NO: 55)    EIGVGYVTDSGSVSRYELSQIKPLHNFLTQLQPFLKLKQKQANLVLKIIEQLPSAKESPD   120
DMD 37-38L.166 (SEQ ID NO: 56)    EIGVGYVSDSGSVSSYVLSEIKPLHNFLTQLQPFLKLKQKQANLVLKIIEQLPSAKESPD   120
DMD 37-38L.478 (SEQ ID NO: 57)    EIGVGYVRDSGSVSSYDLSQIKPLHNFLTQLQPFLKLKQKQANLVLKIIEQLPSAKESPD   120
DMD 37-38L.512 (SEQ ID NO: 58)    EIGVGYVRDSGSVSSYLLSQIKPLHNFLTQLQPFLKLKQKQANLVLKIIEQLPSAKESPD   120
DMD 37-38L.528 (SEQ ID NO: 59)    EIGVGYVRDSGSVSSYNLSEIKPLHNFLTQLQPFLKLKQKQANLVLKIIEQLPSAKESPD   120
                                  ***  ***  *****  **  ********************************************

DMD 37-38x.15  (SEQ ID NO: 53)    KFLEVCTWVDQIAALNDSKTRKTTSETVRAVLDSLPGSVGGLSPSQASSAASSASSSPGS   180
DMD 37-38x.66  (SEQ ID NO: 54)    KFLEVCTWVDQIAALNDSKTRKTTSETVRAVLDSLPGSVGGLSPSQASSAASSASSSPGS   180
DMD 37-38x.79  (SEQ ID NO: 55)    KFLEVCTWVDQIAALNDSKTRKTTSETVRAVLDSLPGSVGGLSPSQASSAASSASSSPGS   180
DMD 37-38L.166 (SEQ ID NO: 56)    KFLEVCTWVDQIAALNDSKTRKTTSETVRAVLDSLPGSVGGLSPSQASSAASSASSSPGS   180
DMD 37-38L.478 (SEQ ID NO: 57)    KFLEVCTWVDQIAALNDSKTRKTTSETVRAVLDSLPGSVGGLSPSQASSAASSASSSPGS   180
DMD 37-38L.512 (SEQ ID NO: 58)    KFLEVCTWVDQIAALNDSKTRKTTSETVRAVLDSLPGSVGGLSPSQASSAASSASSSPGS   180
DMD 37-38L.528 (SEQ ID NO: 59)    KFLEVCTWVDQIAALNDSKTRKTTSETVRAVLDSLPGSVGGLSPSQASSAASSASSSPGS   180
                                  ************************************************************

DMD 37-38x.15  (SEQ ID NO: 53)    GISEALRAGAGSGTGYNKEFLLYLAGFVDGDGSIFACIRPSQRAKFKHVLQLCFRVHQLT   240
DMD 37-38x.66  (SEQ ID NO: 54)    GISEALRAGAGSGTGYNKEFLLYLAGFVDGDGSIFACIRPSQRAKFKHVLQLCFRVHQKT   240
DMD 37-38x.79  (SEQ ID NO: 55)    GISEALRAGAGSGTGYNKEFLLYLAGFVDGDGSIFACIRPSQRAKFKHVLQLCFRVHQST   240
DMD 37-38L.166 (SEQ ID NO: 56)    GISEALRAGAGSGTGYNKEFLLYLAGFVDGDGSIFACIRPSQRAKFKHVLQLCFRVFQKT   240
DMD 37-38L.478 (SEQ ID NO: 57)    GISEALRAGAGSGTGYNKEFLLYLAGFVDGDGSIFACIRPSQRAKFKHVLQLHFRVFQKT   240
DMD 37-38L.512 (SEQ ID NO: 58)    GISEALRAGAGSGTGYNKEFLLYLAGFVDGDGSIFACIRPSQRAKFKHVLQLCFRVFQKT   240
DMD 37-38L.528 (SEQ ID NO: 59)    GISEALRAGAGSGTGYNKEFLLYLAGFVDGDGSIFACIRPSQRAKFKHVLQLCFRVFQKT   240
                                  ***************************************************    ***  *  *

DMD 37-38x.15  (SEQ ID NO: 53)    KRRWFLDKLVDEIGVGYVYDCGSASFYHLSQIKPLHNFTQLQPFLKLKQKQANLVLKII    300
DMD 37-38x.66  (SEQ ID NO: 54)    KRRWFLDKLVDEIGVGYVYDHGSASCYHLSEIKPLHNFLTQLQPFLKLKQKQANLVLKII   300
DMD 37-38x.79  (SEQ ID NO: 55)    RRRWFLDKLVDEIGAGYVYDHGSASLYSLSQIKPLHNFLTQLQPFLKLKQKQANLVLKII   300
DMD 37-38L.166 (SEQ ID NO: 56)    QRRWFLDKLVDEIGVGYVYDHGRASIYQLSQIKPLHNFLTQLQPFLKLKQKQANLVLKII   300
DMD 37-38L.478 (SEQ ID NO: 57)    QRRWFLDKLVDEIGVGYVYDHGRASIYQLSQIKPLHNFLTQLQPFLKLKQKQANLVLKII   300
DMD 37-38L.512 (SEQ ID NO: 58)    QRRWFLDKLVDEIGVGYVYDHGRASIYQLSQIKPLHNFLTQLQPFLKLKQKQANLVLKII   300
DMD 37-38L.528 (SEQ ID NO: 59)    QRRWFLDKLVDEIGVGYVYDHGRASIYQLSQIKPLHNFLTQLQPFLKLKQKQANLVLKII   300
                                  *************  *****    *  **   *  **  *********************************

DMD 37-38x.15  (SEQ ID NO: 53)    EQLPSAKESPDKFLEVCTWVDQIAALNDSKTRKTTSETVRAVLDSLSEKKKSSP       354
DMD 37-38x.66  (SEQ ID NO: 54)    EQLPSAKESPDKFLEVCTWVDQIAALNDSHTRKTTSETVRAVLDSLSEKKKSSP       354
DMD 37-38x.79  (SEQ ID NO: 55)    EQLPSAKESPDKFLEVCTWVDQIAALNDSHTRKTTSETVRAVLDSLSEKKKSSP       354
DMD 37-38L.166 (SEQ ID NO: 56)    EQLPSAKESPDKFLEVCTWVDQIAALNDSHTRKTTSETVRAVLDSLSEKKKSSP       354
DMD 37-38L.478 (SEQ ID NO: 57)    EQLPSAKESPDKFLEVCTWVDQIAALNDSHTRKTTSETVRAVLDSLSEKKKSSP       354
DMD 37-38L.512 (SEQ ID NO: 58)    EQLPSAKESPDKFLEVCTWVDQIAALNDSHTRKTTSETVRAVLDSLSEKKKSSP       354
DMD 37-38L.528 (SEQ ID NO: 59)    EQLPSAKESPDKFLEVCTWVDQIAALNDSHTRKTTSETVRAVLDSLSEKKKSSP       354
                                  *****************************  **********************************
```

FIGURE 4C

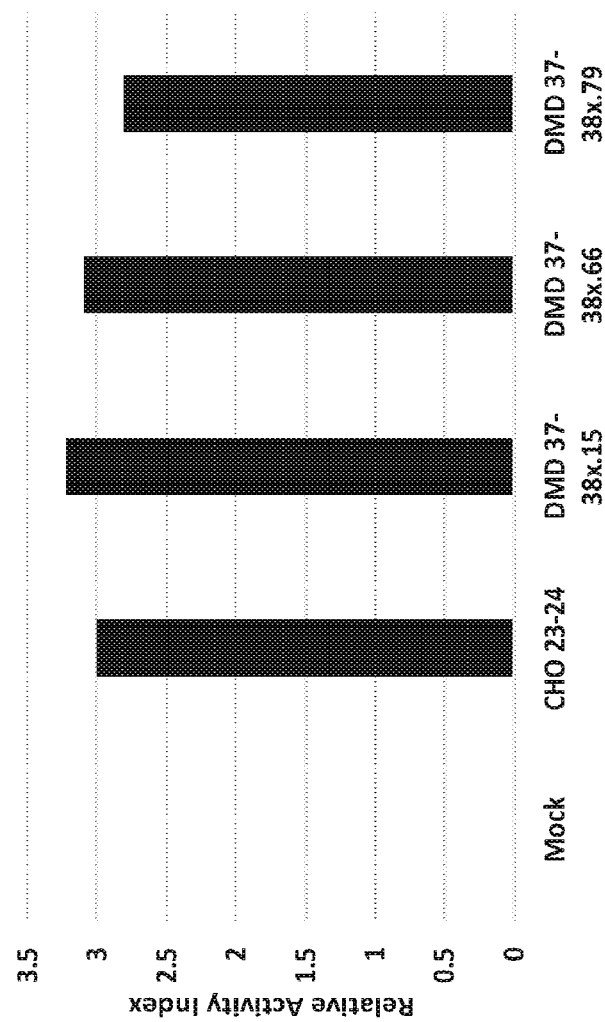

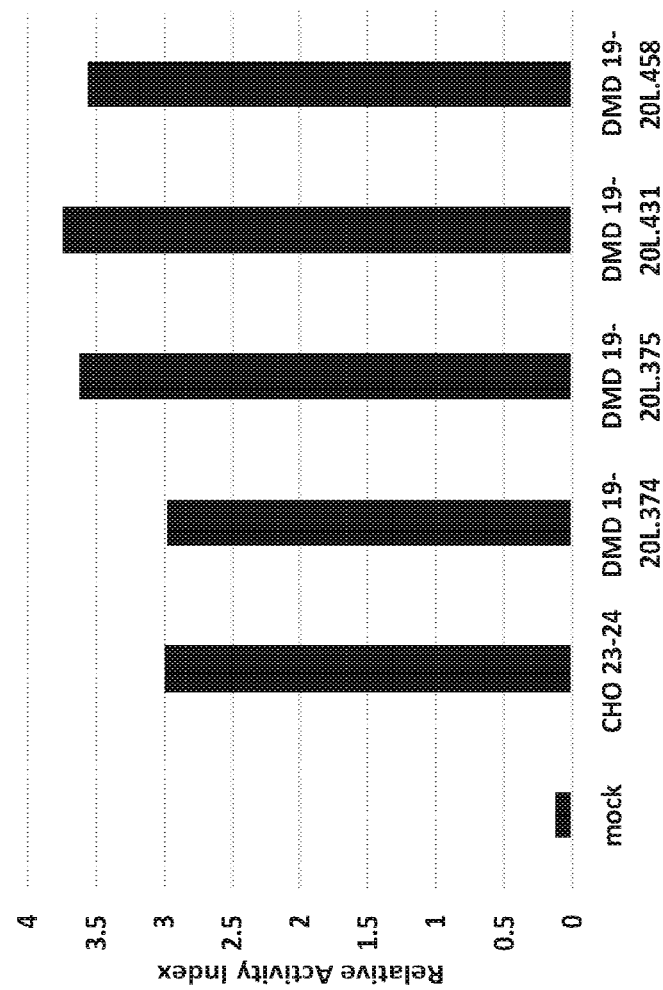

FIGURE 8B

SEQUENCE LISTING

```
Sequence total quantity: 197
SEQ ID NO: 1             moltype = AA  length = 163
FEATURE                  Location/Qualifiers
source                   1..163
                         mol_type = protein
                         organism = Chlamydomonas reinhardtii
SEQUENCE: 1
MNTKYNKEFL LYLAGFVDGD GSIIAQIKPN QSYKFKHQLS LAFQVTQKTQ RRWFLDKLVD    60
EIGVGYVRDR GSVSDYILSE IKPLHNFLTQ LQPFLKLKQK QANLVLKIIW RLPSAKESPD   120
KFLEVCTWVD QIAALNDSKT RKTTSETVRA VLDSLSEKKK SSP                     163

SEQ ID NO: 2             moltype = AA  length = 9
FEATURE                  Location/Qualifiers
source                   1..9
                         mol_type = protein
                         organism = Chlamydomonas reinhardtii
```

```
SEQUENCE: 2
LAGLIDADG                                                                       9

SEQ ID NO: 3            moltype = AA  length = 10
FEATURE                 Location/Qualifiers
REGION                  1..10
                        note = Synthesized
source                  1..10
                        mol_type = protein
                        organism = synthetic construct
SEQUENCE: 3
MAPKKKRKVH                                                                      10

SEQ ID NO: 4            moltype = AA  length = 3685
FEATURE                 Location/Qualifiers
source                  1..3685
                        mol_type = protein
                        organism = Homo sapiens
SEQUENCE: 4
MLWWEEVEDC YEREDVQKKT FTKWVNAQFS KFGKQHIENL FSDLQDGRRL LDLLEGLTGQ   60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILLK WQRLTEEQCL FSAWLSEKED AVNKIHTTGF KDQNEMLSSL  600
QKLAVLKADL EKKKQSMGKL YSLKQDLLST LKNKSVTQKT EAWLDNFARC WDNLVQKLEK  660
STAQISQAVT TTQPSLTQTT VMETVTTVTT REQILVKHAQ EELPPPPPQK KRQITVDSEI  720
RKRLDVDITE LHSWITRSEA VLQSPEFAIF RKEGNFSDLK EKVNAIEREK AEKFRKLQDA  780
SRSAQALVEQ MVNEGVNADS IKQASEQLNS RWIEFCQLLS ERLNWLEYQN NIIAFYNQLQ  840
QLEQMTTTAE NWLKIQPTTP SEPTAIKSQL KICKDEVNRL SDLQPQIERL KIQSIALKEK  900
GQGPMFLDAD FVAFTNHFKQ VFSDVQAREK ELQTIFDTLP PMRYQETMSA IRTWVQQSET  960
KLSIPQLSVT DYEIMEQRLG ELQALQSSLQ EQQSGLYYLS TTVKEMSKKA PSEISRKYQS 1020
EFEEIEGRWK KLSSQLVEHC QKLEEQMNKL RKIQNHIQTL KKWMAEVDVF LKEEWPALGD 1080
SEILKKQLKQ CRLLVSDIQT IQPSLNSVNE GGQKIKNEAE PEFASRLETE LKELNTQWDH 1140
MCQQVYARKE ALKGGLEKTV SLQKDLSEMH EWMTQAEEEY LERDFEYKTP DELQKAVEEM 1200
KRAKEEAQQK EAKVKLLTES VNSVIAQAPP VAQEALKKEL ETLTTNYQWL CTRLNGKCKT 1260
LEEVWACWHE LLSYLEKANK WLNEVEFKLK TTENIPGGAE EISEVLDSLE NLMRHSEDNP 1320
NQIRILAQTL TDGGVMDELI NEELETFNSR WRELHEEAVR RQKLLEQSIQ SAQETEKSLH 1380
LIQESLTFID KQLAAYIADK VDAAQMPQEA QKIQSDLTSH EISLEEMKKH NQGKEAAQRV 1440
LSQIDVAQKK LQDVSMKFRL FQKPANFEQR LQESKMILDE VKMHLPALET KSVEQEVVQS 1500
QLNHCVNLYK SLSEVKSEVE MVIKTGRQIV QKKQTENPKE LDERVTALKL HYNELGAKVT 1560
ERKQQLEKCL KLSRKMRKEM NVLTEWLAAT DMELTKRSAV EGMPSNLDSE VAWGKATQKE 1620
IEKQKVHLKS ITEVGEALKT IAVTSRAEEW DKLSLLNSNW IAVTSRAEEW LNLLLEYQKH 1680
METFDQNVDH ITKWIIQADT LLDESEKKKP QQKEDVLKRL KAELNDIRPK VDSTRDQAAN 1740
LMANRGDHCR KLVEPQISEL NHRFAAISHR IKTGKASIPL KELEQFNSDI QKLLEPLEAE 1800
IQQGVNLKEE DFNKDMNEDN EGTVKELLQR GDNLQQRITD ERKREEIKIK QQLLQTKHNA 1860
LKDLRSQRRK KALEISHQWY QYKRQADDLL KCLDDIEKKL ASLPEPRDER KIKEIDRELQ 1920
KKKEELNAVR RQAEGLSEDG AAMAVEPTQI QLSKRWREIE SKFAQFRRLN FAQIHTVREE 1980
TMMVMTEDMP LEISYVPSTY LTEITHVSQA LLEVEQLLNA PDLCAKDFED LFKQEESLKN 2040
IKDSLQQSSG RIDIIHSKKT AALQSATPVE RVKLQEALSQ LDFQWEKVNK MYKDRQGRFD 2100
RSVEKWRRFH YDIKIFNQWL TEAEQFLRKT QIPENWEHAK EILSKGQHLY KWYKLEQD GIGQRQTVVR 2160
TLNATGEEII QQSSKTDASI LQEKLGSLNL RWQEVCKQLS DRKKRLEEQK NILSEFQRDL 2220
NEFVLWLEEA DNIASIPLEP GKEQQLKEKL EQVKLLVEEL PLRQGILKQL NETGGPVLVS 2280
APISPEEQDK LENKLKQTNL QWIKVSRALP EKQGEIEAQI KDLGQLEKKL EDLEEQLNHL 2340
LLWLSPIRNQ LEIYNQPNQE GPFDVKETEI AVQAKQPVLK EWYKLEQD KEKPATQPVK 2400
RKLEDLSSEW KAVNRLLQEL RAKQPDLAPG LTTIGASPTQ TVTLVTQPVV TKETAISKLE 2460
MPSSLMLEVP ALADFNRAWT ELTDWLSLLD QVIKSQRVMV GDLEDINEMI IKQKATMQDL 2520
EQRRPQLEEL ITAAQNLKNK TSNQEARTII TDRIERIQNQ WDEVQEHLQN RRQQLNEMLK 2580
DSTQWLEAKE EAEQVLGQAR AKLESWKEGP YTVDAIQKKI TETKQLAKDL RQWQTNVDVA 2640
NDLALKLLRD YSADDTRKVH MITENINASW RSIHKRVSER EAALEETHRL LQQFPLDLEK 2700
FLAWLTEAET TANVLQDATR KERLLEDSKG VKELMKQWQD LQGEIEAHTD VYHNLDENSQ 2760
KILRSLEGSD DAVLLQRRLD NMNFKWSELR KKSLNIRSHL EASSDQWKRL HLSLQELLVW 2820
LQLKDDELSR QAPIGGDFPA VQKQNDVHRA FKRELKTKEP VIMSTLETVR IFLTEQPLEG 2880
LEKLYQEPRE LPPEERAQNV TRLLRKQAEE VNTEWEKLNL HSADWQRKID ETLERLRELQ 2940
EATDELDLKL RQAEVIKGSW QPVGDLLIDS LQDHLEKVKA LRGEIAPLKE NVSHVNDLAR 3000
QLTTLGIQLS PYNLSTLEDL NTRWKLLQVA VEDRVRQLHE AHRDFGPASQ HFLSTSVQGP 3060
WERAISPNKV PYYINHETQT TCWDHPKMTE LYQSLADLNN VRFSAYRTAM KLRRLQKALC 3120
LDLLSLSAAC DALDQHNLKQ NDQPMDILQI INCLTTIYDR LEQEHNNLVN VPLCVDMCLN 3180
WLLNVYDTGR TGRIRVLSFK TGIISLCKAH LEDKYRYLFK QVASSTGFCD QRRLGLLLHD 3240
SIQIPRQLGE VASFGGSNIE PSVRSCFQFA NNKPEIEAAL FLDWMRLEPQ SMVWLPVLHR 3300
VAAAETAKHQ AKCNICKECP IIGFRYRSLK HFNYDICQSC FFSGRVAKGH KMHYPMVEYC 3360
TPTTSGEDVR DFAKVLKNKF RTKRYFAKHP RMGYLPVQTV LEGDNMETPV TLINFWPVDS 3420
APASSPQLSH DDTHSRIEHY ASRLAEMENS NGSYLNDSIS PNESIDDEHL LIQHYCQSLN 3480
QDSPLSQPRS PAQILISLES EERGELERIL ADLEEENRNL QAEYDRLKQQ HEHKGLSPLP 3540
SPPEMMPTSP QSPRDAELIA EAKLLRQHKG RLEARMQILE DHNKQLESQL HRLRQLLEQP 3600
```

```
QAEAKVNGTT VSSPSTSLQR SDSSQPMLLR VVGSQTSDSM GEEDLLSPPQ DTSTGLEEVM    3660
EQLNNSFPSS RGRNTPGKPM REDTM                                          3685

SEQ ID NO: 5            moltype = AA   length = 3092
FEATURE                 Location/Qualifiers
source                  1..3092
                        mol_type = protein
                        organism = Homo sapiens
SEQUENCE: 5
MLWWEEVEDC YEREDVQKKT FTKWVNAQFS KFGKQHIENL FSDLQDGRRL LDLLEGLTGQ     60
KLPKEKGSTR VHALNNVNKA LRVLQNNNVD LVNIGSTDIV DGNHKLTLGL IWNIILHWQV    120
KNVMKNIMAG LQQTNSEKIL LSWVRQSTRN YPQVNVINFT TSWSDGLALN ALIHSHRPDL    180
FDWNSVVCQQ SATQRLEHAF NIARYQLGIE KLLDPEDVDT TYPDKKSILM YITSLFQVLP    240
QQVSIEAIQE VEMLRPPKV TKEEHFQLHH QMHYSQQITV SLAQGYERTS SPKPRFKSYA     300
YTQAAYVTTS DPTRSPFPSQ HLEAPEDKSF GSSLMESEVN LDRYQTALEE VLSWLLSAED    360
TLQAQGEISN DVEVVKDQFH THEGYMMDLT AHQGRVGNIL QLGSKLIGTG KLSEDEETEV    420
QEQMNLLNSR WECLRVASME KQSNLHRVLM DLQNQKLKEL NDWLTKTEER TRKMEEEPLG    480
PDLEDLKRQV QQHKVLQEDL EQEQVRVNSL THMVVVVDES SGDHATAALE EQLKVLGDRW    540
ANICRWTEDR WVLLQDILLK WQRLTEEQCL FSAWLSEKED AVNKIHTTGF KDQNEMLSSL    600
QKLAVLKADL EKKKQSMGKL YSLKQDLLST LKNKSVTQKT EAWLDNFARC WDNLVQKLEK    660
STAQISQAVT TTQPSLTQTT VMETVTTVTT REQILVKHAQ EELPPPPPQK KRQITVDSEI    720
RKRLDVDITE LHSWITRSEA VLQSPEFAIF RKEGNFSDLN EKVNAIEREK AEKFRKLQDA    780
SRSAQALVEQ MVNEGVNADS IKQASEQLNS RWIEFCQLLS ERLNWLEYQN NIIAFYNQLQ    840
QLEQMTTTAE NWLKIQPTTP SEPTAIKSQL KICKDEVNRL SDLQPQIERL KIQSIALKEK    900
GQGPMFLDAD FVAFTNHFKQ VFSDVQAREK ELQTIFDTLP PMRYQETMSA IRTWVQQSET    960
KLSIPQLSVT DYEIMEQRLG ELQALQSSLQ EQQSGLYYLS TTVKEMSKKA PSEISRKYQS   1020
EFEEIEGRWK KLSSQLVEHC QKLEEQMNKL RKIQNHIQTL KKWMAEVDVF LKEEWPALGD   1080
SEILKKQLKQ CRLLVSDIQT IQPSLNSVNE GGQKIKNEAE PEFASRLETE LKELNTQWDH   1140
MCQQVYARKE ALKGGLEKTV SLQKDLSEMH EWMTQAEEEY LERDFEYKTP DELQKAVEEM   1200
KRAKEEAQQK EAKVKLLTES VNSVIAQAPP VAQEALKKEL ETLTTNYQWL CTRLNGKCKT   1260
LEEVWACWHE LLSYLEKANK WLNEVEFKLK TTENIPGGAE EISEVLDSLE NLMRHSEDNP   1320
NQIRILAQTL TDGGVMDELI NEELETFNSR WRELHEEAVR RQKLLEQSIQ SAQETEKSLH   1380
LIQESLTFID KQLAAYIADK VDAAQMPQEA QKIQSDLTSH EISLEEMKKH NQGKEAAQRV   1440
LSQIDVAQKK LQDVSMKFRL FQKPANFEQR LQESKMILDE VKMHLPALET KSVEQEVVQS   1500
QLNHCVNLYK SLSEVKSEVE MVIKTGRQIV QKKQTENPKE LDERVTALKL HYNELGAKVT   1560
ERKQQLEKCL KLSRKMRKEM NVLTEWLAAT DMELTKRSAV EGMPSNLDSE VAWGKATQKE   1620
IEKQKVHLKS ITEVGEALKT VLGKKETLVE DKLSLLNSNW IAVTSRAEEW LNLLLEYQKH   1680
METFDQNVDH ITKWIIQADT LLDESEKKKP QQKEDVLKRL KAELNDIRPK VDSTRDQAAN   1740
LMANRGDHCR KLVEPQISEL NHRFAAISHR IKTGKASIPL KELEQFNSDI QKLLEPLEAE   1800
IQQGVNLKEE DFNKDMNEDN EGTVKELLQR GDNLQQRITD ERKREEIKIK QQLLQTKHNA   1860
LKDLRSQRRK KALEISHQWY QYKRQADDLL KCLDDIEKKL ASLPEPRDER KIKEIDRELQ   1920
KKKEELNAVR RQAEGLSEDG AAMAVEPTQI QLSKRWREIE SKFAQFRRLN FAQIHTVREE   1980
TMMVMTEDMP LEISYVPSTY LTEITHVSQA LLEVEQLINA PDLCAKDFED LFKQEESLKN   2040
IKDSLQQSSG RIDIIHSKKT AALQSATPVE RVKLQEALSQ LDFQWEKVNK MYKDRQGRFD   2100
RSVEKWRRFH YDIKIFNQWL TEAEQFLRKT QIPENWEHAK YKWYLKDLQG EIEAHTDVYH   2160
NLDENSQKIL RSLEGSDDAV LLQRRLDNMN FKWSELRKKS LNIRSHLEAS SDQWKRLHLS   2220
LQELLVWLQL KDDELSRQAP IGGDFPPAVQK QNDVHRAFKR ELKTKEPVIM STLETVRIFL   2280
TEQPLEGLEK LYQEPRELPP EERAQNVTRL LRKQAEEVNT EWEKLNLHSA DWQRKIDETL   2340
ERLRELQEAT DELDLKLRQA EVIKGSWQPV GDLLIDSLQD HLEKVKALRG EIAPLKENVS   2400
HVNDLARQLT TLGIQLSPYN LSTLEDLNTR WKLLQVAVED RVRQLHEAHR DFGPASQHFL   2460
STSVQGPWER AISPNKVPYY INHETQTTCW DHPKMTELYQ SLADLNNVRF SAYRTAMKLR   2520
RLQKALCLDL LSLSAACDAL DQHNLKQNDQ PMDILQIINC LTTIYDRLEQ EHNNLVNVPL   2580
CVDMCLNWLL NVYDTGRTGR IRVLSFKTGI ISLCKAHLED KYRYLFKQVA SSTGFCDQRR   2640
LGLLLHDSIQ IPRQLGEVAS FGGSNIEPSV RSCFQFANNK PEIEAALFLD WMRLEPQSMV   2700
WLPVLHRVAA AETAHQAKC NICKECPIIG FRYRSLKHFN YDICQSCFFS GRVAKGHKMH   2760
YPMVEYCTPT TSGEDVRDFA KVLKNKFRTK RYFAKHPRMG YLPVQTVLEG DNMETPVTLI   2820
NFWPVDSAPA SSPQLSHDDT HSRIEHYASR LAEMENSNGS YLNDSISPNE SIDDEHLLIQ   2880
HYCQSLNQDS PLSQPRSPAQ ILISLESEER GELERILADL EEENRNLQAE YDRLKQQHEH   2940
KGLSPLPSPP EMMPTSPQSP RDAELIAEAK LLRQHKGRLE ARMQILEDHN KQLESQLHRL   3000
RQLLEQPQAE AKVNGTTVSS PSTSLQRSDS SQPMLLRVVG SQTSDSMGEE DLLSPPQDTS   3060
TGLEEVMEQL NNSFPSSRGR NTPGKPMRED TM                                 3092

SEQ ID NO: 6            moltype = DNA   length = 22
FEATURE                 Location/Qualifiers
source                  1..22
                        mol_type = genomic DNA
                        organism = Homo sapiens
SEQUENCE: 6
aaggattatg tattacctcc cg                                              22

SEQ ID NO: 7            moltype = DNA   length = 22
FEATURE                 Location/Qualifiers
source                  1..22
                        mol_type = genomic DNA
                        organism = Homo sapiens
SEQUENCE: 7
ttcctaatac ataatggagg gc                                              22

SEQ ID NO: 8            moltype = DNA   length = 22
```

```
FEATURE            Location/Qualifiers
source             1..22
                   mol_type = genomic DNA
                   organism = Homo sapiens
SEQUENCE: 8
taagattggg tatgagggat ag                                              22

SEQ ID NO: 9       moltype = DNA   length = 22
FEATURE            Location/Qualifiers
source             1..22
                   mol_type = genomic DNA
                   organism = Homo sapiens
SEQUENCE: 9
attctaaccc atactcccta tc                                              22

SEQ ID NO: 10      moltype = DNA   length = 22
FEATURE            Location/Qualifiers
source             1..22
                   mol_type = genomic DNA
                   organism = Homo sapiens
SEQUENCE: 10
ctacatggtg tatctgacta ag                                              22

SEQ ID NO: 11      moltype = DNA   length = 22
FEATURE            Location/Qualifiers
source             1..22
                   mol_type = genomic DNA
                   organism = Homo sapiens
SEQUENCE: 11
gatgtaccac atagactgat tc                                              22

SEQ ID NO: 12      moltype = DNA   length = 22
FEATURE            Location/Qualifiers
source             1..22
                   mol_type = genomic DNA
                   organism = Homo sapiens
SEQUENCE: 12
ctggccgaag tataggaata tg                                              22

SEQ ID NO: 13      moltype = DNA   length = 22
FEATURE            Location/Qualifiers
source             1..22
                   mol_type = genomic DNA
                   organism = Homo sapiens
SEQUENCE: 13
gaccggcttc atatccttat ac                                              22

SEQ ID NO: 14      moltype =    length =
SEQUENCE: 14
000

SEQ ID NO: 15      moltype =    length =
SEQUENCE: 15
000

SEQ ID NO: 16      moltype =    length =
SEQUENCE: 16
000

SEQ ID NO: 17      moltype =    length =
SEQUENCE: 17
000

SEQ ID NO: 18      moltype =    length =
SEQUENCE: 18
000

SEQ ID NO: 19      moltype =    length =
SEQUENCE: 19
000

SEQ ID NO: 20      moltype =    length =
SEQUENCE: 20
000

SEQ ID NO: 21      moltype =    length =
SEQUENCE: 21
000
```

```
SEQ ID NO: 22            moltype =    length =
SEQUENCE: 22
000

SEQ ID NO: 23            moltype =    length =
SEQUENCE: 23
000

SEQ ID NO: 24            moltype =    length =
SEQUENCE: 24
000

SEQ ID NO: 25            moltype =    length =
SEQUENCE: 25
000

SEQ ID NO: 26            moltype =    length =
SEQUENCE: 26
000

SEQ ID NO: 27            moltype =    length =
SEQUENCE: 27
000

SEQ ID NO: 28            moltype =    length =
SEQUENCE: 28
000

SEQ ID NO: 29            moltype =    length =
SEQUENCE: 29
000

SEQ ID NO: 30            moltype = DNA  length = 22
FEATURE                  Location/Qualifiers
misc_feature             1..22
                         note = Synthesized
source                   1..22
                         mol_type = other DNA
                         organism = synthetic construct
SEQUENCE: 30
aaggattatg tatgagggat ag                                                  22

SEQ ID NO: 31            moltype = DNA  length = 22
FEATURE                  Location/Qualifiers
misc_feature             1..22
                         note = Synthesized
source                   1..22
                         mol_type = other DNA
                         organism = synthetic construct
SEQUENCE: 31
ttcctaatac atactcccta tc                                                  22

SEQ ID NO: 32            moltype = DNA  length = 22
FEATURE                  Location/Qualifiers
misc_feature             1..22
                         note = Synthesized
source                   1..22
                         mol_type = other DNA
                         organism = synthetic construct
SEQUENCE: 32
aaggattatg tatctgacta ag                                                  22

SEQ ID NO: 33            moltype = DNA  length = 22
FEATURE                  Location/Qualifiers
misc_feature             1..22
                         note = Synthesized
source                   1..22
                         mol_type = other DNA
                         organism = synthetic construct
SEQUENCE: 33
ttcctaatac atagactgat tc                                                  22

SEQ ID NO: 34            moltype = DNA  length = 22
FEATURE                  Location/Qualifiers
misc_feature             1..22
                         note = Synthesized
source                   1..22
                         mol_type = other DNA
                         organism = synthetic construct
```

```
SEQUENCE: 34
aaggattatg tataggaata tg                                                  22

SEQ ID NO: 35             moltype = DNA  length = 22
FEATURE                   Location/Qualifiers
misc_feature              1..22
                          note = Synthesized
source                    1..22
                          mol_type = other DNA
                          organism = synthetic construct
SEQUENCE: 35
ttcctaatac atatccttat ac                                                  22

SEQ ID NO: 36             moltype = AA  length = 354
FEATURE                   Location/Qualifiers
REGION                    1..354
                          note = Synthesized
source                    1..354
                          mol_type = protein
                          organism = synthetic construct
SEQUENCE: 36
MNTKYNKEFL LYLAGFVDSD GSIYATIRPV QSTKFKHTLR LWFAVTQKTQ RRWFLDKLVD   60
EIGVGYVYDN GSVSWYYLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSICACIVP RQDRKFKHQL RLFFEVGQKT  240
KRRWFLDKLV DEIGVGYVED TGRASRYRLS QIKPHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 37             moltype = AA  length = 354
FEATURE                   Location/Qualifiers
REGION                    1..354
                          note = Synthesized
source                    1..354
                          mol_type = protein
                          organism = synthetic construct
SEQUENCE: 37
MNTKYNKEFL LYLAGFVDSD GSIFAVIEPV QSAKFKHRLK LSFVVTQKTQ RRWFLDKLVD   60
EIGVGYVYDQ GSVSFYRLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSICACIVP RQDRKFKHQL RLFFEVGQTT  240
RRRWFLDKLV DEIGVGYVFD KGSASMYRLS EIKPLHNFLT QLQPFLKLKQ KQANLVLKII  300
EQLPSAKESP DKFLEVCTWV DQIAALNDSR TRKTTSETVR AVLDSLSEKK KSSP         354

SEQ ID NO: 38             moltype = AA  length = 354
FEATURE                   Location/Qualifiers
REGION                    1..354
                          note = Synthesized
source                    1..354
                          mol_type = protein
                          organism = synthetic construct
SEQUENCE: 38
MNTKYNKEFL LYLAGFVDSD GSIYASIMPI QTAKFKHRLK LQFAVAQKTQ RRWFLDKLVD   60
EIGVGYVYDF GSVSYYRLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSICACIVP RQDRKFKHQL RLFFEVGQKT  240
QRRWFLDKLV DEIGVGYVRD LGSASTYRLS EIKPLHNFLT QLQPFLKLKQ KQANLVLKII  300
EQLPSAKESP DKFLEVCTWV DQIAALNDSR TRKTTSETVR AVLDSLSEKK KSSP         354

SEQ ID NO: 39             moltype = AA  length = 354
FEATURE                   Location/Qualifiers
REGION                    1..354
                          note = Synthesized
source                    1..354
                          mol_type = protein
                          organism = synthetic construct
SEQUENCE: 39
MNTKYNKEFL LYLAGFVDSD GSIIAFIMPS QTAKFKHRLK LQFAVAQKTQ RRWFLDKLVD   60
EIGVGYVYDF GSVSYYRLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSICACIVP RQDRKFKHQL RLFFEIGQKT  240
QRRWFLDKLV DEIGVGYVRD LGSASTYRLS QIKPLHNFLT QLQPFLKLKQ KQANLVLKII  300
EQLPSAKESP DKFLEVCTWV DQIAALNDSK TRKTTSETVR AVLDSLSEKK KSSP         354

SEQ ID NO: 40             moltype = AA  length = 354
FEATURE                   Location/Qualifiers
REGION                    1..354
                          note = Synthesized
source                    1..354
                          mol_type = protein
```

```
                        organism = synthetic construct
SEQUENCE: 40
MNTKYNKEFL LYLAGFVDSD GSIMAFIMPT QTAKFKHRLK LQFAVAQKTQ RRWFLDKLVD    60
EIGVGYVYDF GSVSYYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSICACIVP RQDRKFKHQL RLFFEVGQKT   240
QRRWFLDKLV DEIGVGYVRD LGSASTYRLS QIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 41           moltype = AA   length = 354
FEATURE                 Location/Qualifiers
REGION                  1..354
                        note = Synthesized
source                  1..354
                        mol_type = protein
                        organism = synthetic construct
SEQUENCE: 41
MNTKYNKEFL LYLAGFVDSD GSIMAFILPE QHMKFKHRLR LQFAVAQKTQ RRWFLDKLVD    60
EIGVGYVYDF GSVSYYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSICACIVP RQDRKFKHQL RLFFEVGQKT   240
QRRWFLDKLV DEIGVGYVRD LGSASTYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 42           moltype = AA   length = 354
FEATURE                 Location/Qualifiers
REGION                  1..354
                        note = Synthesized
source                  1..354
                        mol_type = protein
                        organism = synthetic construct
SEQUENCE: 42
MNTKYNKEFL LYLAGFVDSD GSIMAFILPE QHLKFKHRLR LQFAVAQKTQ RRWFLDKLVD    60
EIGVGYVYDF GSVSYYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSICACIVP RQDRKFKHQL RLFFEVGQKT   240
QRRWFLDKLV DEIGVGYVRD LGSASTYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 43           moltype = AA   length = 354
FEATURE                 Location/Qualifiers
REGION                  1..354
                        note = Synthesized
source                  1..354
                        mol_type = protein
                        organism = synthetic construct
SEQUENCE: 43
MNTKYNKEFL LYLAGFVDSD GSIMAFILPE QGLKFKHRLR LQFAVAQKTQ RRWFLDKLVD    60
EIGVGYVYDF GSVSYYRLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSICACIVP RQDRKFKHQL RLFFEVGQKT   240
QRRWFLDKLV DEIGVGYVRD LGSASTYRLS QIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 44           moltype = AA   length = 354
FEATURE                 Location/Qualifiers
REGION                  1..354
                        note = Synthesized
source                  1..354
                        mol_type = protein
                        organism = synthetic construct
SEQUENCE: 44
MNTKYNKEFL LYLAGFVDSD GSIMAFIMPD QAPKFKHRLR LQFAVAQKTQ RRWFLDKLVD    60
EIGVGYVYDF GSVSYYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSICACIVP RQDRKFKHQL RLFFEVGQKT   240
QRRWFLDKLV DEIGVGYVRD LGSASTYRLS QIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 45           moltype = AA   length = 354
FEATURE                 Location/Qualifiers
REGION                  1..354
                        note = Synthesized
source                  1..354
                        mol_type = protein
                        organism = synthetic construct
SEQUENCE: 45
MNTKYNKEFL LYLAGFVDAD GSIYACIKPH QQLKFKHQLL LYFEVYQKTQ RRWFLDKLVD    60
EIGVGYVADR GSVSEYRLSQ IKPLHNFLTQ LQPFLKLKQK QANLVLKIIE QLPSAKESPD   120
```

```
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFASIMP TQWTKFKHSL LLRFRVTQST    240
RRRWFLDKLM DEIGVGYVSD QGRASYYTLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 46              moltype = AA  length = 354
FEATURE                    Location/Qualifiers
REGION                     1..354
                           note = Synthesized
source                     1..354
                           mol_type = protein
                           organism = synthetic construct
SEQUENCE: 46
MNTKYNKEFL LYLAGFVDAD GSIYACIKPH QQLKFKHQLL LYFEVYQKTQ RRWFLDKLVD     60
EIGVGYVIDS GSVSTYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFASIIP SQLVKFKHTL LLRFRVTQAT    240
RRRWFLDKLV DEIGVGYVTD NGRASYYTLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 47              moltype = AA  length = 354
FEATURE                    Location/Qualifiers
REGION                     1..354
                           note = Synthesized
source                     1..354
                           mol_type = protein
                           organism = synthetic construct
SEQUENCE: 47
MNTKYNKEFL LYLAGFVDAD GSIYACIKPH QQLKFKHQLL LYFEVYQKTQ RRWFLDKLVD     60
EIGVGYVADR GSVSEYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFASIIP SQLVKFKHTL LLRFRVCQAT    240
KRRWFLDKLV DEIGVGYVSD QGSASYYTLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 48              moltype = AA  length = 354
FEATURE                    Location/Qualifiers
REGION                     1..354
                           note = Synthesized
source                     1..354
                           mol_type = protein
                           organism = synthetic construct
SEQUENCE: 48
MNTKYNKEFL LYLAGFVDSD GSIYACIKPH QQLKFKHQLL LYFEVYQKTQ RRWFLDKLVD     60
EIGVGYVADR GSVSEYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFASIIP SQLVKFKHTL LLRFRVCQAT    240
KRRWFLDKLV DEIGVGYVSD QGSASYYTLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 49              moltype = AA  length = 354
FEATURE                    Location/Qualifiers
REGION                     1..354
                           note = Synthesized
source                     1..354
                           mol_type = protein
                           organism = synthetic construct
SEQUENCE: 49
MNTKYNKEFL LYLAGFVDAD GSIYACIKPH QQLKFKHQLL LYFEVYQKTQ RRWFLDKLVD     60
EIGVGYVADR GSVSEYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFASIIP SQEVKFKHTL LLRFRVCQAT    240
KRRWFLDKLV DEIGVGYVSD QGSASYYTLS EIKPLHNFLT QLQPFLKLKQ KQANLVLKII    300
EQLPSAKESP DKFLEVCTWV DQIAALNDSR TRKTTSETVR AVLDSLSEKK KSSP          354

SEQ ID NO: 50              moltype = AA  length = 354
FEATURE                    Location/Qualifiers
REGION                     1..354
                           note = Synthesized
source                     1..354
                           mol_type = protein
                           organism = synthetic construct
SEQUENCE: 50
MNTKYNKEFL LYLAGFVDAD GSIYACIKPH QQLKFKHQLL LYFEVYQKTQ RRWFLDKLVD     60
EIGVGYVADR GSVSEYRLSQ IKPLHNFLTQ LQPFLKLKQK QANLVLKIIE QLPSAKESPD    120
KFLEVCTWVD QIAALNDSKT RKTTSETVRA VLDSLPGSVG GLSPSQASSA ASSASSSPGS    180
GISEALRAGA GSGTGYNKEF LLYLAGFVDG DGSIFASIIP SQEVKFKHTL LLRFRVTQAT    240
KRRWFLDKLV DEIGVGYVSD VGSASYYTLS EIKPLHNFLT QLQPFLKLKQ KQANLVLKII    300
EQLPSAKESP DKFLEVCTWV DQIAALNDSR TRKTTSETVR AVLDSLSEKK KSSP          354
```

```
SEQ ID NO: 51              moltype = AA  length = 354
FEATURE                    Location/Qualifiers
REGION                     1..354
                           note = Synthesized
source                     1..354
                           mol_type = protein
                           organism = synthetic construct
SEQUENCE: 51
MNTKYNKEFL LYLAGFVDSD GSIYACIKPH QQLKFKHQLL LYFEVYQKTQ RRWFLDKLVD   60
EIGVGYVADR GSVSEYRLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIFASIIP SQEVKFKHTL LLRFRVCQAT  240
KRRWFLDKLV DEIGVGYVSD RGSASYYTLS EIKPLHNFLT QLQPFLKLKQ KQANLVLKII  300
EQLPSAKESP DKFLEVCTWV DQIAALNDSR TRKTTSETVR AVLDSLSEKK KSSP        354

SEQ ID NO: 52              moltype = AA  length = 354
FEATURE                    Location/Qualifiers
REGION                     1..354
                           note = Synthesized
source                     1..354
                           mol_type = protein
                           organism = synthetic construct
SEQUENCE: 52
MNTKYNKEFL LYLAGFVDAD GSIYACIKPH QELKFKHQLL LYFEVYQKTQ RRWFLDKLVD   60
EIGVGYVADR GSVSEYRLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIFASIIP SQEVKFKHTL LLRFRVCQAT  240
KRRWFLDKLV DEIGVGYVSD QGSASYYTLS QIKPLHNFLT QLQPFLKLKQ KQANLVLKII  300
EQLPSAKESP DKFLEVCTWV DQIAALNDSR TRKTTSETVR AVLDSLSEKK KSSP        354

SEQ ID NO: 53              moltype = AA  length = 354
FEATURE                    Location/Qualifiers
REGION                     1..354
                           note = Synthesized
source                     1..354
                           mol_type = protein
                           organism = synthetic construct
SEQUENCE: 53
MNTKYNKEFL LYLAGFVDSD GSIVATIRPG QELKFKHGLR LRFYVCQKTQ RRWFLDKLVD   60
EIGVGYVTDS GSVSRYELSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIFACIRP SQEVKFKHVL QLCFRVHQLT  240
KRRWFLDKLV DEIGVGYVYD CGSASFYHLS QIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 54              moltype = AA  length = 354
FEATURE                    Location/Qualifiers
REGION                     1..354
                           note = Synthesized
source                     1..354
                           mol_type = protein
                           organism = synthetic construct
SEQUENCE: 54
MNTKYNKEFL LYLAGFVDAD GSIVATIRPG QELKFKHGLR LRFYVCQKTQ RRWFLDKLVD   60
EIGAGYVTDS GSVSRYELSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIFACIRP SQRAKFKHVL QLCFRVHQKT  240
KRRWFLDKLV DEIGVGYVYD HGSASCYHLS EIKPLHNFLT QLQPFLKLKQ KQANLVLKII  300
EQLPSAKESP DKFLEVCTWV DQIAALNDSH TRKTTSETVR AVLDSLSEKK KSSP        354

SEQ ID NO: 55              moltype = AA  length = 354
FEATURE                    Location/Qualifiers
REGION                     1..354
                           note = Synthesized
source                     1..354
                           mol_type = protein
                           organism = synthetic construct
SEQUENCE: 55
MNTKYNKEFL LYLAGFVDAD GSIVATIRPG QELKFKHGLR LRFYVCQKTQ RRWFLDKLVD   60
EIGVGYVTDS GSVSRYELSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIFACIRP SQRAKFKHVL QLCFRVHQST  240
RRRWFLDKLV DEIGAGYVYD HGSASLYSLS QIKPLHNFLT QLQPFLKLKQ KQANLVLKII  300
EQLPSAKESP DKFLEVCTWV DQIAALNDSH TRKTTSETVR AVLDSLSEKK KSSP        354

SEQ ID NO: 56              moltype = AA  length = 354
FEATURE                    Location/Qualifiers
REGION                     1..354
```

```
                              note = Synthesized
source                        1..354
                              mol_type = protein
                              organism = synthetic construct
SEQUENCE: 56
MNTKYNKEFL LYLAGFVDSD GSIVASIAPA QDCKFKHRLR LRFFVSQKTQ RRWFLDKLVD    60
EIGVGYVSDS GSVSSYVLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFACIRP SQRAKFKHVL QLCFRVFQKT   240
QRRWFLDKLV DEIGVGYVYD HGRASIYQLS QIKPLHNFLT QLQPFLKLKQ KQANLVLKII   300
EQLPSAKESP DKFLEVCTWV DQIAALNDSH TRKTTSETVR AVLDSLSEKK KSSP         354

SEQ ID NO: 57                 moltype = AA  length = 354
FEATURE                       Location/Qualifiers
REGION                        1..354
                              note = Synthesized
source                        1..354
                              mol_type = protein
                              organism = synthetic construct
SEQUENCE: 57
MNTKYNKEFL LYLAGFVDSD GSIVARIEPA QDCKFKHRLR LQFFVSQKTQ RRWFLDKLVD    60
EIGVGYVRDS GSVSSYDLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFACIRP SQRAKFKHVL QLHFRVFQKT   240
QRRWFLDKLV DEIGVGYVYD HGRASIYQLS QIKPLHNFLT QLQPFLKLKQ KQANLVLKII   300
EQLPSAKESP DKFLEVCTWV DQIAALNDSH TRKTTSETVR AVLDSLSEKK KSSP         354

SEQ ID NO: 58                 moltype = AA  length = 354
FEATURE                       Location/Qualifiers
REGION                        1..354
                              note = Synthesized
source                        1..354
                              mol_type = protein
                              organism = synthetic construct
SEQUENCE: 58
MNTKYNKEFL LYLAGFVDSD GSIVARIEPA QDCKFKHRLR LQFFVSQKTQ RRWFLDKLVD    60
EIGVGYVRDS GSVSSYLLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFACIRP SQRAKFKHVL QLCFRVFQKT   240
QRRWFLDKLV DEIGVGYVYD HGRASIYQLS QIKPLHNFLT QLQPFLKLKQ KQANLVLKII   300
EQLPSAKESP DKFLEVCTWV DQIAALNDSH TRKTTSETVR AVLDSLSEKK KSSP         354

SEQ ID NO: 59                 moltype = AA  length = 354
FEATURE                       Location/Qualifiers
REGION                        1..354
                              note = Synthesized
source                        1..354
                              mol_type = protein
                              organism = synthetic construct
SEQUENCE: 59
MNTKYNKEFL LYLAGFVDAD GSIVARIEPA QDCKFKHRLR LQFFVSQKTQ RRWFLDKLVD    60
EIGVGYVRDS GSVSSYNLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFACIRP SQRAKFKHVL QLCFRVFQKT   240
QRRWFLDKLV DEIGVGYVYD HGRASIYQLS QIKPLHNFLT QLQPFLKLKQ KQANLVLKII   300
EQLPSAKESP DKFLEVCTWV DQIAALNDSH TRKTTSETVR AVLDSLSEKK KSSP         354

SEQ ID NO: 60                 moltype = DNA  length = 1065
FEATURE                       Location/Qualifiers
misc_feature                  1..1065
                              note = Synthesized
source                        1..1065
                              mol_type = other DNA
                              organism = synthetic construct
SEQUENCE: 60
atgaatacaa aatataataa agagttctta ctctacttag cagggtttgt agactctgac    60
ggttccatct atgccacgat ccggcctgtt caaagtacta agttcaagca cactctgcgg   120
ctctggttcg cggtcacgca gaagacacag cgccgttggt tcctcgacaa gctggtggac   180
gagatcggtg tgggttacgt gtatgacaat ggcagcgtct cctgctacta tctgtccgag   240
atcaagccct tgcataattt tttaacacaa ctacaacctt ttctaaaact aaaacaaaaa   300
caagcaaatt tagttttaaa aattattgaa caacttccgt cagcaaaaga tccccggac   360
aaattcttag aagtttgtac atgggtggat caaattgcag ctgaatga ttcgaagacg    420
cgtaaaacaa cttctgaaac cgttcgtgct gtgctagaca gtttaccagg atccgtggga   480
ggtctatcgc cattctcagg atccagcgcc gcatcctcaa gctcctcaag cccgggttca   540
gggatcccg aagcactcag agctggagca ggtccggca ctggatacaa caaggaattc    600
ctgctctacc tggcgggctt cgtcgacggg gacggctcca tctgtgcctg tatcgtgcct   660
cgtcaagatc ggaagttcaa gcaccagctg cggctctttt tcgaggtcgg tcagaagaca   720
aagcgccgtt ggttcctcga caagctggtg gacgagatcg tgtgggtta cgtggaggac    780
acgggcaggg cgagcaggta ccggctgtcc cagatcaagc tctgcacaa cttcctgacc   840
```

```
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 61           moltype = DNA   length = 1065
FEATURE                 Location/Qualifiers
misc_feature            1..1065
                        note = Synthesized
source                  1..1065
                        mol_type = other DNA
                        organism = synthetic construct
SEQUENCE: 61
atgaatacaa aatataataa agagttctta ctctacttag cagggtttgt agactctgac     60
ggttccatct tgccgttat cgagcctgtt caaagtgcta agttcaagca ccggctgaag    120
ctctcgttcg ttgtcactca gaagacacag cgccgttggt tcctgacaa gctggtggac    180
gagatcggtg tgggttacgt gtatgaccag ggcagcgtct cctttacag gctgtccgag    240
atcaagcctt tgcataattt tttaacacaa ctacaacctt ttctaaaact aaaacaaaaa    300
caagcaaatt tagttttaaa aattattgaa caacttccgt cagcaaaaga tccccggac     360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcaag cttcctcaag cccgggttca    540
gggatctccg aagcactcag agctggagca ggttccggca ctggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgaggtcgg gcagacgaca    720
aggcgccgtt ggttcctcga caagctggtg gacgagatcg gtgtgggtta cgtgtttgac    780
aagggcagcg cgagcatgta ccggctgtcc gagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 62           moltype = DNA   length = 1065
FEATURE                 Location/Qualifiers
misc_feature            1..1065
                        note = Synthesized
source                  1..1065
                        mol_type = other DNA
                        organism = synthetic construct
SEQUENCE: 62
atgaatacaa aatataataa agagttctta ctctacttag cagggtttgt agactctgac     60
ggttccatct atgccagtat catgcctatt caaacggcta agttcaagca ccgtctgaag    120
ctccagttcg cggtcgctca gaagacacag cgccgttggt tcctgacaa gctggtggac    180
gagatcggtg tgggttacgt gtatgacttt ggcagcgtct cctattacag gctgtcccag    240
atcaagcctt tgcataattt tttaacacaa ctacaacctt ttctaaaact aaaacaaaaa    300
caagcaaatt tagttttaaa aattattgaa caacttccgt cagcaaaaga tccccggac     360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgaggtcgg tcagaagaca    720
cagcgccgtt ggttcctcga caagctggtg gacgagatcg gtgtgggtta cgtgagggac    780
cttggcagcg cgagcactta ccgtctgtcc gagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 63           moltype = DNA   length = 1065
FEATURE                 Location/Qualifiers
misc_feature            1..1065
                        note = Synthesized
source                  1..1065
                        mol_type = other DNA
                        organism = synthetic construct
SEQUENCE: 63
atgaatacaa aatataataa agagttctta ctctacttag cagggtttgt agactctgac     60
ggttccatca ttgcctttat catgcctagt cagacggcta agttcaagca ccgtctgaag    120
ctccagttcg cggtcgctca gaagacacag cgccgttggt tcctgacaa gctggtggac    180
gagatcggtg tgggttacgt gtatgacttt ggcagcgtct cctattacag gctgtcccag    240
atcaagcctt tgcataattt tttaacacaa ctacaacctt ttctaaaact aaaacaaaaa    300
caagcaaatt tagttttaaa aattattgaa caacttccgt cagcaaaaga tccccggac     360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgagatcgg tcagaagaca    720
```

```
cagcgccgtt ggttcctcga caagctggtg gacgagatcg gtgtggggtta cgtgagggac    780
cttggcagcg cgagcactta ccgtctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccaag acccgcaaga ccacttccga aaccgtccgc   1020
gccgttctag acagtctctc cgagaagaag aagtcgtccc cctaa                   1065

SEQ ID NO: 64          moltype = DNA  length = 1065
FEATURE                Location/Qualifiers
misc_feature           1..1065
                       note = Synthesized
source                 1..1065
                       mol_type = other DNA
                       organism = synthetic construct
SEQUENCE: 64
atgaatacaa aatataataa agagttctta ctctacttag cagggtttgt agactctgac     60
ggttccatca tggcctttat catgcctact cagacggcta agttcaagca ccgtctgaag    120
ctccagttcg cggtcgctca gaagacacag cgccgttggt tcctgacaa gctggtggac     180
gagatcggtg tgggttacgt gtatgacttt ggcagcgtct cctattacag gctgtccgag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgaggtcgg tcagaagaca    720
cagcgccgtt ggttcctcga caagctggtg gacgagatcg gtgtggggtta cgtgagggac    780
cttggcagcg cgagcactta ccgtctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 65          moltype = DNA  length = 1065
FEATURE                Location/Qualifiers
misc_feature           1..1065
                       note = Synthesized
source                 1..1065
                       mol_type = other DNA
                       organism = synthetic construct
SEQUENCE: 65
atgaatacaa aatataataa agagttctta ctctacttag cagggtttgt agactctgac     60
ggttccatca tggcctttat cttgcctgag cagcatatga agttcaagca ccgtctgagg    120
ctccagttcg cggtcgctca gaagacacag cgccgttggt tcctgacaa gctggtggac     180
gagatcggtg tgggttacgt gtatgacttt ggcagcgtct cctattacag gctgtccgag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgaggtcgg tcagaagaca    720
cagcgccgtt ggttcctcga caagctggtg gacgagatcg gtgtggggtta cgtgagggac    780
cttggcagcg cgagcactta ccgtctgtcc gagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 66          moltype = DNA  length = 1065
FEATURE                Location/Qualifiers
misc_feature           1..1065
                       note = Synthesized
source                 1..1065
                       mol_type = other DNA
                       organism = synthetic construct
SEQUENCE: 66
atgaatacaa aatataataa agagttctta ctctacttag cagggtttgt agactctgac     60
ggttccatca tggcctttat cttgcctgag cagcatctta agttcaagca ccgtctgagg    120
ctccagttcg cggtcgctca gaagacacag cgccgttggt tcctgacaa gctggtggac     180
gagatcggtg tgggttacgt gtatgacttt ggcagcgtct cctattacag gctgtccgag    240
atcaagcctt tgcataactt ctacaacctt ttctaaaact aaaacaaaaa               300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
```

```
ctgctctacc tggcgggctt cgtcgacggg gacggctcca tctgtgcctg tatcgtgcct    660
cgtcaagatc ggaagttcaa gcaccagctg cggctctttt tcgaggtcgg tcagaagaca    720
cagcgccgat ggttcctcga caagctggtg gacgagatcg gtgtgggtta cgtgagggac    780
cttggcagcg cgagcactta ccgtctgtcc gagatcaagc tctgcacaa cttcctgacc     840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 67           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 67
atgaatacaa aatataataa agagttctta ctctacttag cagggtttgt agactctgac     60
ggttccatca tggcctttat cttgcctgag cagggtctga agttcaagca ccgtctgagg    120
ctccagttcg cggtcgctca gaagacacag cgccgttggt tcctcgacaa gctggtggac    180
gagatcggtg tgggttacgt gtatgacttt ggcagcgtct cctattacag gctgtcccag    240
atcaagcctt tgcataattt tttaaacaaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcaa gcccgggttca             540
gggatctccg aagcactcag agctggagca ggttccggca ccggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgaggtcgg tcagaagaca    720
cagcgccgtt ggttcctcga caagctggtg gacgagatcg gtgtgggtta cgtgagggac    780
cttggcagcg cgagcactta ccgtctgtcc cagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 68           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 68
atgaatacaa aatataataa agagttctta ctctacttag cagggtttgt agactctgac     60
ggttccatca tggcctttat catgcctgat caggcgccta agttcaagca ccgtctgagg    120
ctccagttcg cggtcgctca gaagacacag cgccgttggt tcctcgacaa gctggtggac    180
gagatcggtg tgggttacgt gtatgacttt ggcagcgtct cctattacag gctgtcccag    240
atcaagcctt tgcataattt tttaaacaca ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctgtgcctg tatcgtgcct    660
cgtcaagatc ggaagttcaa gcaccagctg cggctctttt tcgaggtcgg tcagaagaca    720
cagcgccgtt ggttcctcga caagctggtg gacgagatcg gtgtgggtta cgtgagggac    780
cttggcagcg cgagcactta ccgtctgtcc cagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 69           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 69
atgaatacaa aatataataa agagttctta ctctacttag cagggtttgt agacgctgac     60
ggttccatct atggcctgta tcaagcctcat caacagctta agttcaagca ccagctgttg    120
ctctatttcg aggtctatca gaagacacag cgccgttggt tcctcgacaa gctggtggac    180
gagatcggtg tgggttacgt ggctgaccgt ggcagcgtct ccgagtaccg tctgtcccag    240
atcaagcctt tgcataattt tttaaacaca ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
```

```
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgcctc tatcatgccg   660
acgcagtgga cgaagttcaa gcactcgctg ttgctccggt tccgggtcac ccagtcgaca   720
aggcgccgtt ggttcctcga caagctgatg gacgagattg gtgtgggtta cgtgtctgac   780
cagggcaggg cgagctacta caccctgtcc gagatcaagc tctgcacaa cttcctgacc   840
cagctccagc cctcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cctaa                  1065

SEQ ID NO: 70          moltype = DNA   length = 1065
FEATURE                Location/Qualifiers
misc_feature           1..1065
                       note = Synthesized
source                 1..1065
                       mol_type = other DNA
                       organism = synthetic construct
SEQUENCE: 70
atgaatacaa aatataataa agagttctta ctctacttag cagggtttgt agacgctgac    60
ggttccatct atgcctgtat caagcctcat caacagctta agttcaagca ccagctgttg   120
ctctatttcg aggtctatca gaagacacag cgccgttggt tcctcgacaa gctggtggac   180
gagatcggtg tgggttacgt gattgactcg ggcagcgtct ccacgtaccg gctgtcccga   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atcagcgcc gcatcctcgg cttcctcaag cccgggttca    540
gggatctccg aagcactcag agctggagca ggttccggca ctggatacaa caaggaattc   600
ctgctctacc tggcgggctt cgtcgacggg gacggctcca tctttgcctc tatcattccg   660
tcgcagctgg ttaagttcaa gcacactctg ctgctccgtt tccgggtcac ccaggcgaca   720
aggcgccgtt ggttcctcga caagctggtg gacgagatcg gtgtgggtta cgtgacggac   780
aacggcaggg cgagctacta caccctgtcc gagatcaagc tctgcacaa cttcctgacc   840
cagctccagc cctcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cctaa                  1065

SEQ ID NO: 71          moltype = DNA   length = 1065
FEATURE                Location/Qualifiers
misc_feature           1..1065
                       note = Synthesized
source                 1..1065
                       mol_type = other DNA
                       organism = synthetic construct
SEQUENCE: 71
atgaatacaa aatataataa agagttctta ctctacttag cagggtttgt agacgctgac    60
ggttccatct atgcctgtat caagcctcat caacagctta agttcaagca ccagctgttg   120
ctctatttcg aggtctatca gaagacacag cgccgttggt tcctcgacaa gctggtggac   180
gagatcggtg tgggttacgt ggctgaccgt ggcagcgtct ccgagtaccg tctgtcccag   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgcctc tatcattccg   660
tcgcagctgg ttaagttcaa gcacactctg ctgctccgtt tccgggtctg ccaggcgaca   720
aagcgccgtt ggttcctcga caagctggtg gacgagattg gtgtgggtta cgtgtctgac   780
cagggcagcg cgagctacta caccctgtcc gagatcaagc tctgcacaa cttcctgacc   840
cagctccagc cctcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cctaa                  1065

SEQ ID NO: 72          moltype = DNA   length = 1065
FEATURE                Location/Qualifiers
misc_feature           1..1065
                       note = Synthesized
source                 1..1065
                       mol_type = other DNA
                       organism = synthetic construct
SEQUENCE: 72
atgaatacaa aatataataa agagttctta ctctacttag cagggtttgt agactctgac    60
ggttccatct atgcctgtat caagcctcat caacagctta agttcaagca ccagctgttg   120
ctctatttcg aggtctatca gaagacacag cgccgttggt tcctcgacaa gctggtggac   180
gagatcggtg tgggttacgt ggctgaccgt ggcagcgtct ccgagtaccg tctgtcccag   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
```

```
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctc tatcattccg    660
tcgcaggagg ttaagttcaa gcacactctg ctgctccgtt tccgggtctg ccaggcgaca    720
aagcgccgtt ggttcctcga caagctggtg gacgagattg gtgtgggtta cgtgtctgac    780
cagggcagcg cgagctacta caccctgtcc gagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cctaa                   1065

SEQ ID NO: 73           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 73
atgaatacaa aatataataa agagttctta ctctacttag cagggtttgt agacgctgac     60
ggttccatct atgcctgtat caagcctcat caacagctta agttcaagca ccagctgttg    120
ctctatttcg aggtctatca gaagacacag cgccgttggt tcctcgacaa gctggtggac    180
gagatcggtg tgggttacgt ggctgaccgt ggcagcgtct ccgagtaccg tctgtcccag    240
atcaagcctt tgcataattt tttaaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctc tatcattccg    660
tcgcaggagg ttaagttcaa gcacactctg ctgctccgtt tccgggtctg ccaggcgaca    720
aagcgccgtt ggttcctcga caagctggtg gacgagattg gtgtgggtta cgtgtctgac    780
cagggcagcg cgagctacta caccctgtcc gagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cctaa                   1065

SEQ ID NO: 74           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 74
atgaatacaa aatataataa agagttctta ctctacttag cagggtttgt agacgctgac     60
ggttccatct atgcctgtat caagcctcat caacagctta agttcaagca ccagctgttg    120
ctctatttcg aggtctatca gaagacacag cgccgttggt tcctcgacaa gctggtggac    180
gagatcggtg tgggttacgt ggctgaccgt ggcagcgtct ccgagtaccg tctgtcccag    240
atcaagcctt tgcataattt tttaaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctc tatcattccg    660
tcgcaggagg ttaagttcaa gcacactctg ctgctccgtt tcagggtcac tcaggcgaca    720
aagcgccgtt ggttcctcga caagctggtg gacgagattg gtgtgggtta cgtgtctgac    780
gttggcagcg cgagctatta caccctgtcc gagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cctaa                   1065

SEQ ID NO: 75           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 75
atgaatacaa aatataataa agagttctta ctctacttag cagggtttgt agactctgac     60
ggttccatct atgcctgtat caagcctcat caacagctta agttcaagca ccagctgttg    120
ctctatttcg aggtctatca gaagacacag cgccgttggt tcctcgacaa gctggtggac    180
gagatcggtg tgggttacgt ggctgaccgt ggcagcgtct ccgagtaccg tctgtcccag    240
```

```
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctc tatcattccg    660
tcgcaggagg ttaagttcaa gcacactctg ctgctccgtt tccgggtctg ccaggcgaca    720
aagcgccgtt ggttcctcga caagctggtg gacgagattg gtgtgggtta cgtgtctgac    780
cgtggcagcg cgagctatta caccctgtcc gagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 76         moltype = DNA   length = 1065
FEATURE               Location/Qualifiers
misc_feature          1..1065
                      note = Synthesized
source                1..1065
                      mol_type = other DNA
                      organism = synthetic construct
SEQUENCE: 76
atgaatacaa aatataataa agagttctta ctctacttag cagggtttgt agacgctgac     60
ggttccatct atgcctgtat caagcctcat caagagctta agttcaagca ccagctgttg    120
ctctatttcg aggtctatca gaagacacag cgccgttggt tcctcgacaa gctggtggac    180
gagatcggtg tgggttacgt ggctgaccgt ggcagcgtct ccgagtaccg tctgtccgaa    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctc tatcattccg    660
tcgcaggagg ttaagttcaa gcacactctg ctgctccgtt tccgggtctg ccaggcgaca    720
aagcgccgtt ggttcctcga caagctggtg gacgagattg gtgtgggtta cgtgtctgac    780
cagggcagcg cgagctacta caccctgtcc cagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 77         moltype = DNA   length = 1065
FEATURE               Location/Qualifiers
misc_feature          1..1065
                      note = Synthesized
source                1..1065
                      mol_type = other DNA
                      organism = synthetic construct
SEQUENCE: 77
atgaatacaa aatataataa agagttctta ctctacttag cagggtttgt agactctgac     60
ggttccatcg tggccactat ccggccgggg caggagctga agttcaagca cggtctgcgg    120
ctcaggttct atgtctgtca gaagacacag cgccgttggt tcctcgacaa gctggtggac    180
gagatcggtg tgggttacgt gacggacagt ggcagcgtct cccgttacga gctgtcccag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaagacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctg tatccgtccg    660
tcgcagaggg ctaagttcaa gcacgtgctg cagctctgtt tcagggtcca ccagttgaca    720
aagcgccgtt ggttcctcga caagctggtg gacgagatcg tgtaggttta cgtgtatgac    780
tcgggcagcg cgagcttcca ccacctgtcc cagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc   1020
gccgttctag acagtctctc cgagaagaag aagtcgtccc cctaa                   1065

SEQ ID NO: 78         moltype = DNA   length = 1065
FEATURE               Location/Qualifiers
misc_feature          1..1065
                      note = Synthesized
source                1..1065
                      mol_type = other DNA
                      organism = synthetic construct
SEQUENCE: 78
atgaatacaa aatataataa agagttctta ctctacttag cagggtttgt agacgctgac     60
ggttccatcg tggccactat ccggccgggg caggagctga agttcaagca cggtctgcgg    120
```

```
ctcaggttct atgtctgtca gaagacacag cgccgttggt tcctcgacaa gctggtggac    180
gagatcggtg cgggttacgt gacggacagt ggcagcgtct cccgttacga gctgtcccag    240
atcaagcctt tgcataattt tttaacacaa ctacaacctt ttctaaaact aaaacaaaaa    300
caagcaaatt tagttttaaa aattatcgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctg tatccgtccg    660
tcgcagaggg ctaagttcaa gcacgtgctg cagctctgtt tcagggtcca ccagaagaca    720
aagcgccgtt ggttcctcga caagctggtg gacgagatcg tgtgggtta cgtgtatgac    780
cacggcagcg cgagctgcta ccacctgtcc gagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactcccac acccgcaaga ccacttccga aaccgtccgc   1020
gccgttctag acagtctctc cgagaagaag aagtcgtccc cctaa                   1065

SEQ ID NO: 79           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 79
atgaatacaa aatataataa agagttctta ctctacttag cagggtttgt agacgctgac     60
ggttccatcg tggccactat ccggccgggg caggagctga agttcaagca cggtctgcgg    120
ctcaggttct atgtctgtca gaagacacag cgccgttggt tcctcgacaa gctggtggac    180
gagatcggtg tgggttacgt gacggacagt ggcagcgtct cccgttacga gctgtcccag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctg tatccgtccg    660
tcgcagaggg ctaagttcaa gcacgtgctg cagctctgtt tcagggtcca ccagtcgaca    720
aggcgccgtt ggttcctaga caagctggtg gacgagatcg tgcgggtta cgtgtatgac    780
cacggcagcg cgagcctgta cagcctgtcc cagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactcccac acccgcaaga ccacttccga aaccgtccgc   1020
gccgttctag acagtctctc cgagaagaag aagtcgtccc cctaa                   1065

SEQ ID NO: 80           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 80
atgaatacaa aatataataa agagttctta ctctacttag cagggtttgt agactctgac     60
ggttccatcg ttgccagtat cgctccggct caggattgta agttcaagca caggctgagg    120
ctccgtttct ttgtctctca gaagacacag cgccgttggt tcctcgacaa gctggttggac   180
gagatcggtg tgggttacgt gtctgactct ggcagcgtct ccagttacgt tctgtccgag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctttgcctg tatccgtccg    660
tcgcagaggg ctaagttcaa gcacgtgctg cagctctgtt tccgggtctt tcagaagaca    720
cagcgccgtt ggttcctcga caagctggtg gacgagatcg tgtaggtta cgtgtatgac    780
cacggcaggg cgagcatcta ccagctgtcc cagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactcccac acccgcaaga ccacttccga aaccgtccgc   1020
gccgttctag acagtctctc cgagaagaag aagtcgtccc cctaa                   1065

SEQ ID NO: 81           moltype = DNA  length = 1065
FEATURE                 Location/Qualifiers
misc_feature            1..1065
                        note = Synthesized
source                  1..1065
                        mol_type = other DNA
                        organism = synthetic construct
SEQUENCE: 81
```

```
atgaatacaa aatataataa agagttctta ctctacttag cagggtttgt agactctgac    60
ggttccatcg ttgccaggat cgagccggct caggattgta agttcaagca caggctgagg   120
ctccagttct ttgtctctca gaagacacag cgccgttggt tcctcgacaa gctggtggac   180
gagatcggtg tgggttacgt gcgggactct ggcagcgtct ccagttacga tctgtcccag   240
atcaagcctt tgcataattt tttaaacaca ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcag cttcctcaag cccgggttca   540
gggatctccg aagcactcag agctggagca ggttccggca ctggatacaa caaggaattc   600
ctgctctacc tggcgggctt cgtcgacggg gacggctcca tctttgcctg tatccgtccg   660
tcgcagaggg ctaagttcaa gcacgtgctg cagctccatt tccgggtctt tcagaagaca   720
cagcgccgtt ggttcctcga caagctggtg gacgagatcg tgtaggttac gtgtatgac    780
cacggcaggg cgagcatcta ccagctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactcccac acccgcaaga ccacttccga aaccgtccgc  1020
gccgttctag acagtctctc cgagaagaag aagtcgtccc cctaa                  1065

SEQ ID NO: 82          moltype = DNA   length = 1065
FEATURE                Location/Qualifiers
misc_feature           1..1065
                       note = Synthesized
source                 1..1065
                       mol_type = other DNA
                       organism = synthetic construct
SEQUENCE: 82
atgaatacaa aatataataa agagttctta ctctacttag cagggtttgt agactctgac    60
ggttccatcg ttgccaggat cgagccggct caggattgta agttcaagca caggctgagg   120
ctccagttct ttgtctctca gaagacacag cgccgttggt tcctcgacaa gctggtggac   180
gagatcggtg tgggttacgt gcgggactct ggcagcgtct ccagttactt gctgtcccag   240
atcaagcctt tgcataattt tttaaacaca ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgcctg tatccgtccg   660
tcgcagaggg ctaagttcaa gcacgtgctg cagctccatt tccgggtctt tcagaagaca   720
cagcgccgtt ggttcctcga caagctggtg gacgagatcg tgtaggttac gtgtatgac    780
cacggcaggg cgagcatcta ccagctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactcccac acccgcaaga ccacttccga aaccgtccgc  1020
gccgttctag acagtctctc cgagaagaag aagtcgtccc cctaa                  1065

SEQ ID NO: 83          moltype = DNA   length = 1065
FEATURE                Location/Qualifiers
misc_feature           1..1065
                       note = Synthesized
source                 1..1065
                       mol_type = other DNA
                       organism = synthetic construct
SEQUENCE: 83
atgaatacaa aatataataa agagttctta ctctacttag cagggtttgt agacgctgac    60
ggttccatcg ttgccaggat cgagccggct caggattgta agttcaagca caggctgagg   120
ctccagttct ttgtctctca gaagacacag cgccgttggt tcctcgacaa gctggtggac   180
gagatcggtg tgggttacgt gcgggactct ggcagcgtct ccagttacaa tctgtccgag   240
atcaagcctt tgcataattt tttaaacaca ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctttgcctg tatccgtccg   660
tcgcagaggg ctaagttcaa gcacgtgctg cagctctgtt tccgggtctt tcagaagaca   720
cagcgccgtt ggttcctcga caagctggtg gacgagatcg tgtaggttac gtgtatgac    780
cacggcaggg cgagcatcta ccagctgtcc cagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactcccac acccgcaaga ccacttccga aaccgtccgc  1020
gccgttctag acagtctctc cgagaagaag aagtcgtccc cctaa                  1065

SEQ ID NO: 84          moltype = AA   length = 147
FEATURE                Location/Qualifiers
REGION                 1..147
                       note = Synthesized
source                 1..147
                       mol_type = protein
```

```
                                                 organism = synthetic construct
SEQUENCE: 84
KEFLLYLAGF VDSDGSIYAT IRPVQSTKFK HTLRLWFAVT QKTQRRWFLD KLVDEIGVGY         60
VYDNGSVSWY YLSEIKPLHN FLTQLQPFLK LKQKQANLVL KIIEQLPSAK ESPDKFLEVC        120
TWVDQIAALN DSKTRKTTSE TVRAVLD                                           147

SEQ ID NO: 85           moltype = AA  length = 147
FEATURE                 Location/Qualifiers
REGION                  1..147
                        note = Synthesized
source                  1..147
                        mol_type = protein
                        organism = synthetic construct
SEQUENCE: 85
KEFLLYLAGF VDSDGSIFAV IEPVQSAKFK HRLKLSFVVT QKTQRRWFLD KLVDEIGVGY         60
VYDQGSVSFY RLSEIKPLHN FLTQLQPFLK LKQKQANLVL KIIEQLPSAK ESPDKFLEVC        120
TWVDQIAALN DSKTRKTTSE TVRAVLD                                           147

SEQ ID NO: 86           moltype = AA  length = 147
FEATURE                 Location/Qualifiers
REGION                  1..147
                        note = Synthesized
source                  1..147
                        mol_type = protein
                        organism = synthetic construct
SEQUENCE: 86
KEFLLYLAGF VDSDGSIYAS IMPIQTAKFK HRLKLQFAVA QKTQRRWFLD KLVDEIGVGY         60
VYDFGSVSYY RLSQIKPLHN FLTQLQPFLK LKQKQANLVL KIIEQLPSAK ESPDKFLEVC        120
TWVDQIAALN DSKTRKTTSE TVRAVLD                                           147

SEQ ID NO: 87           moltype = AA  length = 147
FEATURE                 Location/Qualifiers
REGION                  1..147
                        note = Synthesized
source                  1..147
                        mol_type = protein
                        organism = synthetic construct
SEQUENCE: 87
KEFLLYLAGF VDSDGSIIAF IMPSQTAKFK HRLKLQFAVA QKTQRRWFLD KLVDEIGVGY         60
VYDFGSVSYY RLSQIKPLHN FLTQLQPFLK LKQKQANLVL KIIEQLPSAK ESPDKFLEVC        120
TWVDQIAALN DSKTRKTTSE TVRAVLD                                           147

SEQ ID NO: 88           moltype = AA  length = 147
FEATURE                 Location/Qualifiers
REGION                  1..147
                        note = Synthesized
source                  1..147
                        mol_type = protein
                        organism = synthetic construct
SEQUENCE: 88
KEFLLYLAGF VDSDGSIMAF IMPTQTAKFK HRLKLQFAVA QKTQRRWFLD KLVDEIGVGY         60
VYDFGSVSYY RLSEIKPLHN FLTQLQPFLK LKQKQANLVL KIIEQLPSAK ESPDKFLEVC        120
TWVDQIAALN DSKTRKTTSE TVRAVLD                                           147

SEQ ID NO: 89           moltype = AA  length = 147
FEATURE                 Location/Qualifiers
REGION                  1..147
                        note = Synthesized
source                  1..147
                        mol_type = protein
                        organism = synthetic construct
SEQUENCE: 89
KEFLLYLAGF VDSDGSIMAF ILPEQHMKFK HRLRLQFAVA QKTQRRWFLD KLVDEIGVGY         60
VYDFGSVSYY RLSEIKPLHN FLTQLQPFLK LKQKQANLVL KIIEQLPSAK ESPDKFLEVC        120
TWVDQIAALN DSKTRKTTSE TVRAVLD                                           147

SEQ ID NO: 90           moltype = AA  length = 147
FEATURE                 Location/Qualifiers
REGION                  1..147
                        note = Synthesized
source                  1..147
                        mol_type = protein
                        organism = synthetic construct
SEQUENCE: 90
KEFLLYLAGF VDSDGSIMAF ILPEQHLKFK HRLRLQFAVA QKTQRRWFLD KLVDEIGVGY         60
VYDFGSVSYY RLSEIKPLHN FLTQLQPFLK LKQKQANLVL KIIEQLPSAK ESPDKFLEVC        120
TWVDQIAALN DSKTRKTTSE TVRAVLD                                           147

SEQ ID NO: 91           moltype = AA  length = 147
```

```
FEATURE                 Location/Qualifiers
REGION                  1..147
                        note = Synthesized
source                  1..147
                        mol_type = protein
                        organism = synthetic construct
SEQUENCE: 91
KEFLLYLAGF VDSDGSIMAF ILPEQGLKFK HRLRLQFAVA QKTQRRWFLD KLVDEIGVGY    60
VYDFGSVSYY RLSQIKPLHN FLTQLQPFLK LKQKQANLVL KIIEQLPSAK ESPDKFLEVC   120
TWVDQIAALN DSKTRKTTSE TVRAVLD                                       147

SEQ ID NO: 92           moltype = AA  length = 147
FEATURE                 Location/Qualifiers
REGION                  1..147
                        note = Synthesized
source                  1..147
                        mol_type = protein
                        organism = synthetic construct
SEQUENCE: 92
KEFLLYLAGF VDSDGSIMAF IMPDQAPKFK HRLRLQFAVA QKTQRRWFLD KLVDEIGVGY    60
VYDFGSVSYY RLSEIKPLHN FLTQLQPFLK LKQKQANLVL KIIEQLPSAK ESPDKFLEVC   120
TWVDQIAALN DSKTRKTTSE TVRAVLD                                       147

SEQ ID NO: 93           moltype = AA  length = 147
FEATURE                 Location/Qualifiers
REGION                  1..147
                        note = Synthesized
source                  1..147
                        mol_type = protein
                        organism = synthetic construct
SEQUENCE: 93
KEFLLYLAGF VDADGSIYAC IKPHQQLKFK HQLLLYFEVY QKTQRRWFLD KLVDEIGVGY    60
VADRGSVSEY RLSQIKPLHN FLTQLQPFLK LKQKQANLVL KIIEQLPSAK ESPDKFLEVC   120
TWVDQIAALN DSKTRKTTSE TVRAVLD                                       147

SEQ ID NO: 94           moltype = AA  length = 147
FEATURE                 Location/Qualifiers
REGION                  1..147
                        note = Synthesized
source                  1..147
                        mol_type = protein
                        organism = synthetic construct
SEQUENCE: 94
KEFLLYLAGF VDADGSIYAC IKPHQQLKFK HQLLLYFEVY QKTQRRWFLD KLVDEIGVGY    60
VIDSGSVSTY RLSQIKPLHN FLTQLQPFLK LKQKQANLVL KIIEQLPSAK ESPDKFLEVC   120
TWVDQIAALN DSKTRKTTSE TVRAVLD                                       147

SEQ ID NO: 95           moltype = AA  length = 147
FEATURE                 Location/Qualifiers
REGION                  1..147
                        note = Synthesized
source                  1..147
                        mol_type = protein
                        organism = synthetic construct
SEQUENCE: 95
KEFLLYLAGF VDADGSIYAC IKPHQQLKFK HQLLLYFEVY QKTQRRWFLD KLVDEIGVGY    60
VADRGSVSEY RLSQIKPLHN FLTQLQPFLK LKQKQANLVL KIIEQLPSAK ESPDKFLEVC   120
TWVDQIAALN DSKTRKTTSE TVRAVLD                                       147

SEQ ID NO: 96           moltype = AA  length = 147
FEATURE                 Location/Qualifiers
REGION                  1..147
                        note = Synthesized
source                  1..147
                        mol_type = protein
                        organism = synthetic construct
SEQUENCE: 96
KEFLLYLAGF VDSDGSIYAC IKPHQQLKFK HQLLLYFEVY QKTQRRWFLD KLVDEIGVGY    60
VADRGSVSEY RLSQIKPLHN FLTQLQPFLK LKQKQANLVL KIIEQLPSAK ESPDKFLEVC   120
TWVDQIAALN DSKTRKTTSE TVRAVLD                                       147

SEQ ID NO: 97           moltype = AA  length = 147
FEATURE                 Location/Qualifiers
REGION                  1..147
                        note = Synthesized
source                  1..147
                        mol_type = protein
                        organism = synthetic construct
SEQUENCE: 97
```

```
KEFLLYLAGF VDADGSIYAC IKPHQQLKFK HQLLLYFEVY QKTQRRWFLD KLVDEIGVGY    60
VADRGSVSEY RLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 98              moltype = AA   length = 147
FEATURE                    Location/Qualifiers
REGION                     1..147
                           note = Synthesized
source                     1..147
                           mol_type = protein
                           organism = synthetic construct
SEQUENCE: 98
KEFLLYLAGF VDADGSIYAC IKPHQQLKFK HQLLLYFEVY QKTQRRWFLD KLVDEIGVGY    60
VADRGSVSEY RLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 99              moltype = AA   length = 147
FEATURE                    Location/Qualifiers
REGION                     1..147
                           note = Synthesized
source                     1..147
                           mol_type = protein
                           organism = synthetic construct
SEQUENCE: 99
KEFLLYLAGF VDSDGSIYAC IKPHQQLKFK HQLLLYFEVY QKTQRRWFLD KLVDEIGVGY    60
VADRGSVSEY RLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 100             moltype = AA   length = 147
FEATURE                    Location/Qualifiers
REGION                     1..147
                           note = Synthesized
source                     1..147
                           mol_type = protein
                           organism = synthetic construct
SEQUENCE: 100
KEFLLYLAGF VDADGSIYAC IKPHQELKFK HQLLLYFEVY QKTQRRWFLD KLVDEIGVGY    60
VADRGSVSEY RLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 101             moltype = AA   length = 147
FEATURE                    Location/Qualifiers
REGION                     1..147
                           note = Synthesized
source                     1..147
                           mol_type = protein
                           organism = synthetic construct
SEQUENCE: 101
KEFLLYLAGF VDSDGSIVAT IRPGQELKFK HGLRLRFYVC QKTQRRWFLD KLVDEIGVGY    60
VTDSGSVSRY ELSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 102             moltype = AA   length = 147
FEATURE                    Location/Qualifiers
REGION                     1..147
                           note = Synthesized
source                     1..147
                           mol_type = protein
                           organism = synthetic construct
SEQUENCE: 102
KEFLLYLAGF VDADGSIVAT IRPGQELKFK HGLRLRFYVC QKTQRRWFLD KLVDEIGAGY    60
VTDSGSVSRY ELSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 103             moltype = AA   length = 147
FEATURE                    Location/Qualifiers
REGION                     1..147
                           note = Synthesized
source                     1..147
                           mol_type = protein
                           organism = synthetic construct
SEQUENCE: 103
KEFLLYLAGF VDADGSIVAT IRPGQELKFK HGLRLRFYVC QKTQRRWFLD KLVDEIGVGY    60
VTDSGSVSRY ELSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 104             moltype = AA   length = 147
FEATURE                    Location/Qualifiers
REGION                     1..147
```

```
                        note = Synthesized
source                  1..147
                        mol_type = protein
                        organism = synthetic construct
SEQUENCE: 104
KEFLLYLAGF VDSDGSIVAS IAPAQDCKFK HRLRLRFFVS QKTQRRWFLD KLVDEIGVGY    60
VSDSGSVSSY VLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 105          moltype = AA  length = 147
FEATURE                 Location/Qualifiers
REGION                  1..147
                        note = Synthesized
source                  1..147
                        mol_type = protein
                        organism = synthetic construct
SEQUENCE: 105
KEFLLYLAGF VDSDGSIVAR IEPAQDCKFK HRLRLQFFVS QKTQRRWFLD KLVDEIGVGY    60
VRDSGSVSSY DLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 106          moltype = AA  length = 147
FEATURE                 Location/Qualifiers
REGION                  1..147
                        note = Synthesized
source                  1..147
                        mol_type = protein
                        organism = synthetic construct
SEQUENCE: 106
KEFLLYLAGF VDSDGSIVAR IEPAQDCKFK HRLRLQFFVS QKTQRRWFLD KLVDEIGVGY    60
VRDSGSVSSY LLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 107          moltype = AA  length = 147
FEATURE                 Location/Qualifiers
REGION                  1..147
                        note = Synthesized
source                  1..147
                        mol_type = protein
                        organism = synthetic construct
SEQUENCE: 107
KEFLLYLAGF VDADGSIVAR IEPAQDCKFK HRLRLQFFVS QKTQRRWFLD KLVDEIGVGY    60
VRDSGSVSSY NLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 108          moltype = AA  length = 147
FEATURE                 Location/Qualifiers
REGION                  1..147
                        note = Synthesized
source                  1..147
                        mol_type = protein
                        organism = synthetic construct
SEQUENCE: 108
KEFLLYLAGF VDGDGSICAC IVPRQDRKFK HQLRLFFEVG QKTKRRWFLD KLVDEIGVGY    60
VEDTGRASRY RLSQIKPLHN FLTQLQPFLK LKQKQANLVL KIIEQLPSAK ESPDKFLEVC   120
TWVDQIAALN DSRTRKTTSE TVRAVLD                                      147

SEQ ID NO: 109          moltype = AA  length = 147
FEATURE                 Location/Qualifiers
REGION                  1..147
                        note = Synthesized
source                  1..147
                        mol_type = protein
                        organism = synthetic construct
SEQUENCE: 109
KEFLLYLAGF VDGDGSICAC IVPRQDRKFK HQLRLFFEVG QTTRRRWFLD KLVDEIGVGY    60
VFDKGSASMY RLSEIKPLHN FLTQLQPFLK LKQKQANLVL KIIEQLPSAK ESPDKFLEVC   120
TWVDQIAALN DSRTRKTTSE TVRAVLD                                      147

SEQ ID NO: 110          moltype = AA  length = 147
FEATURE                 Location/Qualifiers
REGION                  1..147
                        note = Synthesized
source                  1..147
                        mol_type = protein
                        organism = synthetic construct
SEQUENCE: 110
KEFLLYLAGF VDGDGSICAC IVPRQDRKFK HQLRLFFEVG QKTQRRWFLD KLVDEIGVGY    60
VRDLGSASTY RLSEIKPLHN FLTQLQPFLK LKQKQANLVL KIIEQLPSAK ESPDKFLEVC   120
```

TWVDQIAALN DSRTRKTTSE TVRAVLD                                                147

SEQ ID NO: 111          moltype = AA  length = 147
FEATURE                 Location/Qualifiers
REGION                  1..147
                        note = Synthesized
source                  1..147
                        mol_type = protein
                        organism = synthetic construct
SEQUENCE: 111
KEFLLYLAGF VDGDGSICAC IVPRQDRKFK HQLRLFFEIG QKTQRRWFLD KLVDEIGVGY            60
VRDLGSASTY RLSQIKPLHN FLTQLQPFLK LKQKQANLVL KIIEQLPSAK ESPDKFLEVC           120
TWVDQIAALN DSKTRKTTSE TVRAVLD                                              147

SEQ ID NO: 112          moltype = AA  length = 147
FEATURE                 Location/Qualifiers
REGION                  1..147
                        note = Synthesized
source                  1..147
                        mol_type = protein
                        organism = synthetic construct
SEQUENCE: 112
KEFLLYLAGF VDGDGSICAC IVPRQDRKFK HQLRLFFEVG QKTQRRWFLD KLVDEIGVGY            60
VRDLGSASTY RLSQIKPLHN FLTQLQPFLK LKQKQANLVL KIIEQLPSAK ESPDKFLEVC           120
TWVDQIAALN DSKTRKTTSE TVRAVLD                                              147

SEQ ID NO: 113          moltype = AA  length = 147
FEATURE                 Location/Qualifiers
REGION                  1..147
                        note = Synthesized
source                  1..147
                        mol_type = protein
                        organism = synthetic construct
SEQUENCE: 113
KEFLLYLAGF VDGDGSICAC IVPRQDRKFK HQLRLFFEVG QKTQRRWFLD KLVDEIGVGY            60
VRDLGSASTY RLSEIKPLHN FLTQLQPFLK LKQKQANLVL KIIEQLPSAK ESPDKFLEVC           120
TWVDQIAALN DSRTRKTTSE TVRAVLD                                              147

SEQ ID NO: 114          moltype = AA  length = 147
FEATURE                 Location/Qualifiers
REGION                  1..147
                        note = Synthesized
source                  1..147
                        mol_type = protein
                        organism = synthetic construct
SEQUENCE: 114
KEFLLYLAGF VDGDGSICAC IVPRQDRKFK HQLRLFFEVG QKTQRRWFLD KLVDEIGVGY            60
VRDLGSASTY RLSEIKPLHN FLTQLQPFLK LKQKQANLVL KIIEQLPSAK ESPDKFLEVC           120
TWVDQIAALN DSRTRKTTSE TVRAVLD                                              147

SEQ ID NO: 115          moltype = AA  length = 147
FEATURE                 Location/Qualifiers
REGION                  1..147
                        note = Synthesized
source                  1..147
                        mol_type = protein
                        organism = synthetic construct
SEQUENCE: 115
KEFLLYLAGF VDGDGSICAC IVPRQDRKFK HQLRLFFEVG QKTQRRWFLD KLVDEIGVGY            60
VRDLGSASTY RLSQIKPLHN FLTQLQPFLK LKQKQANLVL KIIEQLPSAK ESPDKFLEVC           120
TWVDQIAALN DSRTRKTTSE TVRAVLD                                              147

SEQ ID NO: 116          moltype = AA  length = 147
FEATURE                 Location/Qualifiers
REGION                  1..147
                        note = Synthesized
source                  1..147
                        mol_type = protein
                        organism = synthetic construct
SEQUENCE: 116
KEFLLYLAGF VDGDGSICAC IVPRQDRKFK HQLRLFFEVG QKTQRRWFLD KLVDEIGVGY            60
VRDLGSASTY RLSQIKPLHN FLTQLQPFLK LKQKQANLVL KIIEQLPSAK ESPDKFLEVC           120
TWVDQIAALN DSRTRKTTSE TVRAVLD                                              147

SEQ ID NO: 117          moltype = AA  length = 147
FEATURE                 Location/Qualifiers
REGION                  1..147
                        note = Synthesized
source                  1..147

```
                        mol_type = protein
                        organism = synthetic construct
SEQUENCE: 117
KEFLLYLAGF VDGDGSIFAS IMPTQWTKFK HSLLLRFRVT QSTRRRWFLD KLMDEIGVGY    60
VSDQGRASYY TLSEIKPLHN FLTQLQPFLK LKQKQANLVL KIIEQLPSAK ESPDKFLEVC   120
TWVDQIAALN DSRTRKTTSE TVRAVLD                                      147

SEQ ID NO: 118          moltype = AA  length = 147
FEATURE                 Location/Qualifiers
REGION                  1..147
                        note = Synthesized
source                  1..147
                        mol_type = protein
                        organism = synthetic construct
SEQUENCE: 118
KEFLLYLAGF VDGDGSIFAS IIPSQLVKFK HTLLLRFRVT QATRRRWFLD KLVDEIGVGY    60
VTDNGRASYY TLSEIKPLHN FLTQLQPFLK LKQKQANLVL KIIEQLPSAK ESPDKFLEVC   120
TWVDQIAALN DSRTRKTTSE TVRAVLD                                      147

SEQ ID NO: 119          moltype = AA  length = 147
FEATURE                 Location/Qualifiers
REGION                  1..147
                        note = Synthesized
source                  1..147
                        mol_type = protein
                        organism = synthetic construct
SEQUENCE: 119
KEFLLYLAGF VDGDGSIFAS IIPSQLVKFK HTLLLRFRVC QATKRRWFLD KLVDEIGVGY    60
VSDQGSASYY TLSEIKPLHN FLTQLQPFLK LKQKQANLVL KIIEQLPSAK ESPDKFLEVC   120
TWVDQIAALN DSRTRKTTSE TVRAVLD                                      147

SEQ ID NO: 120          moltype = AA  length = 147
FEATURE                 Location/Qualifiers
REGION                  1..147
                        note = Synthesized
source                  1..147
                        mol_type = protein
                        organism = synthetic construct
SEQUENCE: 120
KEFLLYLAGF VDGDGSIFAS IIPSQEVKFK HTLLLRFRVC QATKRRWFLD KLVDEIGVGY    60
VSDQGSASYY TLSEIKPLHN FLTQLQPFLK LKQKQANLVL KIIEQLPSAK ESPDKFLEVC   120
TWVDQIAALN DSRTRKTTSE TVRAVLD                                      147

SEQ ID NO: 121          moltype = AA  length = 147
FEATURE                 Location/Qualifiers
REGION                  1..147
                        note = Synthesized
source                  1..147
                        mol_type = protein
                        organism = synthetic construct
SEQUENCE: 121
KEFLLYLAGF VDGDGSIFAS IIPSQEVKFK HTLLLRFRVC QATKRRWFLD KLVDEIGVGY    60
VSDQGSASYY TLSEIKPLHN FLTQLQPFLK LKQKQANLVL KIIEQLPSAK ESPDKFLEVC   120
TWVDQIAALN DSRTRKTTSE TVRAVLD                                      147

SEQ ID NO: 122          moltype = AA  length = 147
FEATURE                 Location/Qualifiers
REGION                  1..147
                        note = Synthesized
source                  1..147
                        mol_type = protein
                        organism = synthetic construct
SEQUENCE: 122
KEFLLYLAGF VDGDGSIFAS IIPSQEVKFK HTLLLRFRVT QATKRRWFLD KLVDEIGVGY    60
VSDVGSASYY TLSEIKPLHN FLTQLQPFLK LKQKQANLVL KIIEQLPSAK ESPDKFLEVC   120
TWVDQIAALN DSRTRKTTSE TVRAVLD                                      147

SEQ ID NO: 123          moltype = AA  length = 147
FEATURE                 Location/Qualifiers
REGION                  1..147
                        note = Synthesized
source                  1..147
                        mol_type = protein
                        organism = synthetic construct
SEQUENCE: 123
KEFLLYLAGF VDGDGSIFAS IIPSQEVKFK HTLLLRFRVC QATKRRWFLD KLVDEIGVGY    60
VSDRGSASYY TLSEIKPLHN FLTQLQPFLK LKQKQANLVL KIIEQLPSAK ESPDKFLEVC   120
TWVDQIAALN DSRTRKTTSE TVRAVLD                                      147
```

```
SEQ ID NO: 124         moltype = AA  length = 147
FEATURE                Location/Qualifiers
REGION                 1..147
                       note = Synthesized
source                 1..147
                       mol_type = protein
                       organism = synthetic construct
SEQUENCE: 124
KEFLLYLAGF VDGDGSIFAS IIPSQEVKFK HTLLLRFRVC QATKRRWFLD KLVDEIGVGY    60
VSDQGSASYY TLSQIKPLHN FLTQLQPFLK LKQKQANLVL KIIEQLPSAK ESPDKFLEVC   120
TWVDQIAALN DSRTRKTTSE TVRAVLD                                      147

SEQ ID NO: 125         moltype = AA  length = 147
FEATURE                Location/Qualifiers
REGION                 1..147
                       note = Synthesized
source                 1..147
                       mol_type = protein
                       organism = synthetic construct
SEQUENCE: 125
KEFLLYLAGF VDGDGSIFAC IRPSQRAKFK HVLQLCFRVH QLTKRRWFLD KLVDEIGVGY    60
VYDCGSASFY HLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 126         moltype = AA  length = 147
FEATURE                Location/Qualifiers
REGION                 1..147
                       note = Synthesized
source                 1..147
                       mol_type = protein
                       organism = synthetic construct
SEQUENCE: 126
KEFLLYLAGF VDGDGSIFAC IRPSQRAKFK HVLQLCFRVH QKTKRRWFLD KLVDEIGVGY    60
VYDHGSASCY HLSEIKPLHN FLTQLQPFLK LKQKQANLVL KIIEQLPSAK ESPDKFLEVC   120
TWVDQIAALN DSHTRKTTSE TVRAVLD                                      147

SEQ ID NO: 127         moltype = AA  length = 147
FEATURE                Location/Qualifiers
REGION                 1..147
                       note = Synthesized
source                 1..147
                       mol_type = protein
                       organism = synthetic construct
SEQUENCE: 127
KEFLLYLAGF VDGDGSIFAC IRPSQRAKFK HVLQLCFRVH QSTRRRWFLD KLVDEIGAGY    60
VYDHGSASLY SLSQIKPLHN FLTQLQPFLK LKQKQANLVL KIIEQLPSAK ESPDKFLEVC   120
TWVDQIAALN DSHTRKTTSE TVRAVLD                                      147

SEQ ID NO: 128         moltype = AA  length = 147
FEATURE                Location/Qualifiers
REGION                 1..147
                       note = Synthesized
source                 1..147
                       mol_type = protein
                       organism = synthetic construct
SEQUENCE: 128
KEFLLYLAGF VDGDGSIFAC IRPSQRAKFK HVLQLCFRVF QKTQRRWFLD KLVDEIGVGY    60
VYDHGRASIY QLSQIKPLHN FLTQLQPFLK LKQKQANLVL KIIEQLPSAK ESPDKFLEVC   120
TWVDQIAALN DSHTRKTTSE TVRAVLD                                      147

SEQ ID NO: 129         moltype = AA  length = 147
FEATURE                Location/Qualifiers
REGION                 1..147
                       note = Synthesized
source                 1..147
                       mol_type = protein
                       organism = synthetic construct
SEQUENCE: 129
KEFLLYLAGF VDGDGSIFAC IRPSQRAKFK HVLQLHFRVF QKTQRRWFLD KLVDEIGVGY    60
VYDHGRASIY QLSQIKPLHN FLTQLQPFLK LKQKQANLVL KIIEQLPSAK ESPDKFLEVC   120
TWVDQIAALN DSHTRKTTSE TVRAVLD                                      147

SEQ ID NO: 130         moltype = AA  length = 147
FEATURE                Location/Qualifiers
REGION                 1..147
                       note = Synthesized
source                 1..147
                       mol_type = protein
                       organism = synthetic construct
```

```
SEQUENCE: 130
KEFLLYLAGF VDGDGSIFAC IRPSQRAKFK HVLQLCFRVF QKTQRRWFLD KLVDEIGVGY      60
VYDHGRASIY QLSQIKPLHN FLTQLQPFLK LKQKQANLVL KIIEQLPSAK ESPDKFLEVC     120
TWVDQIAALN DSHTRKTTSE TVRAVLD                                        147

SEQ ID NO: 131          moltype = AA   length = 147
FEATURE                 Location/Qualifiers
REGION                  1..147
                        note = Synthesized
source                  1..147
                        mol_type = protein
                        organism = synthetic construct
SEQUENCE: 131
KEFLLYLAGF VDGDGSIFAC IRPSQRAKFK HVLQLCFRVF QKTQRRWFLD KLVDEIGVGY      60
VYDHGRASIY QLSQIKPLHN FLTQLQPFLK LKQKQANLVL KIIEQLPSAK ESPDKFLEVC     120
TWVDQIAALN DSHTRKTTSE TVRAVLD                                        147

SEQ ID NO: 132          moltype = AA   length = 42
FEATURE                 Location/Qualifiers
REGION                  1..42
                        note = Synthesized
source                  1..42
                        mol_type = protein
                        organism = synthetic construct
SEQUENCE: 132
SLPGSVGGLS PSQASSAASS ASSSPGSGIS EALRAGAGSG TG                         42

SEQ ID NO: 133          moltype = DNA  length = 20
FEATURE                 Location/Qualifiers
misc_feature            1..20
                        note = Synthesized
source                  1..20
                        mol_type = other DNA
                        organism = synthetic construct
SEQUENCE: 133
cgggaggtaa tacataatcc                                                  20

SEQ ID NO: 134          moltype = DNA  length = 21
FEATURE                 Location/Qualifiers
misc_feature            1..21
                        note = Synthesized
source                  1..21
                        mol_type = other DNA
                        organism = synthetic construct
SEQUENCE: 134
gggtgggttg ctttacctct c                                                21

SEQ ID NO: 135          moltype = DNA  length = 20
FEATURE                 Location/Qualifiers
misc_feature            1..20
                        note = Synthesized
source                  1..20
                        mol_type = other DNA
                        organism = synthetic construct
SEQUENCE: 135
tgggctactg caactctgtt                                                  20

SEQ ID NO: 136          moltype = DNA  length = 27
FEATURE                 Location/Qualifiers
misc_feature            1..27
                        note = Synthesized
source                  1..27
                        mol_type = other DNA
                        organism = synthetic construct
SEQUENCE: 136
aggacaaaag aggacggtct gccctgg                                          27

SEQ ID NO: 137          moltype = DNA  length = 20
FEATURE                 Location/Qualifiers
misc_feature            1..20
                        note = Synthesized
source                  1..20
                        mol_type = other DNA
                        organism = synthetic construct
SEQUENCE: 137
taagacccag cttcacggag                                                  20

SEQ ID NO: 138          moltype = DNA  length = 20
FEATURE                 Location/Qualifiers
```

```
misc_feature          1..20
                      note = Synthesized
source                1..20
                      mol_type = other DNA
                      organism = synthetic construct
SEQUENCE: 138
tatgatcgcc tgttcctcca                                                    20

SEQ ID NO: 139        moltype = DNA  length = 18
FEATURE               Location/Qualifiers
misc_feature          1..18
                      note = Synthesized
source                1..18
                      mol_type = other DNA
                      organism = synthetic construct
SEQUENCE: 139
ctggccgaag tataggaa                                                      18

SEQ ID NO: 140        moltype = DNA  length = 21
FEATURE               Location/Qualifiers
misc_feature          1..21
                      note = Synthesized
source                1..21
                      mol_type = other DNA
                      organism = synthetic construct
SEQUENCE: 140
cgcaacatgt gacataaaga g                                                  21

SEQ ID NO: 141        moltype = DNA  length = 20
FEATURE               Location/Qualifiers
misc_feature          1..20
                      note = Synthesized
source                1..20
                      mol_type = other DNA
                      organism = synthetic construct
SEQUENCE: 141
tctggatatc ctcttctggg                                                    20

SEQ ID NO: 142        moltype = DNA  length = 19
FEATURE               Location/Qualifiers
misc_feature          1..19
                      note = Synthesized
source                1..19
                      mol_type = other DNA
                      organism = synthetic construct
SEQUENCE: 142
cctacatggt gtatctgac                                                     19

SEQ ID NO: 143        moltype = DNA  length = 21
FEATURE               Location/Qualifiers
misc_feature          1..21
                      note = Synthesized
source                1..21
                      mol_type = other DNA
                      organism = synthetic construct
SEQUENCE: 143
gaacaccacc agaaaaacaa g                                                  21

SEQ ID NO: 144        moltype = DNA  length = 21
FEATURE               Location/Qualifiers
misc_feature          1..21
                      note = Synthesized
source                1..21
                      mol_type = other DNA
                      organism = synthetic construct
SEQUENCE: 144
cacttcctgt aagacaacca g                                                  21

SEQ ID NO: 145        moltype = DNA  length = 17
FEATURE               Location/Qualifiers
misc_feature          1..17
                      note = Synthesized
source                1..17
                      mol_type = other DNA
                      organism = synthetic construct
SEQUENCE: 145
atccctcata cccaatc                                                       17

SEQ ID NO: 146        moltype = DNA  length = 20
```

| | | |
|---|---|---|
| FEATURE | Location/Qualifiers | |
| misc_feature | 1..20 | |
| | note = Synthesized | |
| source | 1..20 | |
| | mol_type = other DNA | |
| | organism = synthetic construct | |
| SEQUENCE: 146 | | |
| aaaaaccacg gtgctgttga | | 20 |
| | | |
| SEQ ID NO: 147 | moltype = DNA length = 20 | |
| FEATURE | Location/Qualifiers | |
| misc_feature | 1..20 | |
| | note = Synthesized | |
| source | 1..20 | |
| | mol_type = other DNA | |
| | organism = synthetic construct | |
| SEQUENCE: 147 | | |
| atggggtccg agactttcc | | 20 |
| | | |
| SEQ ID NO: 148 | moltype = DNA length = 21 | |
| FEATURE | Location/Qualifiers | |
| misc_feature | 1..21 | |
| | note = Synthesized | |
| source | 1..21 | |
| | mol_type = other DNA | |
| | organism = synthetic construct | |
| SEQUENCE: 148 | | |
| gggtgggttg ctttacctct c | | 21 |
| | | |
| SEQ ID NO: 149 | moltype = DNA length = 19 | |
| FEATURE | Location/Qualifiers | |
| misc_feature | 1..19 | |
| | note = Synthesized | |
| source | 1..19 | |
| | mol_type = other DNA | |
| | organism = synthetic construct | |
| SEQUENCE: 149 | | |
| agagcatgcc atctgagtc | | 19 |
| | | |
| SEQ ID NO: 150 | moltype = DNA length = 20 | |
| FEATURE | Location/Qualifiers | |
| misc_feature | 1..20 | |
| | note = Synthesized | |
| source | 1..20 | |
| | mol_type = other DNA | |
| | organism = synthetic construct | |
| SEQUENCE: 150 | | |
| gtgaagtagc aaagcacctg | | 20 |
| | | |
| SEQ ID NO: 151 | moltype = DNA length = 19 | |
| FEATURE | Location/Qualifiers | |
| misc_feature | 1..19 | |
| | note = Synthesized | |
| source | 1..19 | |
| | mol_type = other DNA | |
| | organism = synthetic construct | |
| SEQUENCE: 151 | | |
| agagcatgcc atctgagtc | | 19 |
| | | |
| SEQ ID NO: 152 | moltype = DNA length = 21 | |
| FEATURE | Location/Qualifiers | |
| misc_feature | 1..21 | |
| | note = Synthesized | |
| source | 1..21 | |
| | mol_type = other DNA | |
| | organism = synthetic construct | |
| SEQUENCE: 152 | | |
| gggtgggttg ctttacctct c | | 21 |
| | | |
| SEQ ID NO: 153 | moltype = DNA length = 20 | |
| FEATURE | Location/Qualifiers | |
| misc_feature | 1..20 | |
| | note = Synthesized | |
| source | 1..20 | |
| | mol_type = other DNA | |
| | organism = synthetic construct | |
| SEQUENCE: 153 | | |
| tttggtatgg ggtccgagac | | 20 |

| | | |
|---|---|---|
| SEQ ID NO: 154<br>FEATURE<br>misc_feature<br><br>source | moltype = DNA   length = 20<br>Location/Qualifiers<br>1..20<br>note = Synthesized<br>1..20<br>mol_type = other DNA<br>organism = synthetic construct | |
| SEQUENCE: 154<br>gtgaagtagc aaagcacctg | | 20 |
| SEQ ID NO: 155<br>FEATURE<br>misc_feature<br><br>source | moltype = DNA   length = 20<br>Location/Qualifiers<br>1..20<br>note = Synthesized<br>1..20<br>mol_type = other DNA<br>organism = synthetic construct | |
| SEQUENCE: 155<br>tttggtatgg ggtccgagac | | 20 |
| SEQ ID NO: 156<br>FEATURE<br>misc_feature<br><br>source | moltype = DNA   length = 21<br>Location/Qualifiers<br>1..21<br>note = Synthesized<br>1..21<br>mol_type = other DNA<br>organism = synthetic construct | |
| SEQUENCE: 156<br>gggtgggttg ctttacctct c | | 21 |
| SEQ ID NO: 157<br>FEATURE<br>misc_feature<br><br>source | moltype = DNA   length = 23<br>Location/Qualifiers<br>1..23<br>note = Synthesized<br>1..23<br>mol_type = other DNA<br>organism = synthetic construct | |
| SEQUENCE: 157<br>gattctcaga aatggagtga ctg | | 23 |
| SEQ ID NO: 158<br>FEATURE<br>misc_feature<br><br>source | moltype = DNA   length = 20<br>Location/Qualifiers<br>1..20<br>note = Synthesized<br>1..20<br>mol_type = other DNA<br>organism = synthetic construct | |
| SEQUENCE: 158<br>gtgaagtagc aaagcacctg | | 20 |
| SEQ ID NO: 159<br>FEATURE<br>misc_feature<br><br>source | moltype = DNA   length = 23<br>Location/Qualifiers<br>1..23<br>note = Synthesized<br>1..23<br>mol_type = other DNA<br>organism = synthetic construct | |
| SEQUENCE: 159<br>gattctcaga aatggagtga ctg | | 23 |
| SEQ ID NO: 160<br>FEATURE<br>misc_feature<br><br>source | moltype = DNA   length = 25<br>Location/Qualifiers<br>1..25<br>note = Synthesized<br>1..25<br>mol_type = other DNA<br>organism = synthetic construct | |
| SEQUENCE: 160<br>atcagaagga ttatgtatag gaata | | 25 |
| SEQ ID NO: 161<br>FEATURE<br>misc_feature<br><br>source | moltype = DNA   length = 20<br>Location/Qualifiers<br>1..20<br>note = Synthesized<br>1..20<br>mol_type = other DNA<br>organism = synthetic construct | |
| SEQUENCE: 161<br>gggtgggttg ctttacctct | | 20 |

```
SEQ ID NO: 162            moltype = DNA  length = 20
FEATURE                   Location/Qualifiers
misc_feature              1..20
                          note = Synthesized
source                    1..20
                          mol_type = other DNA
                          organism = synthetic construct
SEQUENCE: 162
tctggatatc ctcttctggg                                                      20

SEQ ID NO: 163            moltype = DNA  length = 20
FEATURE                   Location/Qualifiers
misc_feature              1..20
                          note = Synthesized
source                    1..20
                          mol_type = other DNA
                          organism = synthetic construct
SEQUENCE: 163
gtgaagtagc aaagcacctg                                                      20

SEQ ID NO: 164            moltype = DNA  length = 20
FEATURE                   Location/Qualifiers
misc_feature              1..20
                          note = Synthesized
source                    1..20
                          mol_type = other DNA
                          organism = synthetic construct
SEQUENCE: 164
gtgaagtagc aaagcacctg                                                      20

SEQ ID NO: 165            moltype = DNA  length = 25
FEATURE                   Location/Qualifiers
misc_feature              1..25
                          note = Synthesized
source                    1..25
                          mol_type = other DNA
                          organism = synthetic construct
SEQUENCE: 165
agtcacttcc taagctaaga caacc                                                25

SEQ ID NO: 166            moltype = DNA  length = 24
FEATURE                   Location/Qualifiers
misc_feature              1..24
                          note = Synthesized
source                    1..24
                          mol_type = other DNA
                          organism = synthetic construct
SEQUENCE: 166
cagaaggatt atgtatgagg gata                                                 24

SEQ ID NO: 167            moltype = DNA  length = 20
FEATURE                   Location/Qualifiers
misc_feature              1..20
                          note = Synthesized
source                    1..20
                          mol_type = other DNA
                          organism = synthetic construct
SEQUENCE: 167
gtgaagtagc aaagcacctg                                                      20

SEQ ID NO: 168            moltype = DNA  length = 20
FEATURE                   Location/Qualifiers
misc_feature              1..20
                          note = Synthesized
source                    1..20
                          mol_type = other DNA
                          organism = synthetic construct
SEQUENCE: 168
atggggtccg agactttcc                                                       20

SEQ ID NO: 169            moltype = DNA  length = 335
FEATURE                   Location/Qualifiers
misc_feature              1..335
                          note = Synthesized
source                    1..335
                          mol_type = other DNA
                          organism = synthetic construct
SEQUENCE: 169
```

```
cggccgtccg ccttcggcac catcctcacg acacccaaat atggcgacgg gtgaggaatg    60
gtggggagtt attttagag cggtgaggaa ggtgggcagg cagcaggtgt tggcgctcta   120
aaaataactc ccgggagtta ttttagagc ggaggaatgg tggacaccca aatatggcga   180
cggttcctca cccgtcgcca tatttgggtg tccgccctcg gccggggccg cattcctggg   240
ggccgggcgg tgctcccgcc cgcctcgata aaaggctccg gggccggcgg cggcccacga   300
gctacccgga ggagcgggag gcgccaagct ctaga                              335
```

SEQ ID NO: 170        moltype = DNA  length = 3357
FEATURE                Location/Qualifiers
source                 1..3357
                        mol_type = genomic DNA
                        organism = Mus musculus
SEQUENCE: 170
```
ccatcctggt ctatagagag agttccagaa cagccagggc tacagataaa cccatctgga    60
aaaacaaagt tgaatgaccc aagaggggtt ctcagagggt ggcgtgtgct ccctggcaag   120
cctatgacat ggccggggcc tgcctctctc tgcctctgac cctcagtggc tcccatgaac   180
tccttgccca atggcatctt tttcctgcgc tccttgggtt attccagtct cccctcagca   240
ttccttcctc agggcctcgc tcttctctct gctccctcct tgcacagctg gctctgtcca   300
cctcagatgt cacagtgctc tctcagagga ggaaggcacc atgtaccctc tgtttcccag   360
gtaagggttc aattttaaa aatggttttt tgtttgtttg tttgtttgtt tgtttgtttg   420
ttttcaaga cagggctcct ctgtgtagtc ctaactgtct tgaaactccc tctgtagacc   480
aggtcgacct cgaactcttg aaacctgcca cggaccacc agtcaggtat ggaggtcct   540
ggaatgagcg tcctcgaagc taggtgggta agggttcggc ggtgacaaac agaaacaaac   600
acagaggcag tttgaatctg agtgtatttt gcagctctca agcagggat tttatacata   660
aaaaaaaaaa aaaaaaaaa accaaacatt acatctctta gaaactatat ccaatgaaac   720
aatcacagat accaaccaaa accattgggc agagtaaaac acaaaaatca tccaagcatt   780
acaactctga aaccatgtat tcagtgaatc acaaacagaa caggtaacat cattattaat   840
ataaatcacc aaaatataac aattctaaaa ggatgtatcc agtgggggct gtcgtccaag   900
gctagtggca gatttccagg agcaggttag taaatcttaa ccactgaact aactctccag   960
ccccatggtc aattattatt tagcatctag tgcctaattt ttttttataa atcttcacta  1020
tgtaatttaa aactatttta attcttccta attaaggctt tctttaccat ataccaaat  1080
tcacctccaa tgacacacgc gtagccatat gaaattttat tgttgggaaa atttgtacct  1140
atcataatg ttttgtaaat gatttaaaaa gcaaagtgtt agccgggcgt ggtggcacac  1200
gcctttaatc cctgcactcg ggaggcaggg gcaggaggat ttctgagttt gaggccagcc  1260
tggtctacag agtgagttcc aggacagcca gggctacaca gagaaaccct gtctcgaacc  1320
cccccacccc caaaaaaagc aaagtgttgg tttccttggg gataaagtca tgttagtggc  1380
ccatctctag gccccatctca cccattattc tcgcttaaga tcttggccta ggctaccagg  1440
aacatgtaaa taagaaaagg aataagagaa aacaaaacag agagattgcc atgagaacta  1500
cggctcaata ttttttctct ccggcgaaga gttccacaac catctccagg aggcctccac  1560
gttttgaggt caatgcctc agtctgtgga acttgtcaca cagatcttac tggaggtggt  1620
gtggcagaaa cccattcctt ttagtgtctt gggctaaaag taaaaggccc agaggaggcc  1680
tttgctcatc tgaccatgct gacaaggaac acgggtgcca ggacagaggc tggacccag  1740
gaacaccta aacacttctt cccttctccg cccctaggc agggctcccc tcaccagcct  1800
gggcagaaat gggggaagat ggagtgaagc catactggct actccagaat caacagaggg  1860
agccgggggc aatactggag aagctggtct ccccccaggg gcaatcctgg cacctccag  1920
gcagaagagg aaacttccac agtgcatctc acttccatga atcccctcct cggactctga  1980
ggtccttggt cacagctgag gtgcaaaagg ctcctgtcat attgtgtcct gctctggtct  2040
gccttccaca gcttgggggc cacctagccc acctctccct agggatgaga gcagccacta  2100
cgggtctagg ctgccccatgt aaggaggcaa ggctgggga cacccgagat gcctggttat  2160
aattaaccca gacatgtggc tgcccccccc ccccaacac ctgctgcctg agcctcaccc  2220
ccacccggt gcctgggtct taggctctgt acaccatgga ggagaagctc gctctaaaaa  2280
taaccctgtc cctggtggat ccagggtgag gggcaggctg agggcggcca ttccctcag  2340
ccgcaggttt gttttcccaa gaatggtttt tctgcttctg tagcttttcc tgtcaattct  2400
gccatggtgg agcagcctgc actgggcttc tgggagaaac caaaccgggt tctaacctt  2460
cagctacagt tattgccttt cctgtagatg ggcgactaca gcccccacc cacccccgct  2520
tcctgtatcc ttcctgggcc tggggatcct aggctttcac tggaaatttc ccccaggtg  2580
ctgtaggcta gagtcacggc tcccaagaac agtgcttgcc tggcatgcat ggttctgaac  2640
ctccaactgc aaaaaatgac acataccttg acccttggaa ggctgaggca ggggattgc  2700
catgagtgca aagccagact gggtggcata gttagaccct gtctcaaaaa accaaaaaca  2760
attaaataac taaagtcagg caagtaatac tactcgggag actgaggcag agggattgtt  2820
acatgtctga ggccagcctg gactacatag ggtttcaggc tagccctgtc tacagagtaa  2880
ggccctattt caaaaacaca aacaaatgg ttctcccagc tgctaatgct caccaggcaa  2940
tgaagcctgg tgagcattag caatgaaggc aatgaaggag ggtgctggct acaatcaagg  3000
ctgtgggaga ctgagggcag gctgtaacag cttggggggc cagggcttat acgtgcctgg  3060
gactcccaaa gtattactgt tccatgttcc cggcgaaggg ccagctgtcc ccgccagct  3120
agactcagca cttagtttag gaaccagtga gcaagtcagc cctggggca gcccatacaa  3180
ggccatgggc ctgggcaagc tgcacgcctg gtccggggt gggcacggtg cccgggcaac  3240
gagctgaaag ctcatctgct ctcaggggcc cctccctggg gacagcccct cctggctagt  3300
cacacccctgt aggctcctct atataaccca ggggcacagg ggctgccccc gggtcac     3357
```

SEQ ID NO: 171        moltype = DNA  length = 655
FEATURE                Location/Qualifiers
source                 1..655
                        mol_type = genomic DNA
                        organism = Homo sapiens
SEQUENCE: 171
```
cctgagtttg aatctctcca actcagccag cctcagtttc cctccactc agtccctagg    60
aggaaggggc gcccaagcgg gtttctgggg ttagactgcc ctccattgca attggtcctt   120
ctcccggcct ctgcttcctc cagctcacag ggtatctgct cctcctggag ccacaccttg   180
```

```
gttccccgag gtgccgctgg gactcgggta ggggtgaggg cccagggcg acaggggag    240
ccgagggcca caggaagggc tggtggctga aggagactca ggggccaggg gacggtggct   300
tctacgtgct tgggacgttc ccagccaccg tccatgttc ccgccgggg ccagctgtcc    360
ccaccgccaa cccaactcag cacttggtta gggtatcagc ttggtggggg cgtgagccca   420
gccctggggc gctcagccca tacaaggcca tggggctggg cgcaaagcat gcctgggttc   480
agggtgggta tggtgccgga gcagggaggg gagaggctca gctgccctcc agaactcctc   540
cctggggaca accctccca gccaatagca cagcctaggt cccctatat aaggccacgg    600
ctgctgccc ttcctttggg tcagtgtcac ctccaggata cagacagccc ccctt         655

SEQ ID NO: 172           moltype = DNA  length = 206
FEATURE                  Location/Qualifiers
source                   1..206
                         mol_type = genomic DNA
                         organism = Mus musculus
SEQUENCE: 172
ccactacggg tctaggctgc ccatgtaagg aggcaaggcc tggggacacc cgagatgcct    60
ggttataatt aacccagaca tgtggctgcc ccccccccc caacacctgc tgcctgagcc   120
tcaccccac cccggtgcct gggtcttagg ctctgtacac catggaggag aagctcgctc   180
taaaaataac cctgtccctg gtggat                                        206

SEQ ID NO: 173           moltype = DNA  length = 211
FEATURE                  Location/Qualifiers
misc_feature             1..211
                         note = Synthesized
source                   1..211
                         mol_type = other DNA
                         organism = synthetic construct
SEQUENCE: 173
ccactacggg tctaggctgc ccatgtaagg aggcaaggcc tggggacacc cgagatgcct    60
ggttataatt aaccccaaca cctgctgccc ccccccccc aacacctgct gcctgagcct   120
gagcggttac cccaccccgg tgcctgggtc ttaggctctg tacaccatgg aggagaagct   180
cgctctaaaa ataaccctgt ccctggtgga t                                  211

SEQ ID NO: 174           moltype = DNA  length = 334
FEATURE                  Location/Qualifiers
misc_feature             1..334
                         note = Synthesized
source                   1..334
                         mol_type = other DNA
                         organism = synthetic construct
SEQUENCE: 174
tggccaccgc cttcggcacc atcctcacga cacccaaata tggcgacggg tgaggaatgg    60
tggggagtta tttttagagc ggtgaggaag gtgggcaggc agcaggtgtt ggcgctctaa   120
aaataactcc cggagttat ttttagagcg gaggaatggt ggacacccaa atatggcgac   180
ggttcctcac ccgtcgccat atttgggtgt ccgccctcgg ccggggccgc attcctgggg   240
gccgggcggt gctcccgccc gcctcgataa aaggctccgg ggccggcggc ggcccacgag   300
ctacccggag gagcgggagg cgccaagctc taga                               334

SEQ ID NO: 175           moltype = DNA  length = 792
FEATURE                  Location/Qualifiers
misc_feature             1..792
                         note = Synthesized
source                   1..792
                         mol_type = other DNA
                         organism = synthetic construct
SEQUENCE: 175
aagcttgcat gtctaagcta gacccttcag attaaaaata actgaggtaa gggcctgggt    60
aggggaggtg gtgtgagacg ctcctgtctc tcctctatct gcccatcggc cctttgggga   120
ggaggaatgt gccaaggac taaaaaaagg ccatggagcc agaggggcga gggcaacaga   180
ccttcatgg gcaaaccttg gggccctgct gtctagcatg ccccactacg ggtctaggct   240
gcccatgtaa ggaggcaagg cctggggaca cccgagatgc ctggttataa ttaacccaga   300
catgtggctg cccccccccc cccaacacct gctgcctcta aaaataaccc tgtccctggt   360
ggatcccctg catgcgaaga tcttcgaaca aggctgtggg ggactgaggg caggctgtaa   420
caggcttggg ggccagggct tatacgtgcc tgggactcca aaagtattac tgttccattg   480
tcccggcgaa gggccagctg tccccgcca gctagactca gcacttagtt taggaaccag   540
tgagcaagtc agcccttggg gcagcccata caaggccatg gggctgggca gctgcacgc   600
ctgggtccgg ggtgggcacg gtgcccgggc aacgagctga aagctcatct gctctcaggg   660
gcccctcct ggggacagcc cctcctggct agtcacaccc tgtaggctcc tctatataac   720
ccaggggcac aggggctgcc ctcattctac caccacctcc acagcacaga cagacactca   780
ggagcagcca gc                                                       792

SEQ ID NO: 176           moltype = DNA  length = 450
FEATURE                  Location/Qualifiers
misc_feature             1..450
                         note = Synthesized
source                   1..450
                         mol_type = other DNA
                         organism = synthetic construct
SEQUENCE: 176
```

```
ctagactagc atgctgccca tgtaaggagg caaggcctgg ggacacccga gatgcctggt    60
tataattaac ccagacatgt ggctgccccc cccccccaa cacctgctgc ctctaaaaat   120
aaccctgcat gccatgttcc cggcgaaggg ccagctgtcc cccgccagct agactcagca   180
cttagtttag gaaccagtga gcaagtcagc ccttggggca gcccatacaa ggccatgggg   240
ctgggcaagc tgcacgcctg ggtccggggt gggcacgtg cccgggcaag gagctgaaag   300
ctcatctgct ctcaggggcc cctccctggg gacagcccct cctggctagt cacaccctgt   360
aggctcctct atataaccca ggggcacagg ggctgccctc attctaccac cacctccaca   420
gcacagacag acactcagga gccagccagc                                    450

SEQ ID NO: 177          moltype = DNA  length = 1417
FEATURE                 Location/Qualifiers
misc_feature            1..1417
                        note = Synthesized
source                  1..1417
                        mol_type = other DNA
                        organism = synthetic construct
SEQUENCE: 177
ttctgagtcc tctaaggtcc ctcactccca actcagcccc atgtcctgtc aattcccact    60
cagtgtctga tctccttctc ctcacctttc ccatctcccg tttgacccag cttcctgagc   120
tctcctccca ttccccttttt tggagtcctc ctcctctccc agaacccagt aataagtggg   180
ctcctccctg gcctggaccc ccgtggtaac cctataaggc gaggcagctg ctgtctgagg   240
caggaggg ctggtgtggg aggctaaggg cagctgctaa gtttagggtg gctccttctc   300
tcttcttaga gacaacaggt ggctgggggc tcagtgccca gaaaagaaaa tgtcttagag   360
gtatcggcat gggcctggag gaggggggac agggcagggg gaggcatctt cctcaggaca   420
tcgggtccta gaggaccttg cttcctagct gggcctttcc ttctcctcta taataccag    480
ctctggtatt tcgccttggc agctgttgct gctagggaga ggctggctt gacatgcatc    540
tcctgacaaa acacaaaccc gtggtgtgag tgggtgtggg cggtgtgagt aggggggatga  600
atcagagagg gggcgaggga gacagggcg caggagtcag gcaaaggcga tgcggggtg    660
cgactacacg cagttggaaa cagtcgtcag aagattctgg aaactatctt gctggctata   720
aacttgaggg aagcagaagg ccaacattcc tcccaaggga aactgaggct cagagttaaa   780
acccaggtat cagtgatatg catgtgcccc ggccagggtc actctctgac taaccggtac   840
ctaccctaca ggcctaccta gagactcttt tgaaaggatg gtagagacct gtccgggctt   900
tgcccacagt cgttggaaac ctcagcattt tctaggcaac ttgtgcgaat aaaacacttc   960
gggggtcctt cttgttcatt ccaataacct aaaacctctc ctcggagaaa ataggggcc  1020
tcaaacaaac gaaattctct agcccgcttt ccccaggata aggcaggcat ccaaatggaa  1080
aaaaagggc cggccggggg tctcctgtca gctccttgcc ctgtgaaacc cagcaggcct  1140
gcctgtcttc tgtcctcttg gggctgtcca ggggcgcagg cctcttgcgg gggagctggc  1200
ctccccgccc cctcgcctgt ggccgccctt ttcctggcag gacagaggga tcctgcagct  1260
gtcagggag gggcgccggg gggtgatgtc aggagggcta caaatagtgc agacagctaa  1320
ggggctccgt cacccatctt cacatccact ccagccggct gcccgcccgc tgcctcctct  1380
gtgcgtccgc ccagccagcc tcgtccacgc cgccacc                          1417

SEQ ID NO: 178          moltype = DNA  length = 579
FEATURE                 Location/Qualifiers
misc_feature            1..579
                        note = Synthesized
source                  1..579
                        mol_type = other DNA
                        organism = synthetic construct
SEQUENCE: 178
accaacgact gattaactct acgtacgaaa cgtatgaaga cggacgaccc ctcggacccc    60
tgaaaggtgt ggccctcaat aaaaatctcg catatggcga cggcccttgg cagtacatca   120
aaacctttca gggcaatcac gataaccgac cccagccaat agcaccaacg actgattaac   180
tctacgtacg aaacgtatga agacggacga ccccctcggac ccctgaaagg tgtggcactc   240
cttaccacgg tccgtatagc ccaaactaca tgacggttcc cagccaatag ccgctctaaa   300
aataactccc ggcagcgta taaacccaca gcgctctaaa aataactccc ccggcagcgg   360
tatagggccc ctccctgggg acagcccaa cctttcaggg caatcacggt ccgcccggta   420
aatggcaccc tcaataaaaa tctcgcatcc ctttggactt cggccccatt gacgtcaatg   480
gggtccaaaa aatatatcag gggcttcagg tttccctaca aggcctgggg acaacccgat   540
atgcctgggt ccaaaaaata tatcaggtgg ttcagtcgt                          579

SEQ ID NO: 179          moltype = DNA  length = 346
FEATURE                 Location/Qualifiers
misc_feature            1..346
                        note = Synthesized
source                  1..346
                        mol_type = other DNA
                        organism = synthetic construct
SEQUENCE: 179
acaggggtcc ggaacggcag cggtataaac ccacagtggt tcagtcgtcc gtccgtcgtc    60
cacaaccgtc caaaaaatat atcaggaact acatgacggt tcaccaacga ctgattaact   120
ctacgtacga aacgtatgaa gacggacgac cccctcggacc cctgaaaggt gtggaccaac   180
gactgattaa ctctacgtac gaaacgtatg aagacggacg accctcgga cccctgaaag   240
gtgtgggtcc aaaaaatata tcagggggaca cccgagatgc ctggttaaac tacatgacgg   300
ttcccccgac agggtcccct cccgggtaa taactgcagt tacccg                  346

SEQ ID NO: 180          moltype = DNA  length = 301
FEATURE                 Location/Qualifiers
misc_feature            1..301
```

-continued

```
                        note = Synthesized
source                  1..301
                        mol_type = other DNA
                        organism = synthetic construct
SEQUENCE: 180
accaacgact gattaactct acgtacgaaa cgtatgaaga cggacgaccc ctcggacccc    60
tgaaaggtgt ggcttggcag tacatcaagc ccattgacgt caataatctt ggcagtacat   120
caaaccaacg actgattaac tctacgtacg aaacgtatga agacgacga ccccctcggac   180
ccctgaaagg tgtggaccaa cgactgatta actctacgta cgaaacgtat gaagacggac   240
gacccctcgg accctgaaa ggtgtgggtc aaaaaatat atcaggcaag gcctggggac     300
a                                                                   301

SEQ ID NO: 181          moltype = DNA  length = 1033
FEATURE                 Location/Qualifiers
misc_feature            1..1033
                        note = Synthesized
source                  1..1033
                        mol_type = other DNA
                        organism = synthetic construct
SEQUENCE: 181
gcggccgcat cgatattcgt aaacgcgttc cttgacacct ctgtctcctc aggtgcctgg    60
ctcccagtcc ccagaacgcc tctcctgtac cttgcttcct agctgggcct ttccttctcc   120
tctataaata ccagctctgg tatttgcct tggcagctgt tgctgctagg gcgcgccgtt    180
taaaccacgt gctcgagagc agccactacg ggtctaggct gcccatgtaa ggaggcaagg   240
cctggggaca cccgagatgc ctggttataa ttaacccaga catgtggctg ccccccccca   300
caacacctgc tgcctgagcc tcaccccac ccggtgcctg gggtcttagg tctgtacac     360
catggaggag aagctcgctc taaaaataac cctgtcgaca cgtgtctaga ctgatcaatc   420
aaggctgtgg gggactgagg gcaggctgta acaggcttgg gggccagggc ttatacgtgc   480
ctgggactcc caaagtatta ctgttccatg ttcccggcga agggccagct gtccccgcc    540
agctagactc agcacttagt ttaggaacca gtgagcaagt cagcccttgg ggcagccat    600
acaaggccat ggggctgggc aagctgcacg cctgggtccg gggtgggcac ggtgcccggg   660
caacgagctg aaagctcatc tgctctcagg ggccctccc tggggacagc ccctcctggc    720
tgatcacacc ctgtaggctc ctctatataa cccaggggca ctagtgggct gccctcagtt   780
caccaccacc tccacagcac agacagtaca tcaggagcca gccaggtacc caggtaggga   840
ctggccaccc cagcccacct gtcccaatgc tgacttagtg caaggcgagc cagcaaggag   900
ggaggacagg tggcagtggg gggtgaggag catctaaaaa tagccacaaa ctgagttctt   960
aagtctgaac ccggtctgct cgcaggtacc ggtcccaaag gccgccaccg ctagcgatat  1020
cggatcctca tga                                                     1033

SEQ ID NO: 182          moltype = AA  length = 738
FEATURE                 Location/Qualifiers
REGION                  1..738
                        note = Synthesized
source                  1..738
                        mol_type = protein
                        organism = synthetic construct
SEQUENCE: 182
MAADGYLPDW LEDNLSEGIR EWWDLKPGAP KPKANQQKQD NGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVESPVKTAP GKKRPVEPSP QRSPDSSTGI GKKGQQPAKK RLNFGQTGDS   180
ESVPDPQPIG EPPAGPSGLG SGTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYNFED   420
VPFHSSYAHS QSLDRLMNPL IDQYLYYLSR TQSTGGTAGT QQLLFSQAGP NNMSAQAKNW   480
LPGPCYRQQR VSTTLSQNNN SNFAWTGATK YHLNGRDSLV NPGVAMATHK DDEERFFPSS   540
GVLMFGKQGA GKDNVDYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP   660
PTTFNQAKLA SFITQYSTGQ VSVEIEWELQ KENSKRWNPE IQYTSNYYKS TNVDFAVNTE   720
GTYSEPRPIG TRYLTRNL                                                738

SEQ ID NO: 183          moltype = AA  length = 736
FEATURE                 Location/Qualifiers
REGION                  1..736
                        note = Synthesized
source                  1..736
                        mol_type = protein
                        organism = synthetic construct
SEQUENCE: 183
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
```

```
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 184            moltype = DNA   length = 24
FEATURE                   Location/Qualifiers
misc_feature              1..24
                          note = Synthesized
source                    1..24
                          mol_type = other DNA
                          organism = synthetic construct
SEQUENCE: 184
gctgaacagt ttctcagaaa gaca                                           24

SEQ ID NO: 185            moltype = DNA   length = 22
FEATURE                   Location/Qualifiers
misc_feature              1..22
                          note = Synthesized
source                    1..22
                          mol_type = other DNA
                          organism = synthetic construct
SEQUENCE: 185
ggctgttttc atccaggttg tg                                             22

SEQ ID NO: 186            moltype = DNA   length = 18
FEATURE                   Location/Qualifiers
misc_feature              1..18
                          note = Synthesized
source                    1..18
                          mol_type = other DNA
                          organism = synthetic construct
SEQUENCE: 186
tcttaaggac ctccaagg                                                  18

SEQ ID NO: 187            moltype = DNA   length = 24
FEATURE                   Location/Qualifiers
misc_feature              1..24
                          note = Synthesized
source                    1..24
                          mol_type = other DNA
                          organism = synthetic construct
SEQUENCE: 187
gggtgggttg ctttacctct ctag                                           24

SEQ ID NO: 188            moltype = DNA   length = 26
FEATURE                   Location/Qualifiers
misc_feature              1..26
                          note = Synthesized
source                    1..26
                          mol_type = other DNA
                          organism = synthetic construct
SEQUENCE: 188
tcacatcatg agatttagtc acttcc                                         26

SEQ ID NO: 189            moltype = DNA   length = 25
FEATURE                   Location/Qualifiers
misc_feature              1..25
                          note = Synthesized
source                    1..25
                          mol_type = other DNA
                          organism = synthetic construct
SEQUENCE: 189
ttgctacttc acagtaacca catgg                                          25

SEQ ID NO: 190            moltype = DNA   length = 20
FEATURE                   Location/Qualifiers
misc_feature              1..20
                          note = Synthesized
source                    1..20
                          mol_type = other DNA
                          organism = synthetic construct
SEQUENCE: 190
gggtgggttg ctttacctct                                                20

SEQ ID NO: 191            moltype = DNA   length = 20
FEATURE                   Location/Qualifiers
misc_feature              1..20
                          note = Synthesized
source                    1..20
```

```
                mol_type = other DNA
                organism = synthetic construct
SEQUENCE: 191
tctggatatc ctcttctggg                                               20

SEQ ID NO: 192      moltype = DNA   length = 25
FEATURE             Location/Qualifiers
misc_feature        1..25
                    note = Synthesized
source              1..25
                    mol_type = other DNA
                    organism = synthetic construct
SEQUENCE: 192
atcagaagga ttatgtatag gaata                                         25

SEQ ID NO: 193      moltype = DNA   length = 24
FEATURE             Location/Qualifiers
misc_feature        1..24
                    note = Synthetic
source              1..24
                    mol_type = other DNA
                    organism = synthetic construct
SEQUENCE: 193
gctatctgga tatcctcttc tggg                                          24

SEQ ID NO: 194      moltype = DNA   length = 98
FEATURE             Location/Qualifiers
source              1..98
                    mol_type = other DNA
                    organism = synthetic construct
SEQUENCE: 194
ataaaatgct caacaaatat tgcttatcag aaggattatg tatctgacta agaagacttt   60
ttgctctggt tgtcttacag gaagtgacta aatctcat                           98

SEQ ID NO: 195      moltype = DNA   length = 98
FEATURE             Location/Qualifiers
source              1..98
                    mol_type = other DNA
                    organism = synthetic construct
SEQUENCE: 195
tattttacga gttgtttata acgaatagtc ttcctaatac atagactgat tcttctgaaa   60
aacgagacca acagaatgtc cttcactgat ttagagta                           98

SEQ ID NO: 196      moltype = DNA   length = 103
FEATURE             Location/Qualifiers
source              1..103
                    mol_type = other DNA
                    organism = synthetic construct
SEQUENCE: 196
agagcagata aaatgctcaa caaatattgc ttatcagaag gattatgtat aggaatatgc   60
aattcccaga agaggatatc cagatagctg gaaaaataaa act                     103

SEQ ID NO: 197      moltype = DNA   length = 103
FEATURE             Location/Qualifiers
source              1..103
                    mol_type = other DNA
                    organism = synthetic construct
SEQUENCE: 197
tctcgtctat tttacgagtt gtttataacg aatagtcttc ctaatacata tccttatacg   60
ttaagggtct tctcctatag gtctatcgac cttttattt tga                      103
```

POLYNUCLEOTIDES ENCODING ENGINEERED MEGANUCLEASES HAVING SPECIFICITY FOR RECOGNITION SEQUENCES IN THE DYSTROPHIN GENE

CROSS-REFERENCE TO RELATED APPLICATIONS

This application is a divisional of U.S. application Ser. No. 17/931,896, filed Sep. 13, 2022, now U.S. Pat. No. 11,753,630, which is a continuation of international application number PCT/US2021/059146, filed Nov. 12, 2021, which claims the benefit of U.S. provisional application Nos. 63/113,131 and 63/233,664, filed Nov. 12, 2020 and Aug. 16, 2021, respectively, each of which is herein incorporated by reference in its entirety.

FIELD OF THE INVENTION

The application relates to the field of engineered meganucleases, molecular biology and recombinant nucleic acid technology. In particular aspects, the invention relates to engineered meganucleases useful for the removal of exons from the dystrophin gene and for the treatment of subjects having Duchenne Muscular Dystrophy.

REFERENCE TO AN ELECTRONIC SEQUENCE LISTING

The contents of the electronic sequence listing (BIO-054US3.xml; Size: 282,023 bytes; and Date of Creation: Feb. 17, 2023) is herein incorporated by reference in its entirety.

BACKGROUND OF THE INVENTION

Duchenne Muscular Dystrophy (DMD) is a rare, X-linked muscle degenerative disorder that affects about 1 in every 3500 boys worldwide. The disease is caused by mutations in the dystrophin gene, which is the largest known gene. The dystrophin gene spans 2.2 Mb of the X chromosome and encodes predominantly a 14-kb transcript derived from 79 exons. The full-length dystrophin protein, as expressed in skeletal muscle, smooth muscle, and cardiomyocytes, is 3685 amino acids and has a molecular weight of 427 kD. The severe Duchenne phenotype is generally associated with the loss of full-length dystrophin protein from skeletal and cardiac muscle, which leads to debilitating muscle degeneration and, ultimately, heart failure. A large number of different dystrophin gene mutations have been described, many of them resulting in either the severe DMD or the milder Becker Muscular Dystrophy.

There are several therapeutic strategies being pursued for the treatment of DMD. First, "gene replacement" strategies are an active area of research (Oshima et al. (2009) *J. Am. Soc. Gene Ther.* 17:73-80; Liu et al. (2005) *Mol. Ther.* 11:245-56; Lai et al. (2006) *Hum Gene Ther.* 17:1036-42; Odom et al. (2008) *Mol. Ther.* 16:1539-45). This approach involves delivering a functional copy of the dystrophin gene to patients using a viral delivery vector, typically adeno-associated virus (AAV). The large size of the dystrophin gene makes it incompatible with the limited carrying capacity of common viral vectors, however. This necessitates the use of a "micro-dystrophin" gene in which most of the repetitive central portion of the gene is removed to leave only the minimally functional protein. It is not clear, however, that expression of "micro-dystrophin" is sufficient for clinical benefit. In addition, this approach suffers from the possibility of random gene integration into the patient genome, which could lead to insertional mutagenesis, and the potential for immune reactions against the delivery vector.

A second approach to treating DMD involves the transplantation of healthy muscle precursor cells into patient muscle fibers (Peault et al. (2007) *Mol. Ther.* 15:867-77; Skuk et al. (2007) *Neuromuscul. Disord.* 17:38-46). This approach suffers from inefficient migration of the transplanted myoblasts and the potential for immune rejection by the patient.

A third approach involves suppression of nonsense mutations using PTC124 (Welch et al. (2007) *Nature* 447:87-91). This would require lifelong dosing of the drug, however, and the approach is yet to show any significant clinical benefit.

A fourth approach for treating DMD is called "Exon Skipping" (Williams et al. (2008) *BMC Biotechnol.* 8:35; Jearawiriyapaisarn et al. (2008) *Mol Ther.* 16:1624-29; Yokota et al. (2007) *Acta Myol.* 26:179-84; van Deutekom et al. (2001) *Hum. Mol. Gen.* 10:1547-54; Benedetti et al. (2013) *FEBS J.* 280:4263-80; Rodino-Klapac (2013) *Curr Neurol Neurosci Rep.* 13:332; Verhaart & Aartsma-Rus (2012) *Curr Opin Neurol.* 25:588-96). In general, the amino (N)- and carboxy (C)-terminal portions of the dystrophin gene are essential for its role as a "scaffold" protein that maintains membrane integrity in muscle fibres, whereas the central "rod domain", which comprises 24 spectrin-like repeats, is at least partially dispensable. Indeed, the severe Duchenne phenotype is typically associated with mutations in the dystrophin gene that introduce frameshifts and/or premature termination codons, resulting in a truncated form of the dystrophin protein lacking the essential C-terminal domain. Mutations in the central rod domain, including large deletions of whole exons, typically result in the much milder Becker phenotype if they maintain the reading frame such that the C-terminal domain of the protein is intact.

DMD is most frequently caused by the deletion of one or more whole exon(s), resulting in reading frame shift. For example, Exon 45 is frequently deleted in Duchenne patients. Because Exon 45 is 176 bp long, which is not divisible by three, deleting the exon shifts Exons 46-79 into the wrong reading frame. The same can be said of Exon 44, which is 148 bp in length. However, if Exons 44 and 45 are deleted, the total size of the deletion is 324 bp, which is divisible by three. Thus, the deletion of both exons does not result in a reading frame shift. Because these exons encode a portion of the non-essential rod domain of the dystrophin protein, deleting them from the protein is expected to result in a mild Becker-like phenotype. Thus, a patient with the Duchenne phenotype due to the deletion of one or more exon(s) can, potentially, be treated by eliminating one or more adjacent exons to restore the reading frame. This is the principle behind "Exon Skipping," in which modified oligonucleotides are used to block splice acceptor sites in dystrophin pre-mRNA so that one or more specific exons are absent from the processed transcript. The approach has been used to restore dystrophin gene expression in the mdx mouse model by skipping Exon 23, which harbored a disease-inducing nonsense mutation (Mann et al. (2001) *Proc. Nat. Acad. Sci. USA* 98:42-47). Oligonucleotide analogs that induce skipping of Exon 51 have also shown promise in early human clinical trials (Benedetti et al. (2013) *FEBS J.* 280:4263-80). The major limitations with this approach are: (1) the exon-skipping process is inefficient, resulting in relatively low levels of functional dystrophin expression; and (2) the exon-skipping oligonucleotide has a relatively short half-life so the affect is transient, necessitating repeated and life-long dosing. Thus, while Exon-Skipping approaches have shown some promise in clinical trials, the improvements in disease progression have been minimal and variable.

The present disclosure improves upon current Exon-Skipping approaches by correcting gene expression at the level of the genomic DNA rather than pre-mRNA. The invention is a permanent treatment for DMD that involves the excision of specific exons from the dystrophin coding sequence using a pair of engineered, site-specific homing endonucleases, often referred to as meganucleases. By targeting a pair of such endonucleases to sites in the intronic regions flanking exons in the dystrophin gene, it is possible to permanently remove the intervening fragment from the genome. The resulting cell, and its progeny, will express a modified dystrophin in which a portion of the non-essential spectrin repeat domain is removed but the essential N- and C-terminal domains are intact.

Homing endonucleases, or meganucleases, are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006) *Q. Rev. Biophys.* 38:49-95). Homing endonucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see, Chevalier et al. (2001) *Nucleic Acids Res.* 29:3757-74). The LAGLIDADG homing endonucleases with a single copy of the LAGLIDADG motif form homodimers, whereas members with two copies of the LAGLIDADG motif are found as monomers.

I-CreI (SEQ ID NO: 1) is a member of the LAGLIDADG family of homing endonucleases that recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004) *J. Mol. Biol.* 342:31-41; Chames et al. (2005) *Nucleic Acids Res.* 33:e178; Seligman et al. (2002) *Nucleic Acids Res.* 30:3870-79, Arnould et al. (2006) *J. Mol. Biol.* 355:443-58). Methods of rationally-designing mono-LAGLIDADG homing endonucleases have been described which are capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009) *Nucleic Acids Res.* 37:1650-62; Grizot et al. (2009) *Nucleic Acids Res.* 37:5405-19). Thus, a functional "single-chain" meganuclease can be expressed from a single transcript. By delivering genes encoding two different single-chain meganucleases to the same cell, it is possible to simultaneously cut two different sites. This, coupled with the extremely low frequency of off-target cutting observed with engineered meganucleases makes them the preferred endonuclease for the present disclosure.

SUMMARY OF THE INVENTION

The present disclosure provides engineered meganucleases that bind and cleave recognition sequences in a dystrophin gene (e.g., a human dystrophin gene), as well as compositions comprising such engineered meganucleases and methods of their use. In some embodiments, pairs of engineered meganucleases are used to remove multiple exons from a dystrophin gene by generating a first cleavage site in an intron upstream of a first exon and a second cleavage site in an intron downstream of a second exon. In particular examples described herein, the first cleavage site is generated in the intron 5' upstream of exon 45 of the dystrophin gene, while the second cleavage site is generated in the intron 3' downstream of exon 55. This process allows for excision and removal of exons 45-55 from the dystrophin gene following annealment of the two cleavage sites and repair of the genome. The recognition sequences targeted by the disclosed engineered meganucleases are selected to have identical four basepair center sequences, such that the first and second cleavage sites will have complementary four basepair 3' overhangs that can perfectly ligate to one another (i.e., each basepair of one overhang pairs with its complement on the other overhang). By removing exons 45-55 from a mutant dystrophin gene that lacks one or more of these exons, this approach results in a restoration of the normal (i.e., wild-type) reading frame of the dystrophin gene. Cells so treated will express a shortened modified form of the dystrophin protein in which a portion of the central spectrin repeat domain is absent but the N- and C-terminal domains are intact. This will, in many cases, reduce the severity of the disease. In some cases, it will result in a milder Becker phenotype.

Thus, in one aspect, the invention provides an engineered meganuclease that binds and cleaves a recognition sequence in a dystrophin gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the recognition sequence comprises SEQ ID NO: 6.

In some such embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of any one of SEQ ID NOs: 36-44. In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 36-44. In some embodiments, the HVR1 region comprises residues corresponding to residues 24, 26, 28, 30, 32, 33, 38, 40, 42, 44, 46, 68, 70, 75, and 77 of any one of SEQ ID NOs: 36-44. In some embodiments, the HVR1 region comprises Y, R, K. or D at a residue corresponding to residue 66 of any one of SEQ ID NOs: 36-44. In some embodiments, the HVR1 region comprises residues 24-79 of any one of SEQ ID NOs: 36-44 with up to 1, 2, 3, 4, 5, 6, 7, 8, 9, 10, or 11 amino acid substitutions. In some embodiments, the HVR1 region comprises residues 24-79 of any one of SEQ ID NOs: 36-44.

In some such embodiments, the first subunit comprises an amino acid sequence having at least 80%, 85%, 90%, 91%, 92%, 93%, 94%, 95%, 96%, 97%, 98%, 99% or more sequence identity to residues 7-153 of any one of SEQ ID NOs: 36-44. In some embodiments, the first subunit comprises G, S, or A at a residue corresponding to residue 19 of any one of SEQ ID NOs: 36-44. In some embodiments, the first subunit comprises a residue corresponding to residue 19 of any one of SEQ ID NOs: 36-44. In some embodiments, the first subunit comprises E, Q, or K at a residue corresponding to residue 80 of any one of SEQ TD NOs: 36-44. In some embodiments, the first subunit comprises a residue corresponding to residue 80 of any one of SEQ ID NOs: 38, 39, or 149. In some embodiments, the first subunit comprises residues 7-153 of any one of SEQ ID NOs: 36-44 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of any one of SEQ ID NOs: 36-44.

In some such embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of any one of SEQ ID NOs: 36-44. In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 36-44. In some embodiments, the HVR2 region comprises residues corresponding to residues 215, 217, 219, 221, 223, 224, 229, 231, 233, 235, 237, 259, 261, 266, and 268 of any one of SEQ ID NOs: 36-44. In some embodiments, the HVR2 region comprises Y, R, K, or D at a residue corresponding to residue 257 of any one of SEQ ID NOs: 36-44. In some embodiments, the HVR2 region comprises a residue corresponding to residue 236 of SEQ ID NO: 39. In some embodiments, the HVR2 region comprises a residue corresponding to residue 239 of SEQ ID NO: 37. In some embodiments, the HVR2 region comprises a residue corresponding to residue 241 of any one of SEQ ID NOs: 36-37. In some embodiments, the HVR2 region comprises a residue corresponding to residue 263 of SEQ ID NO: 36. In some embodiments, the HVR2 region comprises a residue corresponding to residue 264 of any one of SEQ ID NOs: 36-44. In some embodiments, the HVR2 region comprises residues 215-270 of any one of SEQ ID NOs: 36-44 with up to 1, 2, 3, 4, 5, 6, 7, 8, 9, 10, or 11 amino acid substitutions. In some embodiments, the HVR2 region comprises residues 215-270 of any one of SEQ ID NOs: 36-44.

In some such embodiments, the second subunit comprises an amino acid sequence having at least 80%, 85%, 90%, 91%, 92%, 93%, 94%, 95%, 96%, 97%, 98%, 99% or more sequence identity to residues 198-344 of any one of SEQ ID NOs: 36-44. In some embodiments, the second subunit comprises G, S, or A at a residue corresponding to residue 210 of any one of SEQ ID NOs: 36-44. In some embodiments, the second subunit comprises E, Q, or K at a residue corresponding to residue 271 of any one of SEQ ID NOs: 36-44. In some embodiments, the second subunit comprises a residue corresponding to residue 271 of any one of SEQ ID NOs: 36, 39, 40, 43, or 44. In some embodiments, the second subunit comprises a residue corresponding to residue 330 of any one of SEQ ID NOs: 36-38 or 40-44. In some embodiments, the second subunit comprises residues 198-344 of any one of SEQ ID NOs: 36-44 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of any one of SEQ ID NOs: 36-44.

In some such embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity any one of SEQ ID NOs: 36-44. In some embodiments, the engineered meganuclease comprises an amino acid sequence of any one of SEQ ID NOs: 36-44. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in any one of SEQ ID NOs: 60-68. In some embodiments, the engineered meganuclease is encoded by a nucleic acid sequence set forth in any one of SEQ ID NOs: 60-68.

In some embodiments, the recognition sequence comprises SEQ ID NO: 10.

In some such embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of any one of SEQ ID NOs: 45-52. In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 45-52. In some embodiments, the HVR1 region comprises residues corresponding to residues 24, 26, 28, 30, 32, 33, 38, 40, 42, 44, 46, 68, 70, 75, and 77 of any one of SEQ ID NOs: 45-52. In some embodiments, the HVR1 region comprises Y, R, K, or D at a residue corresponding to residue 66 of any one of SEQ ID NOs: 45-52. In some embodiments, the HVR1 region comprises residues 24-79 of any one of SEQ ID NOs: 45-52 with up to 1, 2, 3, 4, 5, 6, 7, 8, 9, 10, or 11 amino acid substitutions. In some embodiments, the HVR1 region comprises residues 24-79 of any one of SEQ ID NOs: 45-52.

In some such embodiments, the first subunit comprises an amino acid sequence having at least 80%, 85%, 90%, 91%, 92%, 93%, 94%, 95%, 96%, 97%, 98%, 99% or more sequence identity to residues 7-153 of any one of SEQ ID NOs: 45-52. In some embodiments, the first subunit comprises G, S, or A at a residue corresponding to residue 19 of any one of SEQ TD NOs: 45-52. In some embodiments, the first subunit comprises a residue corresponding to residue 19 of any one of SEQ ID NOs: 45-52. In some embodiments, the first subunit comprises E, Q, or K at a residue corresponding to residue 80 of any one of SEQ ID NOs: 45-52. In some embodiments, the first subunit comprises a residue corresponding to residue 80 of any one of SEQ ID NOs: 45-51. In some embodiments, the first subunit comprises residues 7-153 of any one of SEQ ID NOs: 45-52 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of any one of SEQ ID NOs: 45-52.

In some such embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of any one of SEQ ID NOs: 45-52. In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 45-52. In some embodiments, the HVR2 region comprises residues corresponding to residues 215, 217, 219, 221, 223, 224, 229, 231, 233, 235, 237, 259, 261, 266, and 268 of any one of SEQ ID NOs: 45-52. In some embodiments, the HVR2 region comprises Y, R, K, or D at a residue corresponding to residue 257 of any one of SEQ ID NOs: 45-52. In some embodiments, the HVR2 region comprises residues corresponding to residues 239, 241, and 264 of any one of SEQ ID NOs: 45-52. In some embodiments, the HVR2 region comprises a residue corresponding to residue 250 of SEQ ID NO: 45. In some embodiments, the HVR2 region comprises a residue corresponding to residue 263 or any one of SEQ ID NOs: 45 or 46. In some embodiments, the HVR2 region comprises residues 215-270 of any one of SEQ ID NOs: 45-52 with up to 1, 2, 3, 4, 5, 6, 7, 8, 9, 10, or 11 amino acid substitutions. In some embodiments, the HVR2 region comprises residues 215-270 of any one of SEQ ID NOs: 45-52.

In some such embodiments, the second subunit comprises an amino acid sequence having at least 80%, 85%, 90%, 91%, 92%, 93%, 94%, 95%, 96%, 97%, 98%, 99% or more sequence identity to residues 198-344 of any one of SEQ ID NOs: 45-52. In some embodiments, the second subunit comprises G, S, or A at a residue corresponding to residue 210 of any one of SEQ ID NOs: 45-52. In some embodiments, the second subunit comprises E, Q, or K at a residue corresponding to residue 271 of any one of SEQ ID NOs: 45-52. In some embodiments, the second subunit comprises a residue corresponding to residue 271 of SEQ ID NO: 52. In some embodiments, the second subunit comprises a residue corresponding to residue 330 of any one of SEQ ID NOs: 45-52. In some embodiments, the second subunit comprises residues 198-344 of any one of SEQ ID NOs: 45-52 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of any one of SEQ ID NOs: 45-52.

In some such embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity any one of SEQ ID NOs: 45-52. In some embodiments, the engineered meganuclease comprises an amino acid sequence of any one of SEQ ID NOs: 45-52. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in any one of SEQ ID NOs: 69-76. In some embodiments, the engineered meganuclease is encoded by a nucleic acid sequence set forth in any one of SEQ ID NOs: 69-76.

In some embodiments, the recognition sequence comprises SEQ ID NO: 12.

In some such embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of any one of SEQ ID NOs: 53-59. In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 53-59. In some embodiments, the HVR1 region comprises residues corresponding to residues 24, 26, 28, 30, 32, 33, 38, 40, 42, 44, 46, 68, 70, 75, and 77 of any one of SEQ ID NOs: 53-59. In some embodiments, the HVR1 region comprises Y, R, K, or D at a residue corresponding to residue 66 of any one of SEQ ID NOs: 53-59. In some embodiments, the HVR1 region comprises a residue corresponding to residue 64 of SEQ ID NO: 54. In some embodiments, the HVR1 region comprises residues 24-79 of any one of SEQ ID NOs: 53-59 with up to 1, 2, 3, 4, 5, 6, 7, 8, 9, 10, or 11 amino acid substitutions. In some embodiments, the HVR1 region comprises residues 24-79 of any one of SEQ ID NOs: 53-59.

In some such embodiments, the first subunit comprises an amino acid sequence having at least 80%, 85%, 90%, 91%, 92%, 93%, 94%, 95%, 96%, 97%, 98%, 99% or more sequence identity to residues 7-153 of any one of SEQ ID NOs: 53-59. In some embodiments, the first subunit comprises G, S, or A at a residue corresponding to residue 19 of any one of SEQ ID NOs: 53-59. In some embodiments, the first subunit comprises a residue corresponding to residue 19 of any one of SEQ ID NOs: 53-59. In some embodiments, the first subunit comprises E, Q, or K at a residue corresponding to residue 80 of any one of SEQ ID NOs: 53-59. In some embodiments, the first subunit comprises a residue corresponding to residue 80 of any one of SEQ ID NOs: 53-55, 57, or 58. In some embodiments, the first subunit comprises residues 7-153 of any one of SEQ ID NOs: 53-59 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of any one of SEQ ID NOs: 53-59.

In some such embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of any one of SEQ ID NOs: 53-59. In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 53-59. In some embodiments, the HVR2 region comprises residues corresponding to residues 215, 217, 219, 221, 223, 224, 229, 231, 233, 235, 237, 259, 261, 266, and 268 of any one of SEQ ID NOs: 53-59. In some embodiments, the HVR2 region comprises Y, R, K, or D at a residue corresponding to residue 257 of any one of SEQ ID NOs: 53-59. In some embodiments, the HVR2 region comprises a residue corresponding to residue 239 of SEQ ID NO: 53 or SEQ ID NO: 55. In some embodiments, the HVR2 region comprises a residue corresponding to residue 241 of any one of SEQ ID NOs: 53-55. In some embodiments, the HVR2 region comprises a residue corresponding to residue 255 of SEQ ID NO: 55. In some embodiments, the HVR2 region comprises a residue corresponding to residue 263 of any one of SEQ ID NOs: 56-59. In some embodiments, the HVR2 region comprises a residue corresponding to residue 264 of any one of SEQ ID NOs: 53-59. In some embodiments, the HVR2 region comprises residues 215-270 of any one of SEQ ID NOs: 53-59 with up to 1, 2, 3, 4, 5, 6, 7, 8, 9, 10, or 11 amino acid substitutions. In some embodiments, the HVR2 region comprises residues 215-270 of any one of SEQ ID NOs: 53-59.

In some such embodiments, the second subunit comprises an amino acid sequence having at least 80%, 85%, 90%, 91%, 92%, 93%, 94%, 95%, 96%, 97%, 98%, 99% or more sequence identity to residues 198-344 of any one of SEQ ID NOs: 53-59. In some embodiments, the second subunit comprises G, S, or A at a residue corresponding to residue 210 of any one of SEQ ID NOs: 53-59. In some embodiments, the second subunit comprises E, Q, or K at a residue corresponding to residue 271 of any one of SEQ ID NOs: 53-59. In some embodiments, the second subunit comprises a residue corresponding to residue 271 of any one of SEQ ID NOs: 53 or 55-59. In some embodiments, the second subunit comprises a residue corresponding to residue 330 of any one of SEQ ID NOs: 54-59. In some embodiments, the second subunit comprises residues 198-344 of any one of SEQ ID NOs: 53-59 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of any one of SEQ ID NOs: 53-59.

In some such embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity any one of SEQ ID NOs: 53-59. In some embodiments, the engineered meganuclease comprises the amino acid sequence of any one of SEQ ID NOs: 53-59. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in any one of SEQ ID NOs: 77-83. In some embodiments, the engineered meganuclease is encoded by a nucleic sequence set forth in any one of SEQ ID NOs: 77-83.

In each of the embodiments above, the engineered meganuclease can comprise a nuclear localization signal. In some embodiments, the nuclear localization signal is at the N-terminus of the engineered meganuclease. In some embodiments, the nuclear localization signal comprises an amino acid sequence having at least 80% or at least 90% sequence identity to SEQ ID NO: 3. In some embodiments, the nuclear localization signal comprises SEQ ID NO: 3.

In another aspect, the invention provides a polynucleotide comprising a nucleic acid sequence encoding an engineered meganuclease described herein. In some embodiments, the polynucleotide is an mRNA.

In another aspect, the invention provides a recombinant DNA construct comprising a polynucleotide comprising a nucleic acid sequence encoding an engineered meganuclease described herein.

In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant AAV. In some embodiments, the recombinant virus is a recombinant AAV. In some embodiments, the recombinant AAV has an rh.74 capsid. In some embodiments, the recombinant AAV has an AAV9 capsid. In some embodiments, the rh.74 capsid comprises an amino acid sequence having at least 80%, 85%, 90%, 91%, 92%, 93%, 94%, 95%, 96%, 97%, 98%, 99% or more identity to SEQ ID NO: 182. In some embodiments, the rh.74 capsid comprises an amino acid sequence of SEQ ID NO: 182. In some embodiments, the AAV9 capsid comprises an amino acid sequence having at least 80%, 85%, 90%, 91%, 92%, 93%, 94%, 95%, 96%, 97%, 98%, 99% or more identity to SEQ ID NO: 183. In some embodiments, the AAV9 capsid comprises an amino acid sequence of SEQ ID NO: 183. In some embodiments, the recombinant AAV has an AAV8 capsid.

In some embodiments, the nucleic acid sequence comprises a promoter operably linked to the nucleic acid sequence encoding an engineered meganuclease described herein. In some embodiments, the promoter is a muscle-specific promoter. In some embodiments, the muscle-specific promoter comprises an MCK promoter, a C5-12 promoter, a spc 5-12 promoter, a MHCK7 promoter, a CK8 promoter, a SK-CRM4 promoter, a SP-301 promoter, a SP-817 promoter, or a SP-905 promoter. In some embodiments, the promoter is capable of expressing an engineered meganuclease described herein in a muscle precursor cell (e.g., a satellite cell or stem cell).

In another aspect, the invention provides a recombinant virus comprising a polynucleotide comprising a nucleic acid sequence encoding an engineered meganuclease described herein.

In some embodiments, the recombinant virus is a recombinant adenovirus, a recombinant lentivirus, a recombinant retrovirus, or a recombinant AAV. In some embodiments, the recombinant virus is a recombinant AAV. In some embodiments, the recombinant AAV has an rh.74 capsid. In some embodiments, the rh.74 capsid comprises an amino acid sequence having at least 80%, 85%, 90%, 91%, 92%, 93%, 94%, 95%, 96%, 97%, 98%, 99% or more identity to SEQ ID NO: 182. In some embodiments, the rh.74 capsid comprises an amino acid sequence of SEQ ID NO: 182. In some embodiments, the recombinant AAV has an AAV9 capsid. In some embodiments, the AAV9 capsid comprises an amino acid sequence having at least 80%, 85%, 90%, 91%, 92%, 93%, 94%, 95%, 96%, 97%, 98%, 99% or more identity to SEQ ID NO: 183. In some embodiments, the AAV9 capsid comprises an amino acid sequence of SEQ ID NO: 183. In some embodiments, the recombinant AAV has an AAV8 capsid.

In some embodiments, the polynucleotide comprises a promoter operably linked to the nucleic acid sequence encoding an engineered meganuclease described herein. In some embodiments, the promoter is a muscle-specific promoter. In some embodiments, the muscle-specific promoter comprises an MCK promoter, a C5-12 promoter, a spc 5-12 promoter, a MHCK7 promoter, a CK8 promoter, a SK-CRM4 promoter, a SP-301 promoter, a SP-817 promoter, or a SP-905 promoter. In some embodiments, the promoter is capable of expressing an engineered meganuclease described herein in a muscle precursor cell (e.g., a satellite cell or stem cell).

In another aspect, the invention provides a lipid nanoparticle composition comprising lipid nanoparticles comprising a polynucleotide, wherein the polynucleotide comprises a nucleic acid sequence encoding an engineered meganuclease described herein. In some embodiments, the polynucleotide is an mRNA.

In another aspect, the invention provides a pharmaceutical composition comprising a pharmaceutically acceptable carrier and an engineered meganuclease described herein.

In another aspect, the invention provides a pharmaceutical composition comprising a pharmaceutically acceptable carrier and a polynucleotide described herein.

In another aspect, the invention provides a pharmaceutical composition comprising a pharmaceutically acceptable carrier and a recombinant DNA construct described herein.

In another aspect, the invention provides a pharmaceutical composition comprising a pharmaceutically acceptable carrier and a recombinant virus described herein.

In another aspect, the invention provides a pharmaceutical composition comprising a pharmaceutically acceptable carrier and a lipid nanoparticle composition described herein.

In another aspect, the invention provides a polynucleotide comprising a first nucleic acid sequence encoding a first engineered meganuclease and a second nucleic acid sequence encoding a second engineered meganuclease, wherein the first engineered meganuclease is an engineered meganuclease described herein that binds and cleaves a recognition sequence comprising SEQ ID NO: 6, and wherein the second engineered meganuclease is an engineered meganuclease described herein that binds and cleaves a recognition sequence comprising SEQ ID NO: 10, or wherein the second engineered meganuclease is an engineered meganuclease described herein that binds and cleaves a recognition sequence comprising SEQ ID NO: 12.

In some embodiments, the first engineered meganuclease is an engineered meganuclease described herein that binds and cleaves a recognition sequence comprising SEQ ID NO: 6, and the second engineered meganuclease is an engineered meganuclease described herein that binds and cleaves a recognition sequence comprising SEQ ID NO: 10. In some embodiments, the first engineered meganuclease and the second engineered meganuclease are selected from the combinations of meganucleases (and variants thereof described herein) provided in Table 1.

TABLE 1

| | Recognition Sequence of SEQ ID NO: 6 | | Recognition Sequence of SEQ ID NO: 10 | |
|---|---|---|---|---|
| Combination | First Meganuclease | SEQ ID NO: | Second Meganuclease | SEQ ID NO: |
| 1 | DMD 19-20x.13 | 36 | DMD 35-36x.63 | 45 |
| 2 | DMD 19-20x.87 | 37 | DMD 35-36x.63 | 45 |
| 3 | DMD 19-20L.249 | 38 | DMD 35-36x.63 | 45 |
| 4 | DMD 19-20L.302 | 39 | DMD 35-36x.63 | 45 |
| 5 | DMD 19-20L.329 | 40 | DMD 35-36x.63 | 45 |
| 6 | DMD 19-20L.374 | 41 | DMD 35-36x.63 | 45 |
| 7 | DMD 19-20L.375 | 42 | DMD 35-36x.63 | 45 |
| 8 | DMD 19-20L.431 | 43 | DMD 35-36x.63 | 45 |
| 9 | DMD 19-20L.458 | 44 | DMD 35-36x.63 | 45 |
| 10 | DMD 19-20x.13 | 36 | DMD 35-36x.81 | 46 |
| 11 | DMD 19-20x.87 | 37 | DMD 35-36x.81 | 46 |
| 12 | DMD 19-20L.249 | 38 | DMD 35-36x.81 | 46 |
| 13 | DMD 19-20L.302 | 39 | DMD 35-36x.81 | 46 |
| 14 | DMD 19-20L.329 | 40 | DMD 35-36x.81 | 46 |
| 15 | DMD 19-20L.374 | 41 | DMD 35-36x.81 | 46 |
| 16 | DMD 19-20L.375 | 42 | DMD 35-36x.81 | 46 |
| 17 | DMD 19-20L.431 | 43 | DMD 35-36x.81 | 46 |
| 18 | DMD 19-20L.458 | 44 | DMD 35-36x.81 | 46 |
| 19 | DMD 19-20x.13 | 36 | DMD 35-36L.195 | 47 |
| 20 | DMD 19-20x.87 | 37 | DMD 35-36L.195 | 47 |
| 21 | DMD 19-20L.249 | 38 | DMD 35-36L.195 | 47 |
| 22 | DMD 19-20L.302 | 39 | DMD 35-36L.195 | 47 |
| 23 | DMD 19-20L.329 | 40 | DMD 35-36L.195 | 47 |
| 24 | DMD 19-20L.374 | 41 | DMD 35-36L.195 | 47 |
| 25 | DMD 19-20L.375 | 42 | DMD 35-36L.195 | 47 |
| 26 | DMD 19-20L.431 | 43 | DMD 35-36L.195 | 47 |
| 27 | DMD 19-20L.458 | 44 | DMD 35-36L.195 | 47 |
| 28 | DMD 19-20x.13 | 36 | DMD 35-36L.282 | 48 |
| 29 | DMD 19-20x.87 | 37 | DMD 35-36L.282 | 48 |
| 30 | DMD 19-20L.249 | 38 | DMD 35-36L.282 | 48 |
| 31 | DMD 19-20L.302 | 39 | DMD 35-36L.282 | 48 |
| 32 | DMD 19-20L.329 | 40 | DMD 35-36L.282 | 48 |
| 33 | DMD 19-20L.374 | 41 | DMD 35-36L.282 | 48 |
| 34 | DMD 19-20L.375 | 42 | DMD 35-36L.282 | 48 |
| 35 | DMD 19-20L.431 | 43 | DMD 35-36L.282 | 48 |
| 36 | DMD 19-20L.458 | 44 | DMD 35-36L.282 | 48 |
| 37 | DMD 19-20x.13 | 36 | DMD 35-36L.349 | 49 |
| 38 | DMD 19-20x.87 | 37 | DMD 35-36L.349 | 49 |
| 39 | DMD 19-20L.249 | 38 | DMD 35-36L.349 | 49 |
| 40 | DMD 19-20L.302 | 39 | DMD 35-36L.349 | 49 |
| 41 | DMD 19-20L.329 | 40 | DMD 35-36L.349 | 49 |
| 42 | DMD 19-20L.374 | 41 | DMD 35-36L.349 | 49 |
| 43 | DMD 19-20L.375 | 42 | DMD 35-36L.349 | 49 |
| 44 | DMD 19-20L.431 | 43 | DMD 35-36L.349 | 49 |
| 45 | DMD 19-20L.458 | 44 | DMD 35-36L.349 | 49 |
| 46 | DMD 19-20x.13 | 36 | DMD 35-36L.376 | 50 |
| 47 | DMD 19-20x.87 | 37 | DMD 35-36L.376 | 50 |
| 48 | DMD 19-20L.249 | 38 | DMD 35-36L.376 | 50 |
| 49 | DMD 19-20L.302 | 39 | DMD 35-36L.376 | 50 |
| 50 | DMD 19-20L.329 | 40 | DMD 35-36L.376 | 50 |
| 51 | DMD 19-20L.374 | 41 | DMD 35-36L.376 | 50 |
| 52 | DMD 19-20L.375 | 42 | DMD 35-36L.376 | 50 |
| 53 | DMD 19-20L.431 | 43 | DMD 35-36L.376 | 50 |
| 54 | DMD 19-20L.458 | 44 | DMD 35-36L.376 | 50 |
| 55 | DMD 19-20x.13 | 36 | DMD 35-36L.457 | 51 |
| 56 | DMD 19-20x.87 | 37 | DMD 35-36L.457 | 51 |
| 57 | DMD 19-20L.249 | 38 | DMD 35-36L.457 | 51 |
| 58 | DMD 19-20L.302 | 39 | DMD 35-36L.457 | 51 |
| 59 | DMD 19-20L.329 | 40 | DMD 35-36L.457 | 51 |
| 60 | DMD 19-20L.374 | 41 | DMD 35-36L.457 | 51 |
| 61 | DMD 19-20L.375 | 42 | DMD 35-36L.457 | 51 |

TABLE 1-continued

| | Recognition Sequence of SEQ ID NO: 6 | | Recognition Sequence of SEQ ID NO: 10 | |
|---|---|---|---|---|
| Combination | First Meganuclease | SEQ ID NO: | Second Meganuclease | SEQ ID NO: |
| 62 | DMD 19-20L.431 | 43 | DMD 35-36L.457 | 51 |
| 63 | DMD 19-20L.458 | 44 | DMD 35-36L.457 | 51 |
| 64 | DMD 19-20x.13 | 36 | DMD 35-36L.469 | 52 |
| 65 | DMD 19-20x.87 | 37 | DMD 35-36L.469 | 52 |
| 66 | DMD 19-20L.249 | 38 | DMD 35-36L.469 | 52 |
| 67 | DMD 19-20L.302 | 39 | DMD 35-36L.469 | 52 |
| 68 | DMD 19-20L.329 | 40 | DMD 35-36L.469 | 52 |
| 69 | DMD 19-20L.374 | 41 | DMD 35-36L.469 | 52 |
| 70 | DMD 19-20L.375 | 42 | DMD 35-36L.469 | 52 |
| 71 | DMD 19-20L.431 | 43 | DMD 35-36L.469 | 52 |
| 72 | DMD 19-20L.458 | 44 | DMD 35-36L.469 | 52 |

In some embodiments, the first engineered meganuclease is DMD 19-20x.13 (SEQ ID NO: 36), or a variant thereof described herein, and the second engineered meganuclease is DMD 35-36x.63 (SEQ ID NO: 45), or a variant thereof described herein. In some embodiments, the first engineered meganuclease is DMD 19-20x.87 (SEQ ID NO: 37), or a variant thereof described herein, and the second engineered meganuclease is DMD 35-36x.81 (SEQ ID NO: 46), or a variant thereof described herein. In some embodiments, the first engineered meganuclease is DMD 19-20x.13 (SEQ ID NO: 36), or a variant thereof described herein, and the second engineered meganuclease is DMD 35-36x.81 (SEQ ID NO: 46), or a variant thereof described herein. In some embodiments, the first engineered meganuclease is DMD 19-20x.87 (SEQ ID NO: 37), or a variant thereof described herein, and the second engineered meganuclease is DMD 35-36x.63 (SEQ ID NO: 45), or a variant thereof described herein. In some embodiments, the first engineered meganuclease is DMD 19-20L.249 (SEQ ID NO: 38), or a variant thereof described herein, and the second engineered meganuclease is DMD 35-36L.195 (SEQ ID NO: 47), or a variant thereof described herein. In some embodiments, the first engineered meganuclease is DMD 19-20L.302 (SEQ ID NO: 39), or a variant thereof described herein, and the second engineered meganuclease is DMD 35-36L.282 (SEQ ID NO: 48), or a variant thereof described herein. In some embodiments, the first engineered meganuclease is DMD 19-20L.329 (SEQ ID NO: 40), or a variant thereof described herein, and the second engineered meganuclease is DMD 35-36L.282 (SEQ ID NO: 48), or a variant thereof described herein. In some embodiments, the first engineered meganuclease is DMD 19-20L.302 (SEQ ID NO: 39), or a variant thereof described herein, and the second engineered meganuclease is DMD 35-36L.349 (SEQ ID NO: 49), or a variant thereof described herein. In some embodiments, the first engineered meganuclease is DMD 19-20L.329 (SEQ ID NO: 40), or a variant thereof described herein, and the second engineered meganuclease is DMD 35-36L.349 (SEQ ID NO: 49), or a variant thereof described herein.

In certain embodiments, the first engineered meganuclease is an engineered meganuclease described herein that binds and cleaves a recognition sequence comprising SEQ ID NO: 6, and the second engineered meganuclease is an engineered meganuclease described herein that binds and cleaves a recognition sequence comprising SEQ ID NO: 12. In some embodiments, the first engineered meganuclease and the second engineered meganuclease are selected from the combinations of meganucleases (and variants thereof described herein) provided in Table 2.

TABLE 2

| | Recognition Sequence of SEQ ID NO: 6 | | Recognition Sequence of SEQ ID NO: 12 | |
|---|---|---|---|---|
| Combination | First Meganuclease | SEQ ID NO: | Second Meganuclease | SEQ ID NO: |
| 1 | DMD 19-20x.13 | 36 | DMD 37-38x.15 | 46 |
| 2 | DMD 19-20x.87 | 37 | DMD 37-38x.15 | 46 |
| 3 | DMD 19-20L.249 | 38 | DMD 37-38x.15 | 46 |
| 4 | DMD 19-20L.302 | 39 | DMD 37-38x.15 | 46 |
| 5 | DMD 19-20L.329 | 40 | DMD 37-38x.15 | 46 |
| 6 | DMD 19-20L.374 | 41 | DMD 37-38x.15 | 46 |
| 7 | DMD 19-20L.375 | 42 | DMD 37-38x.15 | 46 |
| 8 | DMD 19-20L.431 | 43 | DMD 37-38x.15 | 46 |
| 9 | DMD 19-20L.458 | 44 | DMD 37-38x.15 | 46 |
| 10 | DMD 19-20x.13 | 36 | DMD 37-38x.66 | 47 |
| 11 | DMD 19-20x.87 | 37 | DMD 37-38x.66 | 47 |
| 12 | DMD 19-20L.249 | 38 | DMD 37-38x.66 | 47 |
| 13 | DMD 19-20L.302 | 39 | DMD 37-38x.66 | 47 |
| 14 | DMD 19-20L.329 | 40 | DMD 37-38x.66 | 47 |
| 15 | DMD 19-20L.374 | 41 | DMD 37-38x.66 | 47 |
| 16 | DMD 19-20L.375 | 42 | DMD 37-38x.66 | 47 |
| 17 | DMD 19-20L.431 | 43 | DMD 37-38x.66 | 47 |
| 18 | DMD 19-20L.458 | 44 | DMD 37-38x.66 | 47 |
| 19 | DMD 19-20x.13 | 36 | DMD 37-38x.79 | 48 |
| 20 | DMD 19-20x.87 | 37 | DMD 37-38x.79 | 48 |
| 21 | DMD 19-20L.249 | 38 | DMD 37-38x.79 | 48 |
| 22 | DMD 19-20L.302 | 39 | DMD 37-38x.79 | 48 |

TABLE 2-continued

| | Recognition Sequence of SEQ ID NO: 6 | | Recognition Sequence of SEQ ID NO: 12 | |
|---|---|---|---|---|
| Combination | First Meganuclease | SEQ ID NO: | Second Meganuclease | SEQ ID NO: |
| 23 | DMD 19-20L.329 | 40 | DMD 37-38x.79 | 48 |
| 24 | DMD 19-20L.374 | 41 | DMD 37-38x.79 | 48 |
| 25 | DMD 19-20L.375 | 42 | DMD 37-38x.79 | 48 |
| 26 | DMD 19-20L.431 | 43 | DMD 37-38x.79 | 48 |
| 27 | DMD 19-20L.458 | 44 | DMD 37-38x.79 | 48 |
| 28 | DMD 19-20x.13 | 36 | DMD 37-38L.166 | 49 |
| 29 | DMD 19-20x.87 | 37 | DMD 37-38L.166 | 49 |
| 30 | DMD 19-20L.249 | 38 | DMD 37-38L.166 | 49 |
| 31 | DMD 19-20L.302 | 39 | DMD 37-38L.166 | 49 |
| 32 | DMD 19-20L.329 | 40 | DMD 37-38L.166 | 49 |
| 33 | DMD 19-20L.374 | 41 | DMD 37-38L.166 | 49 |
| 34 | DMD 19-20L.375 | 42 | DMD 37-38L.166 | 49 |
| 35 | DMD 19-20L.431 | 43 | DMD 37-38L.166 | 49 |
| 36 | DMD 19-20L.458 | 44 | DMD 37-38L.166 | 49 |
| 37 | DMD 19-20x.13 | 36 | DMD 37-38L.478 | 57 |
| 38 | DMD 19-20x.87 | 37 | DMD 37-38L.478 | 57 |
| 39 | DMD 19-20L.249 | 38 | DMD 37-38L.478 | 57 |
| 40 | DMD 19-20L.302 | 39 | DMD 37-38L.478 | 57 |
| 41 | DMD 19-20L.329 | 40 | DMD 37-38L.478 | 57 |
| 42 | DMD 19-20L.374 | 41 | DMD 37-38L.478 | 57 |
| 43 | DMD 19-20L.375 | 42 | DMD 37-38L.478 | 57 |
| 44 | DMD 19-20L.431 | 43 | DMD 37-38L.478 | 57 |
| 45 | DMD 19-20L.458 | 44 | DMD 37-38L.478 | 57 |
| 46 | DMD 19-20x.13 | 36 | DMD 37-38L.512 | 58 |
| 47 | DMD 19-20x.87 | 37 | DMD 37-38L.512 | 58 |
| 48 | DMD 19-20L.249 | 38 | DMD 37-38L.512 | 58 |
| 49 | DMD 19-20L.302 | 39 | DMD 37-38L.512 | 58 |
| 50 | DMD 19-20L.329 | 40 | DMD 37-38L.512 | 58 |
| 51 | DMD 19-20L.374 | 41 | DMD 37-38L.512 | 58 |
| 52 | DMD 19-20L.375 | 42 | DMD 37-38L.512 | 58 |
| 53 | DMD 19-20L.431 | 43 | DMD 37-38L.512 | 58 |
| 54 | DMD 19-20L.458 | 44 | DMD 37-38L.512 | 58 |
| 55 | DMD 19-20x.13 | 36 | DMD 37-38L.528 | 59 |
| 56 | DMD 19-20x.87 | 37 | DMD 37-38L.528 | 59 |
| 57 | DMD 19-20L.249 | 38 | DMD 37-38L.528 | 59 |
| 58 | DMD 19-20L.302 | 39 | DMD 37-38L.528 | 59 |
| 59 | DMD 19-20L.329 | 40 | DMD 37-38L.528 | 59 |
| 60 | DMD 19-20L.374 | 41 | DMD 37-38L.528 | 59 |
| 61 | DMD 19-20L.375 | 42 | DMD 37-38L.528 | 59 |
| 62 | DMD 19-20L.431 | 43 | DMD 37-38L.528 | 59 |
| 63 | DMD 19-20L.458 | 44 | DMD 37-38L.528 | 59 |

In some embodiments, the first engineered meganuclease is DMD 19-20x.13 (SEQ ID NO: 36), or a variant thereof described herein, and the second engineered meganuclease is DMD 37-38x.15 (SEQ ID NO: 53), or a variant thereof described herein. In some embodiments, the first engineered meganuclease is DMD 19-20x.87 (SEQ ID NO: 37), or a variant thereof described herein, and the second engineered meganuclease is DMD 37-38x.15 (SEQ ID NO: 53), or a variant thereof described herein. In some embodiments, the first engineered meganuclease is DMD 19-20x.13 (SEQ ID NO: 36), or a variant thereof described herein, and the second engineered meganuclease is DMD 37-38x.66 (SEQ ID NO: 54), or a variant thereof described herein. In some embodiments, the first engineered meganuclease is DMD 19-20x.87 (SEQ ID NO: 37), or a variant thereof described herein, and the second engineered meganuclease is DMD 37-38x.66 (SEQ ID NO: 54), or a variant thereof described herein. In some embodiments, the first engineered meganuclease is DMD 19-20x.13 (SEQ ID NO: 36), or a variant thereof described herein, and the second engineered meganuclease is DMD 37-38x.79 (SEQ ID NO: 55), or a variant thereof described herein. In some embodiments, the first engineered meganuclease is DMD 19-20x.87 (SEQ ID NO: 37), or a variant thereof described herein, and the second engineered meganuclease is DMD 37-38x.79 (SEQ ID NO: 55), or a variant thereof described herein. In some embodiments, the first engineered meganuclease is DMD 19-20L.249 (SEQ ID NO: 38), or a variant thereof described herein, and the second engineered meganuclease is DMD 37-38L.166 (SEQ ID NO: 56), or a variant thereof described herein.

In some embodiments, the polynucleotide is an mRNA. In some embodiments, the first nucleic acid sequence and the second nucleic acid sequence are separated by an IRES or 2A sequence. In certain embodiments, the 2A sequence is a T2A, P2A, E2A, or F2A sequence.

In another aspect, the invention provides a recombinant DNA construct comprising a polynucleotide described herein (i.e., that comprises a first nucleic acid sequence encoding a first engineered meganuclease and a second nucleic acid sequence encoding a second engineered meganuclease).

In some embodiments, the first nucleic acid sequence and the second nucleic acid sequence are separated by an IRES or 2A sequence. In certain embodiments, the 2A sequence is a T2A, P2A, E2A, or F2A sequence.

In some embodiments, the polynucleotide comprises a promoter operably linked to the first nucleic acid sequence and the second nucleic acid sequence. In some embodiments, the promoter is a muscle-specific promoter. In some embodiments, the muscle-specific promoter comprises an MCK promoter, a C5-12 promoter, a spc 5-12 promoter, a MHCK7 promoter, a CK8 promoter, a SK-CRM4 promoter, a SP-301 promoter, a SP-817 promoter, or a SP-905 promoter. In some embodiments, the promoter is capable of expressing a first and second engineered meganuclease described herein in a muscle precursor cell (e.g., a satellite cell or stem cell).

In some embodiments, the polynucleotide comprises a first promoter operably linked to the first nucleic acid sequence and a second promoter operably linked to the second nucleic acid sequence. In some embodiments, the first promoter and the second promoter are muscle-specific promoters. In some embodiments, the muscle-specific promoters comprise an MCK promoter, a C5-12 promoter, a spc 5-12 promoter, a MHCK7 promoter, a CK8 promoter, a SK-CRM4 promoter, a SP-301 promoter, a SP-817 promoter, a SP-905 promoter, or a combination thereof. In some embodiments, the promoters are capable of expressing a first and second engineered meganuclease described herein in a muscle precursor cell (e.g., a satellite cell or stem cell).

In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant AAV. In some embodiments, the recombinant virus is a recombinant AAV. In some embodiments, the recombinant AAV has an rh.74 capsid. In some embodiments, the recombinant AAV has an AAV9 capsid. In some embodiments, the rh.74 capsid comprises an amino acid sequence having at least 80%, 85%, 90%, 91%, 92%, 93%, 94%, 95%, 96%, 97%, 98%, 99% or more identity to SEQ ID NO: 182. In some embodiments, the rh.74 capsid comprises an amino acid sequence of SEQ ID NO: 182. In some embodiments, the AAV9 capsid comprises an amino acid sequence having at least 80%, 85%, 90%, 91%, 92%, 93%, 94%, 95%, 96%, 97%, 98%, 99% or more identity to SEQ ID NO: 183. In some embodiments, the AAV9 capsid comprises an amino acid sequence of SEQ ID NO: 183. In some embodiments, the recombinant AAV has an AAV8 capsid.

In another aspect, the invention provides a recombinant virus comprising a polynucleotide described herein (i.e., that comprises a first nucleic acid sequence encoding a first engineered meganuclease and a second nucleic acid sequence encoding a second engineered meganuclease).

In some embodiments, the polynucleotide comprises a promoter operably linked to the first nucleic acid sequence and the second nucleic acid sequence. In some embodiments, the first nucleic acid sequence and the second nucleic acid sequence are separated by an IRES or 2A sequence. In certain embodiments, the 2A sequence is a T2A, P2A, E2A, or F2A sequence.

In some embodiments, the promoter is a muscle-specific promoter. In some embodiments, the muscle-specific promoter comprises an MCK promoter, a C5-12 promoter, a spc 5-12 promoter, a MHCK7 promoter, a CK8 promoter, a SK-CRM4 promoter, a SP-301 promoter, a SP-817 promoter, or a SP-905 promoter. In some embodiments, the promoter is capable of expressing an engineered meganuclease described herein in a muscle precursor cell (e.g., a satellite cell or stem cell).

In some embodiments, the polynucleotide comprises a first promoter operably linked to the first nucleic acid sequence and a second promoter operably linked to the second nucleic acid sequence. In some embodiments, the first promoter and the second promoter are muscle-specific promoters. In some embodiments, the muscle-specific promoters comprise an MCK promoter, a C5-12 promoter, a spc 5-12 promoter, a MHCK7 promoter, a CK8 promoter, a SK-CRM4 promoter, a SP-301 promoter, a SP-817 promoter, a SP-905 promoter, or a combination thereof. In some embodiments, the promoters are capable of expressing an engineered meganuclease described herein in a muscle precursor cell (e.g., a satellite cell or stem cell). In some embodiments, the recombinant virus is a recombinant adenovirus, a recombinant lentivirus, a recombinant retrovirus, or a recombinant AAV. In some embodiments, the recombinant virus is a recombinant AAV. In some embodiments, the recombinant AAV has an rh.74 capsid. In some embodiments, the recombinant AAV has an AAV9 capsid. In some embodiments, the rh.74 capsid comprises an amino acid sequence having at least 80%, 85%, 90%, 91%, 92%, 93%, 94%, 95%, 96%, 97%, 98%, 99% or more identity to SEQ ID NO: 182. In some embodiments, the rh.74 capsid comprises an amino acid sequence of SEQ ID NO: 182. In some embodiments, the AAV9 capsid comprises an amino acid sequence having at least 80%, 85%, 90%, 91%, 92%, 93%, 94%, 95%, 96%, 97%, 98%, 99% or more identity to SEQ ID NO: 183. In some embodiments, the AAV9 capsid comprises an amino acid sequence of SEQ ID NO: 183. In some embodiments, the recombinant AAV has an AAV8 capsid.

In another aspect, the invention provides a lipid nanoparticle composition comprising lipid nanoparticles comprising a polynucleotide described herein (i.e., that comprises a first nucleic acid sequence encoding a first engineered meganuclease and a second nucleic acid sequence encoding a second engineered meganuclease).

In some embodiments, the polynucleotide is an mRNA described herein. In some embodiments, the polynucleotide is a recombinant DNA construct described herein.

In another aspect, the invention provides a pharmaceutical composition comprising a pharmaceutically acceptable carrier and a polynucleotide described herein (i.e., that comprises a first nucleic acid sequence encoding a first engineered meganuclease and a second nucleic acid sequence encoding a second engineered meganuclease).

In some embodiments, the polynucleotide comprises an mRNA described herein. In some embodiments, the polynucleotide comprises a recombinant DNA construct described herein. In some embodiments, the pharmaceutical composition comprises a recombinant virus described herein. In some embodiments, the pharmaceutical composition comprises a lipid nanoparticle composition described herein.

In another aspect, the invention provides a method for producing a genetically modified eukaryotic cell having a modified target sequence in a dystrophin gene of the genetically modified eukaryotic cell, the method comprising: introducing into a eukaryotic cell a polynucleotide comprising a nucleic acid sequence encoding an engineered meganuclease described herein, wherein the engineered meganuclease is expressed in the eukaryotic cell, and wherein the engineered meganuclease produces a cleavage site in the dystrophin gene at a recognition sequence comprising SEQ ID NO: 6. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the polynucleotide is introduced into the eukaryotic cell by a lipid nanoparticle, an mRNA, or a recombinant virus (e.g., a recombinant AAV).

In another aspect, the invention provides a method for producing a genetically modified eukaryotic cell having a modified target sequence in a dystrophin gene of the genetically modified eukaryotic cell, the method comprising: introducing into a eukaryotic cell an engineered meganuclease described herein, wherein the engineered meganuclease produces a cleavage site in the dystrophin gene at a recognition sequence comprising SEQ ID NO: 6. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell.

In another aspect, the invention provides a method for producing a genetically modified eukaryotic cell comprising an exogenous sequence of interest inserted into a dystrophin gene of the genetically modified eukaryotic cell, the method comprising introducing into a eukaryotic cell one or more polynucleotides comprising: a first nucleic acid sequence encoding an engineered meganuclease described herein, wherein the engineered meganuclease is expressed in the eukaryotic cell; and a second nucleic acid sequence comprising the sequence of interest, wherein the engineered meganuclease produces a cleavage site in the dystrophin gene at a recognition sequence comprising SEQ ID NO: 6, and wherein the sequence of interest is inserted into the dystrophin gene at the cleavage site. In some embodiments, the second nucleic acid sequence comprises nucleic acid sequences homologous to nucleic acid sequences flanking the cleavage site and the sequence of interest is inserted at the cleavage site by homologous recombination. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the one or more polynucleotides are introduced into the eukaryotic cell by lipid nanoparticles, mRNA, or recombinant viruses (e.g., recombinant AAVs).

In another aspect, the invention provides a method for producing a genetically modified eukaryotic cell comprising an exogenous sequence of interest inserted into a dystrophin gene of the genetically modified eukaryotic cell, the method comprising introducing into a eukaryotic cell an engineered meganuclease described herein, and a polynucleotide comprising the sequence of interest, wherein the engineered meganuclease produces a cleavage site in the dystrophin gene at a recognition sequence comprising SEQ ID NO: 6, and wherein the sequence of interest is inserted into the dystrophin gene at the cleavage site. In some embodiments, the polynucleotide comprises nucleic acid sequences homologous to nucleic acid sequences flanking the cleavage site and the sequence of interest is inserted at the cleavage site by homologous recombination. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the polynucleotide is introduced into the eukaryotic cell by a lipid nanoparticle, an mRNA, or a recombinant virus (e.g., a recombinant AAV).

In another aspect, the invention provides a method for producing a genetically modified eukaryotic cell having a modified target sequence in a dystrophin gene of the genetically modified eukaryotic cell, the method comprising: introducing into a eukaryotic cell a polynucleotide comprising a nucleic acid sequence encoding an engineered meganuclease described herein, wherein the engineered meganuclease is expressed in the eukaryotic cell, and wherein the engineered meganuclease produces a cleavage site in the dystrophin gene at a recognition sequence comprising SEQ ID NO: 10. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the polynucleotide is introduced into the eukaryotic cell by a lipid nanoparticle, an mRNA, or a recombinant virus (e.g., a recombinant AAV).

In another aspect, the invention provides a method for producing a genetically modified eukaryotic cell having a modified target sequence in a dystrophin gene of the genetically modified eukaryotic cell, the method comprising: introducing into a eukaryotic cell an engineered meganuclease described herein, wherein the engineered meganuclease produces a cleavage site in the dystrophin gene at a recognition sequence comprising SEQ ID NO: 10. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell.

In another aspect, the invention provides a method for producing a genetically modified eukaryotic cell comprising an exogenous sequence of interest inserted into a dystrophin gene of the genetically modified eukaryotic cell, the method comprising introducing into a eukaryotic cell one or more polynucleotides comprising: a first nucleic acid sequence encoding an engineered meganuclease described herein, wherein the engineered meganuclease is expressed in the eukaryotic cell; and a second nucleic acid sequence comprising the sequence of interest, wherein the engineered meganuclease produces a cleavage site in the dystrophin gene at a recognition sequence comprising SEQ TD NO: 10, and wherein the sequence of interest is inserted into the dystrophin gene at the cleavage site. In some embodiments, the second nucleic acid sequence comprises nucleic acid sequences homologous to nucleic acid sequences flanking the cleavage site and the sequence of interest is inserted at the cleavage site by homologous recombination. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the one or more polynucleotides are introduced into the eukaryotic cell by lipid nanoparticles, mRNA, or recombinant viruses (e.g., recombinant AAVs).

In another aspect, the invention provides a method for producing a genetically modified eukaryotic cell comprising an exogenous sequence of interest inserted into a dystrophin gene of the genetically modified eukaryotic cell, the method comprising introducing into a eukaryotic cell an engineered meganuclease described herein, and a polynucleotide comprising the sequence of interest, wherein the engineered meganuclease produces a cleavage site in the dystrophin gene at a recognition sequence comprising SEQ ID NO: 10, and wherein the sequence of interest is inserted into the dystrophin gene at the cleavage site. In some embodiments, the polynucleotide comprises nucleic acid sequences homologous to nucleic acid sequences flanking the cleavage site and the sequence of interest is inserted at the cleavage site by homologous recombination. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the polynucleotide is introduced into the eukaryotic cell by a lipid nanoparticle, an mRNA, or a recombinant virus (e.g., a recombinant AAV).

In another aspect, the invention provides a method for producing a genetically modified eukaryotic cell having a modified target sequence in a dystrophin gene of the genetically modified eukaryotic cell, the method comprising: introducing into a eukaryotic cell a polynucleotide comprising a nucleic acid sequence encoding an engineered meganuclease described herein, wherein the engineered meganuclease is expressed in the eukaryotic cell, and wherein the engineered meganuclease produces a cleavage site in the dystrophin gene at a recognition sequence comprising SEQ ID NO: 12. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the polynucleotide is introduced into the eukaryotic cell by a lipid nanoparticle, an mRNA, or a recombinant virus (e.g., a recombinant AAV).

In another aspect, the invention provides a method for producing a genetically modified eukaryotic cell having a modified target sequence in a dystrophin gene of the genetically modified eukaryotic cell, the method comprising: introducing into a eukaryotic cell an engineered meganuclease described herein, wherein the engineered meganuclease produces a cleavage site in the dystrophin gene at a recognition sequence comprising SEQ ID NO: 12. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell.

In another aspect, the invention provides a method for producing a genetically modified eukaryotic cell comprising an exogenous sequence of interest inserted into a dystrophin gene of the genetically modified eukaryotic cell, the method comprising introducing into a eukaryotic cell one or more polynucleotides comprising: a first nucleic acid sequence encoding an engineered meganuclease described herein, wherein the engineered meganuclease is expressed in the eukaryotic cell; and a second nucleic acid sequence comprising the sequence of interest, wherein the engineered meganuclease produces a cleavage site in the dystrophin gene at a recognition sequence comprising SEQ ID NO: 12, and wherein the sequence of interest is inserted into the dystrophin gene at the cleavage site. In some embodiments, the second nucleic acid sequence comprises nucleic acid sequences homologous to nucleic acid sequences flanking the cleavage site and the sequence of interest is inserted at the cleavage site by homologous recombination. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell or a cardiac muscle cell. In some embodiments, the mammalian cell is a human cell. In some embodiments, the one or more polynucleotides are introduced into the eukaryotic cell by lipid nanoparticles, mRNA, or recombinant viruses (e.g., recombinant AAVs).

In another aspect, the invention provides a method for producing a genetically modified eukaryotic cell comprising an exogenous sequence of interest inserted into a dystrophin gene of the genetically modified eukaryotic cell, the method comprising introducing into a eukaryotic cell an engineered meganuclease described herein, and a polynucleotide comprising the sequence of interest, wherein the engineered meganuclease produces a cleavage site in the dystrophin gene at a recognition sequence comprising SEQ ID NO: 12, and wherein the sequence of interest is inserted into the dystrophin gene at the cleavage site. In some embodiments, the polynucleotide comprises nucleic acid sequences homologous to nucleic acid sequences flanking the cleavage site and the sequence of interest is inserted at the cleavage site by homologous recombination. In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell, or a cardiac muscle cell. In some embodiments, the mammalian cell is a human cell. In some embodiments, the polynucleotide is introduced into the eukaryotic cell by a lipid nanoparticle, an mRNA, or a recombinant virus (e.g., a recombinant AAV).

In another aspect, the invention provides a method for producing a genetically modified eukaryotic cell comprising a modified dystrophin gene, the method comprising: introducing into a eukaryotic cell one or more polynucleotides comprising a first nucleic acid sequence encoding a first engineered nuclease and a second nucleic acid sequence encoding a second engineered nuclease, wherein the first engineered nuclease binds and cleaves a recognition sequence in the intron 5' upstream of exon 45, and wherein the second engineered nuclease binds and cleaves a recognition sequence in the intron 3' downstream of exon 55, wherein the first engineered nuclease and the second engineered nuclease are expressed in the eukaryotic cell, wherein the first engineered nuclease produces a first cleavage site in the dystrophin gene at its recognition sequence, wherein the second engineered nuclease produces a second cleavage site in the dystrophin gene at its recognition sequence, wherein the first cleavage site and the second cleavage site have complementary overhangs, wherein the intervening genomic DNA between the first cleavage site and the second cleavage site is excised from the dystrophin gene, and wherein the dystrophin gene is annealed to generate the modified dystrophin gene.

In some embodiments, the first engineered nuclease is an engineered meganuclease described herein that binds and cleaves a recognition sequence comprising SEQ ID NO: 6, and the second engineered nuclease is an engineered meganuclease described herein that binds and cleaves a recognition sequence comprising SEQ ID NO: 10. In some embodiments, the first engineered meganuclease and the second engineered meganuclease are selected from the combinations of meganucleases (and variants thereof described herein) provided in Table 1. In such embodiments, the first cleavage site and second cleavage site have complementary 3' overhangs. In some embodiments, the first engineered meganuclease is DMD 19-20x.13 (SEQ ID NO: 36), or a variant thereof described herein, and the second engineered meganuclease is DMD 35-36x.63 (SEQ ID NO: 45), or a variant thereof described herein. In some embodiments, the first engineered meganuclease is DMD 19-20x.87 (SEQ ID NO: 37), or a variant thereof described herein, and the second engineered meganuclease is DMD 35-36x.81 (SEQ ID NO: 46), or a variant thereof described herein. In some embodiments, the first engineered meganuclease is DMD 19-20x.13 (SEQ ID NO: 36), or a variant thereof described herein, and the second engineered meganuclease is DMD 35-36x.81 (SEQ ID NO: 46), or a variant thereof described herein. In some embodiments, the first engineered meganuclease is DMD 19-20x.87 (SEQ ID NO: 37), or a variant thereof described herein, and the second engineered meganuclease is DMD 35-36x.63 (SEQ ID NO: 45), or a variant thereof described herein. In some embodiments, the first engineered meganuclease is DMD 19-20L.249 (SEQ ID NO: 38), or a variant thereof described herein, and the second engineered meganuclease is DMD 35-36L.195 (SEQ ID NO: 47), or a variant thereof described herein. In some embodiments, the first engineered meganuclease is DMD 19-20L.302 (SEQ ID NO: 39), or a variant thereof described herein, and the second engineered meganuclease is DMD 35-36L.282 (SEQ ID NO: 48), or a variant thereof described herein. In some embodiments, the first engineered meganuclease is DMD 19-20L.329 (SEQ ID NO: 40), or a variant thereof described herein, and the second engineered meganuclease is DMD 35-36L.282 (SEQ ID NO: 48), or a variant thereof described herein. In some embodiments, the first engineered meganuclease is DMD 19-20L.302 (SEQ ID NO: 39), or a variant thereof described herein, and the second engineered meganuclease is DMD 35-36L.349 (SEQ ID NO: 49), or a variant thereof described herein. In some embodiments, the first engineered meganuclease is DMD 19-20L.329 (SEQ ID NO: 40), or a variant thereof described herein, and the second engineered meganuclease is DMD 35-36L.349 (SEQ ID NO: 49), or a variant thereof described herein.

In some embodiments, the first engineered nuclease is an engineered meganuclease described herein that binds and cleaves a recognition sequence comprising SEQ ID NO: 6, and the second engineered nuclease is an engineered meganuclease described herein that binds and cleaves a recognition sequence comprising SEQ ID NO: 12. In such embodiments, the first cleavage site and second cleavage site have complementary 3' overhangs. In some embodiments, the first engineered meganuclease and the second engineered meganuclease are selected from the combinations of meganucleases (and variants thereof described herein) provided in Table 2. In some embodiments, the first engineered meganuclease is DMD 19-20x.13 (SEQ ID NO: 36), or a variant thereof described herein, and the second engineered meganuclease is DMD 37-38x.15 (SEQ ID NO: 53), or a variant thereof described herein. In some embodiments, the first engineered meganuclease is DMD 19-20x.87 (SEQ ID NO: 37), or a variant thereof described herein, and the second engineered meganuclease is DMD 37-38x.15 (SEQ ID NO: 53), or a variant thereof described herein. In some embodiments, the first engineered meganuclease is DMD 19-20x.13 (SEQ ID NO: 36), or a variant thereof described herein, and the second engineered meganuclease is DMD 37-38x.66 (SEQ ID NO: 54), or a variant thereof described herein. In some embodiments, the first engineered meganuclease is DMD 19-20x.87 (SEQ ID NO: 37), or a variant thereof described herein, and the second engineered meganuclease is DMD 37-38x.66 (SEQ ID NO: 54), or a variant thereof described herein. In some embodiments, the first engineered meganuclease is DMD 19-20x.13 (SEQ ID NO: 36), or a variant thereof described herein, and the second engineered meganuclease is DMD 37-38x.79 (SEQ ID NO: 55), or a variant thereof described herein. In some embodiments, the first engineered meganuclease is DMD 19-20x.87 (SEQ ID NO: 37), or a variant thereof described herein, and the second engineered meganuclease is DMD 37-38x.79 (SEQ ID NO: 55), or a variant thereof described herein. In some embodiments, the first engineered meganuclease is DMD 19-20L.249 (SEQ ID NO: 38), or a variant thereof described herein, and the second engineered meganuclease is DMD 37-38L.166 (SEQ ID NO: 56), or a variant thereof described herein.

In some embodiments, the complementary overhangs (e.g., 3' overhangs) of the first cleavage site and the second cleavage site are perfectly ligated to one another.

In some embodiments, the dystrophin gene comprises a nucleic acid sequence set forth in SEQ ID NO: 32 or 34. In some embodiments, the dystrophin gene comprises a nucleic acid sequence set forth in SEQ ID NO: 32. In some embodiments, the dystrophin gene comprises a nucleic acid sequence set forth in SEQ ID NO: 34.

In some embodiments, a normal reading frame is restored in the modified dystrophin gene is restored as compared to a full-length wild-type dystrophin gene.

In some embodiments, the modified dystrophin gene encodes a modified dystrophin polypeptide lacking the amino acids encoded by exons 45-55 of a wild-type dystrophin gene. In some embodiments, the modified dystrophin polypeptide comprises an amino acid sequence set forth in SEQ ID NO: 5.

In some embodiments, the method comprises introducing into the eukaryotic cell a first polynucleotide comprising a first nucleic acid sequence encoding the first engineered meganuclease and a second polynucleotide comprising a second nucleic acid sequence encoding the second engineered meganuclease. In some embodiments, the first polynucleotide is a first mRNA. In some embodiments, the second polynucleotide is a second mRNA. In some embodiments, the first mRNA and/or the second mRNA is an mRNA described herein (i.e., encoding an engineered meganuclease described herein). In some embodiments, the first polynucleotide is a first recombinant DNA construct. In some embodiments, the second polynucleotide is a second recombinant DNA construct. In some embodiments, the first recombinant DNA construct and/or the second recombinant DNA construct is a recombinant DNA construct described herein (i.e., comprising a nucleic acid sequence encoding an engineered meganuclease described herein). In some embodiments, the first polynucleotide and the second polynucleotide are introduced into the eukaryotic cell by one or more lipid nanoparticles. In some embodiments, the first polynucleotide is introduced into the eukaryotic cell by a first lipid nanoparticle. In some embodiments, the second polynucleotide is introduced into the eukaryotic cell by a second lipid nanoparticle. In some embodiments, the first polynucleotide is introduced into the eukaryotic cell by a first recombinant virus. In some embodiments, the second polynucleotide is introduced into the eukaryotic cell by a second recombinant virus. In some embodiments, the first recombinant and/or the second recombinant virus are a recombinant virus described herein (i.e., comprising a polynucleotide comprising a nucleic acid sequence encoding an engineered meganuclease described herein).

In some embodiments, the method comprises introducing into the eukaryotic cell a polynucleotide comprising a first nucleic acid sequence encoding the first engineered meganuclease and a second nucleic acid sequence encoding the second engineered meganuclease. In some embodiments, the polynucleotide is an mRNA. In some embodiments, the mRNA is an mRNA described herein (i.e., comprising first and second nucleic acid sequences each encoding meganucleases described herein). In some embodiments, the polynucleotide is a recombinant DNA construct. In some embodiments, the recombinant DNA construct is a recombinant DNA construct described herein (i.e., comprising first and second nucleic acid sequences each encoding meganucleases described herein). In some embodiments, the polynucleotide is introduced into the eukaryotic cell by a lipid nanoparticle. In some embodiments, the polynucleotide is introduced into the eukaryotic cell by a recombinant virus. In some embodiments, the recombinant virus is a recombinant virus described herein (i.e., comprising a polynucleotide comprising first and second nucleic acid sequences each encoding meganucleases described herein).

In some embodiments, the eukaryotic cell is a mammalian cell. In some embodiments, the mammalian cell is a muscle cell. In some embodiments, the muscle cell is a muscle precursor cell (e.g., a satellite cell or stem cell), a skeletal muscle cell, or a cardiac muscle cell. In some embodiments, the mammalian cell is a human cell.

In another aspect, the invention provides a method for modifying a dystrophin gene in a target cell in a subject, wherein the dystrophin gene is characterized by a mutation that alters the reading frame of the dystrophin gene from wild-type, the method comprising: delivering to the target cell one or more polynucleotides comprising a first nucleic acid sequence encoding a first engineered nuclease and a second nucleic acid sequence encoding a second engineered nuclease, wherein the first engineered nuclease binds and cleaves a recognition sequence in the intron 5' upstream of exon 45, and wherein the second engineered nuclease binds and cleaves a recognition sequence in the intron 3' downstream of exon 55, wherein the first engineered nuclease and the second engineered nuclease are expressed in the target cell, wherein the first engineered nuclease produces a first cleavage site in the dystrophin gene at its recognition sequence, wherein the second engineered nuclease produces a second cleavage site in the dystrophin gene at its recognition sequence, wherein the first cleavage site and the second cleavage site have complementary overhangs, wherein the intervening genomic DNA between the first cleavage site and the second cleavage site is excised from the dystrophin gene, wherein the dystrophin gene is annealed, and wherein a normal reading frame of the dystrophin gene is restored as compared to a full-length wild-type dystrophin gene.

In some embodiments, the first engineered nuclease is an engineered meganuclease described herein that binds and cleaves a recognition sequence comprising SEQ ID NO: 6, and the second engineered nuclease is an engineered meganuclease described herein that binds and cleaves a recognition sequence comprising SEQ ID NO: 10. In some embodiments, the first engineered meganuclease and the second engineered meganuclease are selected from the combinations of meganucleases (and variants thereof described herein) provided in Table 1. In such embodiments, the first cleavage site and second cleavage site have complementary 3' overhangs. In some embodiments, the first engineered meganuclease is DMD 19-20x.13 (SEQ ID NO: 36), or a variant thereof described herein, and the second engineered meganuclease is DMD 35-36x.63 (SEQ ID NO: 45), or a variant thereof described herein. In some embodiments, the first engineered meganuclease is DMD 19-20x.87 (SEQ ID NO: 37), or a variant thereof described herein, and the second engineered meganuclease is DMD 35-36x.81 (SEQ ID NO: 46), or a variant thereof described herein. In some embodiments, the first engineered meganuclease is DMD 19-20x.13 (SEQ ID NO: 36), or a variant thereof described herein, and the second engineered meganuclease is DMD 35-36x.81 (SEQ ID NO: 46), or a variant thereof described herein. In some embodiments, the first engineered meganuclease is DMD 19-20x.87 (SEQ ID NO: 37), or a variant thereof described herein, and the second engineered meganuclease is DMD 35-36x.63 (SEQ ID NO: 45), or a variant thereof described herein. In some embodiments, the first engineered meganuclease is DMD 19-20L.249 (SEQ ID NO: 38), or a variant thereof described herein, and the second engineered meganuclease is DMD 35-36L.195 (SEQ ID NO: 47), or a variant thereof described herein. In some embodiments, the first engineered meganuclease is DMD 19-20L.302 (SEQ ID NO: 39), or a variant thereof described herein, and the second engineered meganuclease is DMD 35-36L.282 (SEQ ID NO: 48), or a variant thereof described herein. In some embodiments, the first engineered meganuclease is DMD 19-20L.329 (SEQ ID NO: 40), or a variant thereof described herein, and the second engineered meganuclease is DMD 35-36L.282 (SEQ ID NO: 48), or a variant thereof described herein. In some embodiments, the first engineered meganuclease is DMD 19-20L.302 (SEQ ID NO: 39), or a variant thereof described herein, and the second engineered meganuclease is DMD 35-36L.349 (SEQ ID NO: 49), or a variant thereof described herein. In some embodiments, the first engineered meganuclease is DMD 19-20L.329 (SEQ ID NO: 40), or a variant thereof described herein, and the second engineered meganuclease is DMD 35-36L.349 (SEQ ID NO: 49), or a variant thereof described herein.

In some embodiments, the first engineered nuclease is an engineered meganuclease described herein that binds and cleaves a recognition sequence comprising SEQ ID NO: 6, and the second engineered nuclease is an engineered meganuclease described herein that binds and cleaves a recognition sequence comprising SEQ ID NO: 12. In some embodiments, the first engineered meganuclease and the second engineered meganuclease are selected from the combinations of meganucleases (and variants thereof described herein) provided in Table 2. In such embodiments, the first cleavage site and second cleavage site have complementary 3' overhangs. In some embodiments, the first engineered meganuclease is DMD 19-20x.13 (SEQ ID NO: 36), or a variant thereof described herein, and the second engineered meganuclease is DMD 37-38x.15 (SEQ ID NO: 53), or a variant thereof described herein. In some embodiments, the first engineered meganuclease is DMD 19-20x.87 (SEQ ID NO: 37), or a variant thereof described herein, and the second engineered meganuclease is DMD 37-38x.15 (SEQ ID NO: 53), or a variant thereof described herein. In some embodiments, the first engineered meganuclease is DMD 19-20x.13 (SEQ ID NO: 36), or a variant thereof described herein, and the second engineered meganuclease is DMD 37-38x.66 (SEQ ID NO: 54), or a variant thereof described herein. In some embodiments, the first engineered meganuclease is DMD 19-20x.87 (SEQ ID NO: 37), or a variant thereof described herein, and the second engineered meganuclease is DMD 37-38x.66 (SEQ ID NO: 54), or a variant thereof described herein. In some embodiments, the first engineered meganuclease is DMD 19-20x.13 (SEQ ID NO: 36), or a variant thereof described herein, and the second engineered meganuclease is DMD 37-38x.79 (SEQ ID NO: 55), or a variant thereof described herein. In some embodiments, the first engineered meganuclease is DMD 19-20x.87 (SEQ ID NO: 37), or a variant thereof described herein, and the second engineered meganuclease is DMD 37-38x.79 (SEQ ID NO: 55), or a variant thereof described herein. In some embodiments, the first engineered meganuclease is DMD 19-20L.249 (SEQ ID NO: 38), or a variant thereof described herein, and the second engineered meganuclease is DMD 37-38L.166 (SEQ ID NO: 56), or a variant thereof described herein.

In some embodiments, the complementary overhangs (e.g., 3' overhangs) of the first cleavage site and the second cleavage site are perfectly ligated to one another.

In some embodiments, the dystrophin gene comprises a nucleic acid sequence set forth in SEQ ID NO: 32 or 34. In some embodiments, the dystrophin gene comprises a nucleic acid sequence set forth in SEQ ID NO: 32. In some embodiments, the dystrophin gene comprises a nucleic acid sequence set forth in SEQ ID NO: 34.

In some embodiments, the dystrophin gene encodes a modified dystrophin polypeptide lacking the amino acids encoded by exons 45-55 of a wild-type dystrophin gene. In some embodiments, the modified dystrophin polypeptide comprises an amino acid sequence set forth in SEQ ID NO: 5. In some embodiments, the subject is converted to a Becker Muscular Dystrophy phenotype.

In some embodiments, the method comprises delivering to the target cell a first polynucleotide comprising a first nucleic acid encoding the first engineered meganuclease and a second polynucleotide comprising a second nucleic acid sequence encoding the second engineered meganuclease. In some embodiments, the first polynucleotide is a first mRNA. In some embodiments, the second polynucleotide is a second mRNA. In some embodiments, the first mRNA and/or the second mRNA is a described herein (i.e., encoding an engineered meganuclease described herein). In some embodiments, the first polynucleotide is a first recombinant DNA construct. In some embodiments, the second polynucleotide is a second recombinant DNA construct. In some embodiments, the first recombinant DNA construct and/or the second recombinant DNA construct is a recombinant DNA construct described herein (i.e., comprising a nucleic acid sequence encoding an engineered meganuclease described herein). In some embodiments, the first polynucleotide and the second polynucleotide are delivered to the target cells by one or more lipid nanoparticles. In some embodiments, the first polynucleotide is delivered to the target cell by a first lipid nanoparticle. In some embodiments, the second polynucleotide is delivered to the target cell by a second lipid nanoparticle. In some embodiments, the first polynucleotide is delivered to the target cell by a first recombinant virus. In some embodiments, the second polynucleotide is delivered to the target cell by a second recombinant virus. In some embodiments, the first recombinant and/or the second recombinant virus are a recombinant virus described herein (i.e., comprising a polynucleotide comprising a nucleic acid sequence encoding an engineered meganuclease described herein).

In some embodiments, the method comprises delivering to the target cell a polynucleotide comprising a first nucleic acid encoding the first engineered meganuclease and a second nucleic acid sequence encoding the second engineered meganuclease. In some embodiments, the polynucleotide is an mRNA. In some embodiments, the mRNA is an mRNA described herein (i.e., comprising first and second nucleic acid sequences each encoding meganucleases described herein). In some embodiments, the polynucleotide is a recombinant DNA construct. In some embodiments, the recombinant DNA construct is a recombinant DNA construct described herein (i.e., comprising first and second nucleic acid sequences each encoding meganucleases described herein). In some embodiments, the polynucleotide is delivered to the target cell by a lipid nanoparticle. In some embodiments, the polynucleotide is delivered to the target cell by a recombinant virus. In some embodiments, the recombinant virus is a recombinant virus described herein (i.e., comprising a polynucleotide comprising first and second nucleic acid sequences each encoding meganucleases described herein).

In some embodiments, the subject is a mammal. In some embodiments, the target cell is a muscle cell. In some embodiments, the muscle cell is a muscle precursor cell (e.g., a satellite cell or stem cell), a skeletal muscle cell, or a cardiac muscle cell. In some embodiments, the subject is a human.

In another aspect, the invention provides a method for treating DMD in a subject in need thereof, wherein the DMD is characterized by a mutation in a dystrophin gene that alters the reading frame of the dystrophin gene relative to a full-length, wild-type dystrophin gene, the method comprising: administering to the subject an effective amount of one or more polynucleotides comprising a first nucleic acid sequence encoding a first engineered nuclease and a second nucleic acid sequence encoding a second engineered nuclease, wherein the first engineered nuclease binds and cleaves a recognition sequence in the intron 5' upstream of exon 45, and wherein the second engineered nuclease binds and cleaves a recognition sequence in the intron 3' downstream of exon 55, wherein the one or more polynucleotides are delivered to a target cell in the subject, wherein the first engineered nuclease and the second engineered nuclease are expressed in the target cell, wherein the first engineered nuclease produces a first cleavage site in the dystrophin gene at its recognition sequence, wherein the second engineered nuclease produces a second cleavage site in the dystrophin gene at its recognition sequence, wherein the first cleavage site and the second cleavage site have complementary overhangs, wherein the intervening genomic DNA between the first cleavage site and the second cleavage site is excised from the dystrophin gene, wherein the dystrophin gene is annealed, and wherein a normal reading frame of the dystrophin gene is restored as compared to a full-length wild-type dystrophin gene.

In some embodiments, the first engineered nuclease is an engineered meganuclease described herein that binds and cleaves a recognition sequence comprising SEQ ID NO: 6, and the second engineered nuclease is an engineered meganuclease described herein that binds and cleaves a recognition sequence comprising SEQ ID NO: 10. In some embodiments, the first engineered meganuclease and the second engineered meganuclease are selected from the combinations of meganucleases (and variants thereof described herein) provided in Table 1. In such embodiments, the first cleavage site and second cleavage site have complementary 3' overhangs. In some embodiments, the first engineered meganuclease is DMD 19-20x.13 (SEQ ID NO: 36), or a variant thereof described herein, and the second engineered meganuclease is DMD 35-36x.63 (SEQ ID NO: 45), or a variant thereof described herein. In some embodiments, the first engineered meganuclease is DMD 19-20x.87 (SEQ ID NO: 37), or a variant thereof described herein, and the second engineered meganuclease is DMD 35-36x.81 (SEQ ID NO: 46), or a variant thereof described herein. In some embodiments, the first engineered meganuclease is DMD 19-20x.13 (SEQ ID NO: 36), or a variant thereof described herein, and the second engineered meganuclease is DMD 35-36x.81 (SEQ ID NO: 46), or a variant thereof described herein. In some embodiments, the first engineered meganuclease is DMD 19-20x.87 (SEQ ID NO: 37), or a variant thereof described herein, and the second engineered meganuclease is DMD 35-36x.63 (SEQ ID NO: 45), or a variant thereof described herein. In some embodiments, the first engineered meganuclease is DMD 19-20L.249 (SEQ ID NO: 38), or a variant thereof described herein, and the second engineered meganuclease is DMD 35-36L.195 (SEQ ID NO: 47), or a variant thereof described herein. In some embodiments, the first engineered meganuclease is DMD 19-20L.302 (SEQ ID NO: 39), or a variant thereof described herein, and the second engineered meganuclease is DMD 35-36L.282 (SEQ ID NO: 48), or a variant thereof described herein. In some embodiments, the first engineered meganuclease is DMD 19-20L.329 (SEQ ID NO: 40), or a variant thereof described herein, and the second engineered meganuclease is DMD 35-36L.282 (SEQ ID NO: 48), or a variant thereof described herein. In some embodiments, the first engineered meganuclease is DMD 19-20L.302 (SEQ ID NO: 39), or a variant thereof described herein, and the second engineered meganuclease is DMD 35-36L.349 (SEQ ID NO: 49), or a variant thereof described herein. In some embodiments, the first engineered meganuclease is DMD 19-20L.329 (SEQ ID NO: 40), or a variant thereof described herein, and the second engineered meganuclease is DMD 35-36L.349 (SEQ ID NO: 49), or a variant thereof described herein.

In some embodiments, the first engineered nuclease is an engineered meganuclease described herein that binds and cleaves a recognition sequence comprising SEQ ID NO: 6, and the second engineered nuclease is an engineered meganuclease described herein that binds and cleaves a recognition sequence comprising SEQ ID NO: 12. In some embodiments, the first engineered meganuclease and the second engineered meganuclease arm selected from the combinations of meganucleases (and variants thereof described herein) provided in Table 2. In such embodiments, the first cleavage site and second cleavage site have complementary 3' overhangs. In some embodiments, the first engineered meganuclease is DMD 19-20x.13 (SEQ ID NO: 36), or a variant thereof described herein, and the second engineered meganuclease is DMD 37-38x.15 (SEQ ID NO: 53), or a variant thereof described herein. In some embodiments, the first engineered meganuclease is DMD 19-20x.87 (SEQ ID NO: 37), or a variant thereof described herein, and the second engineered meganuclease is DMD 37-38x.15 (SEQ ID NO: 53), or a variant thereof described herein. In some embodiments, the first engineered meganuclease is DMD 19-20x.13 (SEQ ID NO: 36), or a variant thereof described herein, and the second engineered meganuclease is DMD 37-38x.66 (SEQ ID NO: 54), or a variant thereof described herein. In some embodiments, the first engineered meganuclease is DMD 19-20x.87 (SEQ TD NO: 37), or a variant thereof described herein, and the second engineered meganuclease is DMD 37-38x.66 (SEQ ID NO: 54), or a variant thereof described herein. In some embodiments, the first engineered meganuclease is DMD 19-20x.13 (SEQ ID NO: 36), or a variant thereof described herein, and the second engineered meganuclease is DMD 37-38x.79 (SEQ ID NO: 55), or a variant thereof described herein. In some embodiments, the first engineered meganuclease is DMD 19-20x.87 (SEQ ID NO: 37), or a variant thereof described herein, and the second engineered meganuclease is DMD 37-38x.79 (SEQ ID NO: 55), or a variant thereof described herein. In some embodiments, the first engineered meganuclease is DMD 19-20L.249 (SEQ ID NO: 38), or a variant thereof described herein, and the second engineered meganuclease is DMD 37-38L.166 (SEQ ID NO: 56), or a variant thereof described herein.

In some embodiments, the complementary overhangs (e.g., 3' overhangs) of the first cleavage site and the second cleavage site are perfectly ligated to one another.

In some embodiments, the dystrophin gene comprises a nucleic acid sequence set forth in SEQ ID NO: 32 or 34. In some embodiments, the dystrophin gene comprises a nucleic acid sequence set forth in SEQ ID NO: 32. In some embodiments, the dystrophin gene comprises a nucleic acid sequence set forth in SEQ ID NO: 34.

In some embodiments, the dystrophin gene encodes a modified dystrophin polypeptide lacking the amino acids encoded by exons 45-55 of a wild-type dystrophin gene. In some embodiments, the modified dystrophin polypeptide comprises an amino acid sequence set forth in SEQ ID NO: 5. In some embodiments, the subject is converted to a Becker Muscular Dystrophy phenotype.

In some embodiments, the method comprises administering to the subject a first polynucleotide comprising a first nucleic acid encoding the first engineered meganuclease and a second polynucleotide comprising a second nucleic acid sequence encoding the second engineered meganuclease. In some embodiments, the first polynucleotide is a first mRNA. In some embodiments, the second polynucleotide is a second mRNA. In some embodiments, the first mRNA and/or the second mRNA is a mRNA described herein (i.e., encoding an engineered meganuclease described herein). In some embodiments, the first polynucleotide is a first recombinant DNA construct. In some embodiments, the second polynucleotide is a second recombinant DNA construct. In some embodiments, the first recombinant DNA construct and/or the second recombinant DNA construct is a recombinant DNA construct described herein (i.e., comprising a nucleic acid sequence encoding an engineered meganuclease described herein). In some embodiments, the first polynucleotide and the second polynucleotide are administered to the subject by a lipid nanoparticle. In some embodiments, the first polynucleotide is administered to the subject by a first lipid nanoparticle. In some embodiments, the second polynucleotide is administered to the subject by a second lipid nanoparticle. In some embodiments, the first polynucleotide is administered to the subject by a first recombinant virus. In some embodiments, the second polynucleotide is administered to the subject by a second recombinant virus. In some embodiments, the first recombinant and/or the second recombinant virus are a recombinant virus described herein (i.e., comprising a polynucleotide comprising a nucleic acid sequence encoding an engineered meganuclease described herein).

In some embodiments, the method comprises administering to the subject a polynucleotide comprising a first nucleic acid encoding the first engineered meganuclease and a second nucleic acid sequence encoding the second engineered meganuclease. In some embodiments, the polynucleotide is an mRNA. In some embodiments, the mRNA is an mRNA described herein (i.e., comprising first and second nucleic acid sequences each encoding meganucleases described herein). In some embodiments, the polynucleotide is a recombinant DNA construct. In some embodiments, the recombinant DNA construct is a recombinant DNA construct described herein (i.e., comprising first and second nucleic acid sequences each encoding meganucleases described herein). In some embodiments, the polynucleotide is administered to the subject by a lipid nanoparticle. In some embodiments, the polynucleotide is administered to the subject by a recombinant virus. In some embodiments, the recombinant virus is a recombinant virus described herein (i.e., comprising a polynucleotide comprising first and second nucleic acid sequences each encoding meganucleases described herein).

In some embodiments, the subject is a mammal. In some embodiments, the target cell is a muscle cell. In some embodiments, the muscle cell is a muscle precursor cell (e.g., a satellite cell or stem cell), a skeletal muscle cell, or a cardiac muscle cell. In some embodiments, the subject is a human.

In another aspect, the invention provides a polynucleotide comprising a nucleic acid sequence set forth in SEQ ID NO: 32 or SEQ ID NO: 34.

In some embodiments, the polynucleotide comprises a nucleic acid sequence set forth in SEQ ID NO: 32. In some embodiments, the polynucleotide is a dystrophin gene in the genome of a cell (e.g., a human muscle cell) that comprises a nucleic acid sequence set forth in SEQ ID NO: 32. In some embodiments, the polynucleotide is a precursor mRNA in a cell (e.g., a human muscle cell) that comprises a nucleic acid sequence set forth in SEQ ID NO: 32.

In some embodiments, the polynucleotide comprises a nucleic acid sequence set forth in SEQ ID NO: 34. In some embodiments, the polynucleotide is a dystrophin gene in the genome of a cell (e.g., a human muscle cell) that comprises a nucleic acid sequence set forth in SEQ ID NO: 34. In some embodiments, the polynucleotide is a precursor mRNA in a cell (e.g., a human muscle cell) that comprises a nucleic acid sequence set forth in SEQ ID NO: 34.

In another aspect, the invention provides a genetically modified eukaryotic cell comprising in its genome a modified dystrophin gene, wherein the modified dystrophin gene lacks exons 45-55, and wherein the modified dystrophin gene comprises a nucleic acid sequence set forth in SEQ ID NO: 32 or a nucleic acid sequence set forth in SEQ ID NO: 34 positioned within an intron between exon 44 and exon 56.

In some embodiments, the nucleic acid sequence comprises SEQ ID NO: 32. In some embodiments, the nucleic acid sequence comprises SEQ ID NO: 34.

In some embodiments, the genetically modified eukaryotic cell is a mammalian cell. In some embodiments, the genetically modified eukaryotic cell is a human cell. In some embodiments, the genetically modified eukaryotic cell is a muscle cell. In some embodiments, the muscle cell is a muscle precursor cell (e.g., a satellite cell or stem cell), a skeletal muscle cell, or a cardiac muscle cell.

In another aspect, the invention provides a polypeptide comprising an amino acid sequence having at least 80%, 85%, 90%, 91%, 92%, 93%, 94%, 95%, 96%, 97%, 98%, 99% or more sequence identity to SEQ ID NO: 5, wherein said polypeptide is a modified dystrophin protein lacking the amino acids encoded by exons 45-55 of the dystrophin gene, and wherein said polypeptide comprises the C-terminal domain of the dystrophin protein. In some embodiments, the polypeptide comprises an amino acid sequence set forth in SEQ TD NO: 5.

In another aspect, the invention provides engineered meganucleases described herein, or polynucleotides described herein encoding engineered meganucleases, or cells described herein expressing engineered meganucleases, for use as a medicament.

In some embodiments, the medicament is useful for producing a modified dystrophin gene in a subject. In some embodiments, the medicament is useful for the treatment of DMD.

In another aspect, the invention provides the use of engineered meganucleases described herein, or polynucleotides disclosed herein encoding engineered meganucleases, or cells described herein expressing engineered meganucleases, in the manufacture of a medicament for treating DMD, for increasing levels of a modified dystrophin protein (i.e., lacking the amino acids encoded by exons 45-55 of the dystrophin gene), or reducing the symptoms associated with DMD.

BRIEF DESCRIPTION OF THE FIGURES

FIG. 2 is a schematic showing exemplary recognition sequences of the disclosure, which include sense and antisense sequences for the DMD 19-20 (SEQ ID NOs: 6 and 7), DMD 29-30 (SEQ ID NOs: 8 and 9), DMD 35-36 (SEQ ID NOs: 10 and 11), and DMD 37-38 (SEQ ID NOs: 12 and 13) recognition sequences in the human dystrophin gene. Each DMD recognition sequence targeted by engineered meganucleases described herein comprises two recognition half-sites. Each recognition half-site comprises 9 base pairs, separated by a 4 basepair central sequence. For example, the DMD 19-20 recognition sequence has a 5' DMD19 half-site and a 3' DMD20 half-site with a four base pair center sequence GTAT.

FIGS. 4A-4C. FIG. 4A provides an alignment of the sequences of DMD 19-20 meganucleases. FIG. 4B provides an alignment of the sequences of DMD 35-36 engineered meganucleases. FIG. 4C provides an alignment of the sequences of DMD 37-38 engineered meganucleases. Asterisks indicate conserved residues amongst all aligned nucleases, and a space indicates that at least one amino acid differed amongst the meganucleases.

FIGS. 6A-6F. FIGS. 6A, 6B, and 6G provide the efficiency of engineered DMD 19-20 meganucleases for binding and cleaving the DMD 19-20 recognition sequence expressed in the CHO cell reporter assay. FIG. 6C provides the efficiency of engineered DMD 29-30 meganucleases for binding and cleaving the DMD 29-30 recognition sequence expressed in the CHO cell reporter assay. FIG. 6D and FIG. 6H provide the efficiency of engineered DMD 35-36 meganucleases for binding and cleaving the DMD 35-36 recognition sequence expressed in the CHO cell reporter assay. FIG. 6E, FIG. 6F, and FIG. 6I provide the efficiency of engineered DMD 37-38 meganucleases for binding and cleaving the DMD 37-38 recognition sequence expressed in the CHO cell reporter assay. The relative activity index represents % GFP positive cells for each cell line expressing the test meganuclease normalized to the cell line expressing the CHO-23/24 meganuclease accounting for the toxicity of the meganuclease.

FIG. 7A provides the percentage of editing with the DMD 19-20 meganucleases. FIG. 7B provides the percentage of editing with the DMD 35-36 meganucleases. FIG. 7C provides the percentage of editing with the DMD 37-38 meganucleases. FIG. 7D provides the percentage of editing with the DMD 29-30 meganucleases.

FIGS. 8A and 8B provide PCR product and sequencing data for the perfect ligation of the dystrophin gene following cleavage with a pair of engineered meganucleases designed to bind and cleave the DMD 19-20 and DMD 35-36 recognition sequences. FIG. 8A is a gel image of the PCR product using primers specific to amplify ligation of the complementary DMD 19-20 and DMD 35-36 recognition sequences. Lane 5 represents the combination of the DMD 19-20x.13 and DMD 35-36x.63 meganucleases. Lane 6 represents the combination of the DMD 19-20x.87 and DMD 35-36x.81 meganucleases. Lane 7 represents the combination of the DMD 19-20x.13 and DMD 35-36x.81 meganucleases. Lane 8 represents the combination of the DMD 19-20x.87 and DMD 35-36x.63 meganucleases. Lane M represents a mock control. FIG. 8B provides representative sequencing data for perfect ligation of the DMD 19-20 and DMD 35-36 meganuclease recognition sequences following cleavage and excision of the intervening genomic sequence. The sequence of the first row and third through seventh rows is SEQ ID NO: 194. The sequence of the second row is SEQ ID NO: 195.

FIG. 8A is a gel image of the PCR product using primers specific to amplify ligation of the complementary DMD 19-20 and DMD 37-38 recognition sequences. Lane 9 represents the combination of the DMD 19-20x.13 and DMD 37-38x.15 meganucleases. Lane 10 represents the combination of the DMD 19-20x.87 and DMD 37-38x.15 meganucleases. Lane 11 represents the combination of the DMD 19-20x.13 and DMD 37-38x.66 meganucleases. Lane 12 represents the combination of the DMD 19-20x.87 and DMD 37-38x.66 meganucleases. Lane 13 represents the combination of the DMD 19-20x.13 and DMD 37-38x.79 meganucleases. Lane 14 represents the combination of the DMD 19-20x.87 and DMD 37-38x.79 meganucleases. Lane M represents a mock control. FIG. 9B provides a representative sequencing data for perfect ligation of the DMD 19-20 and DMD 37-38 meganuclease recognition sequences following cleavage and excision of the intervening genomic sequence. The sequence of the first row and third through ninth rows is SEQ ID NO: 196. The sequence of the second row is SEQ ID NO: 197.

FIG. 12A provides exon deletion data with the combination of the DMD 19-20x.13 and DMD 35-36x.63 meganucleases, the DMD 19-20x.87 and DMD 35-36x.81 meganucleases, the DMD 19-20x.13 and DMD 35-36x.81 meganucleases, the DMD 19-20x.87 and DMD 35-36x.63 meganucleases, and a mock control. FIG. 12B provides exon deletion data with the combination of the DMD 19-20x.13 and DMD 37-38x.15 meganucleases, the DMD 19-20x.87 and DMD 37-38x.15 meganucleases, the DMD 19-20x.13 and DMD 37-38x.66 meganucleases, the DMD 19-20x.87 and DMD 37-38x.66 meganucleases, the DMD 19-20x.13 and DMD 37-38x.79 meganucleases, the DMD 19-20x.87 and DMD 37-38x.79 meganucleases, and a mock control. FIG. 12C provides exon deletion data for exon 45 alone with the combination of the DMD 19-20x.13 and DMD 29-30x.18 meganucleases, the DMD 19-20x.87 and DMD 29-30x.40 meganucleases, the DMD 19-20x.13 and DMD 29-30x.40 meganucleases, the DMD 19-20x.87 and DMD 29-30x.18 meganucleases, and a mock control.

FIG. 16A is a graph showing dystrophin protein expression following treatment with the combination of engineered meganucleases or the mock control. FIG. 16B provides a gel image of the shortened dystrophin protein band (i.e., lacking the amino acids encoded by exons 45-55) at the correct size. FIG. 16C provides the amount of dystrophin protein relative to a reference vinculin gene.

FIG. 24A provides a bar graph showing the percentage (%) of total ligation of genomic DNA adjacent to exons 45-55 following cleavage of the DMD 19-20 and DMD 37-38 recognition sequences by each of the pairs of indicated engineered DMD 19-20 and DMD 37-38 meganucleases. FIG. 24B provides a bar graph showing the percentage (%) dystrophin restoration for each of the pairs of indicated engineered DMD 19-20 and DMD 37-38 meganucleases compared to an equivalent load of murine quadricep muscle tissue lysate that was based on a standard curve generated from that tissue.

FIG. 25A shows the percent perfect ligation in quadricep tissue. FIG. 25B shows the percent perfect ligation in heart tissue. FIG. 25C shows the percent perfect ligation in diaphragm tissue. FIG. 25D shows the percent perfect ligation in soleus tissue. FIG. 25E shows the percent perfect ligation in liver tissue.

FIG. 26A shows the percent total ligation in quadricep tissue. FIG. 26B shows the percent total ligation in heart tissue. FIG. 26C shows the percent total ligation in diaphragm tissue. FIG. 25D shows the percent total ligation in soleus tissue. FIG. 26E shows the percent total ligation in liver tissue.

FIG. 27A shows the percent total ligation in quadricep tissue. FIG. 27B shows the percent total ligation in heart tissue. FIG. 27C shows the percent total ligation in diaphragm tissue. FIG. 27D shows the percent total ligation in tibialis anterior (TA) tissue. FIG. 27E shows the percent total ligation in liver tissue.

FIG. 28A represents modified shortened dystrophin levels detected at the indicated dosages in heart tissue; FIG. 28B represents modified shortened dystrophin levels detected at the indicated dosages in diaphragm tissue; FIG. 28C represents modified shortened dystrophin levels detected at the indicated dosages in quadricep tissue.

FIG. 30A represents modified shortened dystrophin levels detected at the indicated dosages in heart tissue; FIG. 309B represents modified shortened dystrophin levels detected at the indicated dosages in diaphragm tissue; and FIG. 30C represents modified shortened dystrophin levels detected at the indicated dosages in quadricep tissue.

FIG. 33A provides imaging of Pax7 expression in quadricep tissue from PBS-treated mice. The left panel is a control image that shows any background staining with primary and secondary antibodies that detect meganuclease expression. The middle panel shows cells that express Pax7 indicated by the white arrow heads; and the right panel shows both Pax7 (white arrow heads) and any background staining from antibodies that detect meganuclease expression. FIG. 33B provides imaging of meganuclease and Pax7 expression in quadricep tissue from meganuclease treated mice. The left panel provides meganuclease only expressing cells indicated by the white arrow heads with the full arrow indicating a cell that expresses meganuclease protein and Pax7; the middle panel shows cells that express Pax7 only indicated by the white arrowhead or Pax7 and meganuclease protein indicated by the full arrow. The right panel shows cells that express either meganuclease protein or Pax7 indicated by the arrow heads or a cell that expresses both meganuclease protein and Pax7 indicated by the full arrow.

FIG. 35A shows the BaseScope staining of muscle tissue from PBS treated mice for Pax7 transcript expression and any background staining for the probe used to detect modified human dystrophin transcript expression. FIG. 35B shows the BaseScope staining of muscle tissue from mice treated with the DMD 19-20L.329 and DMD 35-36L.349 pair of meganucleases for Pax7 transcript expression and modified human dystrophin transcript expression.

FIG. 38A provides imaging of Pax7 expression in quadricep tissue from PBS treated mice. The left panel is a control image that provides any background staining with primary and secondary antibodies that detect meganuclease expression; the star indicates non-specific background detection. The middle panel shows cells that express Pax7 indicated by the white arrowhead; and the right panel shows both Pax7 (white arrowhead) and any background staining from antibodies that detect meganuclease expression indicated by the star. FIG. 38B provides imaging of meganuclease and Pax7 expression in quadricep tissue from meganuclease treated mice at a dosage of $1 \times 10^{14}$ VG/kg; FIG. 38C provides imaging from meganuclease treated mice at a dosage of $3 \times 10^{13}$ VG/kg; and FIG. 38D provides imaging from meganuclease-treated mice at a dosage of $1 \times 10^{13}$ VG/kg. The left panel in FIGS. 38B-38D provides meganuclease-only expressing cells; the middle panel shows cells that express Pax7; and the right panel in FIGS. 38B-38D shows cells that express either meganuclease protein or Pax7 or cells that expresses both meganuclease protein and Pax7 indicated by the full arrow. Stars indicate non-specific background staining.

BRIEF DESCRIPTION OF THE SEQUENCES

Figure 1:
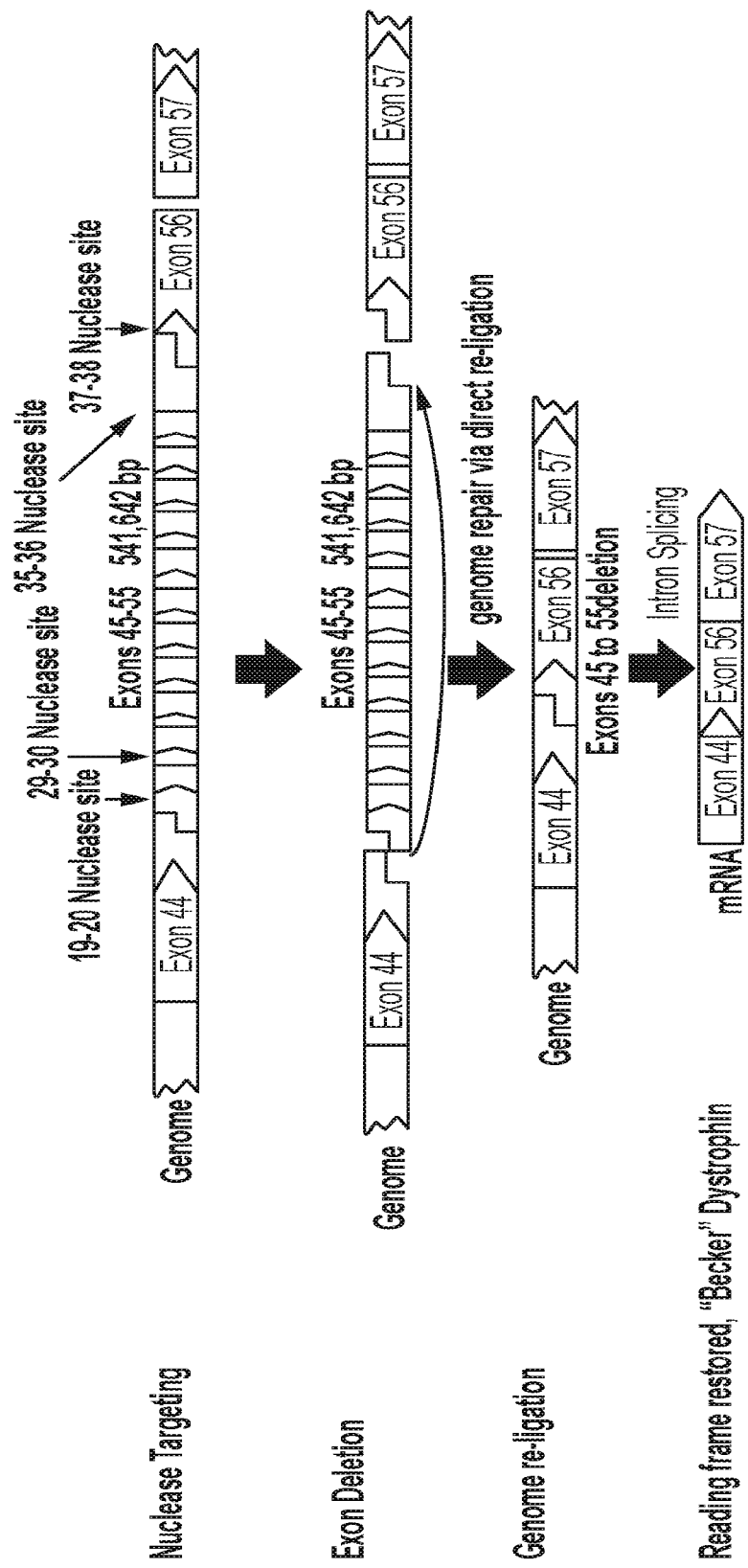
FIG. 1 is a schematic providing the approximate location of the DMD meganuclease recognition sequences and illustrating the dual meganuclease approach for excising multiple exons from the dystrophin gene. As shown, pairs of engineered meganucleases that bind and cleave either the DMD 19-20 recognition sequence and the DMD 35-36 recognition sequence, or the DMD 19-20 recognition sequence and the DMD 37-38 recognition sequence, result in removal of exons 45-55 from the dystrophin gene. These pairs of recognition sequences are located within introns, have identical four basepair center sequences, and produce cleavage sites having complementary overhangs. Therefore, following the removal of the exons, the gene is ligated at the cleavage sites, which will be within an intron located between exon 44 and exon 56. Following post-transcriptional splicing, this genetic modification results in a dystrophin mRNA having exon 44 in frame with exon 56, which restores the dystrophin gene reading frame and results in a Becker type of dystrophin expression. Also shown is the approximate location where a pair of engineered meganucleases bind and cleave the DMD 19-20 recognition sequence and the DMD 29-30 recognition sequence, which results in removal of exon 45 from the dystrophin gene.
Figure 3:
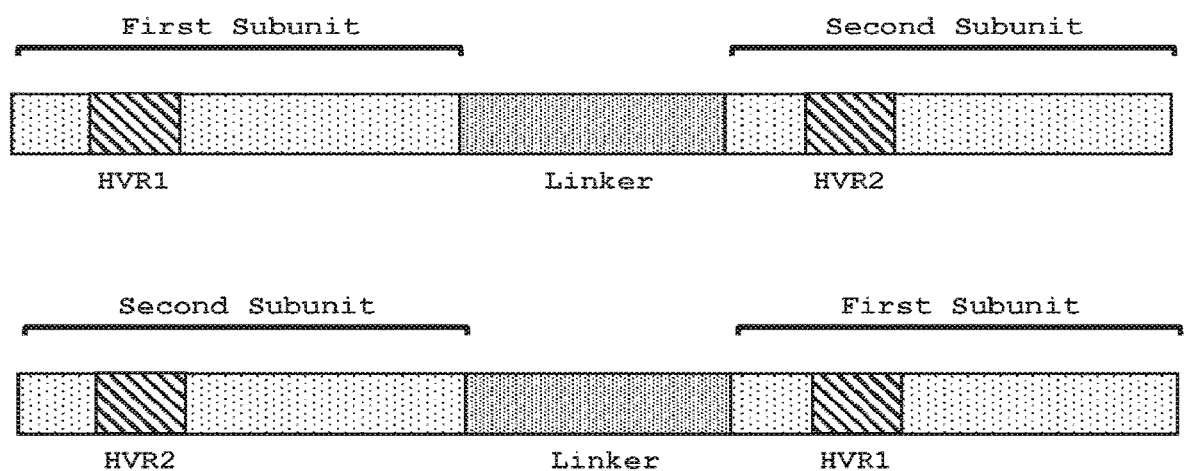
FIG. 3. The engineered meganucleases described herein comprise two subunits, wherein the first subunit comprising the HVR1 region binds to a first recognition half-site (e.g., DMD19) and the second subunit comprising the HVR2 region binds to a second recognition half-site (e.g., DMD20). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth amino acid sequence of the wild-type I-CreI meganuclease from *Chlamydomonas reinhardtii*.

SEQ ID NO: 2 sets forth the amino acid sequence of the LAGLIDADG motif.

SEQ ID NO: 3 sets forth the amino acid sequence of a nuclear localization signal.

SEQ ID NO: 4 sets forth the amino acid sequence of the wild-type dystrophin protein CCDS48091.1 (Gene ID 1756).

SEQ ID NO: 5 sets forth amino acid sequence of the wild-type dystrophin protein CCDS48091.1 (Gene ID 1756) lacking amino acids encoded by exons 45-55.

SEQ ID NO: 6 sets forth the nucleic acid sequence of the sense strand of the DMD 19-20 recognition sequence.

SEQ ID NO: 7 sets forth the nucleic acid sequence of the antisense strand of the DMD 19-20 recognition sequence.

SEQ ID NO: 8 sets forth the nucleic acid sequence of the sense strand of the DMD 29-30 recognition sequence.

SEQ ID NO: 9 sets forth the nucleic acid sequence of the antisense strand of the DMD 29-30 recognition sequence.

SEQ ID NO: 10 sets forth the nucleic acid sequence of the sense strand of the DMD 35-36 recognition sequence.

SEQ ID NO: 11 sets forth the nucleic acid sequence of the antisense strand of the DMD 35-36 recognition sequence.

SEQ ID NO: 12 sets forth the nucleic acid sequence of the sense strand of the DMD 37-38 recognition sequence.

SEQ ID NO: 13 sets forth the nucleic acid sequence of the antisense strand of the DMD 37-38 recognition sequence.

SEQ ID NO: 14 sets forth the nucleic acid sequence of the first half-site sense strand of the DMD 19-20 recognition sequence.

SEQ ID NO: 15 sets forth the nucleic acid sequence of the first half-site antisense strand of the DMD 19-20 recognition sequence.

SEQ ID NO: 16 sets forth the nucleic acid sequence of the first half-site sense strand of the DMD 29-30 recognition sequence.

SEQ ID NO: 17 sets forth the nucleic acid sequence of the first half-site antisense strand of the DMD 29-30 recognition sequence.

SEQ ID NO: 18 sets forth the nucleic acid sequence of the first half-site sense strand of the DMD 35-36 recognition sequence.

SEQ ID NO: 19 sets forth the nucleic acid sequence of the first half-site antisense strand of the DMD 35-36 recognition sequence.

SEQ ID NO: 20 sets forth the nucleic acid sequence of the first half-site sense strand of the DMD 37-38 recognition sequence.

SEQ ID NO: 21 sets forth the nucleic acid sequence of the first half-site antisense strand of the DMD 37-38 recognition sequence.

SEQ ID NO: 22 sets forth the nucleic acid sequence of the second half-site sense strand of the DMD 19-20 recognition sequence.

SEQ ID NO: 23 sets forth the nucleic acid sequence of the second half-site antisense strand of the DMD 19-20 recognition sequence.

SEQ ID NO: 24 sets forth the nucleic acid sequence of the second half-site sense strand of the DMD 29-30 recognition sequence.

SEQ ID NO: 25 sets forth the nucleic acid sequence of the second half-site antisense strand of the DMD 29-30 recognition sequence.

SEQ ID NO: 26 sets forth the nucleic acid sequence of the second half-site sense strand of the DMD 35-36 recognition sequence.

SEQ ID NO: 27 sets forth the nucleic acid sequence of the second half-site antisense strand of the DMD 35-36 recognition sequence.

SEQ ID NO: 28 sets forth the nucleic acid sequence of the second half-site sense strand of the DMD 37-38 recognition sequence.

SEQ ID NO: 29 sets forth the nucleic acid sequence of the second half-site antisense strand of the DMD 37-38 recognition sequence.

SEQ ID NO: 30 sets forth the nucleic acid sequence of the ligated hybrid DMD 19-20/29-30 sense strands.

SEQ ID NO: 31 sets forth the nucleic acid sequence of the ligated hybrid DMD 19-20/29-30 sense strands.

SEQ ID NO: 32 sets forth the nucleic acid sequence of the ligated hybrid DMD 19-20/35-36 sense strands.

SEQ ID NO: 33 sets forth the nucleic acid sequence of the ligated hybrid DMD 19-20/35-36 sense strands.

SEQ ID NO: 34 sets forth the nucleic acid sequence of the ligated hybrid DMD 19-20/37-38 sense strands.

SEQ ID NO: 35 sets forth the nucleic acid sequence of the ligated hybrid DMD 19-20/37-38 sense strands.

SEQ ID NO: 36 sets forth the amino acid sequence of the DMD 19-20x.13 engineered meganuclease.

SEQ ID NO: 37 sets forth the amino acid sequence of the DMD 19-20x.87 engineered meganuclease.

SEQ ID NO: 38 sets forth the amino acid sequence of the DMD 19-20L.249 engineered meganuclease.

SEQ ID NO: 39 sets forth the amino acid sequence of the DMD 19-20L.302 engineered meganuclease.

SEQ ID NO: 40 sets forth the amino acid sequence of the DMD 19-20L.329 engineered meganuclease.

SEQ ID NO: 41 sets forth the amino acid sequence of the DMD 19-20L.374 engineered meganuclease.

SEQ ID NO: 42 sets forth the amino acid sequence of the DMD 19-20L.375 engineered meganuclease.

SEQ ID NO: 43 sets forth the amino acid sequence of the DMD 19-20L.431 engineered meganuclease.

SEQ ID NO: 44 sets forth the amino acid sequence of the DMD 19-20L.458 engineered meganuclease.

SEQ ID NO: 45 sets forth the amino acid sequence of the DMD 35-36x.63 engineered meganuclease.

SEQ ID NO: 46 sets forth the amino acid sequence of the DMD 35-36x.81 engineered meganuclease.

SEQ ID NO: 47 sets forth the amino acid sequence of the DMD 35-36L.195 engineered meganuclease.

SEQ ID NO: 48 sets forth the amino acid sequence of the DMD35-36L.282 engineered meganuclease.

SEQ ID NO: 49 sets forth the amino acid sequence of the DMD35-36L.349 engineered meganuclease.

SEQ ID NO: 50 sets forth the amino acid sequence of the DMD 35-36L.376 engineered meganuclease.

SEQ ID NO: 51 sets forth the amino acid sequence of the DMD 35-36L.457 engineered meganuclease.

SEQ ID NO: 52 sets forth the amino acid sequence of the DMD 35-36L.469 engineered meganuclease.

SEQ ID NO: 53 sets forth the amino acid sequence of the DMD 37-38x.15 engineered meganuclease.

SEQ ID NO: 54 sets forth the amino acid sequence of the DMD 37-38x.66 engineered meganuclease.

SEQ ID NO: 55 sets forth the amino acid sequence of the DMD 37-38x.79 engineered meganuclease.

SEQ ID NO: 56 sets forth the amino acid sequence of the DMD 37-38L.166 engineered meganuclease.

SEQ ID NO: 57 sets forth the amino acid sequence of the DMD 37-38L.478 engineered meganuclease.

SEQ ID NO: 58 sets forth the amino acid sequence of the DMD 37-38L.512 engineered meganuclease.

SEQ ID NO: 59 sets forth the amino acid sequence of the DMD 37-38L.528 engineered meganuclease.

SEQ ID NO: 60 sets forth a nucleic acid sequence encoding the DMD 19-20x.13 engineered meganuclease.

SEQ ID NO: 61 sets forth a nucleic acid sequence encoding the DMD 19-20x.87 engineered meganuclease.

SEQ ID NO: 62 sets forth a nucleic acid sequence encoding the DMD 19-20L.249 engineered meganuclease.

SEQ ID NO: 64 sets forth a nucleic acid sequence encoding the DMD 19-20L.302 engineered meganuclease.

SEQ ID NO: 64 sets forth a nucleic acid sequence encoding the DMD 19-20L.329 engineered meganuclease.

SEQ ID NO: 65 sets forth the nucleic acid sequence of the DMD 19-20L.374 engineered meganuclease.

SEQ ID NO: 66 sets forth the nucleic acid sequence of the DMD 19-20L.375 engineered meganuclease.

SEQ ID NO: 67 sets forth the nucleic acid sequence of the DMD 19-20L.431 engineered meganuclease.

SEQ ID NO: 68 sets forth the nucleic acid sequence of the DMD 19-20L.458 engineered meganuclease.

SEQ ID NO: 69 sets forth a nucleic acid sequence encoding the DMD 35-36x.63 engineered meganuclease.

SEQ ID NO: 70 sets forth a nucleic acid sequence encoding the DMD 35-36x.81 engineered meganuclease.

SEQ ID NO: 71 sets forth a nucleic acid sequence encoding the DMD 35-36L.195 engineered meganuclease.

SEQ ID NO: 72 sets forth a nucleic acid sequence encoding the DMD35-36L.282 engineered meganuclease.

SEQ ID NO: 73 sets forth a nucleic acid sequence encoding the DMD35-36L.349 engineered meganuclease.

SEQ ID NO: 74 sets forth a nucleic acid sequence encoding the DMD35-36L.376 engineered meganuclease.

SEQ ID NO: 75 sets forth a nucleic acid sequence encoding the DMD35-36L.457 engineered meganuclease.

SEQ ID NO: 76 sets forth a nucleic acid sequence encoding the DMD35-36L.469 engineered meganuclease.

SEQ ID NO: 77 sets forth a nucleic acid sequence encoding the DMD 37-38x.15 engineered meganuclease.

SEQ ID NO: 78 sets forth a nucleic acid sequence encoding the DMD 37-38x.66 engineered meganuclease.

SEQ ID NO: 79 sets forth a nucleic acid sequence encoding the DMD 37-38x.79 engineered meganuclease.

SEQ ID NO: 80 sets forth a nucleic acid sequence encoding the DMD 37-38L.166 engineered meganuclease.

SEQ ID NO: 81 sets forth a nucleic acid sequence encoding the DMD 37-38L.478 engineered meganuclease.

SEQ ID NO: 82 sets forth a nucleic acid sequence encoding the DMD 37-38L.512 engineered meganuclease.

SEQ ID NO: 83 sets forth a nucleic acid sequence encoding the DMD 37-38L.528 engineered meganuclease.

SEQ ID NO: 84 sets forth the amino acid sequence of the DMD 19-20x.13 engineered meganuclease DMD19 binding subunit.

SEQ ID NO: 85 sets forth the amino acid sequence of the DMD 19-20x.87 engineered meganuclease DMD19 binding subunit.

SEQ ID NO: 86 sets forth the amino acid sequence of the DMD 19-20L.249 engineered meganuclease DMD19 binding subunit.

SEQ ID NO: 87 sets forth the amino acid sequence of the DMD 19-20L.302 engineered meganuclease DMD19 binding subunit.

SEQ ID NO: 88 sets forth the amino acid sequence of the DMD 19-20L.329 engineered meganuclease DMD19 binding subunit.

SEQ ID NO: 89 sets forth the amino acid sequence of the DMD 19-20L.374 engineered meganuclease DMD19 binding subunit.

SEQ ID NO: 90 sets forth the amino acid sequence of the DMD 19-20L.375 engineered meganuclease DMD19 binding subunit.

SEQ ID NO: 91 sets forth the amino acid sequence of the DMD 19-20L.431 engineered meganuclease DMD19 binding subunit.

SEQ ID NO: 92 sets forth the amino acid sequence of the DMD 19-20L.458 engineered meganuclease DMD19 binding subunit.

SEQ ID NO: 93 sets forth the amino acid sequence of the DMD 35-36x.63 engineered meganuclease DMD35 binding subunit.

SEQ ID NO: 94 sets forth the amino acid sequence of the DMD 35-36x.81 engineered meganuclease DMD35 binding subunit.

SEQ ID NO: 95 sets forth the amino acid sequence of the DMD 35-36L.195 engineered meganuclease DMD35 binding subunit.

SEQ ID NO: 96 sets forth the amino acid sequence of the DMD35-36L.282 engineered meganuclease DMD35 binding subunit.

SEQ ID NO: 97 sets forth the amino acid sequence of the DMD35-36L.349 engineered meganuclease DMD35 binding subunit.

SEQ ID NO: 98 sets forth the amino acid sequence of the DMD35-36L.376 engineered meganuclease DMD35 binding subunit.

SEQ ID NO: 99 sets forth the amino acid sequence of the DMD35-36L.457 engineered meganuclease DMD35 binding subunit.

SEQ ID NO: 100 sets forth the amino acid sequence of the DMD35-36L.469 engineered meganuclease DMD35 binding subunit.

SEQ ID NO: 101 sets forth the amino acid sequence of the DMD 37-38x.15 engineered meganuclease DMD37 binding subunit.

SEQ ID NO: 102 sets forth the amino acid sequence of the DMD 37-38x.66 engineered meganuclease DMD37 binding subunit.

SEQ ID NO: 103 sets forth the amino acid sequence of the DMD 37-38x.79 engineered meganuclease DMD37 binding subunit.

SEQ ID NO: 104 sets forth the amino acid sequence of the DMD 37-38L.166 engineered meganuclease DMD37 binding subunit.

SEQ ID NO: 105 sets forth the amino acid sequence of the DMD 37-38L.478 engineered meganuclease DMD37 binding subunit.

SEQ ID NO: 106 sets forth the amino acid sequence of the DMD 37-38L.512 engineered meganuclease DMD37 binding subunit.

SEQ ID NO: 107 sets forth the amino acid sequence of the DMD 37-38L.528 engineered meganuclease DMD37 binding subunit.

SEQ ID NO: 108 sets forth the amino acid sequence of the DMD 19-20x.13 engineered meganuclease DMD20 binding subunit.

SEQ ID NO: 109 sets forth the amino acid sequence of the DMD 19-20x.87 engineered meganuclease DMD20 binding subunit.

SEQ ID NO: 110 sets forth the amino acid sequence of the DMD 19-20L.249 engineered meganuclease DMD20 binding subunit.

SEQ ID NO: 111 sets forth the amino acid sequence of the DMD 19-20L.302 engineered meganuclease DMD20 binding subunit.

SEQ ID NO: 112 sets forth the amino acid sequence of the DMD 19-20L.329 engineered meganuclease DMD20 binding subunit.

SEQ ID NO: 113 sets forth the amino acid sequence of the DMD 19-20L.374 engineered meganuclease DMD20 binding subunit.

SEQ ID NO: 114 sets forth the amino acid sequence of the DMD 19-20L.375 engineered meganuclease DMD20 binding subunit.

SEQ ID NO: 115 sets forth the amino acid sequence of the DMD 19-20L.431 engineered meganuclease DMD20 binding subunit.

SEQ ID NO: 116 sets forth the amino acid sequence of the DMD 19-20L.458 engineered meganuclease DMD20 binding subunit.

SEQ ID NO: 117 sets forth the amino acid sequence of the DMD 35-36x.63 engineered meganuclease DMD36 binding subunit.

SEQ ID NO: 118 sets forth the amino acid sequence of the DMD 35-36x.81 engineered meganuclease DMD36 binding subunit.

SEQ ID NO: 119 sets forth the amino acid sequence of the DMD 35-36L.195 engineered meganuclease DMD36 binding subunit.

SEQ ID NO: 120 sets forth the amino acid sequence of the DMD35-36L.282 engineered meganuclease DMD36 binding subunit.

SEQ ID NO: 121 sets forth the amino acid sequence of the DMD35-36L.349 engineered meganuclease DMD36 binding subunit.

SEQ ID NO: 122 sets forth the amino acid sequence of the DMD35-36L.376 engineered meganuclease DMD36 binding subunit.

SEQ ID NO: 123 sets forth the amino acid sequence of the DMD35-36L.457 engineered meganuclease DMD36 binding subunit.

SEQ ID NO: 124 sets forth the amino acid sequence of the DMD35-36L.469 engineered meganuclease DMD36 binding subunit.

SEQ ID NO: 125 sets forth the amino acid sequence of the DMD 37-38x.15 engineered meganuclease DMD38 binding subunit.

SEQ ID NO: 126 sets forth the amino acid sequence of the DMD 37-38x.66 engineered meganuclease DMD38 binding subunit.

SEQ ID NO: 127 sets forth the amino acid sequence of the DMD 37-38x.79 engineered meganuclease DMD38 binding subunit.

SEQ ID NO: 128 sets forth the amino acid sequence of the DMD 37-38L.166 engineered meganuclease DMD38 binding subunit.

SEQ ID NO: 129 sets forth the amino acid sequence of the DMD 37-38L.478 engineered meganuclease DMD38 binding subunit.

SEQ ID NO: 130 sets forth the amino acid sequence of the DMD 37-38L.512 engineered meganuclease DMD38 binding subunit.

SEQ ID NO: 131 sets forth the amino acid sequence of the DMD 37-38L.528 engineered meganuclease DMD38 binding subunit.

SEQ ID NO: 132 sets forth the amino acid sequence of a linker sequence.

SEQ ID NO: 133 sets forth the nucleic acid sequence of a probe used in a ddPCR assay for detecting INDELs at the DMD 19-20 recognition sequence.

SEQ ID NO: 134 sets forth the nucleic acid sequence of a forward PCR primer used in a ddPCR assay for detecting INDELs at the DMD 19-20 recognition sequence.

SEQ ID NO: 135 sets forth the nucleic acid sequence of a forward PCR primer used in a ddPCR assay for detecting INDELs at the DMD 19-20 recognition sequence.

SEQ ID NO: 136 sets forth the nucleic acid sequence of a probe used as a reference in a ddPCR assay for detecting INDELs.

SEQ ID NO: 137 sets forth the nucleic acid sequence of a forward PCR primer used as a reference in a ddPCR assay for detecting INDELs.

SEQ ID NO: 138 sets forth the nucleic acid sequence of a forward PCR primer used as a reference in a ddPCR assay for detecting INDELs.

SEQ ID NO: 139 sets forth the nucleic acid sequence of a probe used in a ddPCR assay for detecting INDELs at the DMD 37-38 recognition sequence.

SEQ ID NO: 140 sets forth the nucleic acid sequence of a forward PCR primer used in a ddPCR assay for detecting INDELs at the DMD 37-38 recognition sequence.

SEQ ID NO: 141 sets forth the nucleic acid sequence of a forward PCR primer used in a ddPCR assay for detecting INDELs at the DMD 37-38 recognition sequence.

SEQ ID NO: 142 sets forth the nucleic acid sequence of a probe used in a ddPCR assay for detecting INDELs at the DMD 35-36 recognition sequence.

SEQ ID NO: 143 sets forth the nucleic acid sequence of a forward PCR primer used in a ddPCR assay for detecting INDELs at the DMD 35-36 recognition sequence.

SEQ ID NO: 144 sets forth the nucleic acid sequence of a forward PCR primer used in a ddPCR assay for detecting INDELs at the DMD 35-36 recognition sequence.

SEQ ID NO: 145 sets forth the nucleic acid sequence of a probe used in a ddPCR assay for detecting INDELs at the DMD 29-30 recognition sequence.

SEQ ID NO: 146 sets forth the nucleic acid sequence of a forward PCR primer used in a ddPCR assay for detecting INDELs at the DMD 29-30 recognition sequence.

SEQ ID NO: 147 sets forth the nucleic acid sequence of a forward PCR primer used in a ddPCR assay for detecting INDELs at the DMD 29-30 recognition sequence.

SEQ ID NO: 148 sets forth the nucleic acid sequence of a forward PCR primer used in a PCR amplification assay for the DMD 19-20 to DMD 35-36 ligated recognition sequences.

SEQ ID NO: 149 sets forth the nucleic acid sequence of a reverse PCR primer used in a PCR amplification assay for the DMD 19-20 to DMD 35-36 ligated recognition sequences.

SEQ ID NO: 150 sets forth the nucleic acid sequence of a forward PCR primer used in a PCR amplification assay for the DMD 19-20 to DMD 35-36 ligated recognition sequences.

SEQ ID NO: 151 sets forth the nucleic acid sequence of a reverse PCR primer used in a PCR amplification assay for the DMD 19-20 to DMD 35-36 ligated recognition sequences.

SEQ ID NO: 152 sets forth the nucleic acid sequence of a forward PCR primer used in a PCR amplification assay for the DMD 19-20 to DMD 29-30 ligated recognition sequences.

SEQ ID NO: 153 sets forth the nucleic acid sequence of a reverse PCR primer used in a PCR amplification assay for the DMD 19-20 to DMD 29-30 ligated recognition sequences.

SEQ ID NO: 154 sets forth the nucleic acid sequence of a forward PCR primer used in a PCR amplification assay for the DMD 19-20 to DMD 29-30 ligated recognition sequences.

SEQ ID NO: 155 sets forth the nucleic acid sequence of a reverse PCR primer used in a PCR amplification assay for the DMD 19-20 to DMD 29-30 ligated recognition sequences.

SEQ ID NO: 156 sets forth the nucleic acid sequence of a forward PCR primer used in a PCR amplification assay for the DMD 19-20 to DMD 37-38 ligated recognition sequences.

SEQ ID NO: 157 sets forth the nucleic acid sequence of a reverse PCR primer used in a PCR amplification assay for the DMD 19-20 to DMD 37-38 ligated recognition sequences.

SEQ ID NO: 158 sets forth the nucleic acid sequence of a forward PCR primer used in a PCR amplification assay for the DMD 19-20 to DMD 37-38 ligated recognition sequences.

SEQ ID NO: 159 sets forth the nucleic acid sequence of a reverse PCR primer used in a PCR amplification assay for the DMD 19-20 to DMD 37-38 ligated recognition sequences.

SEQ ID NO: 160 sets forth the nucleic acid sequence of a probe used in a ddPCR assay for the DMD 19-20 to DMD 37-38 ligated recognition sequences.

SEQ ID NO: 161 sets forth the nucleic acid sequence of a forward PCR primer used in a ddPCR assay for the DMD 19-20 to DMD 37-38 ligated recognition sequences.

SEQ ID NO: 162 sets forth the nucleic acid sequence of a reverse PCR primer used in a ddPCR assay for the DMD 19-20 to DMD 37-38 ligated recognition sequences.

SEQ ID NO: 163 sets forth the nucleic acid sequence of a probe used in a ddPCR assay for the DMD 19-20 to DMD 35-36 ligated recognition sequences.

SEQ ID NO: 164 sets forth the nucleic acid sequence of a forward PCR primer used in a ddPCR assay for the DMD 19-20 to DMD 35-36 ligated recognition sequences.

SEQ ID NO: 165 sets forth the nucleic acid sequence of a reverse PCR primer used in a ddPCR assay for the DMD 19-20 to DMD 35-36 ligated recognition sequences.

SEQ ID NO: 166 sets forth the nucleic acid sequence of a probe used in a ddPCR assay for the DMD 19-20 to DMD 29-30 ligated recognition sequences.

SEQ ID NO: 167 sets forth the nucleic acid sequence of a forward PCR primer used in a ddPCR assay for the DMD 19-20 to DMD 29-30 ligated recognition sequences.

SEQ ID NO: 168 sets forth the nucleic acid sequence of a reverse PCR primer used in a ddPCR assay for the DMD 19-20 to DMD 29-30 ligated recognition sequences.

SEQ ID NO: 169 sets forth the nucleic acid sequence of a C5-12 promoter sequence.

SEQ ID NO: 170 sets forth the nucleic acid sequence of a murine MCK promoter and enhancer sequence.

SEQ ID NO: 171 sets forth the nucleic acid sequence of a human MCK promoter sequence.

SEQ ID NO: 172 sets forth the nucleic acid sequence of a wild-type MCK enhancer sequence.

SEQ ID NO: 173 sets forth the nucleic acid sequence of a modified MCK enhancer sequence.

SEQ ID NO: 174 sets forth the nucleic acid sequence of a spc 5-12 promoter sequence.

SEQ ID NO: 175 sets forth the nucleic acid sequence of a MHCK7 promoter sequence.

SEQ ID NO: 176 sets forth the nucleic acid sequence of a CK8 promoter sequence.

SEQ ID NO: 177 sets forth the nucleic acid sequence of a SK-CRM4 promoter sequence.

SEQ ID NO: 178 sets forth the nucleic acid sequence of a SP-301 promoter sequence.

SEQ ID NO: 179 sets forth the nucleic acid sequence of a SP-817 promoter sequence.

SEQ ID NO: 180 sets forth the nucleic acid sequence of a SP-905 promoter sequence.

SEQ ID NO: 181 sets forth the nucleic acid sequence of a Muscle Hybrid promoter sequence.

SEQ ID NO: 182 sets forth the amino acid sequence of an rh.74 AAV capsid.

SEQ ID NO: 183 sets forth the amino acid sequence of an AAV9 capsid.

SEQ ID NO: 184 sets forth the nucleic acid sequence of a forward primer.

SEQ ID NO: 185 sets forth the nucleic acid sequence of a reverse primer.

SEQ ID NO: 186 sets forth the nucleic acid sequence of a probe.

SEQ ID NO: 187 sets forth the nucleic acid sequence of a forward primer.

SEQ ID NO: 188 sets forth the nucleic acid sequence of a reverse primer.

SEQ ID NO: 189 sets forth the nucleic acid sequence of a probe.

SEQ ID NO: 190 sets forth the nucleic acid sequence of a forward primer.

SEQ ID NO: 191 sets forth the nucleic acid sequence of a reverse primer.

SEQ ID NO: 192 sets forth the nucleic acid sequence of a probe.

SEQ ID NO: 193 sets forth the nucleic acid sequence of a reverse primer.

SEQ ID NO: 194 sets forth the nucleic acid sequence of a perfect ligation of the DMD 19-20 and DMD 35-36 meganuclease recognition sequences following cleavage and excision of the intervening genomic sequence.

SEQ ID NO: 195 sets forth the complementary nucleic acid sequence of SEQ ID NO: 194.

SEQ ID NO: 196 sets forth the nucleic acid sequence of a perfect ligation of the DMD 19-20 and DMD 37-38 meganuclease recognition sequences following cleavage and excision of the intervening genomic sequence.

SEQ ID NO: 197 sets forth the complementary nucleic acid sequence of SEQ ID NO: 196.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present disclosure can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the present disclosure, which do not depart from the present invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes, which cleave a phosphodiester bond within a polynucleotide chain. Engineered nucleases can include, without limitation, engineered meganucleases, zinc finger nucleases, TALENs, compact TALENs, CRISPR system nucleases, and megaTALs. In addition, any engineered nuclease is envisioned that is capable of generating overhangs at its cleavage site.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 1), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 132, which sets forth residues 154-195 of any one of SEQ ID NOs: 36-59.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically modified" refers to a cell or organism in which, or in an ancestor of which, a genomic DNA sequence has been deliberately modified by recombinant technology. As used herein, the term "genetically modified" encompasses the term "transgenic."

As used herein, the term with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by a nuclease. In the case of a meganuclease, a recognition sequence comprises a pair of inverted, 9 basepair "half-sites," which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the terms "target site" or "target sequence" refers to a region of the chromosomal DNA of a cell comprising a recognition sequence for a nuclease.

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" means the ability of a nuclease to bind and cleave double-stranded DNA molecules only at a particular sequence of base pairs referred to as the recognition sequence, or only at a particular set of recognition sequences. The set of recognition sequences will share certain conserved positions or sequence motifs but may be degenerate at one or more positions. A highly-specific nuclease is capable of cleaving only one or a very few recognition sequences. Specificity can be determined by any method known in the art.

As used herein, the term "dystrophin gene" refers to the gene associated with National Center for Biotechnology Information (NCBI) gene ID 1756, as well as naturally occurring variants thereof. The term "dystrophin" refers to a polypeptide encoded by the dystrophin gene. The dystrophin isoform expressed in muscle cells and muscle precursor cells is known as the Dp427m dystrophin variant. The amino acid sequence of a full-length, wild type Dp427m dystrophin polypeptide is set forth in SEQ ID NO: 4. NCBI reference numbers NM_004006.3 and NP_003997.2 set forth the dystrophin Dp427m mRNA and polypeptide, respectively. In some embodiments described herein, the dystrophin gene is edited with a pair of engineered meganucleases, resulting in the excision of exons 45-55 and subsequent perfect ligation of the dystrophin gene. Removal of exons 45-55 from the wild-type dystrophin gene can result in a dystrophin polypeptide comprising an amino acid sequence set forth in SEQ ID NO: 5.

As used herein, the term "perfect ligation" refers to the ligation (i.e., annealing) of all four bases of a 3' overhang of a first cleavage site with all four bases of a complementary 3' overhang of a second cleavage site in a dystrophin gene following cleavage by a pair of engineered meganucleases of the invention. The recognition sequences targeted by the disclosed engineered meganucleases have identical four basepair center sequences (e.g., GTAT), such that the first and second cleavage sites will have complementary four basepair 3' overhangs. Accordingly, each basepair of the first 3' overhang pairs with its complement basepair on the second 3' overhang, and ligation occurs through a DNA ligase enzyme. Examples of sequences resulting from such perfect ligations are set forth in SEQ ID NO: 32 (i.e., perfect ligation of the DMD 19-20 and DMD 35-36 recognition sequences) and SEQ ID NO: 34 (i.e., perfect ligation of the DMD 19-20 and DMD 37-38 recognition sequences).

As used herein, the term "Becker Muscular Dystrophy phenotype" refers to a less severe form of muscular dystrophy as compared to DMD. Individuals having Becker Muscular Dystrophy still comprise mutations within the dystrophin gene, but express more functional dystrophin protein in muscle cells (e.g., muscle precursor cells, skeletal muscle cells, and cardiac muscle cells) compared to individuals having DMD, generally leading to a better clinical prognosis.

As used herein, the term "homologous recombination" or "HR" refers to the natural, cellular process in which a double-stranded DNA-break is repaired using a homologous DNA sequence as the repair template (see, e.g., Cahill et al. (2006) Front. Biosci. 11:1958-76). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g., Cahill et al. (2006)). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by non-homologous end joining (NHEJ can introduce mutations into the coding sequence, such as frameshift mutations, that disrupt gene function. Thus, engineered nucleases can be used to effectively knock-out a gene in a population of cells.

As used herein, the term "homology arms" or "sequences homologous to sequences flanking a nuclease cleavage site" refer to sequences flanking the 5' and 3' ends of a nucleic acid molecule, which promote insertion of the nucleic acid molecule into a cleavage site generated by a nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information, and are described in, for example, Altschul et al. (1990) J. Mol. Biol. 215:403-10; Gish & States (1993) Nature Genet. 3:266-72; Madden et al. (1996) Meth. Enzymol. 266:131-41; Altschul et al. (1997) Nucleic Acids Res. 25:3389-3402; and Zhang et al. (2000) J. Comput. Biol. 7:203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 36-59. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 36-59. In certain embodiments, variable residues within a hypervariable region can further correspond to residues 48, 50, and 71-73 of any one of SEQ ID NOs: 36-59. In other embodiments, variable residues within a hypervariable region correspond to one or more of positions 215, 217, 219, 221, 223, 224, 229, 231, 233, 235, 237, 239, 241, 259, 261, 262, 263, 264, 266, and 268 of any one of SEQ ID NOs: 36-59. In certain embodiments, variable residues within a hypervariable region can further correspond to residues 239, 241, and 263-265 of any one of SEQ TD NOs: 36-59.

The terms "increase" in the context of dystrophin protein or mRNA levels refers to any increase in the levels of dystrophin protein or mRNA expression relative to a reference level including an increase of dystrophin protein or mRNA expression of at least 1%, 2%, 3%, 4%, 5%, 10%, 15%, 20%, 25%, 30%, 40%, 50%, 60%, 70%, 80%, 90%, 95%, 100%, or more, when compared to a reference level or control. In some embodiments, an increase in dystrophin protein or mRNA levels refers to an increase in a shortened dystrophin polypeptide or mRNA transcript, for example, missing a portion of the polypeptide encoded by at least one exon (e.g., a portion encoded by exons 45-55) or missing a portion of mRNA corresponding to exons 45-55 compared to the wild-type dystrophin polypeptide or gene.

As used herein, the term "reference level" in the context of dystrophin protein or mRNA levels refers to a level of dystrophin protein or mRNA as measured in, for example, a control cell, control cell population or a control subject, at a previous time point in the control cell, the control cell population or the subject undergoing treatment (e.g., a pre-dose baseline level obtained from the control cell, control cell population or subject), or a pre-defined threshold level of dystrophin protein or mRNA (e.g., a threshold level identified through previous experimentation).

As used herein, the term "a control" or "a control cell" refers to a cell that provides a reference point for measuring changes in genotype or phenotype of a genetically modified cell. A control cell may comprise, for example: (a) a wild-type cell, i.e., of the same genotype as the starting material for the genetic alteration which resulted in the genetically modified cell; (b) a cell of the same genotype as the genetically modified cell but which has been transformed with a null construct (i.e., with a construct which has no known effect on the trait of interest); or, (c) a cell genetically identical to the genetically modified cell but which is not exposed to conditions or stimuli or further genetic modifications that would induce expression of altered genotype or phenotype. A control subject may comprise, for example: a wild-type subject, i.e., of the same genotype as the starting subject for the genetic alteration which resulted in the genetically modified subject (e.g., a subject having the same mutation in a dystrophin gene), which is not exposed to conditions or stimuli or further genetic modifications that would induce expression of altered genotype or phenotype in the subject.

As used herein, the term "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, the term "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the invention. In some embodiments, a "vector" also refers to a viral vector. Viral vectors can include, without limitation, retroviral vectors, lentiviral vectors, adenoviral vectors, and AAV.

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, the terms "treatment" or "treating a subject" refers to the administration of an engineered meganuclease described herein, or a polynucleotide encoding an engineered meganuclease described herein, or a pair of such engineered meganucleases or polynucleotides, to a subject having DMD for the purpose of increasing levels of a dystrophin protein in the subject. In some embodiments, expression of a shortened version (e.g., missing amino acids encoded by multiple exons) of the dystrophin protein is increased. In some embodiments, expression of a version of the dystrophin protein, lacking the amino acids encoded by exons 45-55, is increased. Such treatment, in some embodiments, transitions the DMD phenotype to a Becker Dystrophy phenotype.

As used herein, the term "gc/kg" or "gene copies/kilogram" refers to the number of copies of a nucleic acid sequence encoding an engineered meganuclease described herein per weight in kilograms of a subject that is administered a polynucleotide comprising the nucleic acid sequence.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of an engineered meganuclease or pair of engineered meganucleases described herein, or polynucleotide or pair of polynucleotides encoding the same, or pharmaceutical compositions disclosed herein, increases the level of expression of a dystrophin protein (e.g., a shortened dystrophin protein lacking the amino acids encoded by exons 45-55) and ameliorates at least one symptom associated with DMD.

As used herein, the term "lipid nanoparticle" refers to a lipid composition having a typically spherical structure with an average diameter between 10 and 1000 nm. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values≥0 and ≤2 if the variable is inherently continuous.

2.1 Principle of the Invention

The present disclosure is based, in part, on the hypothesis that certain deletions in the dystrophin gene that give rise to the DMD phenotype can be compensated for by utilizing pairs of endonucleases to strategically delete exons within the dystrophin gene in order to restore a normal reading frame within the gene. The DMD-Leiden Database indicates that most of the mutations that cause DMD are deletions of one or more whole exons that cause a shift in reading frame. In many cases, the reading frame can be restored by eliminating the exon immediately before or after the mutation. As shown in Table 3, 29 different Duchenne-causing mutations, representing ~65% of patients, can be compensated for by deleting a single exon adjacent to the mutation.

TABLE 3

| Exon(s) deleted in patient | Additional Exon to delete | Frequency in DMD-Leiden Database (%) |
| --- | --- | --- |
| 44, 44-47 | 43 | 5 |
| 35-43, 45, 45-54 | 44 | 8 |
| 18-44, 44, 46-47, 46-48, 46-49, 46-51, 46-53 | 45 | 13 |
| 45 | 46 | 7 |
| 51, 51-55 | 50 | 5 |
| 50, 45-50, 48-50, 49-50, 52, 52-63 | 51 | 15 |
| 51, 53, 53-55 | 52 | 3 |
| 45-52, 48-52, 49-52, 50-52, 52 | 53 | 9 |

For example, a patient with disease due to the deletion of exon 45, which occurs in approximately 7% of patients, can be treated with a therapeutic that deletes exon 46. A therapeutic capable of deleting exon 51 or exon 45 could be used to treat 15% and 13% of patients, respectively.

Notably, greater than 50% of all DMD-related mutations within the dystrophin gene are encompassed by exons 45 through 55. Thus, in particular embodiments of the invention, exons 45 through 55 of the dystrophin gene will be removed in order to restore the normal reading frame of the gene. As disclosed herein, exon removal is achieved by the expression of a pair of engineered meganucleases in muscle cells or muscle precursor cells (e.g., a cardiac muscle cell or a skeletal muscle cell) that generate a pair of cleavage sites in introns upstream of exon 45 and downstream of exon 55, allowing for excision of the intervening genomic region. Following this approach, a genetically modified cell (e.g., a muscle cell in a treated subject) will be able to make an amount of a shortened dystrophin protein from the Beckers phenotype, which is similar to micro-dystrophin approaches, without having to express a micro-dystrophin transgene. This shortened dystrophin may be sufficient to rescue disease permanently, unlike other therapies that require a multi-continuous treatment regimen.

Accordingly, it is envisioned that a single treatment will permanently delete exons from a percentage of cells in a subject. In some embodiments, these cells will be myoblasts (i.e., muscle cells) or other muscle precursor cells that are capable of replicating and giving rise to whole muscle fibers that express functional (or semi-functional) dystrophin. If the frequency of exon deletion is low, however, it may be necessary to perform multiple treatments on each patient.

2.2 Meganucleases that Bind and Cleave Recognition Sequences Within a Dystrophin Recognition Sequences It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-strand break in a target locus is known to stimulate homologous recombination, particularly of transgenic DNA sequences flanked by sequences that are homologous to the genomic target. In this manner, exogenous polynucleotides can be inserted into a target locus. Such exogenous polynucleotides can encode any sequence or polypeptide of interest.

In particular embodiments, engineered meganucleases of the invention have been designed to bind and cleave a DMD 19-20 recognition sequence (SEQ ID NO: 6), a DMD 35-36 recognition sequence (SEQ ID NO: 10), or a DMD 37-38 recognition sequence (SEQ ID NO: 12). Exemplary meganucleases that bind and cleave the DMD 19-20 recognition sequence are provided in SEQ ID NOs: 36-44. Exemplary meganucleases that bind and cleave the DMD 35-36 recognition sequence are provided in SEQ ID NOs: 45-52. Exemplary meganucleases that bind and cleave the DMD 37-38 recognition sequence are provided in SEQ ID NOs: 53-59. The sequence of each recognition sequence, and the four base pair 3' overhang produced when cleaved by an engineered meganuclease described herein, is provided in Table 4 below.

TABLE 4

Engineered Meganuclease Recognition Sequences

| Recognition Sequence | SEQ ID NO: | 4 bp 3' Overhang |
|---|---|---|
| AAGGATTATGTATTACCTCCCG | 6 | GTAT |
| TAAGATTGGGTATGAGGGATAG | 8 | GTAT |
| CTACATGGTGTATCTGACTAAG | 10 | GTAT |
| CTGGCCGAAGTATAGGAATATG | 12 | GTAT |

In order to modify the dystrophin gene according to the present disclosure, a pair of engineered meganucleases described herein are utilized together in the same cell. Such pairs of engineered meganucleases were designed to generate a first cleavage site in an intron upstream of exon 45 and a second cleavage site in intron downstream of exon 55, allowing for removal of the intervening genomic sequence. Surprisingly, it was observed that excision of this genomic region from the dystrophin gene, which is greater than 500,000 bp in size, could be accomplished with high efficiency. Moreover, the meganuclease recognition sequences were selected to have complementary four basepair 3' overhangs following cleavage, and it was observed that the dystrophin gene could be repaired at high frequency by a perfect ligation of the 3' overhangs of the two cleavage sites. Such perfectly ligated recognition sequences contemplated herein are provided below in Table 5 below.

TABLE 5

Ligated Recognition Sequences

| Recognition Sequence Pair | Ligated Recognition Sequence | SEQ ID NO: | Exon(s) Removed |
|---|---|---|---|
| DMD 19/20 and DMD 29/30 | AAGGATTATGTATGAGGGATAG | 30 | 45 |
| DMD 19/20 and DMD 35/36 | AAGGATTATGTATCTGACTAAG | 32 | 45-55 |
| DMD 19/20 and DMD 37/38 | AAGGATTATGTATAGGAATATG | 34 | 45-55 |

These recognition sequences are further selected to be within intronic sequences that are normally spliced out during post transcriptional modification cellular processes. This reduces the likelihood of a mutation being introduced into the dystrophin gene and encoded polypeptide.

Exemplary Engineered Meganucleases

Engineered meganucleases of the invention comprise a first subunit, comprising a HVR1 region, and a second subunit, comprising a HVR2 region. Further, the first subunit binds to a first recognition half-site in the recognition sequence (e.g., the DMD19 half-site), and the second subunit binds to a second recognition half-site in the recognition sequence (e.g., the DMD20 half-site).

In particular embodiments, the meganucleases used to practice the invention are single-chain meganucleases. A single-chain meganuclease comprises an N-terminal subunit and a C-terminal subunit (i.e., the first and second subunits discussed above) joined by a linker peptide. Each of the two subunits recognizes and binds to a half-site of the recognition sequence and the site of DNA cleavage is at the middle of the recognition sequence near the interface of the two subunits. As discussed, DNA strand breaks are offset by four base pairs such that DNA cleavage by a meganuclease generates a pair of four basepair 3' single-strand overhangs.

In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit.

Exemplary DMD meganucleases of the invention are provided in SEQ ID NOs: 36-59, and are summarized below in Tables 6-8.

TABLE 6

Exemplary engineered meganucleases that bind and cleave the DMD 19-20 recognition sequence (SEQ ID NO: 6).

| Meganuclease | AA SEQ ID | DMD19 Subunit Residues | DMD19 Subunit SEQ ID | *DMD19 Subunit % | DMD20 Subunit Residues | DMD20 Subunit SEQ ID | *DMD20 Subunit % |
|---|---|---|---|---|---|---|---|
| DMD 19-20x.13 | 36 | 7-153 | 84 | 100 | 198-344 | 108 | 100 |
| DMD 19-20x.87 | 37 | 7-153 | 85 | 92.52 | 198-344 | 109 | 95.24 |
| DMD 19-20L.249 | 38 | 7-153 | 86 | 91.16 | 198-344 | 110 | 95.92 |
| DMD 19-20L.302 | 39 | 7-153 | 87 | 90.48 | 198-344 | 111 | 95.24 |
| DMD 19-20L.329 | 40 | 7-153 | 88 | 91.16 | 198-344 | 112 | 96.6 |
| DMD 19-20L.374 | 41 | 7-153 | 89 | 91.84 | 198-344 | 113 | 95.92 |
| DMD 19-20L.375 | 42 | 7-153 | 90 | 91.84 | 198-344 | 114 | 95.92 |

TABLE 6-continued

Exemplary engineered meganucleases that bind and cleave the DMD 19-20 recognition sequence (SEQ ID NO: 6).

| Meganuclease | AA SEQ ID | DMD19 Subunit Residues | DMD19 Subunit SEQ ID | *DMD19 Subunit % | DMD20 Subunit Residues | DMD20 Subunit SEQ ID | *DMD20 Subunit % |
|---|---|---|---|---|---|---|---|
| DMD 19-20L.431 | 43 | 7-153 | 91 | 91.16 | 198-344 | 115 | 96.60 |
| DMD 19-20L.458 | 44 | 7-153 | 92 | 91.84 | 198-344 | 116 | 96.60 |

"DMD19 Subunit %" and "DMD 20 Subunit %" represent the amino acid sequence identity between the DMD19-binding and DMD20-binding subunit regions of each meganuclease and the DMD19-binding and DMD20-binding subunit regions, respectively, of the DMD 19-20x.13 meganuclease.

TABLE 7

Exemplary engineered meganucleases that bind and cleave the DMD 35-36 recognition sequence (SEQ ID NO: 10).

| Meganuclease | AA SEQ ID | DMD35 Subunit Residues | DMD35 Subunit SEQ ID | *DMD35 Subunit % | DMD36 Subunit Residues | DMD36 Subunit SEQ ID | *DMD36 Subunit % |
|---|---|---|---|---|---|---|---|
| DMD 35-36x.63 | 45 | 7-153 | 93 | 100 | 198-344 | 117 | 100 |
| DMD 35-36x.81 | 46 | 7-153 | 94 | 97.96 | 198-344 | 118 | 93.88 |
| DMD 35-36L.195 | 47 | 7-153 | 95 | 100 | 198-344 | 119 | 93.20 |
| DMD 35-36L.282 | 48 | 7-153 | 96 | 99.32 | 198-344 | 120 | 93.20 |
| DMD 35-36L.349 | 49 | 7-153 | 97 | 100 | 198-344 | 121 | 93.20 |
| DMD 35-36L.376 | 50 | 7-153 | 98 | 100 | 198-344 | 122 | 93.20 |
| DMD 35-36L.457 | 51 | 7-153 | 99 | 99.32 | 198-344 | 123 | 92.52 |
| DMD 35-36L.469 | 52 | 7-153 | 100 | 98.64 | 198-344 | 124 | 95.52 |

"DMD35 Subunit %" and "DMD36 Subunit %" represent the amino acid sequence identity between the DMD35-binding and DMD36-binding subunit regions of each meganuclease and the DMD35-binding and DMD36-binding subunit regions, respectively, of the DMD 35-36x.63 meganuclease.

TABLE 8

Exemplary engineered meganucleases that bind and cleave the DMD 37-38 recognition sequence (SEQ ID NO: 12).

| Meganuclease | AA SEQ ID | DMD37 Subunit Residues | DMD37 Subunit SEQ ID | *DMD37 Subunit % | DMD38 Subunit Residues | DMD38 Subunit SEQ ID | *DMD38 Subunit % |
|---|---|---|---|---|---|---|---|
| DMD 37-38x.15 | 53 | 7-153 | 101 | 100 | 198-344 | 125 | 100 |
| DMD 37-38x.66 | 54 | 7-153 | 102 | 98.64 | 198-344 | 126 | 96.60 |
| DMD 37-38x.79 | 55 | 7-153 | 103 | 99.32 | 198-344 | 127 | 95.24 |
| DMD 37-38.L166 | 56 | 7-153 | 104 | 91.84 | 198-344 | 128 | 94.56 |
| DMD 37-38L.478 | 57 | 7-153 | 105 | 91.84 | 198-344 | 129 | 93.88 |
| DMD 37-38L.512 | 58 | 7-153 | 106 | 91.84 | 198-344 | 130 | 94.56 |
| DMD 37-38L.528 | 59 | 7-153 | 107 | 90.48 | 198-344 | 131 | 94.56 |

"DMD37 Subunit %" and "DMD38 Subunit %" represent the amino acid sequence identity between the DMD37-binding and DMD38-binding subunit regions of each meganuclease and the DMD37-binding and DMD38-binding subunit regions, respectively, of the DMD 37-38x.15 meganuclease.

In certain embodiments of the invention, the engineered meganuclease binds and cleaves a recognition sequence comprising SEQ ID NO: 6 (i.e., the DMD 19-20 recognition sequence) within a dystrophin gene, wherein the engineered meganuclease comprises a first subunit and a second subunit, wherein the first subunit binds to a first recognition half-site of the recognition sequence and comprises a HVR1 region, and wherein the second subunit binds to a second recognition half-site of the recognition sequence and comprises a HVR2 region. Exemplary DMD 19-20 meganucleases are described below.

DMD 19-20x.13 (SEQ ID NO: 36)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 36. In some embodiments, the HVR1 region comprises one or more residues corresponding to residues 24, 26, 28, 30, 32, 33, 38, 40, 42, 44, 46, 68, 70, 75, and 77 of SEQ ID NO: 36. In some embodiments, the HVR1 region comprises residues corresponding to residues 24, 26, 28, 30, 32, 33, 38, 40, 42, 44, 46, 68, 70, 75, and 77 of SEQ ID NO: 36. In some embodiments, the HVR1 region comprises Y, R, K, or D at a residue corresponding to residue 66 of SEQ ID NO: 36. In some embodiments, the HVR1 region comprises residues 24-79 of SEQ ID NO: 36 with up to 1, 2, 3, 4, 5, 6, 7, 8, 9, 10, or 11 amino acid substitutions. In some embodiments, the HVR1 region comprises residues 24-79 of SEQ ID NO: 36.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 36. In some embodiments, the first subunit comprises G, S, or A at a residue corresponding to residue 19 of SEQ ID NO: 36. In some embodiments, the first subunit comprises a residue corresponding to residue 19 of SEQ ID NO: 36. In some embodiments, the first subunit comprises E, Q, or K at a residue corresponding to residue 80 of SEQ ID NO: 36. In some embodiments, the first subunit comprises residues 7-153 of SEQ ID NO: 36 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 36.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 36. In some embodiments, the HVR2 region comprises one or more residues corresponding to residues 215, 217, 219, 221, 223, 224, 229, 231, 233, 235, 237, 259, 261, 266, and 268 of SEQ ID NO: 36. In some embodiments, the HVR2 region comprises residues corresponding to residues 215, 217, 219, 221, 223, 224, 229, 231, 233, 235, 237, 259, 261, 266, and 268 of SEQ ID NO: 36. In some embodiments, the HVR2 region comprises Y, R, K, or D at a residue corresponding to residue 257 of SEQ ID NO: 36. In some embodiments, the HVR2 region comprises a residue corresponding to residue 241 of SEQ ID NO: 36. In some embodiments, the HVR2 region comprises a residue corresponding to residue 263 of SEQ ID NO: 36. In some embodiments, the HVR2 region comprises a residue corresponding to residue 264 of SEQ ID NO: 36. In some embodiments, the HVR2 region comprises residues 215-270 of SEQ ID NO: 36 with up to 1, 2, 3, 4, 5, 6, 7, 8, 9, 10, or 11 amino acid substitutions. In some embodiments, the HVR2 region comprises residues 215-270 of SEQ ID NO: 36.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 36. In some embodiments, the second subunit comprises G, S, or A at a residue corresponding to residue 210 of SEQ ID NO: 36. In some embodiments, the second subunit comprises E, Q, or K at a residue corresponding to residue 271 of SEQ ID NO: 36. In some embodiments, the second subunit comprises a residue corresponding to residue 271 of SEQ ID NO: 36. In some embodiments, the second subunit comprises a residue corresponding to residue 330 of SEQ ID NO: 36. In some embodiments, the second subunit comprises residues 198-344 of SEQ ID NO: 36 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 36.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 36. In some embodiments, the engineered meganuclease comprises an amino acid sequence of SEQ ID NO: 36. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 50. In some embodiments, the engineered meganuclease is encoded by a nucleic acid sequence set forth in SEQ ID NO: 50.

DMD 19-20x.87 (SEQ ID NO: 37)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 37. In some embodiments, the HVR1 region comprises one or more residues corresponding to residues 24, 26, 28, 30, 32, 33, 38, 40, 42, 44, 46, 68, 70, 75, and 77 of SEQ ID NO: 37. In some embodiments, the HVR1 region comprises residues corresponding to residues 24, 26, 28, 30, 32, 33, 38, 40, 42, 44, 46, 68, 70, 75, and 77 of SEQ ID NO: 37. In some embodiments, the HVR1 region comprises Y, R, K, or D at a residue corresponding to residue 66 of SEQ ID NO: 37. In some embodiments, the HVR1 region comprises residues 24-79 of SEQ ID NO: 37 with up to 1, 2, 3, 4, 5, 6, 7, 8, 9, 10, or 11 amino acid substitutions. In some embodiments, the HVR1 region comprises residues 24-79 of SEQ ID NO: 37.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 37. In some embodiments, the first subunit comprises G, S, or A at a residue corresponding to residue 19 of SEQ ID NO: 37. In some embodiments, the first subunit comprises a residue corresponding to residue 19 of SEQ ID NO: 37. In some embodiments, the first subunit comprises E, Q, or K at a residue corresponding to residue 80 of SEQ ID NO: 37. In some embodiments, the first subunit comprises residues 7-153 of SEQ ID NO: 37 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 37.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 37. In some embodiments, the HVR2 region comprises one or more residues corresponding to residues 215, 217, 219, 221, 223, 224, 229, 231, 233, 235, 237, 259, 261, 266, and 268 of SEQ ID NO: 37. In some embodiments, the HVR2 region comprises residues corresponding to residues 215, 217, 219, 221, 223, 224, 229, 231, 233, 235, 237, 259, 261, 266, and 268 of SEQ ID NO: 37. In some embodiments, the HVR2 region comprises Y, R, K, or D at a residue corresponding to residue 257 of SEQ ID NO: 37. In some embodiments, the HVR2 region comprises a residue corresponding to residue 239 of SEQ ID NO: 37. In some embodiments, the HVR2 region comprises a residue corresponding to residue 241 of SEQ ID NO: 37. In some embodiments, the HVR2 region comprises a residue corresponding to residue 264 of SEQ ID NO: 37. In some embodiments, the HVR2 region comprises residues 215-270 of SEQ ID NO: 37 with up to 1, 2, 3, 4, 5, 6, 7, 8, 9, 10, or 11 amino acid substitutions. In some embodiments, the HVR2 region comprises residues 215-270 of SEQ ID NO: 37.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 37. In some embodiments, the second subunit comprises G, S, or A at a residue corresponding to residue 210 of SEQ ID NO: 37. In some embodiments, the second subunit comprises E, Q, or K at a residue corresponding to residue 271 of SEQ ID NO: 37. In some embodiments, the second subunit comprises a residue corresponding to residue 330 of SEQ ID NO: 37. In some embodiments, the second subunit comprises residues 198-344 of SEQ ID NO: 37 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 37.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 37. In some embodiments, the engineered meganuclease comprises an amino acid sequence of SEQ ID NO: 37. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 51. In some embodiments, the engineered meganuclease is encoded by a nucleic acid sequence set forth in SEQ ID NO: 51.

DMD 19-20L.249 (SEQ ID NO: 38)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 38. In some embodiments, the HVR1 region comprises one or more residues corresponding to residues 24, 26, 28, 30, 32, 33, 38, 40, 42, 44, 46, 68, 70, 75, and 77 of SEQ ID NO: 38. In some embodiments, the HVR1 region comprises residues corresponding to residues 24, 26, 28, 30, 32, 33, 38, 40, 42, 44, 46, 68, 70, 75, and 77 of SEQ ID NO: 38. In some embodiments, the HVR1 region comprises Y, R, K, or D at a residue corresponding to residue 66 of SEQ ID NO: 38. In some embodiments, the HVR1 region comprises residues 24-79 of SEQ ID NO: 38 with up to 1, 2, 3, 4, 5, 6, 7, 8, 9, 10, or 11 amino acid substitutions. In some embodiments, the HVR1 region comprises residues 24-79 of SEQ ID NO: 38.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ TD NO: 38. In some embodiments, the first subunit comprises G, S, or A at a residue corresponding to residue 19 of SEQ ID NO: 38. In some embodiments, the first subunit comprises a residue corresponding to residue 19 of SEQ ID NO: 38. In some embodiments, the first subunit comprises E, Q, or K at a residue corresponding to residue 80 of SEQ ID NO: 38. In some embodiments, the first subunit comprises a residue corresponding to residue 80 of SEQ ID NO: 38. In some embodiments, the first subunit comprises residues 7-153 of SEQ ID NO: 38 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 38.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 38. In some embodiments, the HVR2 region comprises one or more residues corresponding to residues 215, 217, 219, 221, 223, 224, 229, 231, 233, 235, 237, 259, 261, 266, and 268 of SEQ ID NO: 38. In some embodiments, the HVR2 region comprises residues corresponding to residues 215, 217, 219, 221, 223, 224, 229, 231, 233, 235, 237, 259, 261, 266, and 268 of SEQ ID NO: 38. In some embodiments, the HVR2 region comprises Y, R, K, or D at a residue corresponding to residue 257 of SEQ ID NO: 38. In some embodiments, the HVR2 region comprises a residue corresponding to residue 264 of SEQ ID NO: 38. In some embodiments, the HVR2 region comprises residues 215-270 of SEQ ID NO: 38 with up to 1, 2, 3, 4, 5, 6, 7, 8, 9, 10, or 11 amino acid substitutions. In some embodiments, the HVR2 region comprises residues 215-270 of SEQ ID NO: 38.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 38. In some embodiments, the second subunit comprises G, S, or A at a residue corresponding to residue 210 of SEQ ID NO: 38. In some embodiments, the second subunit comprises E, Q, or K at a residue corresponding to residue 271 of SEQ ID NO: 38. In some embodiments, the second subunit comprises a residue corresponding to residue 330 of SEQ ID NO: 38. In some embodiments, the second subunit comprises residues 198-344 of SEQ ID NO: 38 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 38.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 38. In some embodiments, the engineered meganuclease comprises an amino acid sequence of SEQ ID NO: 38. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 52. In some embodiments, the engineered meganuclease is encoded by a nucleic acid sequence set forth in SEQ ID NO: 52.

DMD 19-20L.302 (SEQ ID NO: 39)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 39. In some embodiments, the HVR1 region comprises one or more residues corresponding to residues 24, 26, 28, 30, 32, 33, 38, 40, 42, 44, 46, 68, 70, 75, and 77 of SEQ ID NO: 39. In some embodiments, the HVR1 region comprises residues corresponding to residues 24, 26, 28, 30, 32, 33, 38, 40, 42, 44, 46, 68, 70, 75, and 77 of SEQ ID NO: 39. In some embodiments, the HVR1 region comprises Y, R, K, or D at a residue corresponding to residue 66 of SEQ ID NO: 39. In some embodiments, the HVR1 region comprises residues 24-79 of SEQ ID NO: 39 with up to 1, 2, 3, 4, 5, 6, 7, 8, 9, 10, or 11 amino acid substitutions. In some embodiments, the HVR1 region comprises residues 24-79 of SEQ ID NO: 39.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ TD NO: 39. In some embodiments, the first subunit comprises G, S, or A at a residue corresponding to residue 19 of SEQ ID NO: 39. In some embodiments, the first subunit comprises a residue corresponding to residue 19 of SEQ ID NO: 39. In some embodiments, the first subunit comprises E, Q, or K at a residue corresponding to residue 80 of SEQ ID NO: 39. In some embodiments, the first subunit comprises a residue corresponding to residue 80 of SEQ ID NO: 39. In some embodiments, the first subunit comprises residues 7-153 of SEQ ID NO: 39 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ TD NO: 39.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 39. In some embodiments, the HVR2 region comprises one or more residues corresponding to residues 215, 217, 219, 221, 223, 224, 229, 231, 233, 235, 237, 259, 261, 266, and 268 of SEQ ID NO: 39. In some embodiments, the HVR2 region comprises residues corresponding to residues 215, 217, 219, 221, 223, 224, 229, 231, 233, 235, 237, 259, 261, 266, and 268 of SEQ ID NO: 39. In some embodiments, the HVR2 region comprises Y, R, K, or D at a residue corresponding to residue 257 of SEQ ID NO: 39. In some embodiments, the HVR2 region comprises a residue corresponding to residue 236 of SEQ ID NO: 39. In some embodiments, the HVR2 region comprises a residue corresponding to residue 264 of SEQ ID NO: 39. In some embodiments, the HVR2 region comprises residues 215-270 of SEQ ID NO: 39 with up to 1, 2, 3, 4, 5, 6, 7, 8, 9, 10, or 11 amino acid substitutions. In some embodiments, the HVR2 region comprises residues 215-270 of SEQ ID NO: 39.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 39. In some embodiments, the second subunit comprises G, S, or A at a residue corresponding to residue 210 of SEQ ID NO: 39. In some embodiments, the second subunit comprises E, Q, or K at a residue corresponding to residue 271 of SEQ ID NO: 39. In some embodiments, the second subunit comprises a residue corresponding to residue 271 of SEQ ID NO: 39. In some embodiments, the second subunit comprises residues 198-344 of SEQ ID NO: 39 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 39.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 39. In some embodiments, the engineered meganuclease comprises an amino acid sequence of SEQ ID NO: 39. In some embodiments, the engineered meganuclease is encoded by a nucleic acid sequence having at least 80%, 85%, 90%, 91%, 92%, 93%, 94%, 95%, 96%, 97%, 98%, 99% or more sequence identity to a nucleic acid sequence set forth in SEQ ID NOs: 53. In some embodiments, the engineered meganuclease is encoded by a nucleic acid sequence set forth in SEQ ID NO: 53.

DMD 19-20L.329 (SEQ ID NO: 40)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 40. In some embodiments, the HVR1 region comprises one or more residues corresponding to residues 24, 26, 28, 30, 32, 33, 38, 40, 42, 44, 46, 68, 70, 75, and 77 of SEQ ID NO: 40. In some embodiments, the HVR1 region comprises residues corresponding to residues 24, 26, 28, 30, 32, 33, 38, 40, 42, 44, 46, 68, 70, 75, and 77 of SEQ ID NO: 40. In some embodiments, the HVR1 region comprises Y, R, K, or D at a residue corresponding to residue 66 of SEQ ID NO: 40. In some embodiments, the HVR1 region comprises residues 24-79 of SEQ ID NO: 40 with up to 1, 2, 3, 4, 5, 6, 7, 8, 9, 10, or 11 amino acid substitutions. In some embodiments, the HVR1 region comprises residues 24-79 of SEQ ID NO: 40.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 40. In some embodiments, the first subunit comprises G, S, or A at a residue corresponding to residue 19 of SEQ ID NO: 40. In some embodiments, the first subunit comprises a residue corresponding to residue 19 of SEQ ID NO: 40. In some embodiments, the first subunit comprises E, Q, or K at a residue corresponding to residue 80 of SEQ ID NO: 40. In some embodiments, the first subunit comprises residues 7-153 of SEQ ID NO: 40 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 40.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 40. In some embodiments, the HVR2 region comprises one or more residues corresponding to residues 215, 217, 219, 221, 223, 224, 229, 231, 233, 235, 237, 259, 261, 266, and 268 of SEQ ID NO: 40. In some embodiments, the HVR2 region comprises residues corresponding to residues 215, 217, 219, 221, 223, 224, 229, 231, 233, 235, 237, 259, 261, 266, and 268 of SEQ ID NO: 40. In some embodiments, the HVR2 region comprises Y, R, K, or D at a residue corresponding to residue 257 of SEQ ID NO: 40. In some embodiments, the HVR2 region comprises a residue corresponding to residue 264 of SEQ ID NO: 40. In some embodiments, the HVR2 region comprises residues 215-270 of SEQ ID NO: 40 with up to 1, 2, 3, 4, 5, 6, 7, 8, 9, 10, or 11 amino acid substitutions. In some embodiments, the HVR2 region comprises residues 215-270 of SEQ ID NO: 40.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 40. In some embodiments, the second subunit comprises G, S, or A at a residue corresponding to residue 210 of SEQ ID NO: 40. In some embodiments, the second subunit comprises E, Q, or K at a residue corresponding to residue 271 of SEQ ID NO: 40. In some embodiments, the second subunit comprises a residue corresponding to residue 271 of SEQ ID NO: 40. In some embodiments, the second subunit comprises a residue corresponding to residue 330 of SEQ ID NO: 40. In some embodiments, the second subunit comprises residues 198-344 of SEQ ID NO: 40 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 40.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 40. In some embodiments, the engineered meganuclease comprises an amino acid sequence of SEQ ID NO: 40. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 54. In some embodiments, the engineered meganuclease is encoded by a nucleic acid sequence set forth in SEQ ID NO: 54.

DMD 19-20L.374 (SEQ ID NO: 41)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 41. In some embodiments, the HVR1 region comprises one or more residues corresponding to residues 24, 26, 28, 30, 32, 33, 38, 40, 42, 44, 46, 68, 70, 75, and 77 of SEQ ID NO: 41. In some embodiments, the HVR1 region comprises residues corresponding to residues 24, 26, 28, 30, 32, 33, 38, 40, 42, 44, 46, 68, 70, 75, and 77 of SEQ ID NO: 41. In some embodiments, the HVR1 region comprises Y, R, K, or D at a residue corresponding to residue 66 of SEQ ID NO: 40. In some embodiments, the HVR1 region comprises residues 24-79 of SEQ ID NO: 41 with up to 1, 2, 3, 4, 5, 6, 7, 8, 9, 10, or 11 amino acid substitutions. In some embodiments, the HVR1 region comprises residues 24-79 of SEQ ID NO: 41.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 41. In some embodiments, the first subunit comprises G, S, or A at a residue corresponding to residue 19 of SEQ ID NO: 41. In some embodiments, the first subunit comprises a residue corresponding to residue 19 of SEQ ID NO: 41. In some embodiments, the first subunit comprises E, Q, or K at a residue corresponding to residue 80 of SEQ ID NO: 41. In some embodiments, the first subunit comprises residues 7-153 of SEQ ID NO: 41 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 41.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 41. In some embodiments, the HVR2 region comprises one or more residues corresponding to residues 215, 217, 219, 221, 223, 224, 229, 231, 233, 235, 237, 259, 261, 266, and 268 of SEQ ID NO: 41. In some embodiments, the HVR2 region comprises residues corresponding to residues 215, 217, 219, 221, 223, 224, 229, 231, 233, 235, 237, 259, 261, 266, and 268 of SEQ ID NO: 41. In some embodiments, the HVR2 region comprises Y, R, K, or D at a residue corresponding to residue 257 of SEQ TD NO: 41. In some embodiments, the HVR2 region comprises a residue corresponding to residue 264 of SEQ ID NO: 41. In some embodiments, the HVR2 region comprises residues 215-270 of SEQ ID NO: 41 with up to 1, 2, 3, 4, 5, 6, 7, 8, 9, 10, or 11 amino acid substitutions. In some embodiments, the HVR2 region comprises residues 215-270 of SEQ ID NO: 41.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 41. In some embodiments, the second subunit comprises G, S, or A at a residue corresponding to residue 210 of SEQ ID NO: 41. In some embodiments, the second subunit comprises E, Q, or K at a residue corresponding to residue 271 of SEQ ID NO: 41. In some embodiments, the second subunit comprises a residue corresponding to residue 330 of SEQ ID NO: 41. In some embodiments, the second subunit comprises residues 198-344 of SEQ ID NO: 41 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 41.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 41. In some embodiments, the engineered meganuclease comprises an amino acid sequence of SEQ ID NO: 41. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 65. In some embodiments, the engineered meganuclease is encoded by a nucleic acid sequence set forth in SEQ ID NO: 65.

DMD 19-20L.375 (SEQ ID NO: 42)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 42. In some embodiments, the HVR1 region comprises one or more residues corresponding to residues 24, 26, 28, 30, 32, 33, 38, 40, 42, 44, 46, 68, 70, 75, and 77 of SEQ ID NO: 42. In some embodiments, the HVR1 region comprises residues corresponding to residues 24, 26, 28, 30, 32, 33, 38, 40, 42, 44, 46, 68, 70, 75, and 77 of SEQ ID NO: 42. In some embodiments, the HVR1 region comprises Y, R, K, or D at a residue corresponding to residue 66 of SEQ ID NO: 42. In some embodiments, the HVR1 region comprises residues 24-79 of SEQ ID NO: 42 with up to 1, 2, 3, 4, 5, 6, 7, 8, 9, 10, or 11 amino acid substitutions. In some embodiments, the HVR1 region comprises residues 24-79 of SEQ ID NO: 42.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 42. In some embodiments, the first subunit comprises G, S, or A at a residue corresponding to residue 19 of SEQ ID NO: 42. In some embodiments, the first subunit comprises a residue corresponding to residue 19 of SEQ ID NO: 42. In some embodiments, the first subunit comprises E, Q, or K at a residue corresponding to residue 80 of SEQ ID NO: 42. In some embodiments, the first subunit comprises residues 7-153 of SEQ ID NO: 42 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 42.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 42. In some embodiments, the HVR2 region comprises one or more residues corresponding to residues 215, 217, 219, 221, 223, 224, 229, 231, 233, 235, 237, 259, 261, 266, and 268 of SEQ ID NO: 42. In some embodiments, the HVR2 region comprises residues corresponding to residues 215, 217, 219, 221, 223, 224, 229, 231, 233, 235, 237, 259, 261, 266, and 268 of SEQ ID NO: 42. In some embodiments, the HVR2 region comprises Y, R, K, or D at a residue corresponding to residue 257 of SEQ ID NO: 42. In some embodiments, the HVR2 region comprises a residue corresponding to residue 264 of SEQ ID NO: 42. In some embodiments, the HVR2 region comprises residues 215-270 of SEQ ID NO: 42 with up to 1, 2, 3, 4, 5, 6, 7, 8, 9, 10, or 11 amino acid substitutions. In some embodiments, the HVR2 region comprises residues 215-270 of SEQ ID NO: 42.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 42. In some embodiments, the second subunit comprises G, S, or A at a residue corresponding to residue 210 of SEQ ID NO: 42. In some embodiments, the second subunit comprises E, Q, or K at a residue corresponding to residue 271 of SEQ ID NO: 42. In some embodiments, the second subunit comprises a residue corresponding to residue 330 of SEQ TD NO: 42. In some embodiments, the second subunit comprises residues 198-344 of SEQ ID NO: 42 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 42.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 42. In some embodiments, the engineered meganuclease comprises an amino acid sequence of SEQ ID NO: 42. In some embodiments, the engineered meganuclease is encoded by a nucleic acid sequence having at least 80%, 85%, 90%, 91%, 92%, 93%, 94%, 95%, 96%, 97%, 98%, 99% or more sequence identity to a nucleic acid sequence set forth in SEQ ID NO: 66. In some embodiments, the engineered meganuclease is encoded by a nucleic acid sequence set forth in SEQ ID NO: 66.

DMD 19-20L.431 (SEQ ID NO: 43)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 43. In some embodiments, the HVR1 region comprises one or more residues corresponding to residues 24, 26, 28, 30, 32, 33, 38, 40, 42, 44, 46, 68, 70, 75, and 77 of SEQ ID NO: 43. In some embodiments, the HVR1 region comprises residues corresponding to residues 24, 26, 28, 30, 32, 33, 38, 40, 42, 44, 46, 68, 70, 75, and 77 of SEQ ID NO: 43. In some embodiments, the HVR1 region comprises Y, R, K, or D at a residue corresponding to residue 66 of SEQ ID NO: 43. In some embodiments, the HVR1 region comprises residues 24-79 of SEQ ID NO: 43 with up to 1, 2, 3, 4, 5, 6, 7, 8, 9, 10, or 11 amino acid substitutions. In some embodiments, the HVR1 region comprises residues 24-79 of SEQ ID NO: 43.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 43. In some embodiments, the first subunit comprises G, S, or A at a residue corresponding to residue 19 of SEQ ID NO: 43. In some embodiments, the first subunit comprises a residue corresponding to residue 19 of SEQ ID NO: 43. In some embodiments, the first subunit comprises E, Q, or K at a residue corresponding to residue 80 of SEQ ID NO: 43. In some embodiments, the first subunit comprises a residue corresponding to residue 80 of SEQ ID NO: 43. In some embodiments, the first subunit comprises residues 7-153 of SEQ ID NO: 43 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 43.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 43. In some embodiments, the HVR2 region comprises one or more residues corresponding to residues 215, 217, 219, 221, 223, 224, 229, 231, 233, 235, 237, 259, 261, 266, and 268 of SEQ ID NO: 43. In some embodiments, the HVR2 region comprises residues corresponding to residues 215, 217, 219, 221, 223, 224, 229, 231, 233, 235, 237, 259, 261, 266, and 268 of SEQ ID NO: 43. In some embodiments, the HVR2 region comprises Y, R, K, or D at a residue corresponding to residue 257 of SEQ ID NO: 43. In some embodiments, the HVR2 region comprises a residue corresponding to residue 264 of SEQ ID NO: 43. In some embodiments, the HVR2 region comprises residues 215-270 of SEQ ID NO: 43 with up to 1, 2, 3, 4, 5, 6, 7, 8, 9, 10, or 11 amino acid substitutions. In some embodiments, the HVR2 region comprises residues 215-270 of SEQ ID NO: 43.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 43. In some embodiments, the second subunit comprises G, S, or A at a residue corresponding to residue 210 of SEQ ID NO:

43. In some embodiments, the second subunit comprises E, Q, or K at a residue corresponding to residue 271 of SEQ ID NO: 43. In some embodiments, the second subunit comprises a residue corresponding to residue 271 of SEQ ID NO: 43. In some embodiments, the second subunit comprises a residue corresponding to residue 330 of SEQ ID NO: 43. In some embodiments, the second subunit comprises residues 198-344 of SEQ ID NO: 43 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 43.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 43. In some embodiments, the engineered meganuclease comprises an amino acid sequence of SEQ ID NO: 43. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 67. In some embodiments, the engineered meganuclease is encoded by a nucleic acid sequence set forth in SEQ ID NO: 67.

DMD 19-20L.458 (SEQ ID NO: 44)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 44. In some embodiments, the HVR1 region comprises one or more residues corresponding to residues 24, 26, 28, 30, 32, 33, 38, 40, 42, 44, 46, 68, 70, 75, and 77 of SEQ ID NO: 44. In some embodiments, the HVR1 region comprises residues corresponding to residues 24, 26, 28, 30, 32, 33, 38, 40, 42, 44, 46, 68, 70, 75, and 77 of SEQ ID NO: 44. In some embodiments, the HVR1 region comprises Y, R, K, or D at a residue corresponding to residue 66 of SEQ ID NO: 44. In some embodiments, the HVR1 region comprises residues 24-79 of SEQ ID NO: 44 with up to 1, 2, 3, 4, 5, 6, 7, 8, 9, 10, or 11 amino acid substitutions. In some embodiments, the HVR1 region comprises residues 24-79 of SEQ ID NO: 44.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 44. In some embodiments, the first subunit comprises G, S. or A at a residue corresponding to residue 19 of SEQ ID NO: 44. In some embodiments, the first subunit comprises a residue corresponding to residue 19 of SEQ ID NO: 44. In some embodiments, the first subunit comprises E, Q, or K at a residue corresponding to residue 80 of SEQ ID NO: 44. In some embodiments, the first subunit comprises residues 7-153 of SEQ ID NO: 44 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 44.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 44. In some embodiments, the HVR2 region comprises one or more residues corresponding to residues 215, 217, 219, 221, 223, 224, 229, 231, 233, 235, 237, 259, 261, 266, and 268 of SEQ ID NO: 44. In some embodiments, the HVR2 region comprises residues corresponding to residues 215, 217, 219, 221, 223, 224, 229, 231, 233, 235, 237, 259, 261, 266, and 268 of SEQ ID NO: 44. In some embodiments, the HVR2 region comprises Y, R, K, or D at a residue corresponding to residue 257 of SEQ ID NO: 44. In some embodiments, the HVR2 region comprises a residue corresponding to residue 264 of SEQ ID NO: 44. In some embodiments, the HVR2 region comprises residues 215-270 of SEQ ID NO: 44 with up to 1, 2, 3, 4, 5, 6, 7, 8, 9, 10, or 11 amino acid substitutions. In some embodiments, the HVR2 region comprises residues 215-270 of SEQ ID NO: 44.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 44. In some embodiments, the second subunit comprises G, S, or A at a residue corresponding to residue 210 of SEQ ID NO: 44. In some embodiments, the second subunit comprises E, Q, or K at a residue corresponding to residue 271 of SEQ ID NO: 44. In some embodiments, the second subunit comprises a residue corresponding to residue 271 of SEQ ID NO: 44. In some embodiments, the second subunit comprises a residue corresponding to residue 330 of SEQ ID NO: 44. In some embodiments, the second subunit comprises residues 198-344 of SEQ ID NO: 44 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 44.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 44. In some embodiments, the engineered meganuclease comprises an amino acid sequence of SEQ ID NO: 44. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 68. In some embodiments, the engineered meganuclease is encoded by a nucleic acid sequence set forth in SEQ ID NO: 68.

In certain embodiments of the invention, the engineered meganuclease binds and cleaves a recognition sequence comprising SEQ ID NO: 10 (i.e., the DMD 35-36 recognition sequence) within a dystrophin gene, wherein the engineered meganuclease comprises a first subunit and a second subunit, wherein the first subunit hinds to a first recognition half-site of the recognition sequence and comprises a first hypervariable (HVR1) region, and wherein the second subunit binds to a second recognition half-site of the recognition sequence and comprises a second hypervariable (HVR2) region. Exemplary DMD 35-36 meganucleases are described below.

DMD 35-36x.63 (SEQ ID NO: 45)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 45. In some embodiments, the HVR1 region comprises one or more residues corresponding to residues 24, 26, 28, 30, 32, 33, 38, 40, 42, 44, 46, 68, 70, 75, and 77 of SEQ ID NO: 45. In some embodiments, the HVR1 region comprises residues corresponding to residues 24, 26, 28, 30, 32, 33, 38, 40, 42, 44, 46, 68, 70, 75, and 77 of SEQ ID NO: 45. In some embodiments, the HVR1 region comprises Y, R, K, or D at a residue corresponding to residue 66 of SEQ ID NO: 45. In some embodiments, the HVR1 region comprises residues 24-79 of SEQ ID NO: 45 with up to 1, 2, 3, 4, 5, 6, 7, 8, 9, 10, or 11 amino acid substitutions. In some embodiments, the HVR1 region comprises residues 24-79 of SEQ ID NO: 45.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 45. In some embodiments, the first subunit comprises G, S, or A at a residue corresponding to residue 19 of SEQ ID NO: 45. In some embodiments, the first subunit comprises a residue corresponding to residue 19 of SEQ ID NO: 45. In some embodiments, the first subunit comprises E, Q, or K at a residue corresponding to residue 80 of SEQ ID NO: 45. In some embodiments, the first subunit comprises a residue corresponding to residue 80 of SEQ ID NO: 45. In some embodiments, the first subunit comprises residues 7-153 of SEQ ID NO: 45 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 45.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 45. In some embodiments, the HVR2 region comprises one or more residues corresponding to residues 215, 217, 219, 221, 223, 224, 229, 231, 233, 235, 237, 259, 261, 266, and 268 of SEQ ID NO: 45. In some embodiments, the HVR2 region comprises residues corresponding to residues 215, 217, 219, 221, 223, 224, 229, 231, 233, 235, 237, 259, 261, 266, and 268 of SEQ ID NO: 45. In some embodiments, the HVR2 region comprises Y, R, K, or D at a residue corresponding to residue 257 of SEQ ID NO: 45. In some embodiments, the HVR2 region comprises a residue corresponding to residue 239 of SEQ ID NO: 45. In some embodiments, the HVR2 region comprises a residue corresponding to residue 241 of SEQ ID NO: 45. In some embodiments, the HVR2 region comprises a residue corresponding to residue 250 of SEQ ID NO: 45. In some embodiments, the HVR2 region comprises a residue corresponding to residue 263 of SEQ ID NO: 45. In some embodiments, the HVR2 region comprises a residue corresponding to residue 264 of SEQ ID NO: 45. In some embodiments, the HVR2 region comprises residues 215-270 of SEQ ID NO: 45 with up to 1, 2, 3, 4, 5, 6, 7, 8, 9, 10, or 11 amino acid substitutions. In some embodiments, the HVR2 region comprises residues 215-270 of SEQ ID NO: 45. In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 45. In some embodiments, the second subunit comprises G, S, or A at a residue corresponding to residue 210 of SEQ ID NO: 45. In some embodiments, the second subunit comprises E, Q, or K at a residue corresponding to residue 271 of SEQ ID NO: 45. In some embodiments, the second subunit comprises a residue corresponding to residue 330 of SEQ ID NO: 45. In some embodiments, the second subunit comprises residues 198-344 of SEQ ID NO: 45 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 45.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 45. In some embodiments, the engineered meganuclease comprises an amino acid sequence of SEQ ID NO: 45. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 69. In some embodiments, the engineered meganuclease is encoded by a nucleic acid sequence set forth in SEQ ID NO: 69.

DMD 35-36x.81 (SEQ ID NO: 46)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 46. In some embodiments, the HVR1 region comprises one or more residues corresponding to residues 24, 26, 28, 30, 32, 33, 38, 40, 42, 44, 46, 68, 70, 75, and 77 of SEQ ID NO: 46. In some embodiments, the HVR1 region comprises residues corresponding to residues 24, 26, 28, 30, 32, 33, 38, 40, 42, 44, 46, 68, 70, 75, and 77 of SEQ ID NO: 46. In some embodiments, the HVR1 region comprises Y, R, K, or D at a residue corresponding to residue 66 of SEQ ID NO: 46. In some embodiments, the HVR1 region comprises residues 24-79 of SEQ ID NO: 46 with up to 1, 2, 3, 4, 5, 6, 7, 8, 9, 10, or 11 amino acid substitutions. In some embodiments, the HVR1 region comprises residues 24-79 of SEQ ID NO: 46.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 46. In some embodiments, the first subunit comprises G, S, or A at a residue corresponding to residue 19 of SEQ ID NO: 46. In some embodiments, the first subunit comprises a residue corresponding to residue 19 of SEQ ID NO: 46. In some embodiments, the first subunit comprises E, Q, or K at a residue corresponding to residue 80 of SEQ ID NO: 46. In some embodiments, the first subunit comprises a residue corresponding to residue 80 of SEQ ID NO: 46. In some embodiments, the first subunit comprises residues 7-153 of SEQ ID NO: 46 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 46.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 46. In some embodiments, the HVR2 region comprises one or more residues corresponding to residues 215, 217, 219, 221, 223, 224, 229, 231, 233, 235, 237, 259, 261, 266, and 268 of SEQ ID NO: 46. In some embodiments, the HVR2 region comprises residues corresponding to residues 215, 217, 219, 221, 223, 224, 229, 231, 233, 235, 237, 259, 261, 266, and 268 of SEQ ID NO: 46. In some embodiments, the HVR2 region comprises Y, R. K, or D at a residue corresponding to residue 257 of SEQ ID NO: 46. In some embodiments, the HVR2 region comprises a residue corresponding to residue 239 of SEQ ID NO: 46. In some embodiments, the HVR2 region comprises a residue corresponding to residue 241 of SEQ ID NO: 46. In some embodiments, the HVR2 region comprises a residue corresponding to residue 263 of SEQ ID NO: 46. In some embodiments, the HVR2 region comprises a residue corresponding to residue 264 of SEQ ID NO: 46. In some embodiments, the HVR2 region comprises residues 215-270 of SEQ ID NO: 46 with up to 1, 2, 3, 4, 5, 6, 7, 8, 9, 10, or 11 amino acid substitutions. In some embodiments, the HVR2 region comprises residues 215-270 of SEQ ID NO: 46.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 46. In some embodiments, the second subunit comprises G, S, or A at a residue corresponding to residue 210 of SEQ ID NO: 46. In some embodiments, the second subunit comprises E, Q, or K at a residue corresponding to residue 271 of SEQ ID NO: 46. In some embodiments, the second subunit comprises a residue corresponding to residue 330 of SEQ ID NO: 46. In some embodiments, the second subunit comprises residues 198-344 of SEQ ID NO: 46 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 46.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 46. In some embodiments, the engineered meganuclease comprises an amino acid sequence of SEQ ID NO: 46. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 70. In some embodiments, the engineered meganuclease is encoded by a nucleic acid sequence set forth in SEQ ID NO: 70.

DMD 35-36L.195 (SEQ ID NO: 47)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 47. In some embodiments, the HVR1 region comprises one or more residues corresponding to residues 24, 26, 28, 30, 32, 33, 38, 40, 42, 44, 46, 68, 70, 75, and 77 of SEQ ID NO: 47. In some embodiments, the HVR1 region comprises residues corresponding to residues 24, 26, 28, 30, 32, 33, 38, 40, 42, 44, 46, 68, 70, 75, and 77 of SEQ ID NO: 47. In some embodiments, the HVR1 region comprises Y, R, K, or D at a residue corresponding to residue 66 of SEQ ID NO: 47. In some embodiments, the HVR1 region comprises residues 24-79 of SEQ ID NO: 47 with up to 1, 2, 3, 4, 5, 6, 7, 8, 9, 10, or 11 amino acid substitutions. In some embodiments, the HVR1 region comprises residues 24-79 of SEQ ID NO: 47.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 47. In some embodiments, the first subunit comprises G, S, or A at a residue corresponding to residue 19 of SEQ ID NO: 47. In some embodiments, the first subunit comprises a residue corresponding to residue 19 of SEQ ID NO: 47. In some embodiments, the first subunit comprises E, Q, or K at a residue corresponding to residue 80 of SEQ ID NO: 47. In some embodiments, the first subunit comprises a residue corresponding to residue 80 of SEQ ID NO: 47. In some embodiments, the first subunit comprises residues 7-153 of SEQ ID NO: 47 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 47.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 47. In some embodiments, the HVR2 region comprises one or more residues corresponding to residues 215, 217, 219, 221, 223, 224, 229, 231, 233, 235, 237, 259, 261, 266, and 268 of SEQ ID NO: 47. In some embodiments, the HVR2 region comprises residues corresponding to residues 215, 217, 219, 221, 223, 224, 229, 231, 233, 235, 237, 259, 261, 266, and 268 of SEQ ID NO: 47. In some embodiments, the HVR2 region comprises Y, R, K, or D at a residue corresponding to residue 257 of SEQ ID NO: 47. In some embodiments, the HVR2 region comprises a residue corresponding to residue 239 of SEQ ID NO: 47. In some embodiments, the HVR2 region comprises a residue corresponding to residue 241 of SEQ ID NO: 47. In some embodiments, the HVR2 region comprises a residue corresponding to residue 264 of SEQ ID NO: 47. In some embodiments, the HVR2 region comprises residues 215-270 of SEQ ID NO: 47 with up to 1, 2, 3, 4, 5, 6, 7, 8, 9, 10, or 11 amino acid substitutions. In some embodiments, the HVR2 region comprises residues 215-270 of SEQ ID NO: 47.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 47. In some embodiments, the second subunit comprises G, S, or A at a residue corresponding to residue 210 of SEQ ID NO: 47. In some embodiments, the second subunit comprises E, Q, or K at a residue corresponding to residue 271 of SEQ ID NO: 47. In some embodiments, the second subunit comprises a residue corresponding to residue 330 of SEQ ID NO: 47. In some embodiments, the second subunit comprises residues 198-344 of SEQ TD NO: 47 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 47.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 47. In some embodiments, the engineered meganuclease comprises an amino acid sequence of SEQ ID NO: 47. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 71. In some embodiments, the engineered meganuclease is encoded by a nucleic acid sequence set forth in SEQ ID NO: 71.

DMD 35-36L.282 (SEQ ID NO: 48)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 48. In some embodiments, the HVR1 region comprises one or more residues corresponding to residues 24, 26, 28, 30, 32, 33, 38, 40, 42, 44, 46, 68, 70, 75, and 77 of SEQ ID NO: 48. In some embodiments, the HVR1 region comprises residues corresponding to residues 24, 26, 28, 30, 32, 33, 38, 40, 42, 44, 46, 68, 70, 75, and 77 of SEQ ID NO: 48. In some embodiments, the HVR1 region comprises Y, R, K, or D at a residue corresponding to residue 66 of SEQ ID NO: 48. In some embodiments, the HVR1 region comprises residues 24-79 of SEQ ID NO: 48 with up to 1, 2, 3, 4, 5, 6, 7, 8, 9, 10, or 11 amino acid substitutions. In some embodiments, the HVR1 region comprises residues 24-79 of SEQ ID NO: 48.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 48. In some embodiments, the first subunit comprises G, S, or A at a residue corresponding to residue 19 of SEQ ID NO: 48. In some embodiments, the first subunit comprises a residue corresponding to residue 19 of SEQ ID NO: 48. In some embodiments, the first subunit comprises E, Q, or K at a residue corresponding to residue 80 of SEQ ID NO: 48. In some embodiments, the first subunit comprises a residue corresponding to residue 80 of SEQ ID NO: 48. In some embodiments, the first subunit comprises residues 7-153 of SEQ ID NO: 48 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 48.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 48. In some embodiments, the HVR2 region comprises one or more residues corresponding to residues 215, 217, 219, 221, 223, 224, 229, 231, 233, 235, 237, 259, 261, 266, and 268 of SEQ ID NO: 48. In some embodiments, the HVR2 region comprises residues corresponding to residues 215, 217, 219, 221, 223, 224, 229, 231, 233, 235, 237, 259, 261, 266, and 268 of SEQ ID NO: 48. In some embodiments, the HVR2 region comprises Y, R, K, or D at a residue corresponding to residue 257 of SEQ ID NO: 48. In some embodiments, the HVR2 region comprises a residue corresponding to residue 239 of SEQ ID NO: 48. In some embodiments, the HVR2 region comprises a residue corresponding to residue 241 of SEQ ID NO: 48. In some embodiments, the HVR2 region comprises a residue corresponding to residue 264 of SEQ TD NO: 48. In some embodiments, the HVR2 region comprises residues 215-270 of SEQ ID NO: 48 with up to 1, 2, 3, 4, 5, 6, 7, 8, 9, 10, or 11 amino acid substitutions. In some embodiments, the HVR2 region comprises residues 215-270 of SEQ ID NO: 48.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 48. In some embodiments, the second subunit comprises G, S, or A at a residue corresponding to residue 210 of SEQ ID NO: 48. In some embodiments, the second subunit comprises E, Q, or K at a residue corresponding to residue 271 of SEQ ID NO: 48. In some embodiments, the second subunit comprises a residue corresponding to residue 330 of SEQ ID NO: 48. In some embodiments, the second subunit comprises residues 198-344 of SEQ ID NO: 48 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 48.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 48. In some embodiments, the engineered meganuclease comprises an amino acid sequence of SEQ ID NO: 48. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 72. In some embodiments, the engineered meganuclease is encoded by a nucleic acid sequence set forth in SEQ ID NO: 72.

DMD 35-36L.349 (SEQ ID NO: 49)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 49. In some embodiments, the HVR1 region comprises one or more residues corresponding to residues 24, 26, 28, 30, 32, 33, 38, 40, 42, 44, 46, 68, 70, 75, and 77 of SEQ ID NO: 49. In some embodiments, the HVR1 region comprises residues corresponding to residues 24, 26, 28, 30, 32, 33, 38, 40, 42, 44, 46, 68, 70, 75, and 77 of SEQ ID NO: 49. In some embodiments, the HVR1 region comprises Y, R, K, or D at a residue corresponding to residue 66 of SEQ ID NO: 49. In some embodiments, the HVR1 region comprises residues 24-79 of SEQ ID NO: 49 with up to 1, 2, 3, 4, 5, 6, 7, 8, 9, 10, or 11 amino acid substitutions. In some embodiments, the HVR1 region comprises residues 24-79 of SEQ ID NO: 49.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 49. In some embodiments, the first subunit comprises G, S, or A at a residue corresponding to residue 19 of SEQ ID NO: 49. In some embodiments, the first subunit comprises a residue corresponding to residue 19 of SEQ ID NO: 49. In some embodiments, the first subunit comprises E, Q, or K at a residue corresponding to residue 80 of SEQ ID NO: 49. In some embodiments, the first subunit comprises a residue corresponding to residue 80 of SEQ ID NO: 49. In some embodiments, the first subunit comprises residues 7-153 of SEQ ID NO: 49 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 49.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 49. In some embodiments, the HVR2 region comprises one or more residues corresponding to residues 215, 217, 219, 221, 223, 224, 229, 231, 233, 235, 237, 259, 261, 266, and 268 of SEQ ID NO: 49. In some embodiments, the HVR2 region comprises residues corresponding to residues 215, 217, 219, 221, 223, 224, 229, 231, 233, 235, 237, 259, 261, 266, and 268 of SEQ ID NO: 49. In some embodiments, the HVR2 region comprises Y, R, K, or D at a residue corresponding to residue 257 of SEQ ID NO: 49. In some embodiments, the HVR2 region comprises a residue corresponding to residue 239 of SEQ ID NO: 49. In some embodiments, the HVR2 region comprises a residue corresponding to residue 241 of SEQ ID NO: 49. In some embodiments, the HVR2 region comprises a residue corresponding to residue 264 of SEQ ID NO: 49. In some embodiments, the HVR2 region comprises residues 215-270 of SEQ ID NO: 49 with up to 1, 2, 3, 4, 5, 6, 7, 8, 9, 10, or 11 amino acid substitutions. In some embodiments, the HVR2 region comprises residues 215-270 of SEQ ID NO: 49.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 49. In some embodiments, the second subunit comprises G, S, or A at a residue corresponding to residue 210 of SEQ ID NO: 49. In some embodiments, the second subunit comprises E, Q, or K at a residue corresponding to residue 271 of SEQ ID NO: 49. In some embodiments, the second subunit comprises a residue corresponding to residue 330 of SEQ ID NO: 49. In some embodiments, the second subunit comprises residues 198-344 of SEQ ID NO: 49 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 49.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 49. In some embodiments, the engineered meganuclease comprises an amino acid sequence of SEQ ID NO: 49. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 73. In some embodiments, the engineered meganuclease is encoded by a nucleic acid sequence set forth in SEQ ID NO: 73.

DMD 35-36L.376 (SEQ ID NO: 50)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 50. In some embodiments, the HVR1 region comprises one or more residues corresponding to residues 24, 26, 28, 30, 32, 33, 38, 40, 42, 44, 46, 68, 70, 75, and 77 of SEQ ID NO: 50. In some embodiments, the HVR1 region comprises residues corresponding to residues 24, 26, 28, 30, 32, 33, 38, 40, 42, 44, 46, 68, 70, 75, and 77 of SEQ ID NO: 50. In some embodiments, the HVR1 region comprises Y, R, K, or D at a residue corresponding to residue 66 of SEQ ID NO: 50. In some embodiments, the HVR1 region comprises residues 24-79 of SEQ ID NO: 50 with up to 1, 2, 3, 4, 5, 6, 7, 8, 9, 10, or 11 amino acid substitutions. In some embodiments, the HVR1 region comprises residues 24-79 of SEQ ID NO: 50.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 50. In some embodiments, the first subunit comprises G, S, or A at a residue corresponding to residue 19 of SEQ ID NO: 50. In some embodiments, the first subunit comprises a residue corresponding to residue 19 of SEQ ID NO: 50. In some embodiments, the first subunit comprises E, Q, or K at a residue corresponding to residue 80 of SEQ ID NO: 50. In some embodiments, the first subunit comprises a residue corresponding to residue 80 of SEQ ID NO: 50. In some embodiments, the first subunit comprises residues 7-153 of SEQ ID NO: 50 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 50.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 50. In some embodiments, the HVR2 region comprises one or more residues corresponding to residues 215, 217, 219, 221, 223, 224, 229, 231, 233, 235, 237, 259, 261, 266, and 268 of SEQ ID NO: 50. In some embodiments, the HVR2 region comprises residues corresponding to residues 215, 217, 219, 221, 223, 224, 229, 231, 233, 235, 237, 259, 261, 266, and 268 of SEQ ID NO: 50. In some embodiments, the HVR2 region comprises Y, R, K, or D at a residue corresponding to residue 257 of SEQ ID NO: 50. In some embodiments, the HVR2 region comprises a residue corresponding to residue 239 of SEQ ID NO: 50. In some embodiments, the HVR2 region comprises a residue corresponding to residue 241 of SEQ ID NO: 50. In some embodiments, the HVR2 region comprises a residue corresponding to residue 264 of SEQ ID NO: 50. In some embodiments, the HVR2 region comprises residues 215-270 of SEQ ID NO: 50 with up to 1, 2, 3, 4, 5, 6, 7, 8, 9, 10, or 11 amino acid substitutions. In some embodiments, the HVR2 region comprises residues 215-270 of SEQ ID NO: 50.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 50. In some embodiments, the second subunit comprises G, S, or A at a residue corresponding to residue 210 of SEQ ID NO: 50. In some embodiments, the second subunit comprises E, Q, or K at a residue corresponding to residue 271 of SEQ ID NO: 50. In some embodiments, the second subunit comprises a residue corresponding to residue 330 of SEQ ID NO: 50. In some embodiments, the second subunit comprises residues 198-344 of SEQ ID NO: 50 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 50.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 50. In some embodiments, the engineered meganuclease comprises an amino acid sequence of SEQ ID NO: 50. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 74. In some embodiments, the engineered meganuclease is encoded by a nucleic acid sequence set forth in SEQ ID NO: 74.

DMD 35-36L.457 (SEQ ID NO: 51)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 51. In some embodiments, the HVR1 region comprises one or more residues corresponding to residues 24, 26, 28, 30, 32, 33, 38, 40, 42, 44, 46, 68, 70, 75, and 77 of SEQ ID NO: 51. In some embodiments, the HVR1 region comprises residues corresponding to residues 24, 26, 28, 30, 32, 33, 38, 40, 42, 44, 46, 68, 70, 75, and 77 of SEQ ID NO: 51. In some embodiments, the HVR1 region comprises Y, R, K, or D at a residue corresponding to residue 66 of SEQ ID NO: 51. In some embodiments, the HVR1 region comprises residues 24-79 of SEQ ID NO: 51 with up to 1, 2, 3, 4, 5, 6, 7, 8, 9, 10, or 11 amino acid substitutions. In some embodiments, the HVR1 region comprises residues 24-79 of SEQ ID NO: 51.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 51. In some embodiments, the first subunit comprises G, S, or A at a residue corresponding to residue 19 of SEQ ID NO: 51. In some embodiments, the first subunit comprises a residue corresponding to residue 19 of SEQ ID NO: 51. In some embodiments, the first subunit comprises E, Q, or K at a residue corresponding to residue 80 of SEQ ID NO: 51. In some embodiments, the first subunit comprises a residue corresponding to residue 80 of SEQ ID NO: 51. In some embodiments, the first subunit comprises residues 7-153 of SEQ ID NO: 51 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 51.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 51. In some embodiments, the HVR2 region comprises one or more residues corresponding to residues 215, 217, 219, 221, 223, 224, 229, 231, 233, 235, 237, 259, 261, 266, and 268 of SEQ ID NO: 51. In some embodiments, the HVR2 region comprises residues corresponding to residues 215, 217, 219, 221, 223, 224, 229, 231, 233, 235, 237, 259, 261, 266, and 268 of SEQ ID NO: 51. In some embodiments, the HVR2 region comprises Y, R, K, or D at a residue corresponding to residue 257 of SEQ ID NO: 51. In some embodiments, the HVR2 region comprises a residue corresponding to residue 239 of SEQ ID NO: 51. In some embodiments, the HVR2 region comprises a residue corresponding to residue 241 of SEQ ID NO: 51. In some embodiments, the HVR2 region comprises a residue corresponding to residue 264 of SEQ ID NO: 51. In some embodiments, the HVR2 region comprises residues 215-270 of SEQ ID NO: 51 with up to 1, 2, 3, 4, 5, 6, 7, 8, 9, 10, or 11 amino acid substitutions. In some embodiments, the HVR2 region comprises residues 215-270 of SEQ ID NO: 51.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 51. In some embodiments, the second subunit comprises G, S, or A at a residue corresponding to residue 210 of SEQ ID NO: 51. In some embodiments, the second subunit comprises E, Q, or K at a residue corresponding to residue 271 of SEQ ID NO: 51. In some embodiments, the second subunit comprises a residue corresponding to residue 330 of SEQ ID NO: 51. In some embodiments, the second subunit comprises residues 198-344 of SEQ ID NO: 51 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 51.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 51. In some embodiments, the engineered meganuclease comprises an amino acid sequence of SEQ ID NO: 51. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 75. In some embodiments, the engineered meganuclease is encoded by a nucleic acid sequence set forth in SEQ ID NO: 75.

DMD 35-36L.469 (SEQ ID NO: 52)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 52. In some embodiments, the HVR1 region comprises one or more residues corresponding to residues 24, 26, 28, 30, 32, 33, 38, 40, 42, 44, 46, 68, 70, 75, and 77 of SEQ ID NO: 52. In some embodiments, the HVR1 region comprises residues corresponding to residues 24, 26, 28, 30, 32, 33, 38, 40, 42, 44, 46, 68, 70, 75, and 77 of SEQ ID NO: 52. In some embodiments, the HVR1 region comprises Y, R, K, or D at a residue corresponding to residue 66 of SEQ ID NO: 52. In some embodiments, the HVR1 region comprises residues 24-79 of SEQ ID NO: 52 with up to 1, 2, 3, 4, 5, 6, 7, 8, 9, 10, or 11 amino acid substitutions. In some embodiments, the HVR1 region comprises residues 24-79 of SEQ ID NO: 52.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 52. In some embodiments, the first subunit comprises G, S, or A at a residue corresponding to residue 19 of SEQ ID NO: 52. In some embodiments, the first subunit comprises a residue corresponding to residue 19 of SEQ ID NO: 52. In some embodiments, the first subunit comprises E, Q, or K at a residue corresponding to residue 80 of SEQ ID NO: 52. In some embodiments, the first subunit comprises residues 7-153 of SEQ ID NO: 52 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 52.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 52. In some embodiments, the HVR2 region comprises one or more residues corresponding to residues 215, 217, 219, 221, 223, 224, 229, 231, 233, 235, 237, 259, 261, 266, and 268 of SEQ ID NO: 52. In some embodiments, the HVR2 region comprises residues corresponding to residues 215, 217, 219, 221, 223, 224, 229, 231, 233, 235, 237, 259, 261, 266, and 268 of SEQ ID NO: 52. In some embodiments, the HVR2 region comprises Y, R, K, or D at a residue corresponding to residue 257 of SEQ ID NO: 52. In some embodiments, the HVR2 region comprises a residue corresponding to residue 239 of SEQ ID NO: 52. In some embodiments, the HVR2 region comprises a residue corresponding to residue 241 of SEQ ID NO: 52. In some embodiments, the HVR2 region comprises a residue corresponding to residue 264 of SEQ ID NO: 52. In some embodiments, the HVR2 region comprises residues 215-270 of SEQ ID NO: 52 with up to 1, 2, 3, 4, 5, 6, 7, 8, 9, 10, or 11 amino acid substitutions. In some embodiments, the HVR2 region comprises residues 215-270 of SEQ ID NO: 52.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 52. In some embodiments, the second subunit comprises G, S, or A at a residue corresponding to residue 210 of SEQ ID NO: 52. In some embodiments, the second subunit comprises E, Q, or K at a residue corresponding to residue 271 of SEQ ID NO: 52. In some embodiments, the second subunit comprises a residue corresponding to residue 271 of SEQ ID NO: 52. In some embodiments, the second subunit comprises a residue corresponding to residue 330 of SEQ ID NO: 52. In some embodiments, the second subunit comprises residues 198-344 of SEQ ID NO: 52 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 52.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 52. In some embodiments, the engineered meganuclease comprises an amino acid sequence of SEQ ID NO: 52. In some embodiments, the engineered meganuclease is encoded by a nucleic acid sequence having at least 80%, 85%, 90%, 91%, 92%, 93%, 94%, 95%, 96%, 97%, 98%, 99% or more sequence identity to a nucleic acid sequence set forth in SEQ ID NO: 76. In some embodiments, the engineered meganuclease is encoded by a nucleic acid sequence set forth in SEQ ID NO: 76.

In certain embodiments of the invention, the engineered meganuclease binds and cleaves a recognition sequence comprising SEQ ID NO: 12 (i.e., the DMD 37-38 recognition sequence) within a dystrophin gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region. Exemplary DMD 37-38 meganucleases are described below.

DMD 37-38x.15 (SEQ ID NO: 53)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 53. In some embodiments, the HVR1 region comprises one or more residues corresponding to residues 24, 26, 28, 30, 32, 33, 38, 40, 42, 44, 46, 68, 70, 75, and 77 of SEQ ID NO: 53. In some embodiments, the HVR1 region comprises residues corresponding to residues 24, 26, 28, 30, 32, 33, 38, 40, 42, 44, 46, 68, 70, 75, and 77 of SEQ ID NO: 53. In some embodiments, the HVR1 region comprises Y, R, K, or D at a residue corresponding to residue 66 of SEQ ID NO: 53. In some embodiments, the HVR1 region comprises residues 24-79 of SEQ ID NO: 53 with up to 1, 2, 3, 4, 5, 6, 7, 8, 9, 10, or 11 amino acid substitutions. In some embodiments, the HVR1 region comprises residues 24-79 of SEQ ID NO: 53.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 53. In some embodiments, the first subunit comprises G, S, or A at a residue corresponding to residue 19 of SEQ ID NO: 53. In some embodiments, the first subunit comprises a residue corresponding to residue 19 of SEQ ID NO: 53. In some embodiments, the first subunit comprises E, Q, or K at a residue corresponding to residue 80 of SEQ ID NO: 53. In some embodiments, the first subunit comprises a residue corresponding to residue 80 of SEQ ID NO: 53. In some embodiments, the first subunit comprises residues 7-153 of SEQ ID NO: 53 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ TD NO: 53.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 53. In some embodiments, the HVR2 region comprises one or more residues corresponding to residues 215, 217, 219, 221, 223, 224, 229, 231, 233, 235, 237, 259, 261, 266, and 268 of SEQ ID NO: 53. In some embodiments, the HVR2 region comprises residues corresponding to residues 215, 217, 219, 221, 223, 224, 229, 231, 233, 235, 237, 259, 261, 266, and 268 of SEQ ID NO: 53. In some embodiments, the HVR2 region comprises Y, R, K, or D at a residue corresponding to residue 257 of SEQ ID NO: 53. In some embodiments, the HVR2 region comprises a residue corresponding to residue 239 of SEQ ID NO: 53. In some embodiments, the HVR2 region comprises a residue corresponding to residue 241 of SEQ ID NO: 53. In some embodiments, the HVR2 region comprises a residue corresponding to residue 264 of SEQ ID NO: 53. In some embodiments, the HVR2 region comprises residues 215-270 of SEQ ID NO: 53 with up to 1, 2, 3, 4, 5, 6, 7, 8, 9, 10, or 11 amino acid substitutions. In some embodiments, the HVR2 region comprises residues 215-270 of SEQ ID NO: 53.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 53. In some embodiments, the second subunit comprises G, S, or A at a residue corresponding to residue 210 of SEQ ID NO: 53. In some embodiments, the second subunit comprises E, Q, or K at a residue corresponding to residue 271 of SEQ ID NO: 53. In some embodiments, the second subunit comprises a residue corresponding to residue 271 of SEQ ID NO: 53. In some embodiments, the second subunit comprises residues 198-344 of SEQ ID NO: 53 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 53.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 53. In some embodiments, the engineered meganuclease comprises the amino acid sequence of SEQ ID NO: 53. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 77. In some embodiments, the engineered meganuclease is encoded by a nucleic sequence set forth in SEQ ID NO: 77. DMD 37-38x.66 (SEQ ID NO: 54)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 54. In some embodiments, the HVR1 region comprises one or more residues corresponding to residues 24, 26, 28, 30, 32, 33, 38, 40, 42, 44, 46, 68, 70, 75, and 77 of SEQ ID NO: 54. In some embodiments, the HVR1 region comprises residues corresponding to residues 24, 26, 28, 30, 32, 33, 38, 40, 42, 44, 46, 68, 70, 75, and 77 of SEQ ID NO: 54. In some embodiments, the HVR1 region comprises Y, R, K, or D at a residue corresponding to residue 66 of SEQ ID NO: 54. In some embodiments, the HVR1 region comprises a residue corresponding to residue 64 of SEQ ID NO: 54. In some embodiments, the HVR1 region comprises residues 24-79 of SEQ ID NO: 54 with up to 1, 2, 3, 4, 5, 6, 7, 8, 9, 10, or 11 amino acid substitutions. In some embodiments, the HVR1 region comprises residues 24-79 of SEQ ID NO: 54.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 54. In some embodiments, the first subunit comprises G, S. or A at a residue corresponding to residue 19 of SEQ ID NO: 54. In some embodiments, the first subunit comprises a residue corresponding to residue 19 of SEQ ID NO: 54. In some embodiments, the first subunit comprises E, Q, or K at a residue corresponding to residue 80 of SEQ ID NO: 54. In some embodiments, the first subunit comprises a residue corresponding to residue 80 of SEQ ID NO: 54. In some embodiments, the first subunit comprises residues 7-153 of SEQ ID NO: 54 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 54.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 54. In some embodiments, the HVR2 region comprises one or more residues corresponding to residues 215, 217, 219, 221, 223, 224, 229, 231, 233, 235, 237, 259, 261, 266, and 268 of SEQ ID NO: 54. In some embodiments, the HVR2 region comprises residues corresponding to residues 215, 217, 219, 221, 223, 224, 229, 231, 233, 235, 237, 259, 261, 266, and 268 of SEQ ID NO: 54. In some embodiments, the HVR2 region comprises Y, R, K, or D at a residue corresponding to residue 257 of SEQ ID NO: 54. In some embodiments, the HVR2 region comprises a residue corresponding to residue 241 of SEQ ID NO: 54. In some embodiments, the HVR2 region comprises a residue corresponding to residue 264 of SEQ ID NO: 54. In some embodiments, the HVR2 region comprises residues 215-270 of SEQ ID NO: 54 with up to 1, 2, 3, 4, 5, 6, 7, 8, 9, 10, or 11 amino acid substitutions. In some embodiments, the HVR2 region comprises residues 215-270 of SEQ ID NO: 54.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 54. In some embodiments, the second subunit comprises G, S, or A at a residue corresponding to residue 210 of SEQ ID NO: 54. In some embodiments, the second subunit comprises E, Q, or K at a residue corresponding to residue 271 of SEQ ID NO: 54. In some embodiments, the second subunit comprises a residue corresponding to residue 330 of SEQ ID NO: 54. In some embodiments, the second subunit comprises residues 198-344 of SEQ ID NO: 54 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 54.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 54. In some embodiments, the engineered meganuclease comprises the amino acid sequence of SEQ ID NO: 54. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 78. In some embodiments, the engineered meganuclease is encoded by a nucleic sequence set forth in SEQ ID NO: 78.

DMD 37-38x.79 (SEQ ID NO: 55)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 55. In some embodiments, the HVR1 region comprises one or more residues corresponding to residues 24, 26, 28, 30, 32, 33, 38, 40, 42, 44, 46, 68, 70, 75, and 77 of SEQ ID NO: 55. In some embodiments, the HVR1 region comprises residues corresponding to residues 24, 26, 28, 30, 32, 33, 38, 40, 42, 44, 46, 68, 70, 75, and 77 of SEQ ID NO: 55. In some embodiments, the HVR1 region comprises Y, R, K, or D at a residue corresponding to residue 66 of SEQ ID NO: 55. In some embodiments, the HVR1 region comprises residues 24-79 of SEQ ID NO: 55 with up to 1, 2, 3, 4, 5, 6, 7, 8, 9, 10, or 11 amino acid substitutions. In some embodiments, the HVR1 region comprises residues 24-79 of SEQ ID NO: 55.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 55. In some embodiments, the first subunit comprises G, S, or A at a residue corresponding to residue 19 of SEQ ID NO: 55. In some embodiments, the first subunit comprises a residue corresponding to residue 19 of SEQ ID NO: 55. In some embodiments, the first subunit comprises E, Q, or K at a residue corresponding to residue 80 of SEQ ID NO: 55. In some embodiments, the first subunit comprises a residue corresponding to residue 80 of SEQ ID NO: 55. In some embodiments, the first subunit comprises residues 7-153 of SEQ ID NO: 55 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 55.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 55. In some embodiments, the HVR2 region comprises one or more residues corresponding to residues 215, 217, 219, 221, 223, 224, 229, 231, 233, 235, 237, 259, 261, 266, and 268 of SEQ ID NO: 55. In some embodiments, the HVR2 region comprises residues corresponding to residues 215, 217, 219, 221, 223, 224, 229, 231, 233, 235, 237, 259, 261, 266, and 268 of SEQ ID NO: 55. In some embodiments, the HVR2 region comprises Y, R, K, or D at a residue corresponding to residue 257 of SEQ ID NO: 55. In some embodiments, the HVR2 region comprises a residue corresponding to residue 239 of SEQ ID NO: 55. In some embodiments, the HVR2 region comprises a residue corresponding to residue 241 of SEQ ID NO: 55. In some embodiments, the HVR2 region comprises a residue corresponding to residue 255 of SEQ ID NO: 55. In some embodiments, the HVR2 region comprises a residue corresponding to residue 264 of SEQ ID NO: 55. In some embodiments, the HVR2 region comprises residues 215-270 of SEQ ID NO: 55 with up to 1, 2, 3, 4, 5, 6, 7, 8, 9, 10, or 11 amino acid substitutions. In some embodiments, the HVR2 region comprises residues 215-270 of SEQ ID NO: 55.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 55. In some embodiments, the second subunit comprises G, S, or A at a residue corresponding to residue 210 of SEQ ID NO: 55. In some embodiments, the second subunit comprises E, Q, or K at a residue corresponding to residue 271 of SEQ ID NO: 55. In some embodiments, the second subunit comprises a residue corresponding to residue 271 of SEQ ID NO: 55. In some embodiments, the second subunit comprises a residue corresponding to residue 330 of SEQ ID NO: 55. In some embodiments, the second subunit comprises residues 198-344 of SEQ ID NO: 55 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 55.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 55. In some embodiments, the engineered meganuclease comprises the amino acid sequence of SEQ ID NO: 55. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 79. In some embodiments, the engineered meganuclease is encoded by a nucleic sequence set forth in SEQ ID NO: 79.

DMD 37-38L.166 (SEQ ID NO: 56)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 56. In some embodiments, the HVR1 region comprises one or more residues corresponding to residues 24, 26, 28, 30, 32, 33, 38, 40, 42, 44, 46, 68, 70, 75, and 77 of SEQ ID NO: 56. In some embodiments, the HVR1 region comprises residues corresponding to residues 24, 26, 28, 30, 32, 33, 38, 40, 42, 44, 46, 68, 70, 75, and 77 of SEQ ID NO: 56. In some embodiments, the HVR1 region comprises Y, R, K, or D at a residue corresponding to residue 66 of SEQ ID NO: 56. In some embodiments, the HVR1 region comprises residues 24-79 of SEQ ID NO: 56 with up to 1, 2, 3, 4, 5, 6, 7, 8, 9, 10, or 11 amino acid substitutions. In some embodiments, the HVR1 region comprises residues 24-79 of SEQ ID NO: 56.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 56. In some embodiments, the first subunit comprises G, S, or A at a residue corresponding to residue 19 of SEQ ID NO: 56. In some embodiments, the first subunit comprises a residue corresponding to residue 19 of SEQ ID NO: 56. In some embodiments, the first subunit comprises E, Q, or K at a residue corresponding to residue 80 of SEQ ID NO: 56. In some embodiments, the first subunit comprises residues 7-153 of SEQ ID NO: 56 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ TD NO: 56.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 56. In some embodiments, the HVR2 region comprises one or more residues corresponding to residues 215, 217, 219, 221, 223, 224, 229, 231, 233, 235, 237, 259, 261, 266, and 268 of SEQ ID NO: 56. In some embodiments, the HVR2 region comprises residues corresponding to residues 215, 217, 219, 221, 223, 224, 229, 231, 233, 235, 237, 259, 261, 266, and 268 of SEQ ID NO: 56. In some embodiments, the HVR2 region comprises Y, R, K, or D at a residue corresponding to residue 257 of SEQ ID NO: 56. In some embodiments, the HVR2 region comprises a residue corresponding to residue 263 of SEQ ID NO: 56. In some embodiments, the HVR2 region comprises a residue corresponding to residue 264 of SEQ ID NO: 56. In some embodiments, the HVR2 region comprises residues 215-270 of SEQ ID NO: 56 with up to 1, 2, 3, 4, 5, 6, 7, 8, 9, 10, or 11 amino acid substitutions. In some embodiments, the HVR2 region comprises residues 215-270 of SEQ ID NO: 56.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 56. In some embodiments, the second subunit comprises G, S, or A at a residue corresponding to residue 210 of SEQ ID NO: 56. In some embodiments, the second subunit comprises E, Q, or K at a residue corresponding to residue 271 of SEQ ID NO: 56. In some embodiments, the second subunit comprises a residue corresponding to residue 271 of SEQ ID NO: 56. In some embodiments, the second subunit comprises a residue corresponding to residue 330 of SEQ ID NO: 56. In some embodiments, the second subunit comprises residues 198-344 of SEQ ID NO: 56 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 56.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 56. In some embodiments, the engineered meganuclease comprises the amino acid sequence of SEQ ID NO: 56. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 80. In some embodiments, the engineered meganuclease is encoded by a nucleic sequence set forth in SEQ ID NO: 80. DMD 37-38L.478 (SEQ ID NO: 57)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 57. In some embodiments, the HVR1 region comprises one or more residues corresponding to residues 24, 26, 28, 30, 32, 33, 38, 40, 42, 44, 46, 68, 70, 75, and 77 of SEQ ID NO: 57. In some embodiments, the HVR1 region comprises residues corresponding to residues 24, 26, 28, 30, 32, 33, 38, 40, 42, 44, 46, 68, 70, 75, and 77 of SEQ ID NO: 57. In some embodiments, the HVR1 region comprises Y, R, K, or D at a residue corresponding to residue 66 of SEQ ID NO: 57. In some embodiments, the HVR1 region comprises residues 24-79 of SEQ ID NO: 57 with up to 1, 2, 3, 4, 5, 6, 7, 8, 9, 10, or 11 amino acid substitutions. In some embodiments, the HVR1 region comprises residues 24-79 of SEQ ID NO: 57.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 57. In some embodiments, the first subunit comprises G, S, or A at a residue corresponding to residue 19 of SEQ ID NO: 57. In some embodiments, the first subunit comprises a residue corresponding to residue 19 of SEQ ID NO: 57. In some embodiments, the first subunit comprises E, Q, or K at a residue corresponding to residue 80 of SEQ ID NO: 57. In some embodiments, the first subunit comprises a residue corresponding to residue 80 of SEQ ID NO: 57. In some embodiments, the first subunit comprises residues 7-153 of SEQ ID NO: 57 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 57.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 57. In some embodiments, the HVR2 region comprises one or more residues corresponding to residues 215, 217, 219, 221, 223, 224, 229, 231, 233, 235, 237, 259, 261, 266, and 268 of SEQ ID NO: 57. In some embodiments, the HVR2 region comprises residues corresponding to residues 215, 217, 219, 221, 223, 224, 229, 231, 233, 235, 237, 259, 261, 266, and 268 of SEQ ID NO: 57. In some embodiments, the HVR2 region comprises Y, R, K, or D at a residue corresponding to residue 257 of SEQ ID NO: 57. In some embodiments, the HVR2 region comprises a residue corresponding to residue 263 of SEQ ID NO: 57. In some embodiments, the HVR2 region comprises a residue corresponding to residue 264 of SEQ ID NO: 57. In some embodiments, the HVR2 region comprises residues 215-270 of SEQ ID NO: 57 with up to 1, 2, 3, 4, 5, 6, 7, 8, 9, 10, or 11 amino acid substitutions. In some embodiments, the HVR2 region comprises residues 215-270 of SEQ ID NO: 57.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 57. In some embodiments, the second subunit comprises G, S, or A at a residue corresponding to residue 210 of SEQ ID NO: 57. In some embodiments, the second subunit comprises E, Q, or K at a residue corresponding to residue 271 of SEQ ID NO: 57. In some embodiments, the second subunit comprises a residue corresponding to residue 271 of SEQ ID NO: 57. In some embodiments, the second subunit comprises a residue corresponding to residue 330 of SEQ ID NO: 57. In some embodiments, the second subunit comprises residues 198-344 of SEQ ID NO: 57 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 57.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 57. In some embodiments, the engineered meganuclease comprises the amino acid sequence of SEQ TD NO: 57. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 81. In some embodiments, the engineered meganuclease is encoded by a nucleic sequence set forth in SEQ ID NO: 81.

DMD 37-38L.512 (SEQ ID NO: 58)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 58. In some embodiments, the HVR1 region comprises one or more residues corresponding to residues 24, 26, 28, 30, 32, 33, 38, 40, 42, 44, 46, 68, 70, 75, and 77 of SEQ ID NO: 58. In some embodiments, the HVR1 region comprises residues corresponding to residues 24, 26, 28, 30, 32, 33, 38, 40, 42, 44, 46, 68, 70, 75, and 77 of SEQ ID NO: 58. In some embodiments, the HVR1 region comprises Y, R, K, or D at a residue corresponding to residue 66 of SEQ ID NO: 58. In some embodiments, the HVR1 region comprises residues 24-79 of SEQ ID NO: 58 with up to 1, 2, 3, 4, 5, 6, 7, 8, 9, 10, or 11 amino acid substitutions. In some embodiments, the HVR1 region comprises residues 24-79 of SEQ ID NO: 58.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 58. In some embodiments, the first subunit comprises G, S, or A at a residue corresponding to residue 19 of SEQ ID NO: 58. In some embodiments, the first subunit comprises a residue corresponding to residue 19 of SEQ ID NO: 58. In some embodiments, the first subunit comprises E, Q, or K at a residue corresponding to residue 80 of SEQ ID NO: 58. In some embodiments, the first subunit comprises a residue corresponding to residue 80 of SEQ ID NO: 58. In some embodiments, the first subunit comprises residues 7-153 of SEQ ID NO: 58 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 58.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 58. In some embodiments, the HVR2 region comprises one or more residues corresponding to residues 215, 217, 219, 221, 223, 224, 229, 231, 233, 235, 237, 259, 261, 266, and 268 of SEQ ID NO: 58. In some embodiments, the HVR2 region comprises residues corresponding to residues 215, 217, 219, 221, 223, 224, 229, 231, 233, 235, 237, 259, 261, 266, and 268 of SEQ ID NO: 58. In some embodiments, the HVR2 region comprises Y, R, K, or D at a residue corresponding to residue 257 of SEQ ID NO: 58. In some embodiments, the HVR2 region comprises a residue corresponding to residue 263 of SEQ ID NO: 58. In some embodiments, the HVR2 region comprises a residue corresponding to residue 264 of SEQ ID NO: 58. In some embodiments, the HVR2 region comprises residues 215-270 of SEQ ID NO: 58 with up to 1, 2, 3, 4, 5, 6, 7, 8, 9, 10, or 11 amino acid substitutions. In some embodiments, the HVR2 region comprises residues 215-270 of SEQ ID NO: 58.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 58. In some embodiments, the second subunit comprises G, S, or A at a residue corresponding to residue 210 of SEQ ID NO: 58. In some embodiments, the second subunit comprises E, Q, or K at a residue corresponding to residue 271 of SEQ ID NO: 58. In some embodiments, the second subunit comprises a residue corresponding to residue 271 of SEQ ID NO: 58. In some embodiments, the second subunit comprises a residue corresponding to residue 330 of SEQ ID NO: 58. In some embodiments, the second subunit comprises residues 198-344 of SEQ ID NO: 58 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 58.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 58. In some embodiments, the engineered meganuclease comprises the amino acid sequence of SEQ ID NO: 58. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 82. In some embodiments, the engineered meganuclease is encoded by a nucleic sequence set forth in SEQ ID NO: 82.

DMD 37-38L.528 (SEQ ID NO: 59)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 59. In some embodiments, the HVR1 region comprises one or more residues corresponding to residues 24, 26, 28, 30, 32, 33, 38, 40, 42, 44, 46, 68, 70, 75, and 77 of SEQ ID NO: 59. In some embodiments, the HVR1 region comprises residues corresponding to residues 24, 26, 28, 30, 32, 33, 38, 40, 42, 44, 46, 68, 70, 75, and 77 of SEQ ID NO: 59. In some embodiments, the HVR1 region comprises Y, R, K, or D at a residue corresponding to residue 66 of SEQ ID NO: 59. In some embodiments, the HVR1 region comprises residues 24-79 of SEQ ID NO: 59 with up to 1, 2, 3, 4, 5, 6, 7, 8, 9, 10, or 11 amino acid substitutions. In some embodiments, the HVR1 region comprises residues 24-79 of SEQ ID NO: 59.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 59. In some embodiments, the first subunit comprises G, S. or A at a residue corresponding to residue 19 of SEQ ID NO: 59. In some embodiments, the first subunit comprises a residue corresponding to residue 19 of SEQ ID NO: 59. In some embodiments, the first subunit comprises E, Q, or K at a residue corresponding to residue 80 of SEQ ID NO: 59. In some embodiments, the first subunit comprises residues 7-153 of SEQ ID NO: 59 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 59.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 59. In some embodiments, the HVR2 region comprises one or more residues corresponding to residues 215, 217, 219, 221, 223, 224, 229, 231, 233, 235, 237, 259, 261, 266, and 268 of SEQ ID NO: 59. In some embodiments, the HVR2 region comprises residues corresponding to residues 215, 217, 219, 221, 223, 224, 229, 231, 233, 235, 237, 259, 261, 266, and 268 of SEQ ID NO: 59. In some embodiments, the HVR2 region comprises Y, R, K, or D at a residue corresponding to residue 257 of SEQ ID NO: 59. In some embodiments, the HVR2 region comprises a residue corresponding to residue 263 of SEQ ID NO: 59. In some embodiments, the HVR2 region comprises a residue corresponding to residue 264 of SEQ ID NO: 59. In some embodiments, the HVR2 region comprises residues 215-270 of SEQ ID NO: 59 with up to 1, 2, 3, 4, 5, 6, 7, 8, 9, 10, or 11 amino acid substitutions. In some embodiments, the HVR2 region comprises residues 215-270 of SEQ ID NO: 59.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 59. In some embodiments, the second subunit comprises G, S, or A at a residue corresponding to residue 210 of SEQ ID NO: 59. In some embodiments, the second subunit comprises E, Q, or K at a residue corresponding to residue 271 of SEQ ID NO: 59. In some embodiments, the second subunit comprises a residue corresponding to residue 271 of SEQ ID NO: 59. In some embodiments, the second subunit comprises a residue corresponding to residue 330 of SEQ ID NO: 59. In some embodiments, the second subunit comprises residues 198-344 of SEQ ID NO: 59 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 59.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 59. In some embodiments, the engineered meganuclease comprises the amino acid sequence of SEQ ID NO: 59. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 83. In some embodiments, the engineered meganuclease is encoded by a nucleic sequence set forth in SEQ ID NO: 83.

2.3 Methods for Delivering and Expressing Engineered Meganucleases

In different aspects, the invention provides engineered meganucleases described herein that are useful for binding and cleaving recognition sequences within a dystrophin gene of a cell (e.g., the human dystrophin gene). The invention provides various methods for modifying a dystrophin gene in cells using engineered meganucleases described herein, methods for making genetically modified cells comprising a modified dystrophin gene, and methods of modifying a dystrophin gene in a target cell in a subject. In further aspects, the invention provides methods for treating DMD in a subject by administering the engineered meganucleases described herein, or polynucleotides encoding the same, to a subject, in some cases as part of a pharmaceutical composition.

In each case, it is envisioned that the engineered meganucleases, or polynucleotides encoding the same, are introduced into cells, such as muscle cells or muscle precursor cells capable of expressing a dystrophin protein. Engineered meganucleases described herein can be delivered into a cell in the form of protein or, preferably, as a polynucleotide encoding the engineered meganuclease. Such polynucleotides can be, for example, DNA (e.g., circular or linearized plasmid DNA, PCR products, or a viral genome) or RNA (e.g., mRNA).

Detection and Expression

Expression of a modified dystrophin (i.e., a gene lacking exons 45-55, or a protein lacking amino acids encoded by exons 45-55) in a genetically modified cell or subject can be detected using standard methods in the art. For example, levels of such modified dystrophin may be assessed based on the level of any variable associated with dystrophin gene expression, e.g., dystrophin mRNA levels or dystrophin protein levels. Increased levels or expression of such modified dystrophin may be assessed by an increase in an absolute or relative level of one or more of these variables compared with a reference level. Such modified dystrophin levels may be measured in a biological sample isolated from a subject, such as a tissue biopsy or a bodily fluid including blood, serum, plasma, cerebrospinal fluid, or urine. Optionally, such modified dystrophin levels are normalized to a standard protein or substance in the sample. Further, such modified dystrophin levels can be assessed any time before, during, or after treatment in accordance with the methods herein.

In various aspects, the methods described herein can increase protein levels of a modified dystrophin (i.e., lacking amino acids encoded by exons 45-55) in a genetically modified cell, target cell, or subject (e.g., as measured in a cell, a tissue, an organ, or a biological sample obtained from the subject), to at least 1%, 2%, 3%, 4%, 5%, 10%, 15%, 20%, 25%, 30%, 40%, 50%, 60%, 70%, 80%, 90%, 95%, 100%, or more, of a reference level (i.e., protein level of dystrophin in a wild-type cell or subject). In some embodiments, the methods herein are effective to increase the level of such modified dystrophin protein to about 10% to about 100% (e.g., 10%-20%, 20%-30%, 30%-40%, 40%-50%, 50%-60%, 60%-70%, 70%-80%, 80%-90%, 90%-100%, or more) of a reference level of dystrophin (i.e., protein level of dystrophin in a wild-type cell or subject).

Introduction of Engineered Meganucleases into Cells

Engineered meganuclease proteins disclosed herein, or polynucleotides encoding the same, can be delivered into cells to cleave genomic DNA by a variety of different mechanisms known in the art, including those further detailed herein below.

Engineered meganucleases disclosed herein can be delivered into a cell in the form of protein or, preferably, as a polynucleotide comprising a nucleic acid sequence encoding the engineered meganuclease. Such polynucleotides can be, for example, DNA (e.g., circular or linearized plasmid DNA, PCR products, or viral genomes) or RNA (e.g., mRNA).

For embodiments in which the engineered meganuclease coding sequence is delivered in DNA form, it should be operably linked to a promoter to facilitate transcription of the meganuclease gene. Mammalian promoters suitable for the invention include constitutive promoters such as the cytomegalovirus early (CMV) promoter (Thomsen et al. (1984) *Proc Natl Acad Sci USA*. 81:659-63) or the SV40 early promoter (Benoist & Chambon (1981) *Nature* 290: 304-10) as well as inducible promoters such as the tetracycline-inducible promoter (Dingermann et al. (1992) *Mol Cell Biol*. 12:4038-45). An engineered meganuclease of the invention can also be operably linked to a synthetic promoter. Synthetic promoters can include, without limitation, the JeT promoter (WO 2002/012514).

In specific embodiments, a nucleic acid sequence encoding an engineered nuclease of the invention is operably linked to a tissue-specific promoter, such as a muscle-specific promoter. In some particular embodiments, the promoter is capable of expressing an engineered meganuclease described herein in a muscle precursor cell (e.g., satellite cell or stem cell). Exemplary and non-limiting muscle promoters include C5-12 (Liu et al. (2004) *Hum Gene Ther*. 15:783-92), the muscle-specific creatine kinase (MCK) promoter (Yuasa et al. (2002) *Gene Ther*. 9:1576-88), or the smooth muscle 22 (SM22) promoter (Haase et al. (2013) *BMC Biotechnol*. 13:49-54). In some embodiments, the muscle-specific promoter comprises the sequence according to any one of SEQ ID NOs: 169-181. In some embodiments, the muscle-specific promoter comprises a sequence 90%, 91%, 92%, 93%, 94%, 95%, 96%, 97%, 98%, 99% or 100% identical to a C5-12 promoter comprising SEQ ID NO: 169. In some embodiments, the muscle-specific promoter comprises a sequence 90%, 91%, 92%, 93%, 94%, 95%, 96%, 97%, 98%, 99% or 100% identical to a murine MCK promoter comprising SEQ ID NO: 170. In some embodiments, the muscle-specific promoter comprises a sequence 90%, 91%, 92%, 93%, 94%, 95%, 96%, 97%, 98%, 99% or 100% identical to a human MCK promoter comprising SEQ ID NO: 171. In some embodiments, the muscle-specific promoter comprises a sequence 90%, 91%, 92%, 93%, 94%, 95%, 96%, 97%, 98%, 99% or 100% identical to a MCK enhancer comprising SEQ ID NO: 172. In some embodiments, the muscle-specific promoter comprises a sequence 90%, 91%, 92%, 93%, 94%, 95%, 96%, 97%, 98%, 99% or 100% identical to a modified MCK enhancer comprising SEQ ID NO: 173. In some embodiments, the muscle-specific promoter comprises a sequence 90%, 91%, 92%, 93%, 94%, 95%, 96%, 97%, 98%, 99% or 100% identical to a spc 5-12 promoter comprising SEQ ID NO: 174. In some embodiments, the muscle-specific promoter comprises a sequence 90%, 91%, 92%, 93%, 94%, 95%, 96%, 97%, 98%, 99% or 100% identical to a MHCK7 promoter comprising SEQ ID NO: 175. In some embodiments, the muscle-specific promoter comprises a sequence 90%, 91%, 92%, 93%, 94%, 95%, 96%, 97%, 98%, 99% or 100% identical to a CK8 promoter comprising SEQ ID NO: 176. In some embodiments, the muscle-specific promoter comprises a sequence 90%, 91%, 92%, 93%, 94%, 95%, 96%, 97%, 98%, 99% or 100% identical to a SK-CRM4 promoter comprising SEQ ID NO: 177. In some embodiments, the muscle-specific promoter comprises a sequence 90%, 91%, 92%, 93%, 94%, 95%, 96%, 97%, 98%, 99% or 100% identical to a SP-301 promoter comprising SEQ ID NO: 178. In some embodiments, the muscle-specific promoter comprises a sequence 90%, 91%, 92%, 93%, 94%, 95%, 96%, 97%, 98%, 99% or 100% identical to a SP-817 promoter comprising SEQ ID NO: 179. In some embodiments, the muscle-specific promoter comprises a sequence 90%, 91%, 92%, 93%, 94%, 95%, 96%, 97%, 98%, 99% or 100% identical to a SP-905 promoter comprising SEQ ID NO: 180. In some embodiments, the muscle-specific promoter comprises a sequence 90%, 91%, 92%, 93%, 94%, 95%, 96%, 97%, 98%, 99% or 100% identical to a muscle hybrid promoter comprising SEQ ID NO: 181.

In some embodiments, wherein a single polynucleotide comprises two separate nucleic acid sequences each encoding an engineered meganuclease described herein, the meganuclease genes are operably linked to two separate promoters. In alternative embodiments, the two meganuclease genes are operably linked to a single promoter, and in some examples can be separated by an internal-ribosome entry site (IRES) or a 2A peptide sequence (Szymezak & Vignali (2005) *Expert Opin Biol Ther*. 5:627-38). Such 2A peptide sequences can include, for example, a T2A, P2A, E2A, or F2A sequence.

In specific embodiments, a polynucleotide comprising a nucleic acid sequence encoding an engineered meganuclease described herein is delivered on a recombinant DNA construct or expression cassette. For example, the recombinant DNA construct can comprise an expression cassette (i.e., "cassette") comprising a promoter and a nucleic acid sequence encoding an engineered meganuclease described herein.

In another particular embodiment, a polynucleotide comprising a nucleic acid sequence encoding an engineered meganuclease described herein is introduced into the cell using a single-stranded DNA template. The single-stranded DNA can further comprise a 5' and/or a 3' AAV inverted terminal repeat (ITR) upstream and/or downstream of the sequence encoding the engineered nuclease. The single-stranded DNA can further comprise a 5' and/or a 3' homology arm upstream and/or downstream of the sequence encoding the engineered meganuclease.

In another particular embodiment, a polynucleotide comprising a nucleic acid sequence encoding an engineered meganuclease described herein can be introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

In some embodiments, mRNA encoding an engineered meganuclease described herein is delivered to a cell because this reduces the likelihood that the gene encoding the engineered meganuclease will integrate into the genome of the cell. Such mRNA can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine.

Additional nucleoside analogs include, for example, those described in U.S. Pat. No. 8,278,036.

In some embodiments, the meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisarn et al. (2008) *Mol Ther.* 16:1624-29), TAT peptide from the HIV virus (Hudecz et al. (2005) *Med. Res. Rev.* 25:679-736), MPG (Simeoni et al. (2003) *Nucleic Acids Res.* 31:2717-24), Pep-1 (Deshayes et al. (2004) *Biochemistry* 43:7698-7706, and HSV-1 VP-22 (Deshayes et al. (2005) *Cell Mol Life Sci.* 62:1839-49). In an alternative embodiment, engineered nucleases, or DNA/mRNA encoding nucleases, are coupled covalently or non-covalently to an antibody that recognizes a specific cell-surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell-surface receptor. (McCall et al. (2014) *Tissue Barriers.* 2(4):e944449; Dinda et al. (2013) *Curr. Pharm. Biotechnol.* 14:1264-74; Kang et al. (2014) *Curr. Pharm. Biotechnol.* 15:220-30; and Qian et al. (2014) *Expert Opin. Drug Metab Toxicol.* 10:1491-508).

In some embodiments, meganuclease proteins, or DNA/mRNA encoding meganucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Derwent et al. (2008) *Trans Am. Ophthalmol. Soc.* 106:206-14).

In some embodiments, meganuclease proteins, or DNA/mRNA encoding meganucleases, are coupled covalently or, preferably, non-covalently to a nanoparticle or encapsulated within such a nanoparticle using methods known in the art (Sharma et al. (2014) *Biomed. Res. Int.* 2014:156010). A nanoparticle is a nanoscale delivery system whose length scale is <1 μm, preferably <100 nm. Such nanoparticles may be designed using a core composed of metal, lipid, polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33:7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins, or DNA/mRNA encoding meganucleases, are encapsulated within liposomes or complexed using cationic lipids (see, e.g., LIPOFECTAMINE™, Life Technologies Corp., Carlsbad, CA; Zuris et al. (2015) *Nat. Biotechnol.* 33:73-80; Mishra et al. (2011) *J. Drug Deliv.* 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) *Ther Deliv.* 2:523-36). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding meganucleases, are combined with amphiphilic molecules that self-assemble into micelles (Tong et al. (2007) *J. Gene Med.* 9:956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, for example, as described in U.S. Pat. Nos. 6,015,832, 6,506,803, 6,635,676, 6,559,189, and 7,767,216, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) *Nanoscale.* 7:3845-56; Cheng et al. (2008) *J. Pharm Sci.* 97:123-43). The dendrimer generation can control the payload capacity and size and can provide a high payload capacity. Moreover, display of multiple surface groups can be leveraged to improve stability, reduce nonspecific interactions, and enhance cell-specific targeting and drug release.

In some embodiments, polynucleotides comprising a nucleic acid sequence encoding an engineered meganuclease described herein are introduced into a cell using a recombinant virus (i.e., a recombinant viral vector). Such recombinant viruses are known in the art and include recombinant retroviruses, recombinant lentiviruses, recombinant adenoviruses, and recombinant AAVs (reviewed in Vannucci et al. (2013) *New Microbiol.* 36:1-22). Recombinant AAVs useful in the invention can have any serotype that allows for transduction of the virus into a target cell type and expression of the meganuclease gene in the target cell. For example, in some embodiments, recombinant AAVs have a serotype (i.e., a capsid) of AAV1, AAV2, AAV5 AAV6, AAV7, AAV8, AAV9, AAV12, or AAVrh.74. It is known in the art that different AAVs tend to localize to different tissues (Wang et al. (2014) *Expert Opin Drug Deliv* 11:345-34.). The AAVrh.74 serotype, which is closely related to AAV8, has further been described as targeting muscle tissue including skeletal muscle and cardiac muscle tissue (Mendell et al. (2020) *JAMA Neurol.* 77:1122-31). Accordingly, in some embodiments, the AAV serotype is AAV1. In some embodiments, the AAV serotype is AAV2. In some embodiments, the AAV serotype is AAV5. In some embodiments, the AAV serotype is AAV6. In some embodiments, the AAV serotype is AAV7. In some embodiments, the AAV serotype is AAV8. In some embodiments, the AAV serotype is AAV9. In some embodiments, the AAV serotype is AAV12. In some embodiments, the AAV serotype is AAVrh.74. AAVs can also be self-complementary such that they do not require second-strand DNA synthesis in the host cell (McCarty et al. (2001) *Gene Ther.* 8:1248-54). Polynucleotides delivered by recombinant AAVs can include left (5') and right (3') inverted terminal repeats as part of the viral genome. In some embodiments, the recombinant viruses are injected directly into target tissues. In alternative embodiments, the recombinant viruses are delivered systemically via the circulatory system.

In one embodiment, a recombinant virus used for meganuclease gene delivery is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide a coding sequence for a promoter, an engineered meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome, and cut the recombinant viral genome at this target site. Once cut, the 5' and 3' ends of the viral genome will be exposed and degraded by exonucleases, thus killing the virus and ceasing production of the meganuclease.

If a polynucleotide comprising a nucleic acid sequence encoding an engineered meganuclease described herein is delivered to a cell by a recombinant virus (e.g. an AAV), the nucleic acid sequence encoding the engineered meganuclease can be operably linked to a promoter. In some embodiments, this can be a viral promoter such as endogenous promoters from the recombinant virus (e.g. the LTR of a lentivirus) or the well-known cytomegalovirus- or SV40 virus-early promoters. In particular embodiments, nucleic acid sequences encoding the engineered meganucleases are operably linked to a promoter that drives gene expression preferentially in the target cells (e.g., muscle cells or muscle precursor cells). Examples of muscle-specific tissue promoters include but are not limited to those muscle-specific promoters previously described, including C5-12, the muscle-specific creatine kinase (MCK) promoter, or the smooth muscle 22 (SM22) promoter. In some embodiments, the muscle-specific promoter comprises the sequence according to any one of SEQ ID NOs: 169-181. In some embodiments, the muscle-specific promoter comprises a sequence 90%, 91%, 92%, 93%, 94%, 95%, 96%, 97%, 98%, 99% or 100% identical to a C5-12 promoter comprising SEQ ID NO: 169. In some embodiments, the muscle-specific promoter comprises a sequence 90%, 91%, 92%, 93%, 94%, 95%, 96%, 97%, 98%, 99% or 100% identical to a murine MCK promoter comprising SEQ ID NO: 170. In some embodiments, the muscle-specific promoter comprises a sequence 90%, 91%, 92%, 93%, 94%, 95%, 96%, 97%, 98%, 99% or 100% identical to a human MCK promoter comprising SEQ ID NO: 171. In some embodiments, the muscle-specific promoter comprises a sequence 90%, 91%, 92%, 93%, 94%, 95%, 96%, 97%, 98%, 99% or 100% identical to a MCK enhancer comprising SEQ ID NO: 172. In some embodiments, the muscle-specific promoter comprises a sequence 90%, 91%, 92%, 93%, 94%, 95%, 96%, 97%, 98%, 99% or 100% identical to a modified MCK enhancer comprising SEQ ID NO: 173. In some embodiments, the muscle-specific promoter comprises a sequence 90%, 91%, 92%, 93%, 94%, 95%, 96%, 97%, 98%, 99% or 100% identical to a spc 5-12 promoter comprising SEQ ID NO: 174. In some embodiments, the muscle-specific promoter comprises a sequence 90%, 91%, 92%, 93%, 94%, 95%, 96%, 97%, 98%, 99% or 100% identical to a MHCK7 promoter comprising SEQ ID NO: 175. In some embodiments, the muscle-specific promoter comprises a sequence 90%, 91%, 92%, 93%, 94%, 95%, 96%, 97%, 98%, 99% or 100% identical to a CK8 promoter comprising SEQ ID NO: 176. In some embodiments, the muscle-specific promoter comprises a sequence 90%, 91%, 92%, 93%, 94%, 95%, 96%, 97%, 98%, 99% or 100% identical to a SK-CRM4 promoter comprising SEQ ID NO: 177. In some embodiments, the muscle-specific promoter comprises a sequence 90%, 91%, 92%, 93%, 94%, 95%, 96%, 97%, 98%, 99% or 100% identical to a SP-301 promoter comprising SEQ ID NO: 178. In some embodiments, the muscle-specific promoter comprises a sequence 90%, 91%, 92%, 93%, 94%, 95%, 96%, 97%, 98%, 99% or 100% identical to a SP-817 promoter comprising SEQ ID NO: 179. In some embodiments, the muscle-specific promoter comprises a sequence 90%, 91%, 92%, 93%, 94%, 95%, 96%, 97%, 98%, 99% or 100% identical to a SP-905 promoter comprising SEQ ID NO: 180. In some embodiments, the muscle-specific promoter comprises a sequence 90%, 91%, 92%, 93%, 94%, 95%, 96%, 97%, 98%, 99% or 100% identical to a muscle hybrid promoter comprising SEQ ID NO: 181. In some embodiments, wherein a single polynucleotide comprises two separate nucleic acid sequences each encoding an engineered meganuclease described herein, the meganuclease genes are operably linked to two separate promoters. In alternative embodiments, the two meganuclease genes are operably linked to a single promoter, and in some examples can be separated by an internal-ribosome entry site (IRES) or a 2A peptide sequence (Szymezak & Vignali (2005) *Expert Opin Biol Ther.* 5:627-38). Such 2A peptide sequences can include, for example, a T2A, P2A, E2A, or F2A sequence.

In some embodiments, the methods include delivering an engineered meganuclease described herein, or a polynucleotide encoding the same, to a cell in combination with a second polynucleotide comprising an exogenous nucleic acid sequence encoding a sequence of interest, wherein the engineered meganuclease is expressed in the cells, recognizes and cleaves a recognition sequence described herein (e.g., SEQ ID NO: 6, SEQ ID NO: 10, or SEQ ID NO: 12) within a dystrophin gene of the cell, and generates a cleavage site, wherein the exogenous nucleic acid and sequence of interest are inserted into the genome at the cleavage site (e.g., by homologous recombination). In some such examples, the polynucleotide can comprise sequences homologous to nucleic acid sequences flanking the meganuclease cleavage site in order to promote homologous recombination of the exogenous nucleic acid and sequence of interest into the genome.

Such polynucleotides comprising exogenous nucleic acids can be introduced into a cell and/or delivered to a target cell in a subject by any of the means previously discussed. In particular embodiments, such polynucleotides comprising exogenous nucleic acid molecules are introduced by way of a recombinant virus (i.e., a viral vector), such as a recombinant lentivirus, recombinant retrovirus, recombinant adenovirus, or a recombinant AAV. Recombinant AAVs useful for introducing a polynucleotide comprising an exogenous nucleic acid molecule can have any serotype (i.e., capsid) that allows for transduction of the virus into the cell and insertion of the exogenous nucleic acid molecule sequence into the cell genome. In some embodiments, recombinant AAVs have a serotype of AAV1, AAV2, AAV5 AAV6, AAV7, AAV8, AAV9, AAV12, or AAVrh.74. In some embodiments, the AAV serotype is AAV1. In some embodiments, the AAV serotype is AAV2. In some embodiments, the AAV serotype is AAV5. In some embodiments, the AAV serotype is AAV6. In some embodiments, the AAV serotype is AAV7. In some embodiments, the AAV serotype is AAV8. In some embodiments, the AAV serotype is AAV9. In some embodiments, the AAV serotype is AAV12. In some embodiments, the AAV serotype is AAVrh.74. The recombinant AAV can also be self-complementary such that it does not require second-strand DNA synthesis in the host cell. Exogenous nucleic acid molecules introduced using a recombinant AAV can be flanked by a 5' (left) and 3' (right) inverted terminal repeat in the viral genome.

In another particular embodiment, an exogenous nucleic acid molecule can be introduced into a cell using a single-stranded DNA template. The single-stranded DNA can comprise the exogenous nucleic acid molecule and, in particular embodiments, can comprise 5' and 3' homology arms to promote insertion of the nucleic acid sequence into the nuclease cleavage site by homologous recombination. The single-stranded DNA can further comprise a 5' AAV ITR sequence 5' upstream of the 5' homology arm, and a 3' AAV ITR sequence 3' downstream of the 3' homology arm.

In another particular embodiment, genes encoding a nuclease of the invention and/or an exogenous nucleic acid molecule of the invention can be introduced into a cell by transfection with a linearized DNA template. A plasmid DNA encoding an engineered nuclease and/or an exogenous nucleic acid molecule can, for example, be digested by one or more restriction enzymes such that the circular plasmid DNA is linearized prior to transfection into the cell.

When delivered to a cell, an exogenous nucleic acid of the invention can be operably linked to any promoter suitable for expression of the encoded polypeptide in the cell, including those mammalian promoters and inducible promoters previously discussed. An exogenous nucleic acid of the invention can also be operably linked to a synthetic promoter. Synthetic promoters can include, without limitation, the JeT promoter (WO 2002/012514). In specific embodiments, a nucleic acid sequence encoding an engineered meganuclease as disclosed herein can be operably linked to a muscle-specific promoter discussed herein.

Administration

The target tissue(s) or target cell(s) include, without limitation, muscle cells, such as skeletal muscle cells, cardiac muscle cells, or muscle cells of the diaphragm. In some embodiments, the target cell is a muscle progenitor cell such as a skeletal muscle progenitor cell or a cardiac muscle progenitor cell. Such muscle progenitor cells have been described in the art and can either be present in a subject or derived from another stem cell population such as an induced pluripotent stem cell or an embryonic stem cell (Tey et al. (2019) *Front. Cell Dev. Biol.* 7:284 and Amini et al. (2017) *J. Cardiovasc. Thorac. Res.* 9:127-32).

In some embodiments, engineered meganucleases described herein, or polynucleotides encoding the same, are delivered to a cell in vitro. In some embodiments, engineered meganucleases described herein, or polynucleotides encoding the same, are delivered to a cell in a subject in vivo. As discussed herein, meganucleases of the invention can be delivered as purified protein or as a polynucleotide (e.g., RNA or DNA) comprising a nucleic acid sequence encoding the meganuclease. In some embodiments, meganuclease proteins, or polynucleotides encoding meganucleases, are supplied to target cells (e.g., a muscle cell or muscle progenitor cell) via injection directly to the target tissue. Alternatively, meganuclease proteins, or polynucleotides encoding meganucleases, can be delivered systemically via the circulatory system.

In various embodiments of the methods, compositions described herein, such as the engineered meganucleases described herein, polynucleotides encoding the same, recombinant viruses comprising such polynucleotides, or lipid nanoparticles comprising such polynucleotides, can be administered via any suitable route of administration known in the art. Such routes of administration can include, for example, intravenous, intramuscular, intraperitoneal, subcutaneous, intrahepatic, transmucosal, transdermal, intraarterial, and sublingual. In some embodiments, the engineered meganuclease proteins, polynucleotides encoding the same, recombinant viruses comprising such polynucleotides, or lipid nanoparticles comprising such polynucleotides, are supplied to target cells (e.g., muscle cells or muscle precursor cells) via injection directly to the target tissue (e.g., muscle tissue). Other suitable routes of administration can be readily determined by the treating physician as necessary.

In some embodiments, a therapeutically effective amount of an engineered nuclease described herein, or a polynucleotide encoding the same, is administered to a subject in need thereof for the treatment of a disease. As appropriate, the dosage or dosing frequency of the engineered meganuclease, or the polynucleotide encoding the same, may be adjusted over the course of the treatment, based on the judgment of the administering physician. Appropriate doses will depend, among other factors, on the specifics of any AAV chosen (e.g., serotype, etc.), any lipid nanoparticle chosen, on the route of administration, on the subject being treated (i.e., age, weight, sex, and general condition of the subject), and the mode of administration. Thus, the appropriate dosage may vary from patient to patient. An appropriate effective amount can be readily determined by one of skill in the art or treating physician. Dosage treatment may be a single dose schedule or, if multiple doses are required, a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

In some embodiments, the methods further include administration of a polynucleotide comprising a nucleic acid sequence encoding a secretion-impaired hepatotoxin, or encoding tPA, which stimulates hepatocyte regeneration without acting as a hepatotoxin.

In some embodiments, a subject is administered a pharmaceutical composition comprising a polynucleotide comprising a nucleic acid sequence encoding an engineered meganuclease described herein, wherein the encoding nucleic acid sequence is administered at a dose of about $1\times10^{10}$ gc/kg to about $1\times10^{14}$ gc/kg (e.g., about $1\times10^{10}$ gc/kg, about $1\times10^{11}$ gc/kg, about $1\times10^{12}$ gc/kg, about $1\times10^{13}$ gc/kg, or about $1\times10^{14}$ gc/kg). In some embodiments, a subject is administered a pharmaceutical composition comprising a polynucleotide comprising a nucleic acid sequence encoding an engineered meganuclease described herein, wherein the encoding nucleic acid sequence is administered at a dose of about $1\times10^{10}$ gc/kg, about $1\times10^{11}$ gc/kg, about $1\times10^{12}$ gc/kg, about $1\times10^{13}$ gc/kg, or about $1\times10^{14}$ gc/kg. In some embodiments, a subject is administered a pharmaceutical composition comprising a polynucleotide comprising a nucleic acid sequence encoding an engineered meganuclease described herein, wherein the encoding nucleic acid sequence is administered at a dose of about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg. It should be understood that these doses can relate to the administration of a single polynucleotide comprising a single nucleic acid sequence encoding a single engineered meganuclease described herein or, alternatively, can relate to a single polynucleotide comprising a first nucleic acid sequence encoding a first engineered meganuclease described herein and a second nucleic acid sequence encoding a second engineered meganuclease described herein, wherein each of the two encoding nucleic acid sequences is administered at the indicated dose.

In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 3 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg.

2.4 Pharmaceutical Compositions

In some embodiments, the invention provides a pharmaceutical composition comprising a pharmaceutically acceptable carrier and an engineered meganuclease described herein, or a pharmaceutically acceptable carrier and a polynucleotide described herein that comprises a nucleic acid sequence encoding an engineered meganuclease described herein. Such polynucleotides can be, for example, mRNA or DNA as described herein. In some such examples, the polynucleotide in the pharmaceutical composition can be comprised by a lipid nanoparticle or can be comprised by a recombinant virus (e.g., a recombinant AAV). In other embodiments, the disclosure provides a pharmaceutical composition comprising a pharmaceutically acceptable carrier and a genetically modified cell of the invention, which can be delivered to a target tissue where the cell expresses the engineered meganuclease as disclosed herein. Such pharmaceutical compositions are formulated, for example, for systemic administration, or administration to target tissues.

In various embodiments of the invention, the pharmaceutical compositions can be useful for treating DMD, converting a DMD disease phenotype to a Becker Muscular Dystrophy phenotype, and/or reducing the symptoms associated with DMD in a subject.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, engineered meganucleases described herein, polynucleotides encoding the same, or cells expressing the same, are typically admixed with a pharmaceutically acceptable carrier and the resulting composition is administered to a subject. The carrier must be acceptable in the sense of being compatible with any other ingredients in the formulation and must not be deleterious to the subject. The carrier can be a solid or a liquid, or both, and can be formulated with the compound as a unit-dose formulation.

In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

The pharmaceutical compositions described herein can include a therapeutically effective amount of any engineered meganuclease disclosed herein, or any polynucleotide described herein encoding any engineered meganuclease described herein. For example, in some embodiments, the pharmaceutical composition can include polynucleotides described herein at any of the doses (e.g., gc/kg of an encoding nucleic acid sequence or mg/kg of mRNA) described herein.

In particular embodiments of the invention, the pharmaceutical composition can comprise one or more recombinant viruses (e.g., recombinant AAVs) described herein that comprise one or more polynucleotides described herein (i.e., packaged within the viral genome). In particular embodiments, the pharmaceutical composition comprises two or more recombinant viruses (e.g., recombinant AAVs) described herein, each comprising a polynucleotide comprising a nucleic acid sequence encoding a different engineered meganuclease described herein. For example, a first recombinant virus (e.g., recombinant AAV) may comprise a first polynucleotide comprising a first nucleic acid sequence encoding a first engineered meganuclease described herein having specificity for the DMD 19-20 recognition sequence, and a second recombinant virus (e.g., recombinant AAV) comprising a second polynucleotide comprising a second nucleic acid sequence encoding a second engineered meganuclease described herein having specificity for the DMD 35-36 recognition sequence or the DMD 37-38 recognition sequence. The expression of such a pair of engineered meganucleases in the same cell (e.g., a muscle cell) would allow for the excision of exons 45-55 from the dystrophin gene according to the invention.

In other particular embodiments, the pharmaceutical composition can comprise a recombinant virus (e.g., recombinant AAV) described herein that comprises a polynucleotide (i.e., packaged within the viral genome) that comprises two nucleic acid sequences encoding two separate engineered meganucleases described herein. For example, the recombinant virus (e.g., recombinant AAV) can comprise a polynucleotide comprising a first nucleic acid sequence encoding a first engineered meganuclease described herein having specificity for the DMD 19-20 recognition sequence, and a second nucleic acid sequence encoding a second engineered meganuclease described herein having specificity for the DMD 35-36 recognition sequence or the DMD 37-38 recognition sequence. The expression of such a pair of engineered meganucleases would allow for the excision of exons 45-55 from the dystrophin gene according to the invention.

In particular embodiments of the invention, the pharmaceutical composition can comprise one or more polynucleotides (e.g., mRNAs) described herein encapsulated within lipid nanoparticles. In particular embodiments, lipid nanoparticles can comprise two or more polynucleotides (e.g., mRNAs) described herein, each comprising a nucleic acid sequence encoding a different engineered meganuclease described herein. For example, a first polynucleotide (e.g., mRNA) in the lipid nanoparticle may encode a first engineered meganuclease described herein having specificity for the DMD 19-20 recognition sequence, and a second polynucleotide (e.g., mRNA) in the lipid nanoparticle may encode a second engineered meganuclease described herein having specificity for the DMD 35-36 recognition sequence or the DMD 37-38 recognition sequence. The expression of such a pair of engineered meganucleases in the same cell (e.g., a muscle cell) would allow for the excision of exons 45-55 from the dystrophin gene according to the invention. Alternatively, the pharmaceutical composition can comprise two separate populations of lipid nanoparticles, each comprising a different polynucleotide (e.g., mRNA) described herein, wherein a first population of lipid nanoparticles comprise a first polynucleotide (e.g., mRNA) described herein encoding a first engineered meganuclease having specificity for the DMD 19-20 recognition sequence, and the second population of lipid nanoparticles comprise a second polynucleotide (e.g., mRNA) described herein encoding a second engineered meganuclease having specificity for the DMD 35-36 recognition sequence or the DMD 37-38 recognition sequence.

In other particular embodiments, lipid nanoparticles can comprise one polynucleotide (e.g., mRNA) described herein that comprises two nucleic acid sequences encoding two separate engineered meganucleases described herein. For example, the lipid nanoparticle can comprise a polynucleotide (e.g., mRNA) comprising a first nucleic acid sequence encoding a first engineered meganuclease described herein having specificity for the DMD 19-20 recognition sequence, and a second nucleic acid sequence encoding a second engineered meganuclease described herein having specificity for the DMD 35-36 recognition sequence or the DMD 37-38 recognition sequence. The expression of such a pair of engineered meganucleases in the same cell (e.g., a muscle cell) would allow for the excision of exons 45-55 from the dystrophin gene according to the invention.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.C1), 1,2-dilinoleoyl-3-trimethylaminopropane chloride salt (DLin-TAP.C1), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in WO 2009/086558. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N', N', N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethylamronium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+N, N-dioctadecylamido-glycine, CTAB cetyltrimethylammonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CCHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particular examples are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition, which specifically enhances delivery and uptake in the liver, and specifically within hepatocytes.

In some embodiments, pharmaceutical compositions of the invention can further comprise one or more additional agents useful in the treatment of DMD in the subject.

The present disclosure also provides engineered meganucleases described herein, or polynucleotides described herein encoding the same, or cells described herein expressing engineered meganucleases described herein for use as a medicament. The present disclosure further provides the use of engineered meganucleases described herein, or polynucleotides disclosed herein encoding the same, or cells described herein expressing engineered meganucleases described herein in the manufacture of a medicament for treating DMD, for increasing levels of a modified dystrophin protein (i.e., lacking the amino acids encoded by exons 45-55 of the dystrophin gene), or reducing the symptoms associated with DMD.

2.5 Methods for Producing Recombinant Viruses

In some embodiments, the invention provides recombinant viruses, such as recombinant AAVs, for use in the methods of the invention. Recombinant AAVs are typically produced in mammalian cell lines such as HEK-293. Because the viral cap and rep genes are removed from the recombinant virus to prevent its self-replication to make room for the therapeutic gene(s) to be delivered (e.g., the meganuclease gene), it is necessary to provide these in trans in the packaging cell line. In addition, it is necessary to provide the "helper" (e.g., adenoviral) components necessary to support replication (Cots et al. (2013) *Curr. Gene Ther.* 13:370-81). Frequently, recombinant AAVs are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the engineered meganuclease is not expressed in the packaging cells. Because the recombinant viral genomes of the invention may comprise a recognition sequence for the meganuclease, any meganuclease expressed in the packaging cell line may be capable of cleaving the viral genome before it can be packaged into viral particles. This will result in reduced packaging efficiency and/or the packaging of fragmented genomes. Several approaches can be used to prevent meganuclease expression in the packaging cells.

The nuclease can be placed under the control of a tissue-specific promoter that is not active in the packaging cells. Any tissue specific promoter described herein for expression of the engineered meganuclease or for a nucleic acid sequence of interest can be used. For example, if a recombinant virus is developed for delivery of genes encoding an engineered meganuclease to muscle tissue, a muscle-specific promoter can be used. Examples of muscle-specific promoters include, without limitation, those muscle-specific promoters described elsewhere herein.

Alternatively, the recombinant virus can be packaged in cells from a different species in which the meganuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a particular embodiment, viral particles are produced in insect cells using the baculovirus system as described by Gao et al. (2007) *J. Biotechnol.* 131:138-43. A meganuclease under the control of a mammalian promoter is unlikely to be expressed in these cells (Airenne et al. (2013) *Mol. Ther.* 21:739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA transcripts in insect cells, insect cells will not express a functional meganuclease and will package the full-length genome. In contrast, mammalian cells to which the resulting recombinant AAV particles are delivered will properly splice the pre-mRNA and will express functional meganuclease protein. Chen has reported using HGH and SV40 large T antigen introns to attenuate expression of the toxic proteins barnase and diphtheria toxin fragment A in insect packaging cells, enabling the production of recombinant AAV vectors carrying these toxin genes (Chen (2012) *Mol. Ther. Nucleic Acids.* 1: e57).

The engineered meganuclease gene can be operably linked to an inducible promoter such that a small-molecule inducer is required for meganuclease expression. Examples of inducible promoters include the Tet-On system (Clontech; Chen et al. (2015) *BMC Biotechnol.* 15:4) and the Rheo-Switch system (Intrexon; Sowa i (2011) *Spine* 36:E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the engineered meganuclease gene under the control of a promoter that responds to the corresponding transcription factor, the meganuclease gene having (a) binding site(s) for the transcription factor; and 2) including the gene encoding the transcription factor in the packaged viral genome. The latter step is necessary because the engineered meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector, or it can be stably integrated into the genome of the packaging cell such that it is expressed constitutively. Methods to modify common mammalian promoters to incorporate transcription repressor sites are known in the art. For example, Chang & Roninson modified the strong, constitutive CMV and RSV promoters to comprise operators for the Lac repressor and showed that gene expression from the modified promoters was greatly attenuated in cells expressing the repressor (Chang & Roninson (1996) *Gene* 183:137-42). The use of a non-human transcription repressor ensures that transcription of the meganuclease gene will be repressed only in the packaging cells expressing the repressor and not in target cells or tissues transduced with the resulting recombinant AAV.

2.6 Engineered Meganuclease Variants

Embodiments of the invention encompass the engineered meganucleases described herein, and variants thereof. Further embodiments of the invention encompass polynucleotides comprising a nucleic acid sequence encoding the engineered meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to bind and cleave a dystrophin gene recognition sequence described herein (e.g., a DMD 19-20, DMD 35-36, or DMD 37-38 recognition sequence). Such variants may result, for example, from human manipulation. Biologically active variants of a native polypeptide of the embodiments (e.g., SEQ ID NOs: 36-59), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, native subunit, native HVR1 region, and/or native HVR2 region, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, e.g., Kunkel (1985) *Proc. Natl. Acad. Sci. USA* 82:488-92; Kunkel et al. (1987) *Methods Enzymol.* 154:367-82; U.S. Pat. No. 4,873,192; Walker & Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases of the invention comprise an HVR1 that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NOs: 36-59.

In certain embodiments, engineered meganucleases of the invention comprise an HVR2 that has 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 215-270 of any one of SEQ ID NOs: 36-59.

A substantial number of amino acid modifications to the DNA recognition domain of the wild-type I-CreI meganuclease have previously been identified (e.g., U.S. Pat. No. 8,021,867), which singly or in combination, result in engineered meganucleases with specificities altered at individual bases within the DNA recognition sequence half-site, such that the resulting rationally-designed meganucleases have half-site specificities different from the wild-type enzyme. Table 9 provides potential substitutions that can be made in an engineered meganuclease monomer or subunit to enhance specificity based on the base present at each half-site position (−1 through −9) of a recognition half-site.

TABLE 9

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |

TABLE 9-continued

| Posn. | \multicolumn{11}{c}{Favored Sense-Strand Base} |
|---|---|---|---|---|---|---|---|---|---|---|---|
|  | A | C | G | T | A/T | A/C | A/G | C/T | G/T | A/G/T | A/C/G/T |
| −2 | Q70<br>T44*<br>A44*<br>V44*<br>I44*<br>L44*<br>N44* | E70<br>D70<br>K44*<br>R44* | H70<br>D44*<br>E44* | Q44* | C44* |  |  |  |  |  |  |
| −3 | Q68<br>C24*<br>I24* | E68<br>F68<br>K24*<br>R24* | R68 | M68<br>C68<br>L68<br>F68 |  | H68 |  | Y68 | K68 |  |  |
| −4 | A26*<br>Q77 | E77<br>K26* | R77<br>E26* |  |  |  |  | S77 |  | Q26* | S26* |
| −5 |  | E42 | R42 |  |  | K28* | C28*<br>Q42 |  |  |  | M66<br>K66 |
| −6 | Q40<br>C28* | E40<br>R28* | R40 | C40<br>I40<br>V40<br>C79<br>I79<br>V79<br>Q28* | A40<br>A79<br>A28*<br>H28* |  |  |  |  |  | S40<br>S28* |
| −7 | N30*<br>Q38 | E38<br>K30*<br>R30* | K38<br>R38<br>E30* | I38<br>L38 |  |  | C38 |  |  |  | H38<br>N38<br>Q30* |
| −8 | F33<br>Y33 | E33<br>D33 | F33<br>H33 | L33<br>V33<br>I33<br>F33<br>C33 |  | R32* | R33 |  |  |  |  |
| −9 |  | E32 | R32<br>K32 | L32<br>V32<br>A32<br>C32 |  |  |  | D32<br>I32 |  |  | S32<br>N32<br>H32<br>Q32<br>T32 |

Bold entries are wild-type contact residues and do not constitute "modifications" as used herein. An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or any one of SEQ ID NOs: 36-59 (WO 2009/001159), a Y, R, K, or D at a residue corresponding to position 66 of I-CreI or any one of SEQ ID NOs: 36-59, and/or an E, Q, or K at a residue corresponding to position 80 of I-CreI or any one of SEQ ID NOs: 36-59 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide its intended activity. For example, variants of an engineered meganuclease would be screened for their ability to preferentially bind and cleave recognition sequences found within a dystrophin gene.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases that Bind and Cleave Recognition Sequences in the Dystrophin Gene

1. Meganucleases that Bind and Cleave the DMD 19-20, DMD 29-30, DMD 35-36, and DMD 37-38 Recognition Sequences These experiments were designed to utilize pairs of engineered meganucleases that allow for the removal of a segment of the dystrophin gene. This strategy of employing two engineered meganucleases to edit at two locations simultaneously allows for the excision of multiple exons, specifically exons 45 through 55. In some cases, two engineered meganucleases delivered on a single AAV vector can make double-stranded breaks in the intron sequences upstream of exon 45 and downstream of exon 55; i.e., the introns flanking exons 45-55 of the gene.

As described herein, the pairs of engineered meganucleases selected for use are designed to cleave recognition sequences with identical 4 base pair center sequences. As a result, cleavage by the engineered meganucleases will leave complementary sticky ends (i.e., 4 base pair, 3' overhangs) so that the genomic sequence will be perfectly ligated following excision of the "hot spot" of exons 45-55, where over 50% of DMD-causing mutations are found. Removal of these exons results in the excision of over 500,000 base pairs of genomic sequence from the gene, returns the reading frame of the gene back to normal relative to wild-type, and creates a shorter "Becker's" dystrophin that has been shown to be therapeutically relevant in preclinical models. FIG. 1 provides the approximate location of the recognition sequences and the resulting ligation of the intron between exon 44 and exon 56. Subsequent splicing during transcription provides an mRNA transcript where exon 44 is in frame with exon 56 resulting in the shortened but functional dystrophin protein.

Hundreds of potential pairs of engineered meganucleases were evaluated for activity and efficacy. Of these, a select number were further characterized for their ability to cleave within the dystrophin gene and generate a perfect ligation of the genetic material.

Engineered meganucleases designed to bind and cleave the DMD 19-20 (SEQ ID NO: 6), DMD 29-30 (SEQ ID NO: 8), DMD 35-36 (SEQ ID NO: 10), and DMD 37-38 (SEQ ID NO: 12) recognition sequences within introns of the dystrophin gene are referred to herein as DMD 19-20 meganucleases, DMD 29-30 meganucleases, DMD 35-36 meganucleases, and DMD 37-38 meganucleases, respectively. The DMD 19-20 recognition sequence is positioned in the intron 5' upstream of exon 45. The DMD 29-30 recognition sequence is positioned in the intron 5' upstream of exon 46. Both the DMD 35-36 and DMD 37-38 recognition sequences are positioned in the intron 3' downstream of exon 55.

Each DMD engineered meganuclease comprises an N-terminal nuclear localization signal derived from SV40, a first meganuclease subunit, a linker sequence, and a second meganuclease subunit. A first subunit in each DMD meganuclease binds to a first DMD recognition half-site, while a second subunit binds to a second DMD recognition half-site. For example, a first subunit in the DMD 19-20 meganuclease binds to a first DMD recognition half-site, while a second subunit binds to a second DMD 19-20 recognition half-site (FIG. 1).

The DMD meganuclease subunits each comprise a 56 base pair hypervariable region, referred to as HVR1 and HVR2, respectively. The HVR1 region of each DMD meganuclease binding subunit consists of residues 24-79 of SEQ ID NOs: 36-59. The HVR2 region of each DMD meganuclease consists of residues 215-270 of SEQ ID NOs: 36-59.

Figure 5:
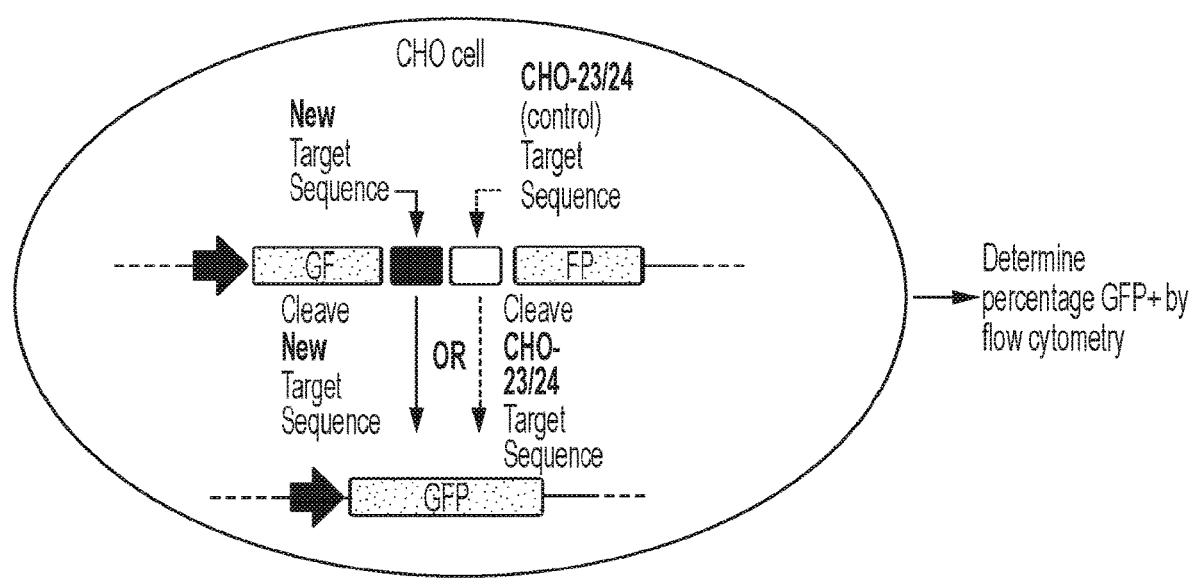
FIG. 5 is a schematic of a reporter assay in CHO cells for evaluating engineered meganucleases targeting recognition sequences found in the dystrophin gene. For the engineered meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease described herein (e.g., the DMD 19-20, DMD 29-30, DMD 35-36, or DMD 37-38 recognition sequences); the recognition sequence for the CHO-23/24 meganuclease (WO 2012/167192); and the 3' 2/3 of the GFP gene. Cells stably transfected with this cassette did not express GFP in the absence of a DNA break-inducing agent. Meganucleases were introduced by transduction of an mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.
Figure 6A:
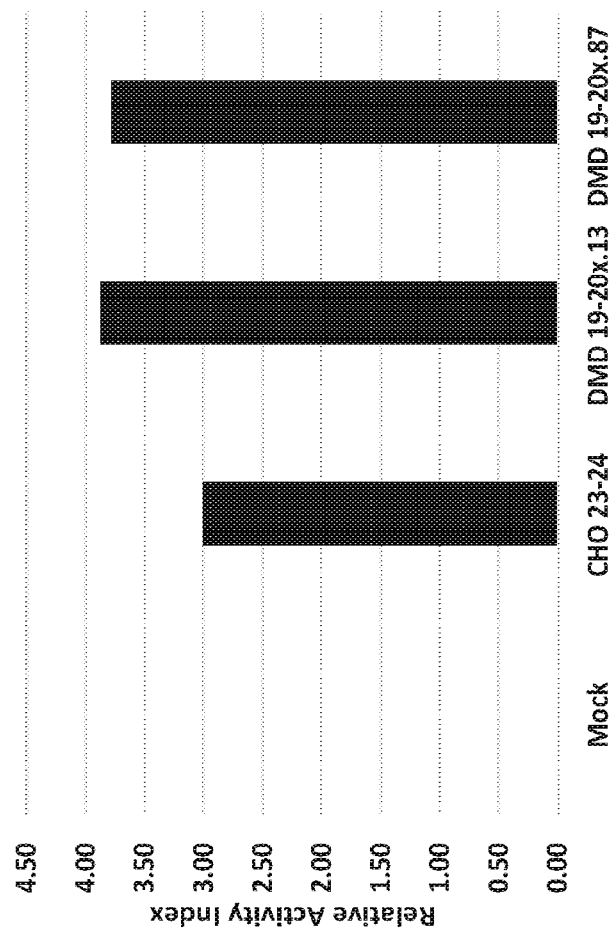
Figure 6B:
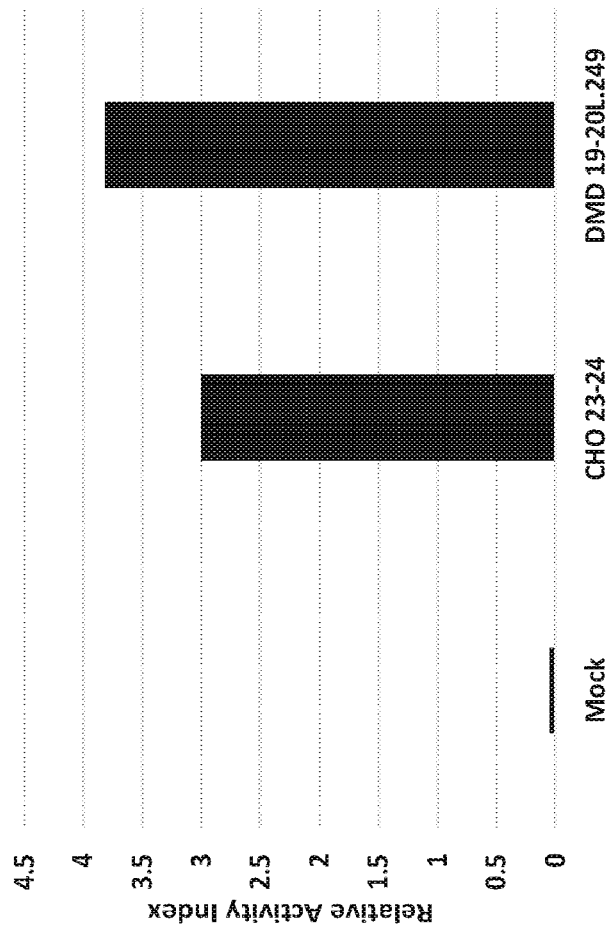
Figure 6C:
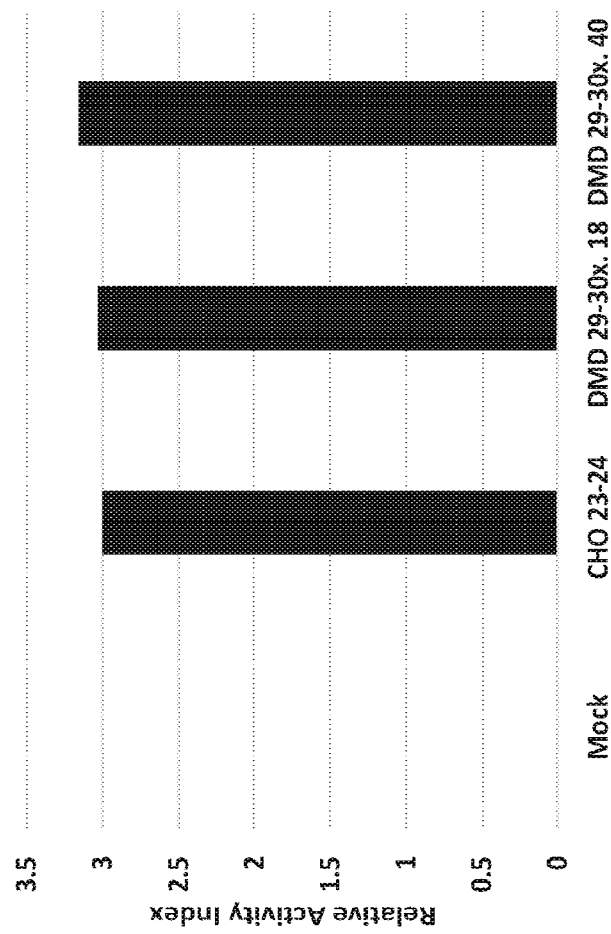
Figure 6D:
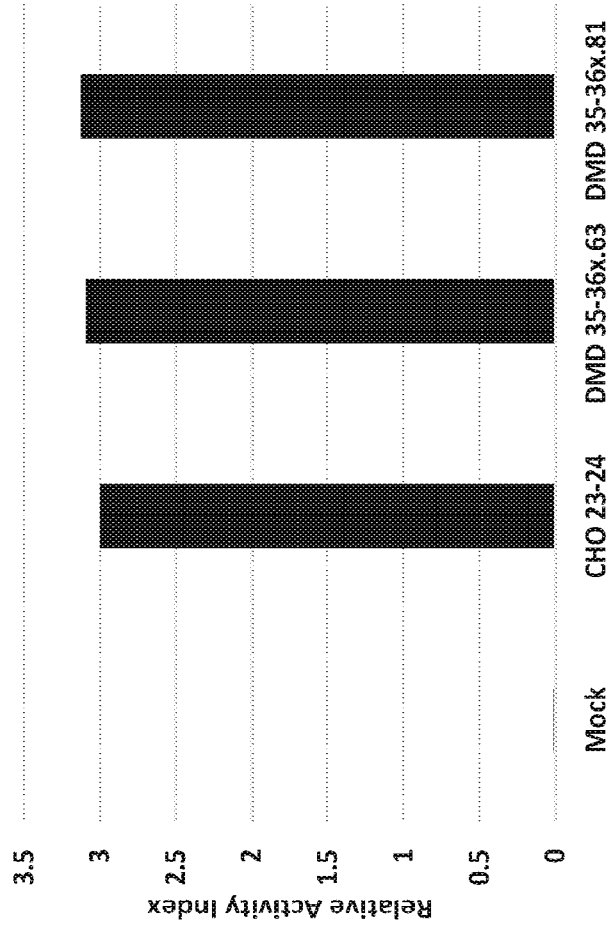
Figure 6F:
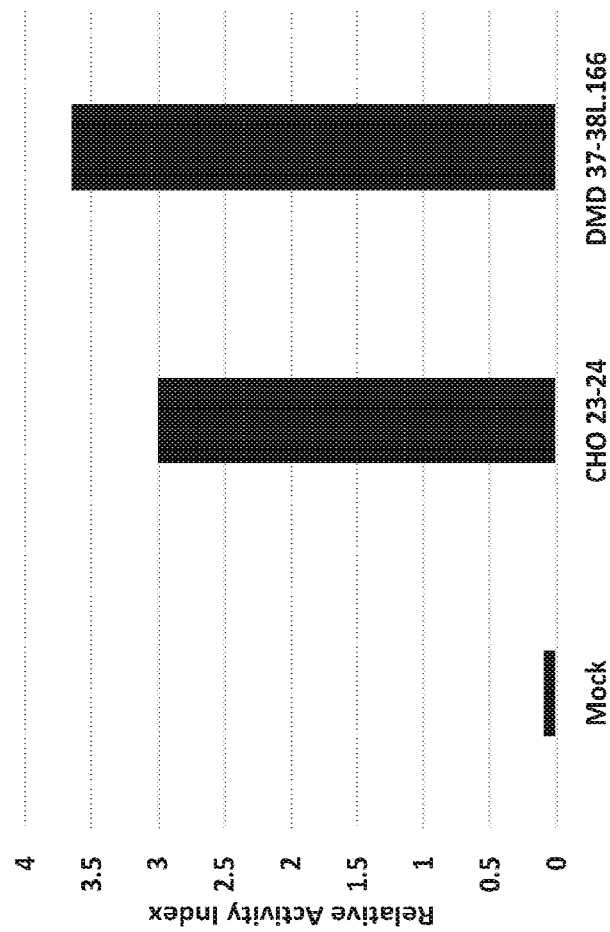
Figure 6H:
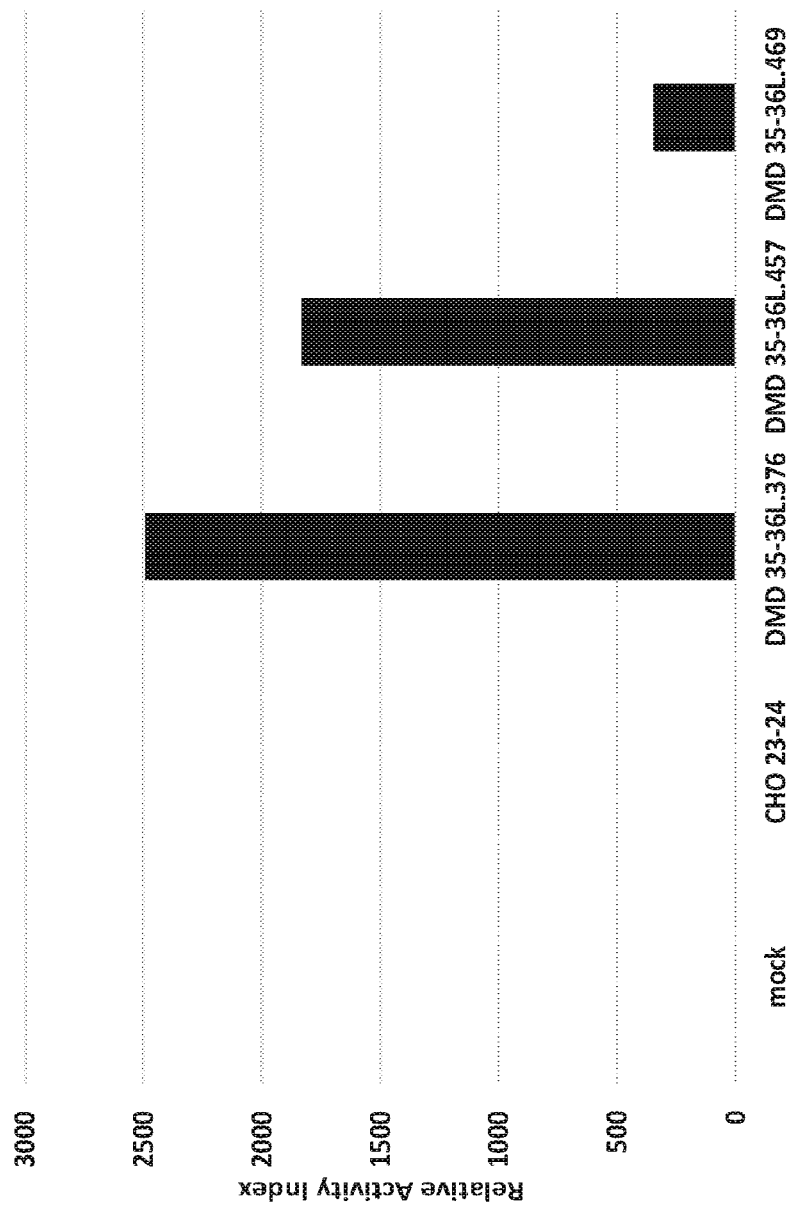
Figure 6I:
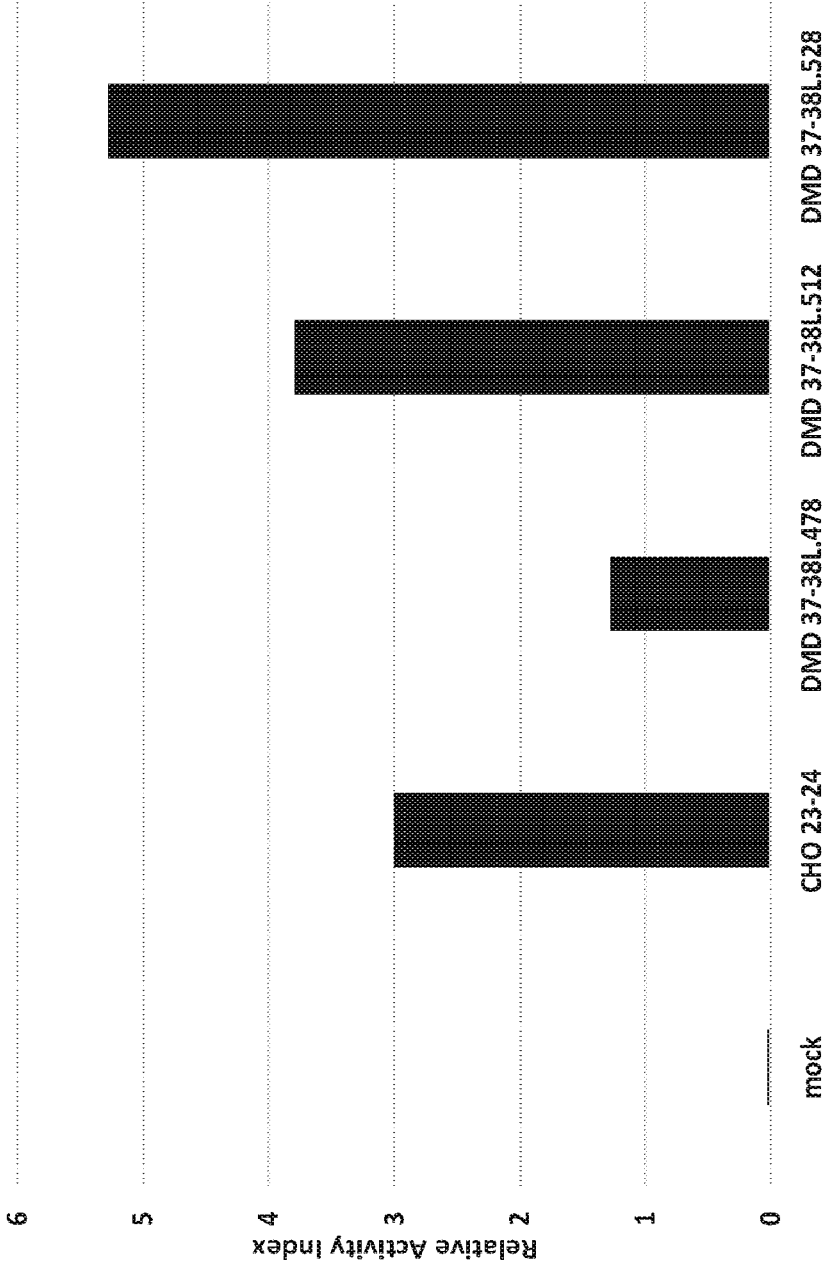

2. Cleavage of DMD 19-20, DMD 29-30, DMD 35-36, and DMD 37-38 Recognition Sequences in a CHO Cell Reporter Assay To determine whether the DMD 19-20, DMD 29-30, DMD 35-36, and DMD 37-38 meganucleases could bind and cleave their respective human recognition sequences, each engineered meganuclease was evaluated using the CHO cell reporter assay previously described (see, WO 2012/167192 and FIG. 5). To perform the assays, CHO cell reporter lines were produced, which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the human DMD 19-20, DMD 29-30, DMD 35-36, and DMD 37-38 recognition sequences. The second recognition sequence inserted into the GFP gene was a CHO-23/24 recognition sequence, which is recognized and cleaved by a control meganuclease called "CHO-23/24."

CHO reporter cells were transfected with mRNA encoding the DMD 19-20x.13, DMD 19-20x.87, DMD 19-20L.249, DMD 19-20L.374, DMD 19-20L.375, DMD 19-20L.431, DMD 19-20L.458, DMD 29-30x.18, DMD 29-30x.40, DMD 35-36x.63, DMD 35-36x.81, DMD 35-36L.376, DMD 35-36L.457, DMD 35-36L.469, DMD 37-38x.15, DMD 37-38x.66, DMD 37-38x.79, DMD 37-38L.166, DMD 37-38L.478, DMD 37-38L.512, and DMD 37-38L.528 meganucleases. CHO reporter cells were also transfected with mRNA encoding the CHO-23/24 meganuclease. In each assay, 5e4 CHO reporter cells were transfected with 90 ng of mRNA in a 96-well plate using Lipofectamine® MessengerMax (ThermoFisher) according to the manufacturer's instructions. The transfected CHO cells were evaluated by flow cytometry at 2 days, 5 days, and 7 days post transfection to determine the percentage of GFP-positive cells compared to an untransfected negative control. Data obtained at each time point was normalized to the % GFP positive cells observed using the CHO-23/24 meganuclease to determine an "activity score," and the normalized data from the earliest time point was subtracted from that of the latest time point to determine a "toxicity score." The activity and toxicity scores were then added together to determine an "activity index," which was then normalized to the activity index of the CHO-23/24 meganuclease to compare data between cell lines ("normalized activity index").

3. Results

As shown in FIG. 6A-6I, each of the respective meganucleases were able to bind and cleave their respective recognition sequence. Each meganuclease provided a level of GFP expression that was as high or higher than the positive control CHO 23-24 meganuclease.

4. Conclusions

These studies demonstrated that engineered meganucleases of the invention could efficiently bind and cleave their respective human recognition sequences (e.g., recognition sequences of SEQ ID NOs: 6, 8, 10, and 12) in cells.

Example 2

Characterization of Insertions and Deletions Induced by DMD Meganucleases

1. Methods

DMD 19-20, DMD 29-30, DMD 35-36, and DMD 37-38 meganucleases were each evaluated for their ability to generate insertions or deletions ("indels") at their respective recognition sequences in MRC5 cells.

In these experiments, 1e6 MRC5 cells were electroporated with 2 ng or 100 ng mRNA encoding DMD meganucleases (DMD 19-20x.13, DMD 19-20x.87, DMD 29-30x.18, DMD 29-30x.40, DMD 35-36x.63, DMD 35-36x.81, DMD 37-38x.15, DMD 37-38x.66, or DMD 37-38x.79), or GFP using the Lonza Amaxa 4D system. Cells were collected at two days post electroporation for cDNA preparation and evaluated for transfection efficiency using a Beckman Coulter CytoFlex S cytometer. Transfection efficiency exceeded 90%. Additional time points were collected at five- and eight-days post electroporation for gDNA extractions. gDNA was prepared using the Machercy Nagel NucleoSpin Blood QuickPure kit.

Digital droplet PCR was utilized to determine the frequency of target insertions and deletions (indel %) using primers P1, F1, and R1 at the DMD 19-20 binding site; primers P3, F3 & R3 at the DMD 37-38 binding site; Primers P4, F4 and R4 at the 35-36 target site to generate an amplicon surrounding the binding site, primers P5, F5 & R5 at the DMD 29-30 binding site, as well as primers P2, F2, R2 to generate a reference amplicon. Amplifications were multiplexed in a 20 uL reaction containing 1×ddPCR Supermix for Probes (no dUTP, BioRad), 250 nM of each probe, 900 nM of each primer, 5 U of HindIII-HF, and about 50 ng cellular gDNA. Droplets were generated using a QX100 droplet generator (BioRad). Cycling conditions were as follows: 1 cycle of 95° C. (2° C./s ramp) for 10 minutes, 44 cycles of 94° C. (1° C./s ramp) for 30 seconds, X° C. (1° C./s ramp) for 45 seconds (See below per "X" target site annealing temperatures), 72° C. (0.2° C./s ramp) for 2 minutes, 1 cycle of 98° C. for 10 minutes, 4° C. hold. Droplets were analyzed using a QX200 droplet reader (BioRad) and QuantaSoft analysis software (BioRad) was used to acquire and analyze data. Indel frequencies were calculated by dividing the number of positive copies for the binding site probe by the number of positive copies for the reference probe and comparing loss of FAM+ copies in nuclease-treated cells to mock-transfected cells.

Cycling annealing temperatures: DMD 19-20: 57° C.; DMD 35-36 59° C.; DMD 37-38 57° C.; and DMD 29-30 62° C.

TABLE 10

Primer and Probe Sets

| Sites | Primer Seq Id No. | Primer Sequence |
| --- | --- | --- |
| Probe 19-20 | SEQ ID NO: 133 | CGGGAGGTAATACATAATCC |
| 19-20 F1 | SEQ ID NO: 134 | GGGTGGGTTGCTTTACCTCTC |
| 19-20 R1 | SEQ ID NO: 135 | TGGGCTACTGCAACTCTGTT |
| P2 Reference | SEQ ID NO: 136 | AGGACAAAAGAGGACGGTCTGCCCTGG |
| Reference F2 | SEQ ID NO: 137 | TAAGACCCAGCTTCACGGAG |
| Reference R2 | SEQ ID NO: 138 | TATGATCGCCTGTTCCTCCA |
| P3 37-38 | SEQ ID NO: 139 | CTGGCCGAAGTATAGGAA |
| 37-38 F3 | SEQ ID NO: 140 | CGCAACATGTGACATAAAGAG |
| 37-38 R3 | SEQ ID NO: 141 | TCTGGATATCCTCTTCTGGG |
| P4 35-36 | SEQ ID NO: 142 | CCTACATGGTGTATCTGAC |
| 35-36 F4 | SEQ ID NO: 143 | GAACACCACCAGAAAAACAAG |
| 35-36 R4 | SEQ ID NO: 144 | CACTTCCTGTAAGACAACCAG |
| P5 29-30 | SEQ ID NO: 145 | ATCCCTCATACCCAATC |
| 29-30 F5 | SEQ ID NO: 146 | AAAAACCACGGTGCTGTTGA |
| 29-30 R5 | SEQ ID NO: 147 | ATGGGGTCCGAGACTTTTCC |

2. Results

Figure 7A:
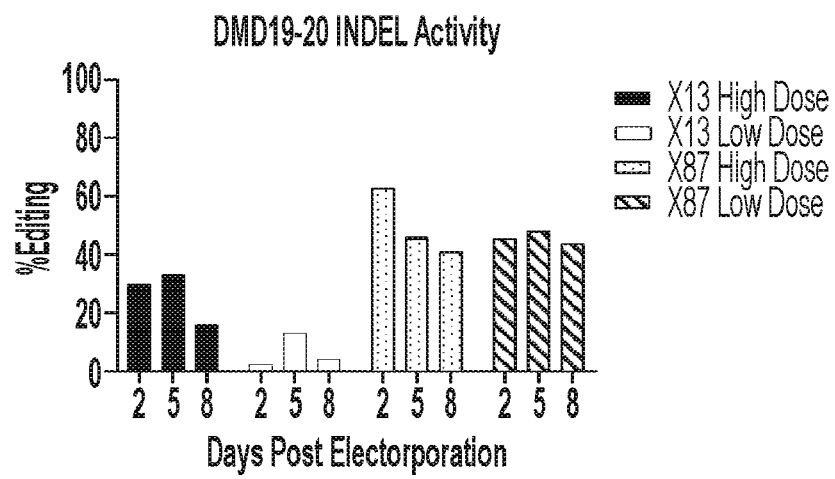
FIGS. 7A-7D show bar graphs showing the percentage frequency of insertions and deletions (indel) of the tested meganucleases targeting the indicated recognition sequences at two doses in MRC5 cells. Each meganuclease was tested at three time points (days 2, 5, and 8) following transfection of the meganuclease.
Figure 7B:
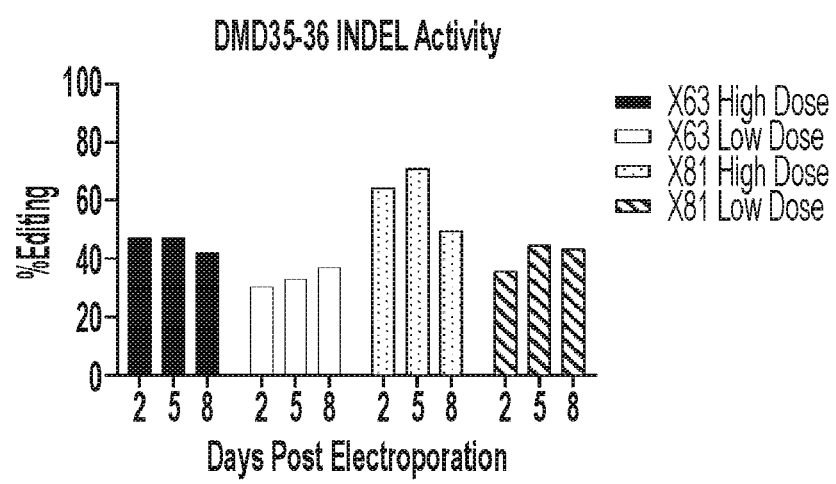
Figure 7C:
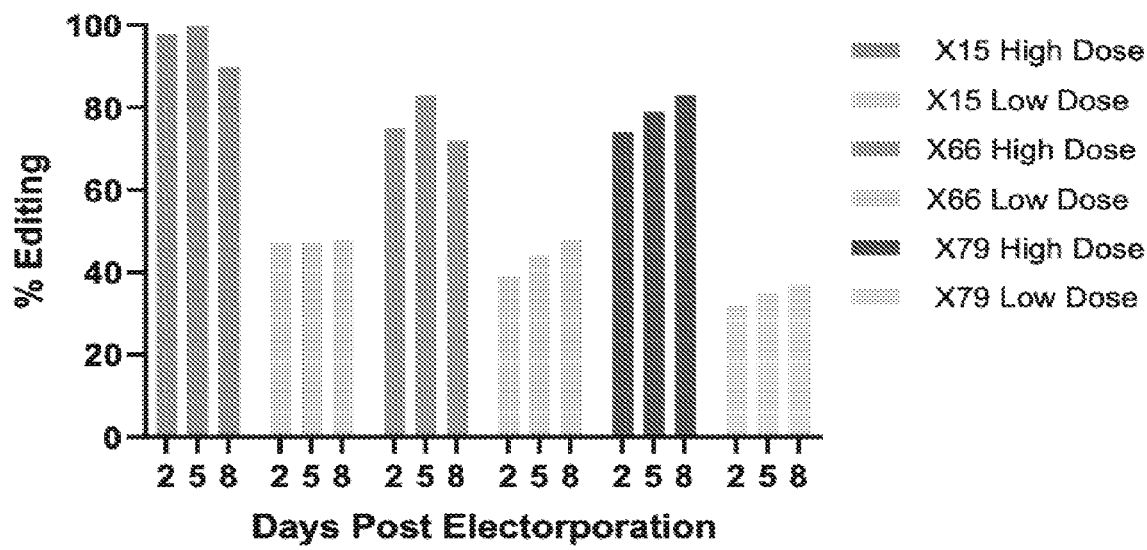
Figure 7D:
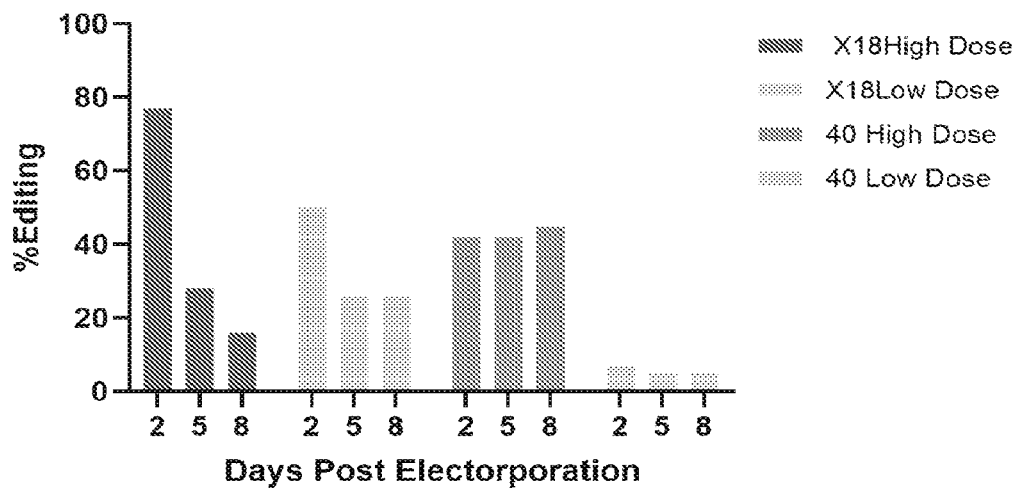

Meganucleases targeting the DMD 19-20, DMD 29-30, DMD 35-36, and DMD 37-38 recognition sequences were screened for their ability to generate indels in the MRC5 cell line. The DMD 19-20x.13 and DMD 19-20x.87 meganucleases each returned a measurable amount of indel activity at the low mRNA dose, with the DMD 19-20x.87 meganuclease showing more potency in this single nuclease assay (FIG. 7A). The DMD 35-36x.63 and DMD 35-36x.81 meganucleases each returned greater that 30% genomic editing in MRC5 cells at the low mRNA dose (FIG. 7B). The DMD 37-38x.15, DMD 37-38x.66, and DMD 37-38x.79 meganucleases returned a >30% genomic editing at the low mRNA dose with no editing reduction over time (FIG. 7C). The DMD 29-30x.18 meganuclease initially had high % indels, but these were reduced significantly at day 8, while the DMD 29-30x.40 meganuclease had a lower % of indels that were stable out to day 8 (FIG. 7D).

3. Conclusions

These experiments demonstrated that engineered DMD meganucleases of the invention were capable of generating indels at their recognition sequences in cultured cells, with many capable of producing high frequencies of indels that were stable over time, even when cells were transfected with low concentration of mRNA.

Example 3

Characterization of Pairs of Meganucleases for Removing Exons 45-55 of the Dystrophin Gene

1. Methods

These experiments evaluated pairs of engineered meganucleases targeting the DMD 19-20, DMD 35-36, and DMD 37-38 recognition sequences for their ability to excise exons 45-55 of the dystrophin gene from the genome of MRC5 cells. To accomplish this, MRC5 cells were transfected with separate mRNAs encoding DMD 19-20 and DMD 35-36 meganucleases, or separate mRNAs encoding DMD 19-20 and DMD 37-38 meganucleases. The pairs of DMD 19-20 and DMD 35-36 meganucleases tested included the following: DMD 19-20x.13 and DMD 35-36x.63; DMD 19-20x.87 and DMD 35-36x.81; DMD 19-20x.13 and DMD 35-36x.81; DMD 19-20x.87 and DMD 35-36x.63. The pairs of DMD 19-20 and DMD 37-38 meganucleases tested included the following: DMD 19-20x.13 and DMD 37-38x.15; DMD 19-20x.87 and DMD 37-38x.15; DMD 19-20x.13 and DMD 37-38x.66; DMD 19-20x.87 and DMD 37-38x.66; DMD 19-20x.13 and DMD 37-38x.79; and DMD 19-20x.87 and DMD 37-38x.79. Additionally, these experiments also evaluated pairs of DMD 19-20 and DMD 29-30 meganucleases for their ability to excise only exon 45 of the dystrophin gene from the genome of MRC5 cells. The pairs of DMD 19-20 and DMD 29-30 meganucleases tested included the following: DMD 19-20x.13 and DMD 29-30x.18; DMD 19-20x.87 and DMD 29-30x.40; DMD 19-20x.13 and DMD 29-30x.40; and DMD 19-20x.87 and DMD 29-30x.18.

1e6 MRC5 cells were electroporated with 40 ng mRNA encoding each DMD meganuclease or GFP using the Lonza Amaxa 4D system. Cells were collected at two days post electroporation for gDNA preparation and evaluated for transfection efficiency using a Beckman Coulter CytoFlex S cytometer. Transfection efficiency exceeded 90%. gDNA was prepared using the Macherey Nagel NucleoSpin Blood QuickPure kit.

gDNA was PCR amplified with primer sets spanning the deletion sites to amplify any deletion event. The following PCR Primers sets in the table below were used:

TABLE 11

| Primer Sets | | | |
|---|---|---|---|
| Sites | Primer Seq Id No. | | Primer Sequence |
| 19-20 to 35-36 | SEQ ID NO: 148 | | GGGTGGGTTGCTTTACCTCTC |
|  | SEQ ID NO: 149 | | AGAGCATGCCATCTGAGTC |
| 19-20 to 35-36 | SEQ ID NO: 150 | | GTGAAGTAGCAAAGCACCTG |
|  | SEQ ID NO: 151 | | AGAGCATGCCATCTGAGTC |
| 19-20 to 29-30 | SEQ ID NO: 152 | | GGGTGGGTTGCTTTACCTCTC |
|  | SEQ ID NO: 153 | | TTTGGTATGGGGTCCGAGAC |
| 19-20 to 29-30 | SEQ ID NO: 154 | | GTGAAGTAGCAAAGCACCTG |
|  | SEQ ID NO: 155 | | TTTGGTATGGGGTCCGAGAC |
| 19-20 to 37-38 | SEQ ID NO: 156 | | GGGTGGGTTGCTTTACCTCTC |
|  | SEQ ID NO: 157 | | GATTCTCAGAAATGGAGTGACTG |
| 19-20 to 37-38 | SEQ ID NO: 158 | | GTGAAGTAGCAAAGCACCTG |
|  | SEQ ID NO: 159 | | GATTCTCAGAAATGGAGTGACTG |

Q5 Taq Polymerase (New England Biolabs) was used in conjunction with the primers above and dNTPs (New England Biolabs) to amplify gDNA. The cycling conditions were as follows: 1 cycle of 98° C. for 4 minutes, 35 cycles of 98° C. for 10 seconds, X° C. (see above TM for anneal) for 20 seconds, 72° C. for 1.5 minutes, 1 cycle of 72° C. for 2 minutes, 4° C. hold. PCR products were run out on a 2% agarose gel and visualized by UV camera. The remaining PCR products were used for sanger sequencing using the same primers utilized in the amplification step. DNA sequence was analyzed using the SnapGene Software and compared to the anticipated template file.

Figure 11:
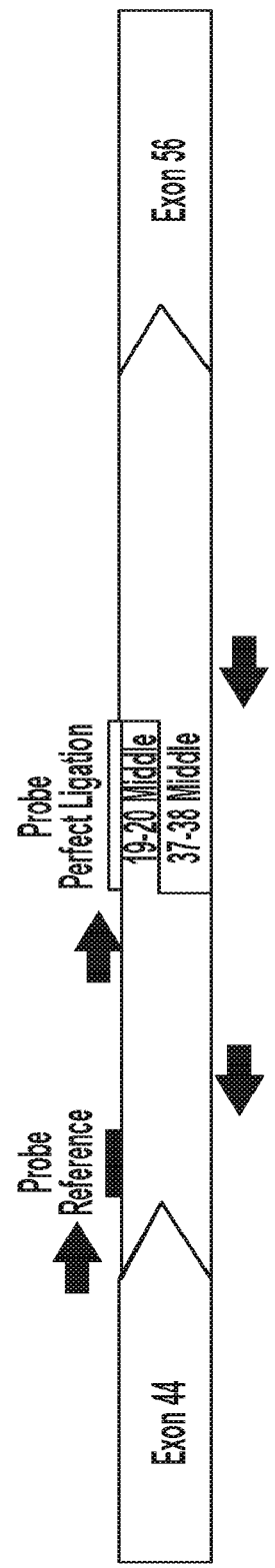
FIG. 11 provides a schematic showing the approximate location of the forward and reverse primers and the probe for the reference and perfect ligation primer sets used in the Digital droplet PCR (ddPCR) assay for detecting ligation events following cleavage. The schematic exemplifies the DMD 19-20 and DMD 37-38 ligated recognition sequences.

Digital droplet PCR was utilized to determine the frequency of large deletions (indel %) utilizing primer pairs and probes that span the junction of the 19-20 target site and the corresponding DMD nuclease for either 29-30, 35-36, or 37-38. This assay measures the perfect ligation event of the left half-site of 19-20 with the corresponding right half-site of either the 29-30, 35-36, or 37-38 nuclease site. With each dual nuclease assay, the same reference amplicon assay from Example 2 as using primers P2, F2, R2 was included allowing us to quantify the ratio of large deletion to a region unaffected by the nuclease activity. A summary schematic can be found in FIG. 11, which illustrates this assay for the 19-20 to 37-38 dual nuclease delivery. The perfect ligation for DMD 19-20 and DMD 37-38 utilized primers P6, F6, and R6. The perfect ligation for the DMD 19-20 and DMD 35-36 utilized primers P7, F7 and R7. The perfect ligation for DMD 19-20 to 29-30 utilized primers and probes P8, F8 and R8. Amplifications were multiplexed in a 20 uL reaction containing 1×ddPCR Supermix for Probes (no dUTP, Bio-Rad), 250 nM of each probe, 900 nM of each primer, 5 U of HindIII-HF, and about 50 ng cellular gDNA. Droplets were generated using a QX100 droplet generator (BioRad). Cycling conditions were as follows: 1 cycle of 95° C. (2° C./s ramp) for 10 minutes, 44 cycles of 94° C. (1° C./s ramp) for 30 seconds, X° C. (1° C./s ramp) for 45 seconds (see annealing temperature below per target site), 72° C. (0.2° C./s ramp) for 2 minutes, 1 cycle of 98° C. for 10 minutes, 4° C. hold. Droplets were analyzed using a QX200 droplet reader (BioRad) and QuantaSoft analysis software (BioRad) was used to acquire and analyze data. Indel frequencies were calculated by dividing the number of positive copies for the binding site probe by the number of positive copies for the reference probe and comparing loss of FAM+ copies in nuclease-treated cells to mock-transfected cells.

Cycling annealing temperatures: DMD 19-20-DMD 37-38 at 53° C., DMD19-20-DMD 37-38 at 59° C., and DMD 19-20-DMD 29-30 at 55° C.

TABLE 12

Primer and Probe Sets

| Sites | Primer Seq ID NO. | Primer Sequence |
| --- | --- | --- |
| P6 19/38 | SEQ ID NO: 160 | ATCAGAAGGATTATGTATAGGAATA |
| 19-20 F6 | SEQ ID NO: 161 | GGGTGGGTTGCTTTACCTCT |
| 37-38 R6 | SEQ ID NO: 162 | TCTGGATATCCTCTTCTGGG |
| P7 19/36 | SEQ ID NO: 163 | GTGAAGTAGCAAAGCACCTG |
| 19-20 F7 | SEQ ID NO: 164 | GTGAAGTAGCAAAGCACCTG |
| 35-36 R7 | SEQ ID NO: 165 | AGTCACTTCCTAAGCTAAGACAACC |
| P8 19/30 | SEQ ID NO: 166 | CAGAAGGATTATGTATGAGGGATA |
| 19-20 F8 | SEQ ID NO: 167 | GTGAAGTAGCAAAGCACCTG |
| 29-30 R8 | SEQ ID NO: 168 | ATGGGGTCCGAGACTTTTCC |

2. Results

Figure 8A:
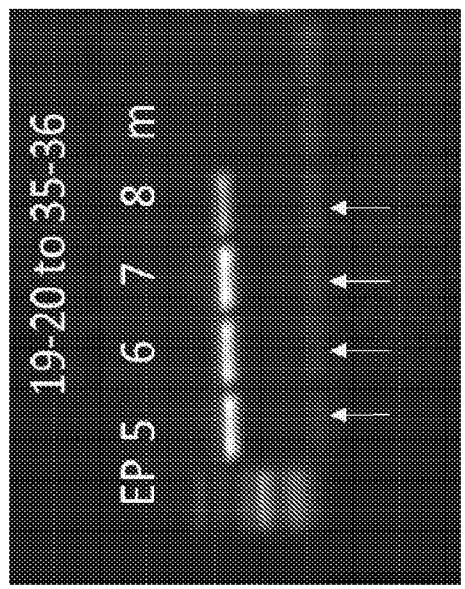
Figure 8B:
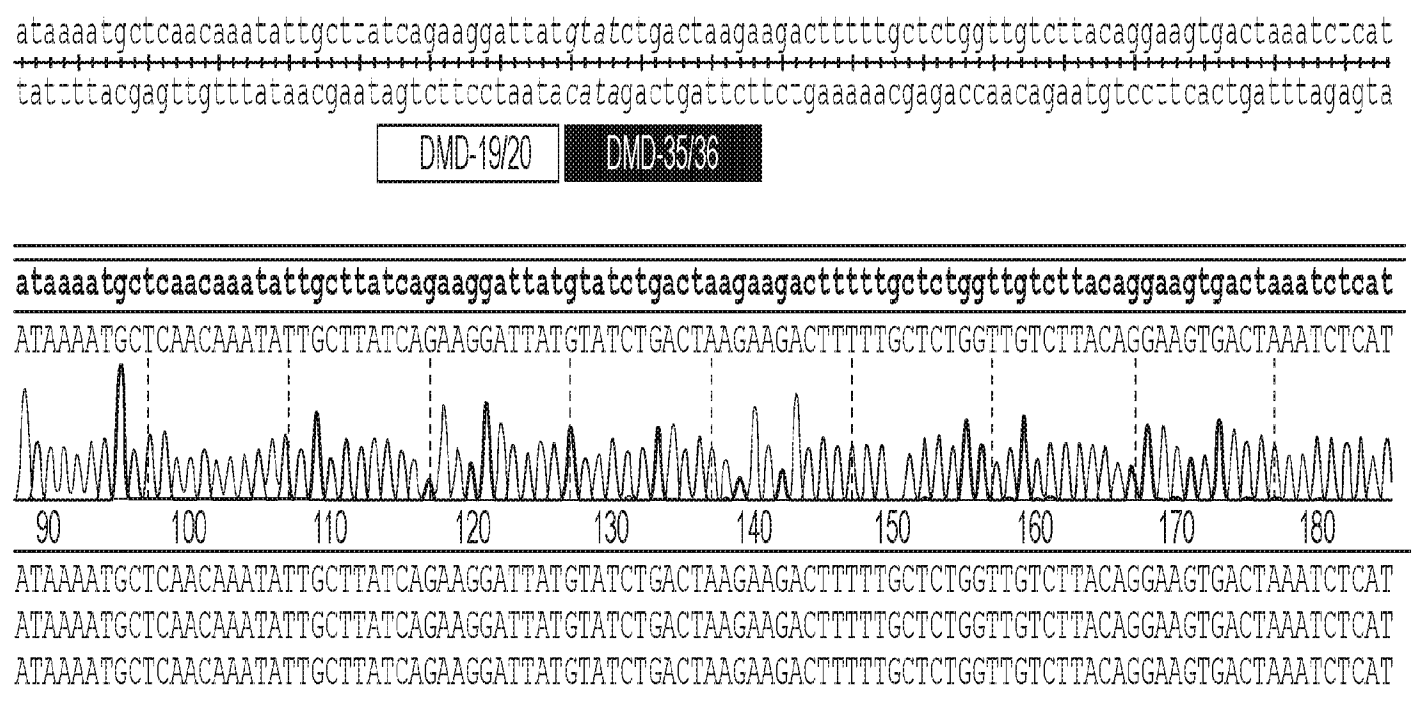
Figure 9A:
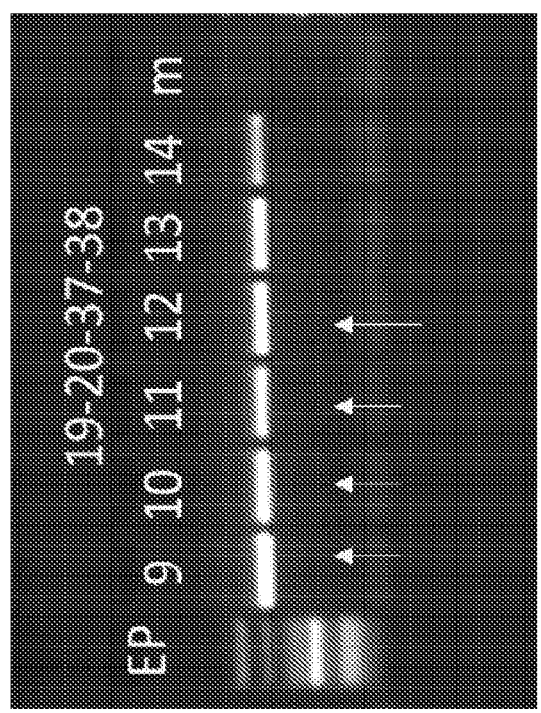
FIGS. 9A and 9B provide PCR product and sequencing data for the perfect ligation of the dystrophin gene following cleavage with a pair of engineered meganucleases designed to bind and cleave the DMD 19-20 and DMD 37-38 recognition sequences.
Figure 9B:
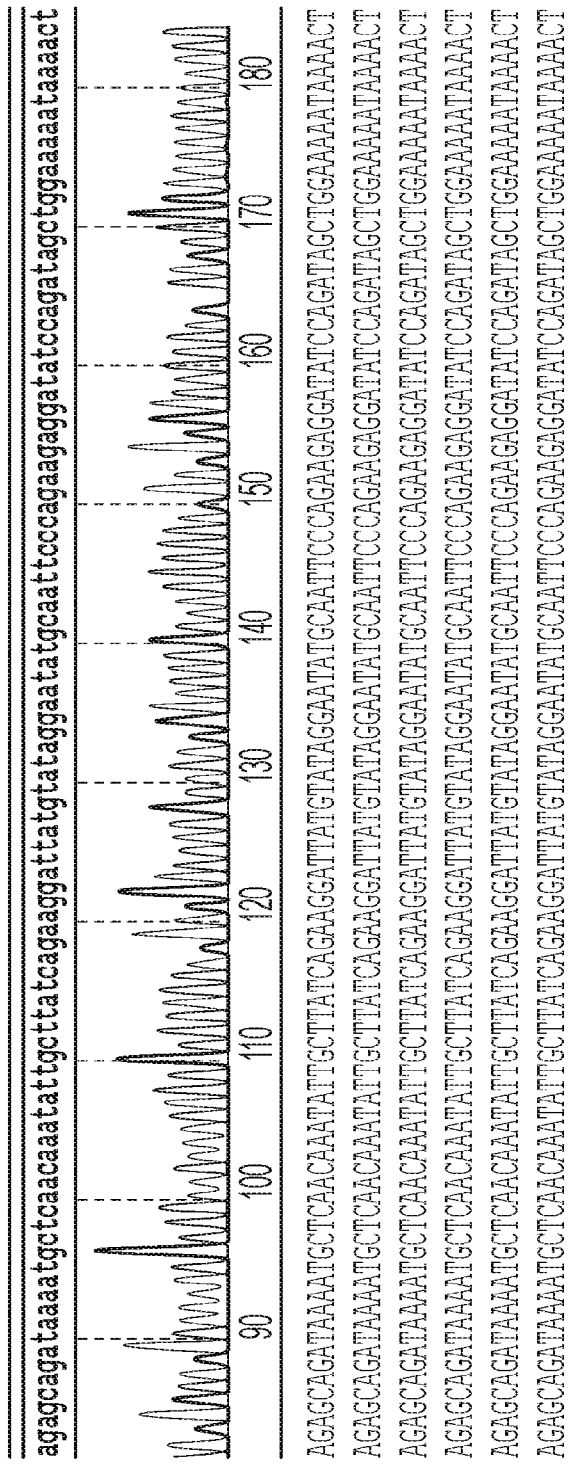
Figure 10:
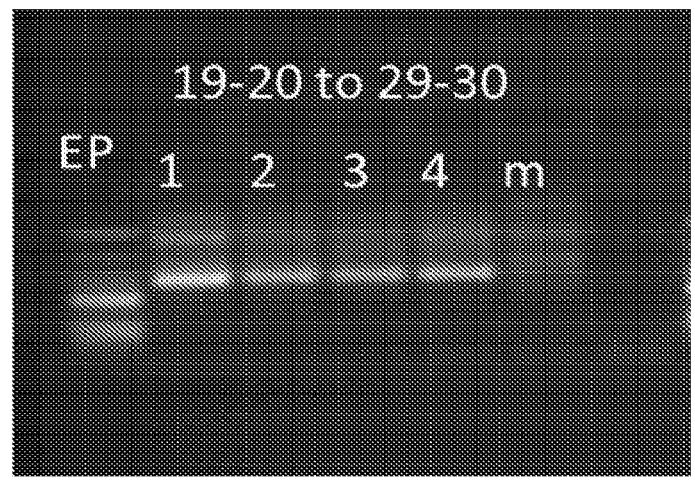
FIG. 10 provides PCR product for the perfect ligation of the dystrophin gene following cleavage with a pair of engineered meganucleases designed to bind and cleave the DMD 19-20 and DMD 29-30 recognition sequences. Shown is a gel image of the PCR product using primers specific to amplify ligation of the complementary DMD 19-20 and DMD 29-30 recognition sequences. Lane 1 represents the combination of the DMD 19-20x.13 and DMD 29-30x.18 meganucleases. Lane 2 represents the combination of the DMD 19-20x.87 and DMD 29-30x.40 meganucleases. Lane 3 represents the combination of the DMD 19-20x.13 and DMD 29-30x.40 meganucleases. Lane 4 represents the combination of the DMD 19-20x.87 and DMD 29-30x.18 meganucleases. Lane M represents a mock control.

Correct sized PCR products were visualized for 19-20 to 35-36 amplifications (FIG. 8A) with the corresponding sequence data showing the perfect ligation between the 19-20/35-36 nuclease binding sites (FIG. 8B). The correct sized PCR products were also visualized for 19-20 to 37-38 amplifications (FIG. 9A) with the corresponding sequence data showing the perfect ligation between the 19-20/37-38 nuclease binding sites (FIG. 9B). Furthermore, the correct sized PCR products were visualized for 19-20 to 29-30 amplifications (FIG. 10).

Figure 12A:
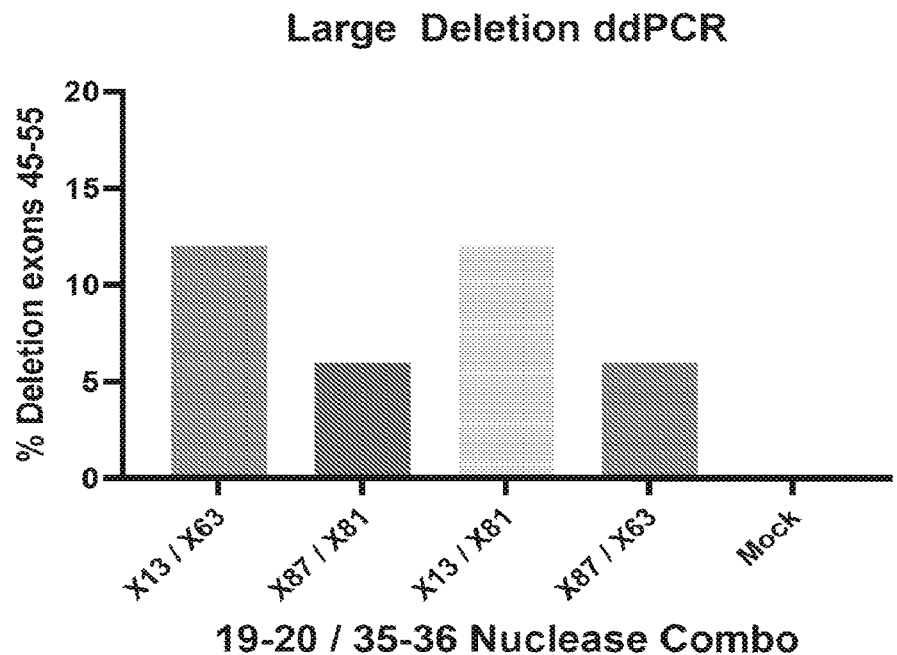
FIGS. 12A-12C provide bar graphs showing the percentage of deletion of exons 45-55, or exon 45 alone, as assessed by ddPCR.
Figure 12B:
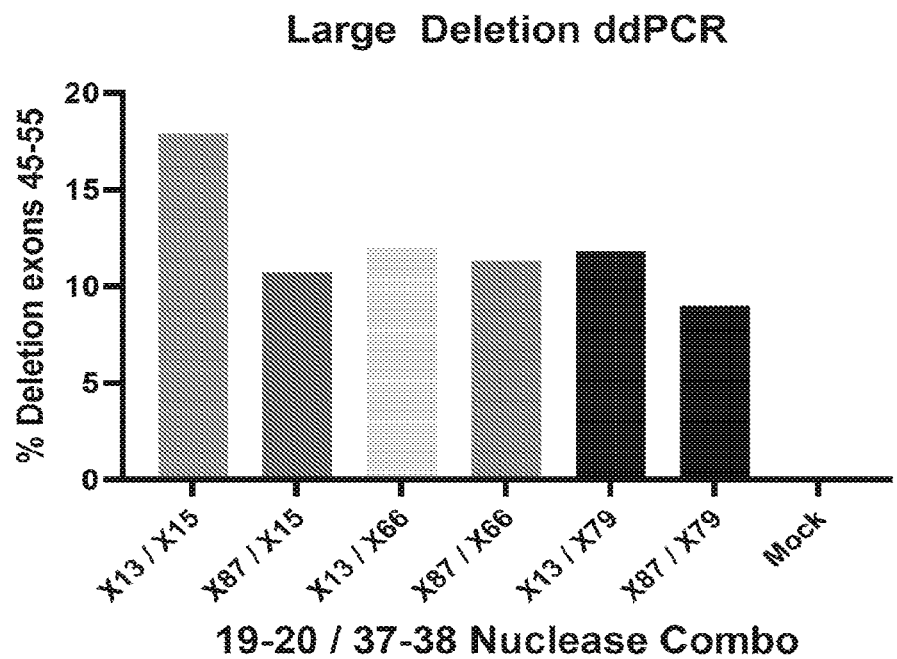
Figure 12C:
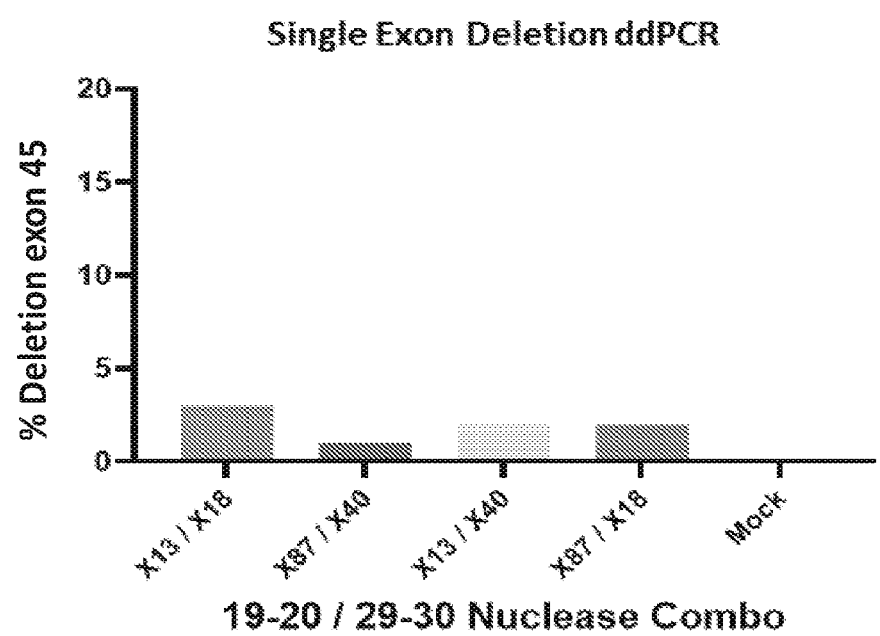

The Digital droplet PCR (ddPCR) assays for all three deletion events were successful in measuring the perfect ligation between the 19-20 recognition sequence and the corresponding sequence from either 29-30, 35-36, or 37-38 with clean mock reactions. The perfect ligation for DMD 19-20 to DMD 35-36 quantified deletion and ligation events ranged from 6 to 12% (FIG. 12A). The perfect ligation for DMD 19-20 to DMD 37-38 quantified deletion and ligation events ranged from 9 to 17.9% (FIG. 12B) and the perfect ligation for DMD 19-20 to DMD 29-30 quantified deletion and ligation events ranged from 1 to 3% (FIG. 12C).

3. Conclusions

Figure 13:
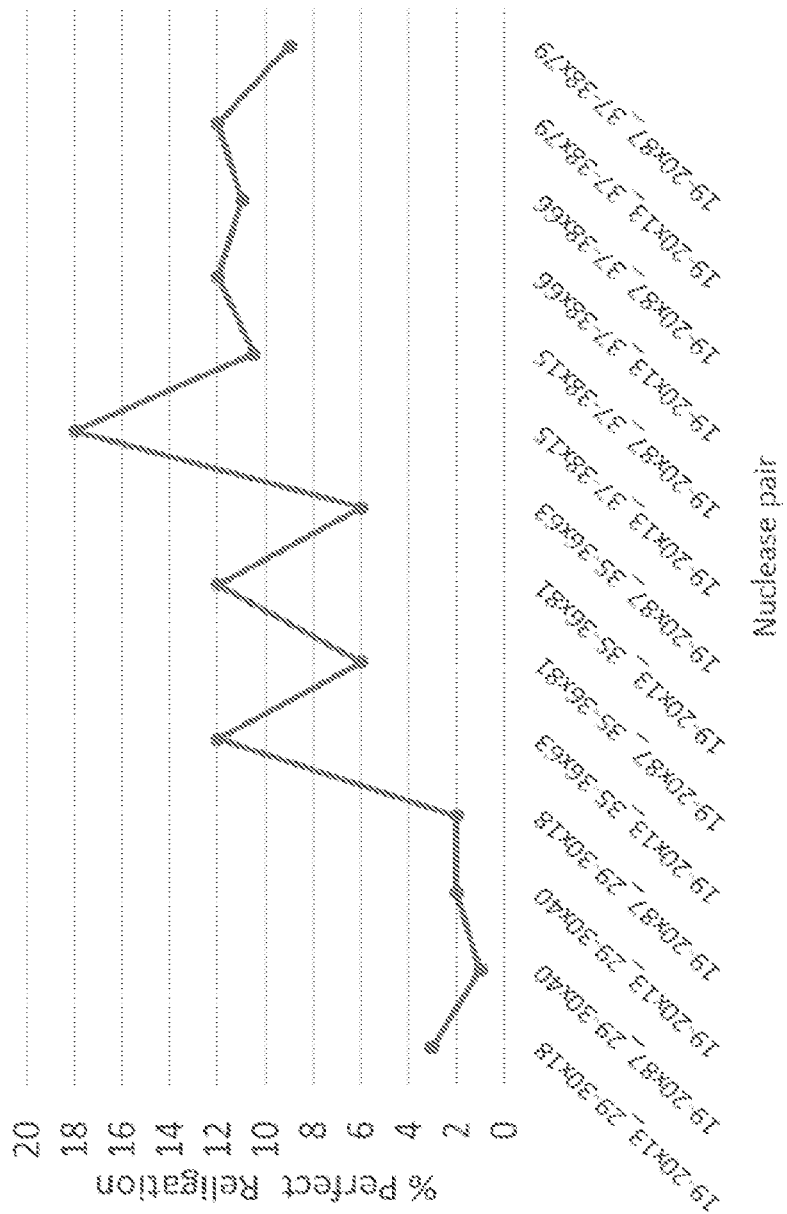
FIG. 13 provides a line graph of perfect ligation events assessed by ddPCR with additional different combinations of engineered meganucleases.

These results provide in vitro proof of concept for dual editing with removal of the hot spot exons associated with multiple DMD disease-associated mutations. These editing events were measured to be as high as 17.9%. However, the frequency of these edits, and the removal of either exon 45 alone or exons 45-55, are underestimated because this assay only picks up the perfect ligation events, as opposed to ligations that result in minor indels at the target sites. Furthermore, it was shown that this can be accomplished with multiple different engineered meganucleases and target sites with varying levels of success (FIG. 13). Unexpectedly, these data showed that the percentage of perfect ligation was significantly higher for the removal of exons 45-55 and over 500,000 bp of genetic sequence with the DMD 19-20 and DMD 35-36/DMD 37-38 meganuclease pairings, as compared to the removal of a single exon 45 with the DMD 19-20 and DMD 29-30 meganuclease pairing (FIG. 12C and FIG. 13).

Example 4

Analysis of Perfect Ligation Events in the Dystrophin Gene Following Removal of Exons 45-55 in Primary Human Skeletal Muscle Myoblasts 1. Methods In these experiments, the editing ability of meganucleases targeting the DMD 19-20 and DMD 37-38 recognition sequences was evaluated in human skeletal muscle myoblasts, a human primary muscle cell. Human skeletal muscle myoblasts were purchased from Lonza (HSMM CC-2580). Cells were thawed and seeded at 3500 cells/cm² in Skeletal muscle cell growth medium-2 (SkGM-2) and maintained to a confluency not more than 70% until electroporation. Transfections were performed with 1e6 cells. Cells were electroporated with either 20, 40, 80 or 160 ng mRNA encoding each DMD meganuclease in pairs (DMD 19-20L.249 and DMD 37-38L.166 pair) or GFP using the Lonza Amaxa 4D system. After electroporation cells were seeded into growth media in individual wells of a 6 well plate. One day after electroporation, cells to be differentiated were changed to DMEMF12 (Thermo) with 2% horse serum, while cells to be maintained as undifferentiated were maintained in growth media. Cells were harvested 2- and 8-days post electroporation for DNA and protein extraction. gDNA isolation and Digital droplet PCR was utilized to determine the frequency of large deletions (indel %) for the DMD 19-20-DMD 37-38 perfect ligation as specified in Example 3 above.

2. Results

Figure 14:
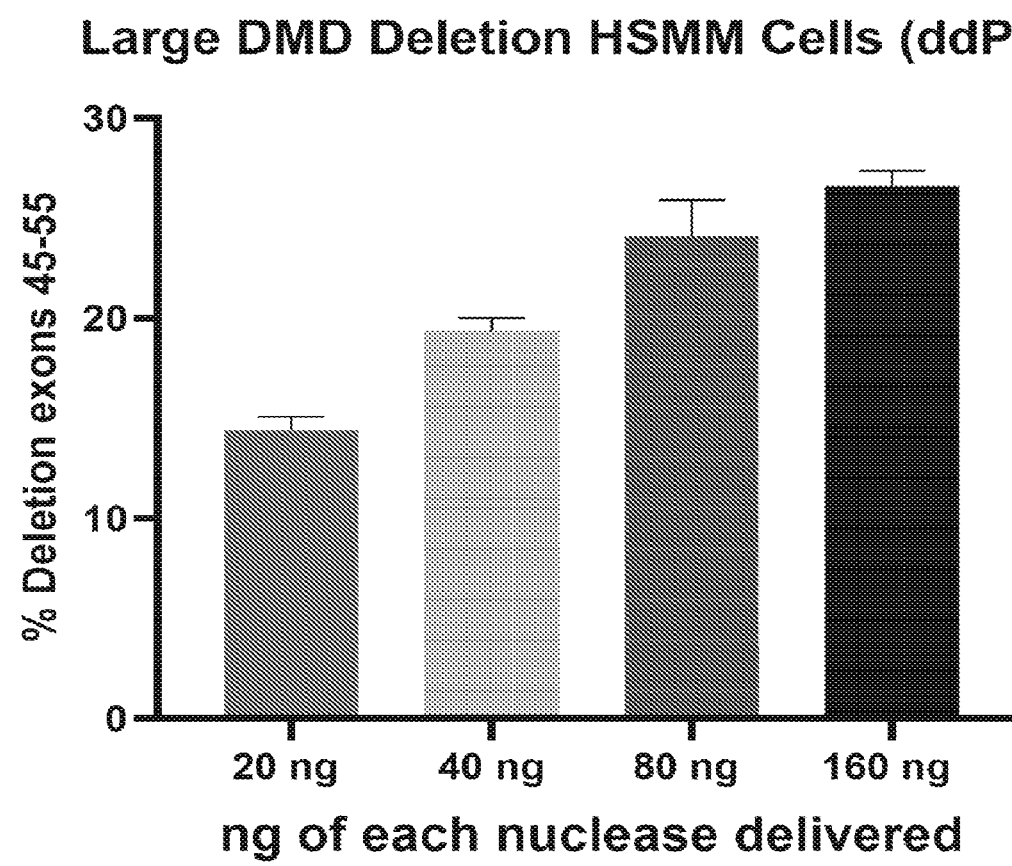
FIG. 14 provides a bar graph showing the percentage of deletion of exons 45-55 as assessed by ddPCR using the pair of DMD 19-20L.249 and DMD 37-38L.166 engineered meganucleases in human skeletal muscle myoblasts (HSMM). The HSMM cells were transfected with either 20 ng, 40 ng, 80 ng, or 160 ng of mRNA encoding each engineered meganuclease.

A dose-dependent increase in the large deletion/perfect ligation was seen with increasing amounts of DMD 19-20L.249 and DMD 37-38L.166 engineered meganuclease mRNA in the HSMM cell lines (FIG. 14). Perfect ligations following excision of exons 45-55 ranged from 14% to 27% for the low to high dose mRNA.

3. Conclusions

Previous results of dual delivery large deletion were carried out in a human MRC5 cell line. By contrast, this experiment measured the ability of engineered meganucleases of the invention to edit the genome at recognition sites needed to excise the exons that contain the "Hot Spot" regions in a relevant muscle cell line. Increasing amounts of engineered meganuclease mRNA that targeted the DMD 19-20 and DMD 37-38 recognition sequences were able excise a fragment greater than 500,000 bp and perfectly ligate the gene back together at frequencies up to 27%, as quantified by digital droplet PCR. These data support in vitro proof of concept of large-scale editing/deletion with a pair engineered meganucleases.

Example 5

Analysis of Large Deletion and Restoration of Dystrophin In Vitro Following Increasing Amounts of Pairs of DMD Meganucleases in an Immortalized Cell Line Isolated from a DMD Patient 1. Methods Pairs of DMD 19-20 and DMD 37-38 nucleases were further evaluated in a DMD patient cell line AB1098. The DMD patient myoblast cell line was obtained from the Center for Research in Myology (Sorbonne University). This cell line was immortalized from the spinal muscle of a patient with a deletion of exons 48-50 and are dystrophin protein deficient due to the deleted exons.

Cells were seeded at 3000 cells/cm² and grown in Promocell muscle growth media (Promocell). Transfections were performed with 1e6 cells in P5 electroporation solution (Lonza) and transfected with the EY100 program using the Lonza 4D-Nucleofector X unit. Nuclease mRNA dose was 10 ng, 20 ng, 40 ng, 80 ng, or 160 ng for each of the DMD 19-20L.249 and DMD 37-38L.166 meganucleases. After electroporation, cells were seeded into growth media in individual wells of a 6 well plate. One day after electroporation, cells to be differentiated were changed to DMEM (Thermo) 10 ug/ml Insulin, and 50 ug/ml gentamycin, while cells to be maintained as undifferentiated were maintained in growth media. Cells were harvested 2- and 8-days post electroporation for DNA and protein extraction. gDNA isolation and Digital droplet PCR was utilized to determine the frequency of large deletions (indel %) for the DMD 19-20-DMD 37-38 perfect ligation as specified in Example 3 above. For protein extraction, cells were harvested from the plates with TrypLE, pelleted, then rinsed with PBS and lysed with 1×RIPA buffer with protease inhibitors (Millipore). Protein concentration was determined by BCA assay (Thermo). For analysis by WES (Protein simple) lysates were normalized to 250 ng/ul and run on the 66-440 kDa module using the standard program. Primary antibody used for detection of dystrophin was ab154168 at 1:1000. Primary antibody vs Vinculin (Abcam) was used (1:200) as a loading control.

2. Results

Figure 15:
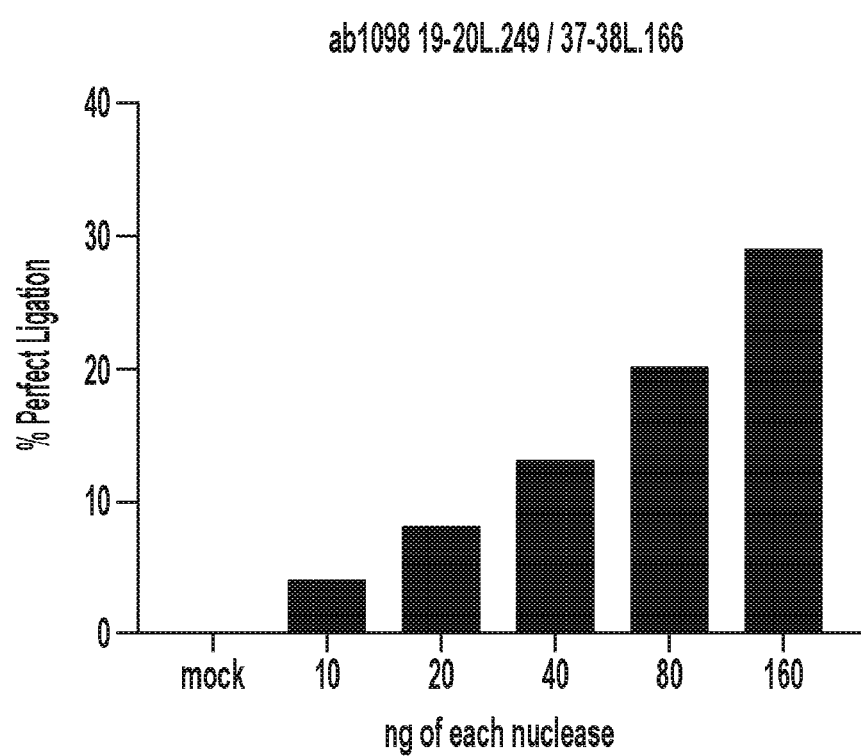
FIG. 15 provides a bar graph showing the percentage of perfect ligation assessed by ddPCR using the pair of DMD 19-20L.249 and DMD 37-38L.166 engineered meganucleases in an immortalized myoblast cell line from a patient having DMD (AB1098 cells). The AB1098 cells were transfected with either 10 ng, 20 ng, 40 ng, 80 ng, or 160 ng of mRNA encoding each meganuclease.

A dose dependent increase in the large deletion/perfect ligation was seen with increasing amounts of mRNA encoding the DMD 19-20L.249 and DMD 37-38L.166 engineered meganucleases in this DMD patient cell line. Perfect ligations ranged from 4% to 29% (low to high dose mRNA) (FIG. 15).

Figure 16A:
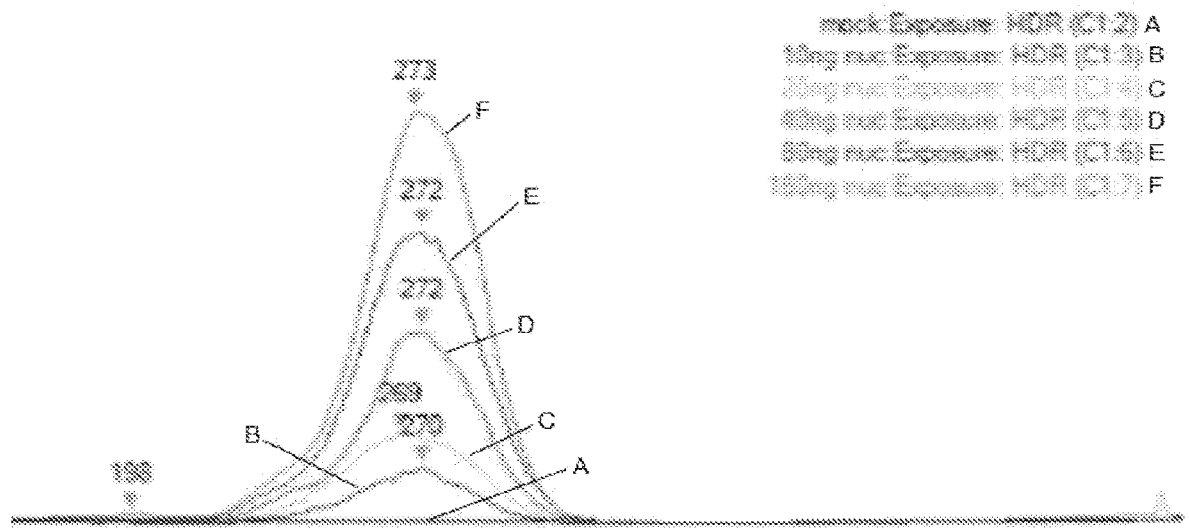
FIGS. 16A-16C provide protein expression data following treatment with either 10 ng, 20 ng, 40 ng, 80 ng, or 160 ng of mRNA encoding each of the DMD 19-20L.249 and DMD 37-38L.166 engineered meganucleases, or a mock control, in AB1098 cells.
Figure 16B:
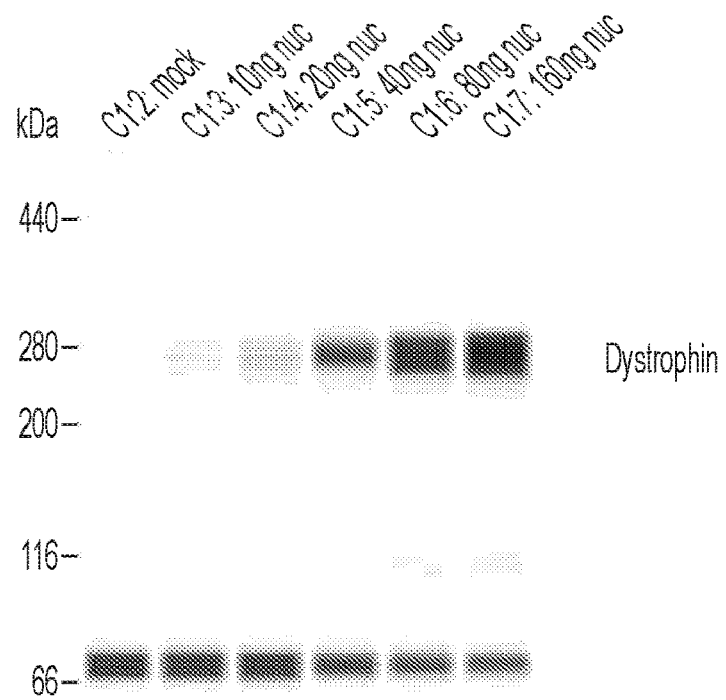
Figure 16C:
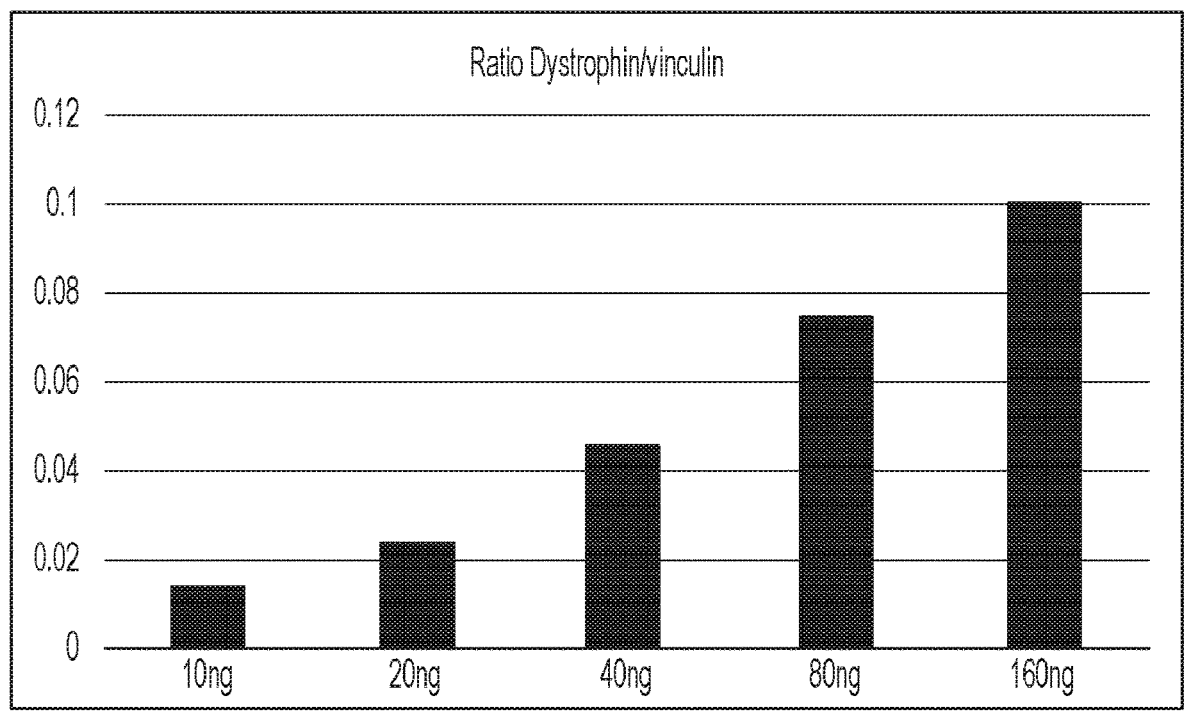

Expression of the shortened modified dystrophin protein, lacking the amino acids encoded by exons 45-55, was measured by WES automated western blot analysis. A dose dependent increase in the amount of modified dystrophin is viewed in the WES Chromatic readout, with the highest dose 160 ng (line F), 80 ng (line E), 40 ng (line D), 20 ng (line C), ng (line B) and mock (line A) (FIG. 16A). The WES system converted the chromatic data generated into a more traditional Western Blot figure and duplicated the read out. No dystrophin was detected in mock untreated AB1098 cells, with increasing intensity of bands for dystrophin across the dose range (FIG. 16B). Dystrophin restoration was normalized to a loading control Vinculin Protein and the amount of protein restoration was calculated relative to loading (FIG. 16C). No dystrophin was measured in mock, while a seven-fold increase in dystrophin was observed across the dose curve.

3. Conclusions

These experiments report the large deletion of exons 45 to 55 in a cell line isolated from a patient missing exons 48 to 50 in the dystrophin gene. This cell line does not express detectable levels of dystrophin and is a good in vitro model for the DMD disease. The WES protein data in FIG. 16 shows restored expression of a shortened modified dystrophin protein, with no protein expression in untreated mock cells to a detectable level across all engineered meganuclease dose ranges. This is further confirmation and in vitro proof of concept of using dual engineered meganucleases for the purpose of treating DMD patients by excising exons 45-55 and converting the dystrophin gene to a Beckers dystrophin phenotype.

Example 6

Analysis of RNA Splice Message

1. Methods

This study characterized pairs of DMD 19-20 and DMD 37-38 meganucleases in the patient cell line AB1098 looking at the RNA splice message post meganuclease delivery.

Cells were cultured and electroporated as described in Example 5. The dose of nuclease mRNA dose was 10 ng, 20 ng, 40 ng, 80 ng, or 160 ng for each meganuclease (DMD 19-20L.249 and DMD 37-36L.166). Cells were harvested on day 8 for RNA extraction using phenol chloroform and the Purelink RNA mini kit (Thermo). Post RNA isolation, cDNA synthesis was performed with the iSCRIPT cDNA synthesis kit (Bio-Rad) and ddPCR was utilized to determine the frequency of the splicing of exon 44 to exon 56. Dystrophin splice message of treated cells was normalized to a reference message assay for the gene, Ankyrin Repeat Domain containing protein 27 (ANKRD27) purchased from Thermo Fisher (assay #Hs01047624_g1).

CDNA Synthesis conditions: Primed for 5 minutes at 25° C., RT for 20 minutes at 46° C. and inactivated for 1 minute at 95° C. ddPCR cycling 95° C. for 10 minutes followed by cycles of 95° C. 45 seconds, 57° C. 45 seconds, 72° C. for 1 minute and final inactivation of 98° C. for 10 minutes.

TABLE 13

Primer and Probe Sets

| Sites | Primer Seq Id No. | Primer Sequence |
|---|---|---|
| 95 DMD Splice RNA For2 | SEQ ID NO: 184 | GCTGAACAGTTTCTCAGAAAGACA |
| 98 DMD RNA Splice Rev 2 | SEQ ID NO: 185 | GGCTGTTTTCATCCAGGTTGTG |
| 96 DMD 4456 RNA SPLICE PB | SEQ ID NO: 186 | TCTTAAGGACCTCCAAGG |

2. Results

Figure 17:
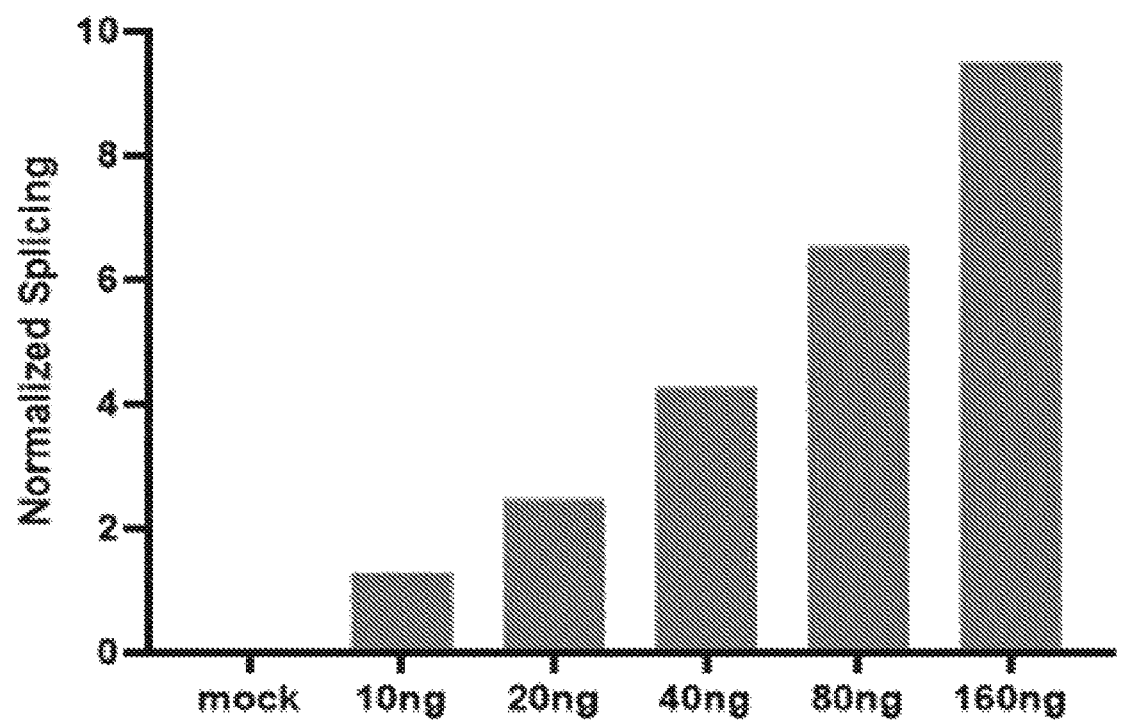
FIG. 17 provides a bar graph showing RNA splicing of exon 44 to exon 56 in AB1098 cell mRNA following transfection with 10 ng, 20 ng, 40 ng, 80 ng, or 160 ng of mRNA encoding each of the DMD 19-20L.249 and DMD 37-38L.166 engineered meganucleases, or a mock control.

A dose-dependent increase in the exon 44 to exon 56 splice message was seen with increasing amounts of DMD19-20L.249 and DMD 37-38L.166 engineered meganuclease mRNA in the patient cell line. Splice message to reference gene message ratio ranged from 0.01% in the mock to 9.51% at high dose mRNA (FIG. 17).

3. Conclusions

These experiments demonstrated the large deletion of exons 45 to 55 of the dystrophin RNA message in a cell line isolated from a DMD patient. This cell line does not express detectable levels of dystrophin and is a good in vitro model for DMD disease. The splice message data in FIG. 17 shows the targeted deletion of exons 45 to 55. This is further confirmation and in vitro proof of concept of using a dual engineered meganuclease strategy for the purpose of treating DMD patients by excising exons 45-55, and restoring a "Beckers" dystrophin phenotype.

Example 7

Analysis of Perfect Ligation Events in the Dystrophin Gene Following Removal of Exons 45-55 in Primary Human Skeletal Muscle Myoblasts

1. Methods

These experiments evaluated the ability of meganucleases targeting the DMD 19-20 and DMD 35-36 recognition sequences to excise exons 45 to 55 of the dystrophin gene in human skeletal muscle myoblasts, a human primary muscle cell, as described in Example 4. Cells were thawed and seeded at 3500 cells/cm$^2$ in Skeletal muscle cell growth medium-2 (SkGM-2) and maintained to a confluency not more than 70% until electroporation. Transfections were performed with 1e6 cells. Cells were electroporated with either 40 ng mRNA encoding each DMD meganuclease in pairs (DMD 19-20x.13 and DMD 35-36x.63; DMD 19-20L.249 and DMD 35-36L.195; DMD 19-20L.302 and DMD 35-36L.282; DMD 19-20L.329 and DMD 35-36L.282; DMD 19-20L.302 and DMD 35-36L.349; or DMD 19-20L.329 and DMD 35-36L.349) or GFP using the Lonza Amaxa 4D system. After electroporation, cells were seeded into growth media in individual wells of a 6 well plate. Cells were harvested 2 days post electroporation for DNA. gDNA isolation and digital droplet PCR was utilized to determine the frequency of large deletions (indel %) for the DMD 19-20-DMD 35-36 perfect ligation as specified in Example 3 above.

2. Results

Figure 18:
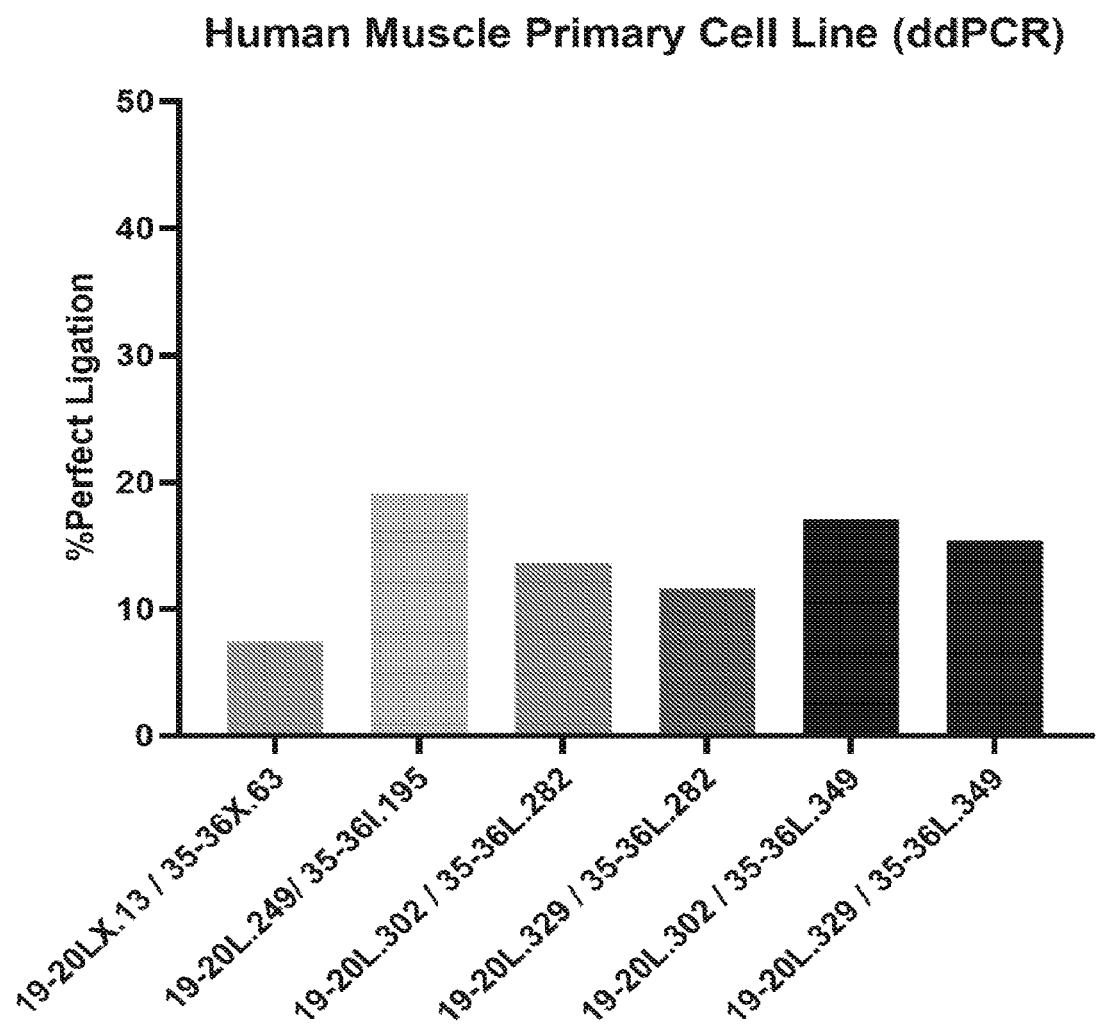
FIG. 18 provides a bar graph showing the percentage of perfect ligation as assessed by ddPCR using the indicated pairs of engineered meganucleases in HSMM cells. The HSMM cells were transfected with 40 ng of mRNA encoding each engineered meganuclease.

As shown in FIG. 18, each pair of engineered meganucleases demonstrated a deletion of exons 45-55 and perfect ligation of the dystrophin gene in this primary myoblast cell line.

3. Conclusions

These results further demonstrate that pairs of engineered meganucleases of the invention, which target the DMD 19-20 and DMD 35-36 recognition sequences within the dystrophin gene, can excise exons 45-55 from the dystrophin gene and subsequently induce a perfect ligation of the dystrophin gene. These data are consistent with data provided in Example 4 and further support in vitro proof of concept of large-scale editing and deletion with engineered meganucleases.

Example 8

Generation of Additional DMD 19-20 Meganucleases

1. Methods

Figure 19:
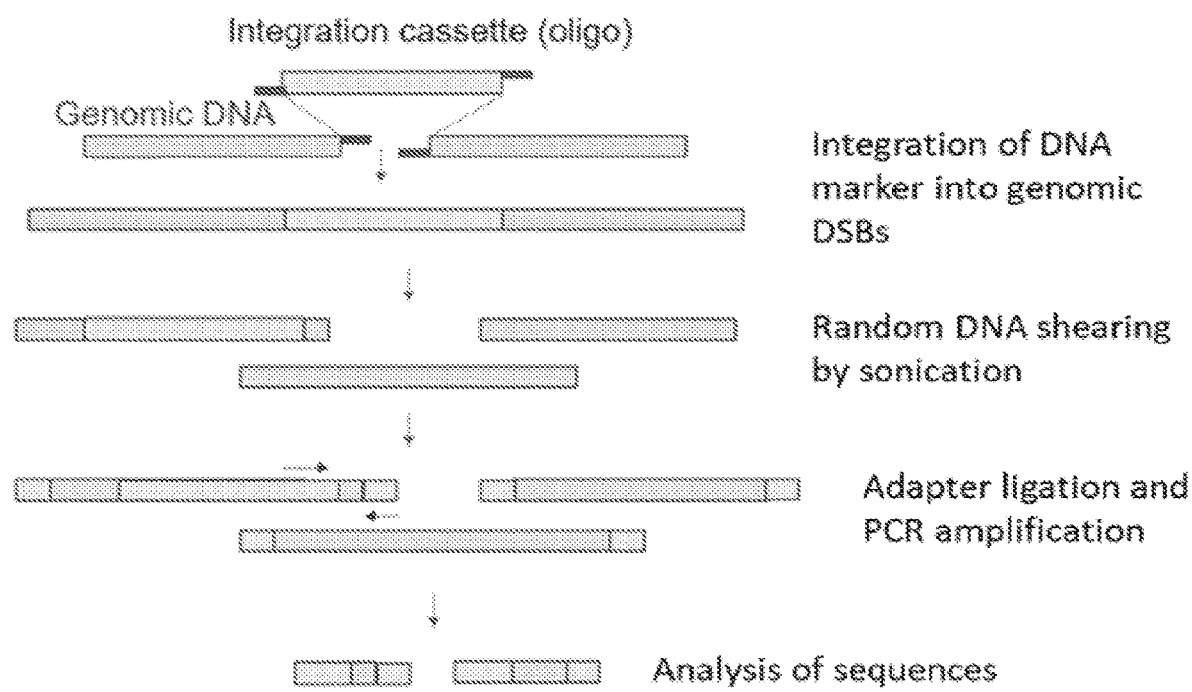
FIG. 19 provides a schematic of the oligo capture assay utilized to determine off-target effects of an engineered nuclease (e.g., an engineered meganuclease described herein). As shown, the integration cassette or oligo anneals with a double stranded break in the genome that may be due to engineered nuclease cleavage. The DNA is then sheared by sonication, adapters are ligated and PCR amplified followed by sequence analysis to determine location of the double strand break.

Additional DMD 19-20 meganucleases were created after three rounds of development to increase meganuclease potency and specificity. Meganuclease specificity was measured using the OligoCapture assay. This is a cell-based, in vitro assay that relies on the integration of a synthetic oligonucleotide (oligo) cassette at DSBs within the genome. Using the oligo as an anchor, genomic DNA to either side of the integration site can be amplified, sequenced, and mapped (FIG. 19). This allows for a minimally biased assessment of potential off-target editing sites of the nuclease. This technique was adapted from GuideSeq (Tsai et al. (2015) *Nat. Biotech.* 33:187-97) with specific modification to increase sensitivity and accommodate the 3' complementary overhangs induced by the meganucleases. The OligoCapture analysis software is sequence agnostic. That is, no a priori assumptions are made regarding which DNA sequences the nuclease is capable of cutting. In the OligoCapture assay, cells are transfected with nuclease mRNA and double-stranded DNA oligonucleotides. After 2 days, the cellular genomic DNA was isolated and sheared into smaller sizes. An oligonucleotide adapter was ligated to the sheared DNA and polymerase chain reaction was used to amplify any DNA pieces that contain an adapter at one end and the captured oligonucleotide at the other end. The amplified DNA was purified, and sequencing libraries were prepared and sequenced. The data were filtered and analyzed for valid sites that captured an oligonucleotide to identify potential off-target sites. The sequence reads were aligned to a reference genome, and grouped sequences within thousand-base pair windows scanned for a potential meganuclease cleavage site. HEK293 cells were transfected with mRNA for multiple DMD19-20 nucleases at each round of optimization (rounds 1-3) gDNA was isolated and processed as written above in the assay description.

2. Results

Figure 20:
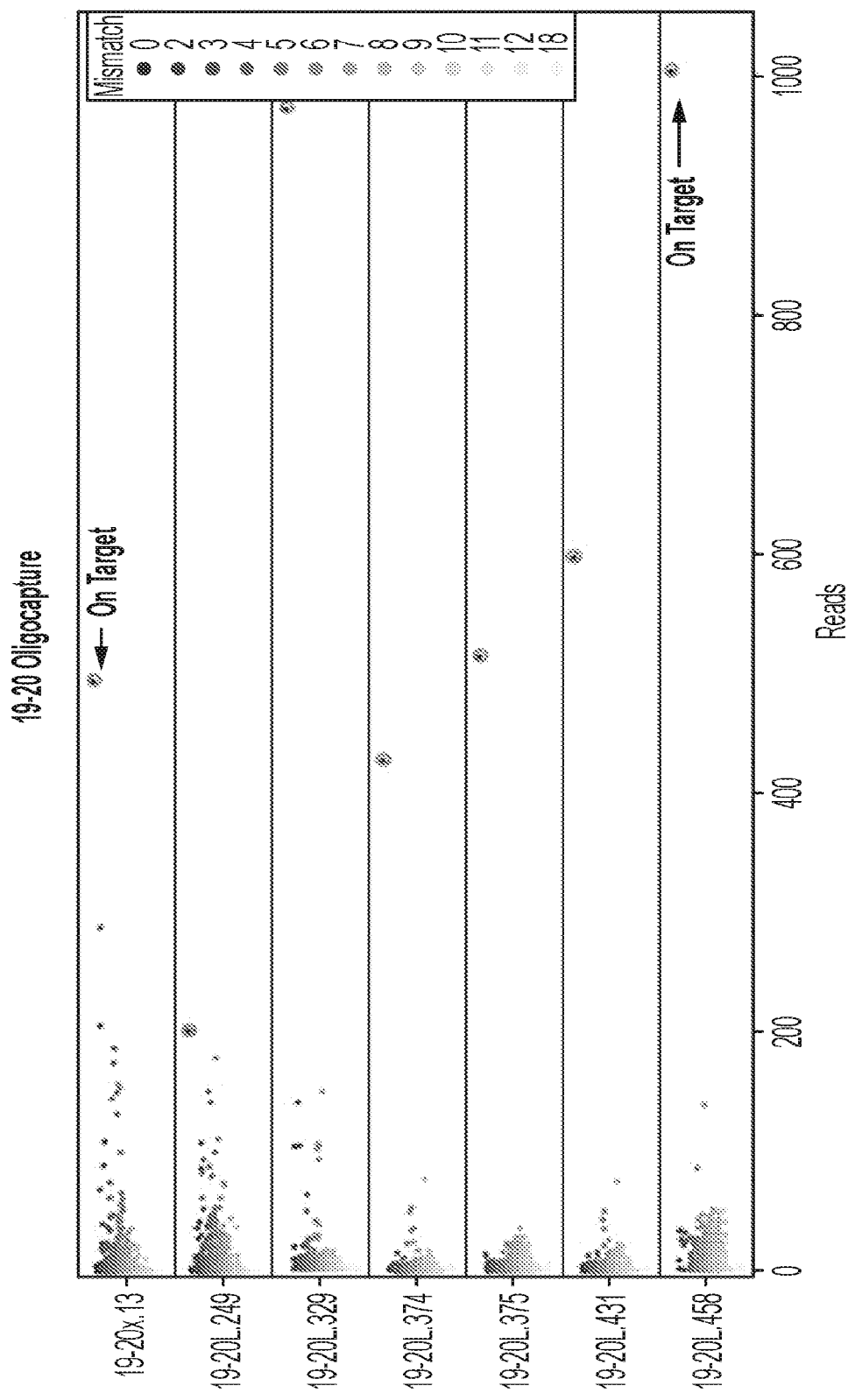
FIG. 20 provides a graph depicting results from an oligo (oligonucleotide) capture assay to identify off-target cutting induced by the DMD 19-20x.13, DMD 19-20L.249, DMD 19-20L.329, DMD 19-20L.374, DMD 19-20L.375, DMD 19-20L.431, and DMD 19-20L.458 meganucleases transfected in HEK 293 cells. The circled dots indicate the on-target site and the non-circled dots indicate off-target sites with the X axis representing the number of sequencing reads for each detected off-target site. The shade of the dot indicates the number of base-pair mismatches between the on target site and each of the detected off-target sites. The closer to the top of the row the dot is located, the lower the number of mismatches.

As shown in FIG. 20, each off-target site generated by each DMD 19-20 meganuclease in HEK293 cells is plotted based on the number of unique sequence reads for a probe oligo being captured at that site with the dot cluster on the left representing low read counts and dots to the right representing high read counts. The specificity of the DMD 19-20 meganucleases can be judged by how many intermediate sites are found in the middle region of the graph and how low their read counts are. Fewer dots correlate to fewer detected potential off-target sites overall, and dots closer to the left correlate to lower read counts and less confidence that they are legitimate off-targets. The intended DMD target sites should have the highest read counts, which is the case for both nucleases selected for inclusion in DMD 19-20 meganuclease dots within the circles; also corresponding to fewer sequence mismatches compared to the target site sequence shown by darker blue spots.

3. Conclusions

Meganuclease specificity for the 19-20 target site increased over three development rounds. These meganucleases had a specificity profile that warranted characterizing targeted off-targets.

Example 9

Generation of Additional DMD 35-36 Meganucleases

1. Methods

Additional DMD 35-36 meganucleases were created after three rounds of development to increase meganuclease potency and specificity. Nuclease specificity was measured using the OligoCapture assay as described in Example 8.

2. Results

Figure 21:
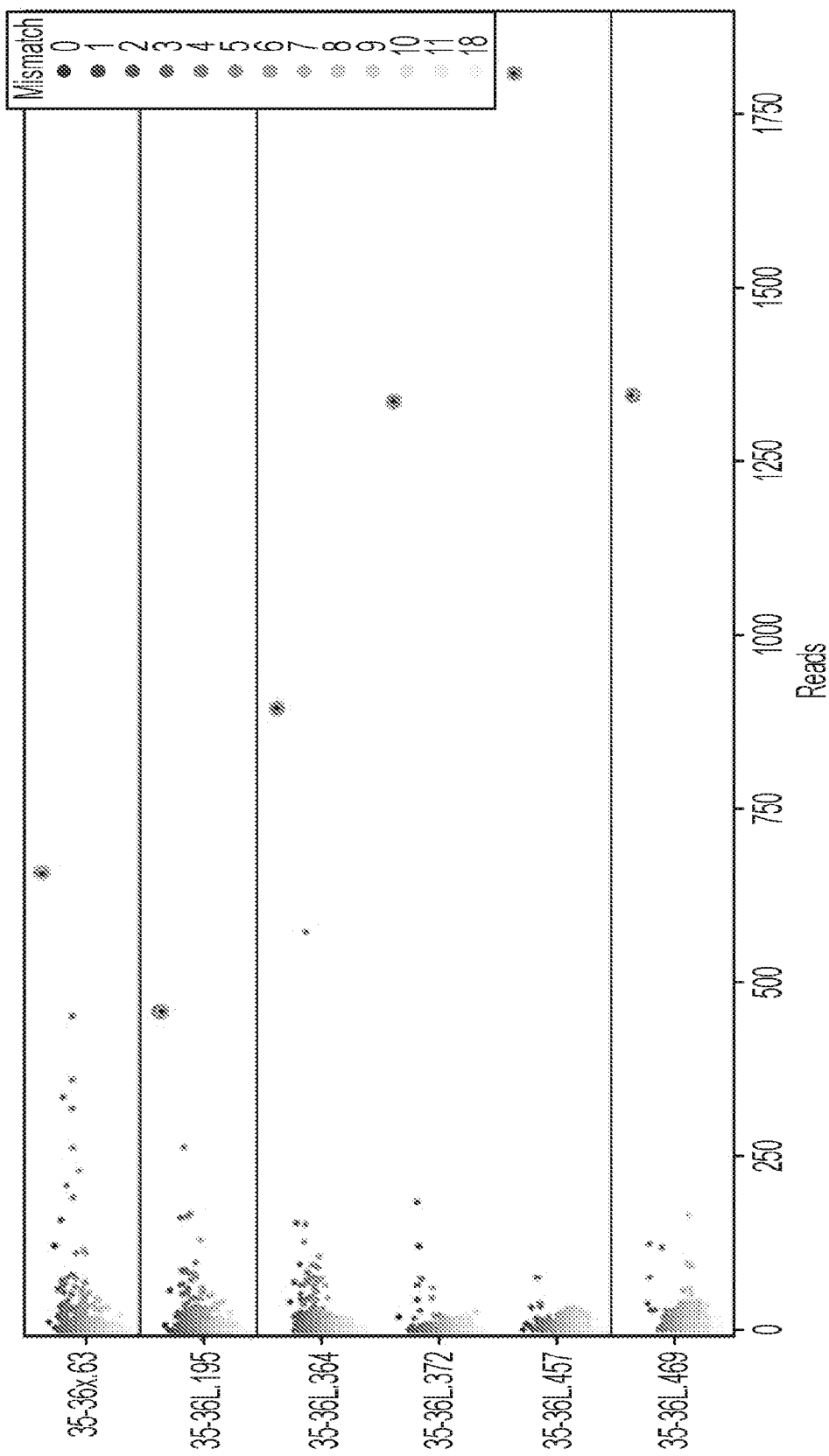
FIG. 21 provides a graph depicting results from an oligo capture assay to identify off-target cutting induced by the DMD 35-36x.63, DMD 35-36L.195, DMD 35-36L.364, DMD 35-36L.372, DMD 35-36L.457, and DMD 35-36L.469 meganucleases transfected in HEK 293 cells. The circled dots indicate the on-target site and the non-circled dots indicate off-target sites with the X axis representing the number of sequencing reads for each off-target site. The shade and proximity to the top of the row of the dot indicates the number of base-pair mismatches between the on target site and each of the detected off-target sites.

As shown in FIG. 21, each off-target site generated by each DMD 35-36 meganuclease in HEK293 cells is plotted based on the number of unique sequence reads for a probe oligo being captured at that site with the dot cluster on the left representing low read counts and dots to the right representing high read counts. The specificity of the DMD 35-36 meganucleases can be judged by how many intermediate sites are found in the middle region of the graph and how low their read counts are. Fewer dots correlate to fewer detected potential off-target sites overall, and dots closer to the left correlate to lower read counts and less confidence that they are legitimate off-targets. The intended DMD target sites should have the highest read counts, which is the case for both nucleases selected for inclusion in DMD35-36 meganuclease dots within the circles also corresponding to fewer sequence mismatches compared to the target site sequence shown by darker blue spots.

3. Conclusions

Meganuclease specificity for the 35-36 target site increased over 3 development rounds. These generated meganucleases had a specificity profile that warranted characterizing targeted off-targets.

Example 10

Editing of Dystrophin Gene in DMD Patient Cell Line Using Pairs of DMD Meganucleases

1. Methods

Pairs of improved DMD 19-20, DMD 35-36 and DMD 37-38 meganucleases were further evaluated in a DMD patient cell line AB1098. The DMD patient myoblast cell line was obtained from the Center for Research in Myology (Sorbonne University). This cell line was immortalized from the spinal muscle of a patient with a deletion of exons 48-50 and are dystrophin protein deficient due to the deleted exons. Cells were transduced with pairs of the engineered meganucleases targeting the DMD 19-20 and DMD 35-36 or the DMD 19-20 and DMD 37-38 recognition sequences as shown in Table 14 below.

TABLE 14

| Pairs of Engineered Meganucleases | |
|---|---|
| EP | 19-20/35-36 Pair |
| 1 | 19-20 L.374/35-36 L.376 |
| 2 | 19-20 L.374/35-36 L.457 |
| 3 | 19-20 L.374/35-36 L.469 |
| 4 | 19-20 L.375/35-36 L.376 |

TABLE 14-continued

Pairs of Engineered Meganucleases

| EP | 19-20/35-36 Pair |
|---|---|
| 5 | 19-20 L.375/35-36 L.457 |
| 6 | 19-20 L.375/35-36 L.469 |
| 7 | 19-20 L.431/35-36 L.376 |
| 8 | 19-20 L.431/35-36 L.457 |
| 9 | 19-20 L.431/35-36 L.469 |
| 10 | 19-20 L.458/35-36 L.376 |
| 11 | 19-20 L.458/35-36 L.457 |
| 12 | 19-20 L.458/35-36 L.469 |
| 13 | Mock |
| 14 | 19-20 L.374/37-38 L.478 |
| 15 | 19-20 L.374/37-38 L.512 |
| 16 | 19-20 L.374/37-38 L.528 |
| 17 | 19-20 L.375/37-38 L.528 |
| 18 | 19-20 L.375/37-38 L.528 |
| 19 | 19-20 L.375/37-38 L.528 |

TABLE 14-continued

Pairs of Engineered Meganucleases

| EP | 19-20/35-36 Pair |
|---|---|
| 20 | 19-20 L.431/37-38 L.528 |
| 21 | 19-20 L.431/37-38 L.528 |
| 22 | 19-20 L.431/37-38 L.528 |

Cells were seeded at 3000 cells/cm² and grown in Promocell muscle growth media (Promocell). Transfections were performed with 1e6 cells in P5 electroporation solution (Lonza) and transfected with the EY100 program using the Lonza 4D-Nucleofector X unit. Meganuclease mRNA dose was 40 ng for each of the DMD 19-20, DMD 35-36, and DMD 37-38 mcganuclcases. After electroporation, cells were seeded into growth media in individual wells of a 6 well plate. One day after electroporation, cells to be differentiated were changed to DMEM (Thermo) 10 ug/ml insulin, and 50 ug/ml gentamycin, while cells to be maintained as undifferentiated were maintained in growth media. Cells were harvested 2- and 8-days post electroporation for DNA and protein extraction. gDNA was isolated and Digital droplet PCR was utilized to determine the frequency of large deletions (indel %) for the DMD 19-20-DMD 35-36 and DMD 19-20-DMD 37-38 meganucleases. The reagents, cycling conditions and reference assay were conducted as described in example 2 switching out the PCR primers and probes to measure total ligation. This ddPCR assay used a forward primer 5' of the 19-20 binding site and a reverse primer 3' to the 35-36 site or to the 37-38 site and a probe specific to the sequence 51 base pairs 5' to the ligated 19-20/35-36 site or the 19-20/37-38 site (see, Table 15 below). With each dual meganuclease assay, the same reference amplicon assay from Example 2 was included allowing quantification of the ratio of large deletion to a region unaffected by the pair of meganucleases (see, Table 15 below).

For protein extraction, cells were harvested from the plates with TrypLE, pelleted, then rinsed with PBS and lysed with 1×RIPA buffer with protease inhibitors (Millipore). Protein concentration was determined by BCA assay (Thermo). For analysis by WES (Protein simple) lysates were normalized to 250 ng/ul and run on the 66-440 kDa module using the standard program. Primary antibody used for detection of dystrophin was 1:50 mandyS10. Primary antibody vs Vinculin (Abeam) was used (1:100) as a loading control.

TABLE 15

Primers used in ddPCR assay for total ligation determination

| Primer Name | Primer Sequence | SEQ ID NO. |
|---|---|---|
| 143 DMDligfor4 | GGGTGGGTTGCTTTACCTCTCTAG | SEQ ID NO: 187 |
| 145 DMD1936REV | TCACATCATGAGATTTAGTCACTTCC | SEQ ID NO: 188 |
| 141 DMD 38 revers2 | GCTATCTGGATATCCTCTTCTGGG | SEQ ID NO: 193 |
| 134 DMDimpLIG probe | TTGCTACTTCACAGTAACCACATGG | SEQ ID NO: 189 |
| P2 Reference | AGGACAAAAGAGGACGGTCTGCCCTGG | SEQ ID NO: 136 |
| Reference F2 | TAAGACCCAGCTTCACGGAG | SEQ ID NO: 137 |
| Reference R2 | TATGATCGCCTGTTCCTCCA | SEQ ID NO: 138 |

2. Results

Figure 22:
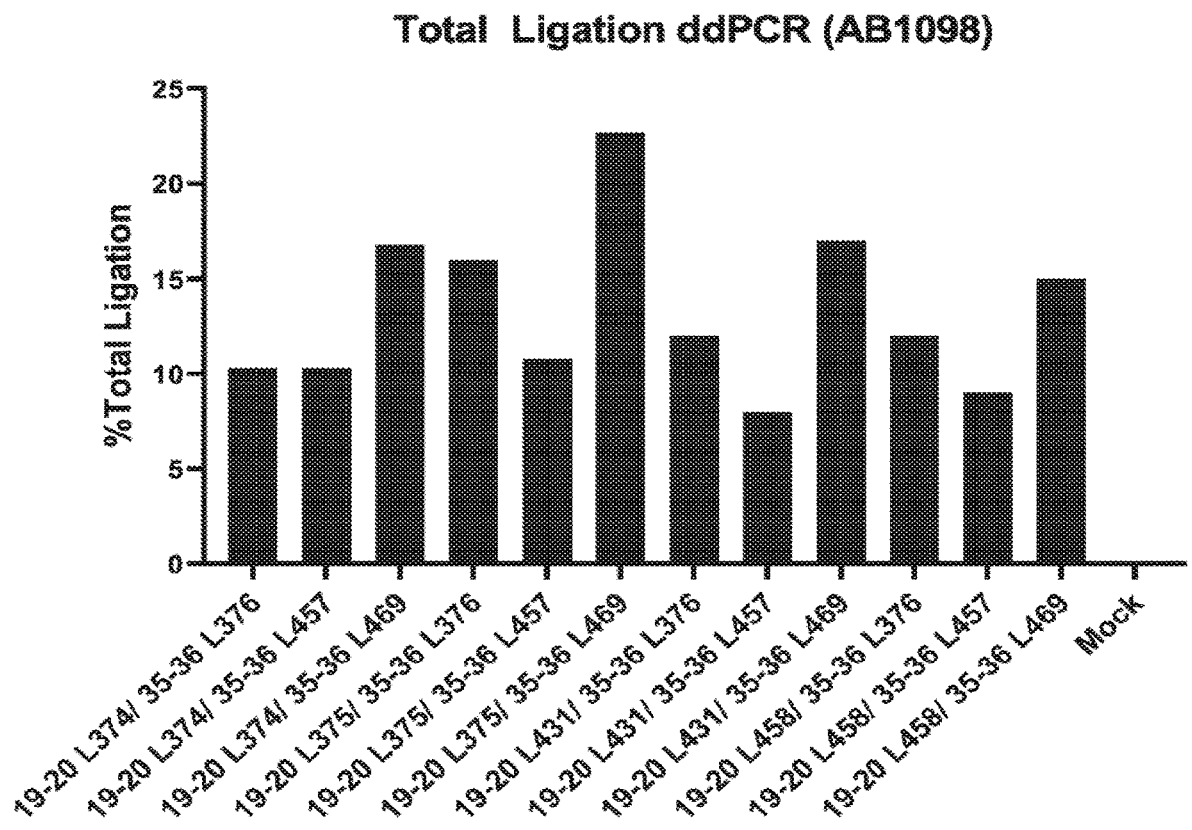
FIG. 22 provides a bar graph showing the percentage (%) of total ligation of genomic DNA adjacent to exons 45-55 following cleavage of the DMD 19-20 and DMD 35-36 recognition sequences by each of the pairs of indicated engineered DMD 19-20 and DMD 35-36 meganucleases.
Figure 23A:
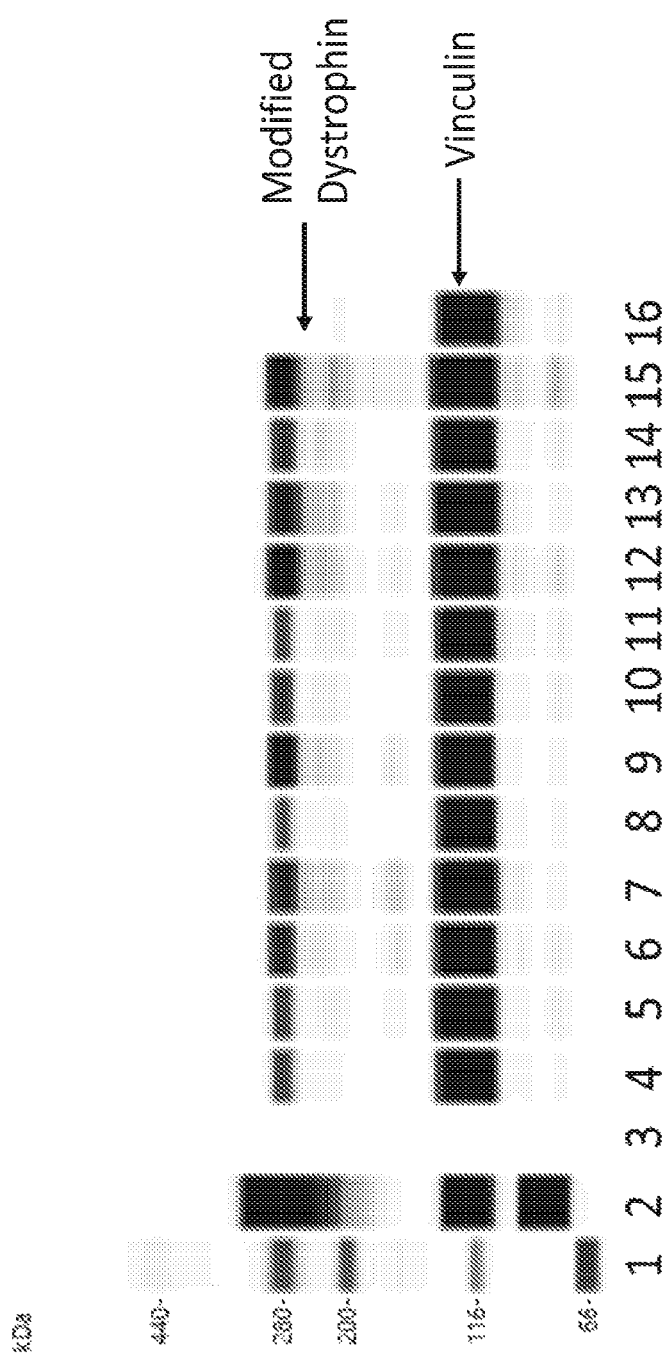
FIG. 23A provides a WES protein intensity read out for shortened modified dystrophin protein levels lacking exons 45-55 of the dystrophin gene in AB1098 cells treated with combinations of the DMD 19-20 and DMD 35-36 meganucleases. Lane 1 is the marker control; lane 2 is the heart positive control for dystrophin protein; lane 3 is the blank control; lane 4 is the combination of the DMD 19-20L.374 and DMD 35-36L.376 meganucleases; lane 5 is the combination of the DMD 19-20L.374 and DMD 35-36L.457 meganucleases; lane 6 is the combination of the DMD 19-20L.374 and DMD 35-36L.469 meganucleases; lane 7 is the combination of the DMD 19-20L.375 and DMD 35-36L.376 meganucleases; lane 8 is the combination of the DMD 19-20L.375 and DMD 35-36L.457 meganucleases; lane 9 is the combination of the DMD 19-20L.375 and DMD 35-36L.469 meganucleases; lane 10 is the combination of the DMD 19-20L.431 and DMD 35-36L.376 meganucleases; lane 11 is the combination of the DMD 19-20L.431 and DMD 35-36L.457 meganucleases; lane 12 is the combination of the DMD 19-20L.431 and DMD 35-36L.469 meganucleases; lane 13 is the combination of the DMD 19-20L.458 and DMD 35-36L.376 meganucleases; lane 14 is the combination of the DMD 19-20L.458 and DMD 35-36L.457 meganucleases; lane 15 is the combination of the DMD 19-20L.458 and DMD 35-36L.469 meganucleases; and lane 16 is the mock AB1098 cell line control that lacks expression of dystrophin protein.
Figure 23B:
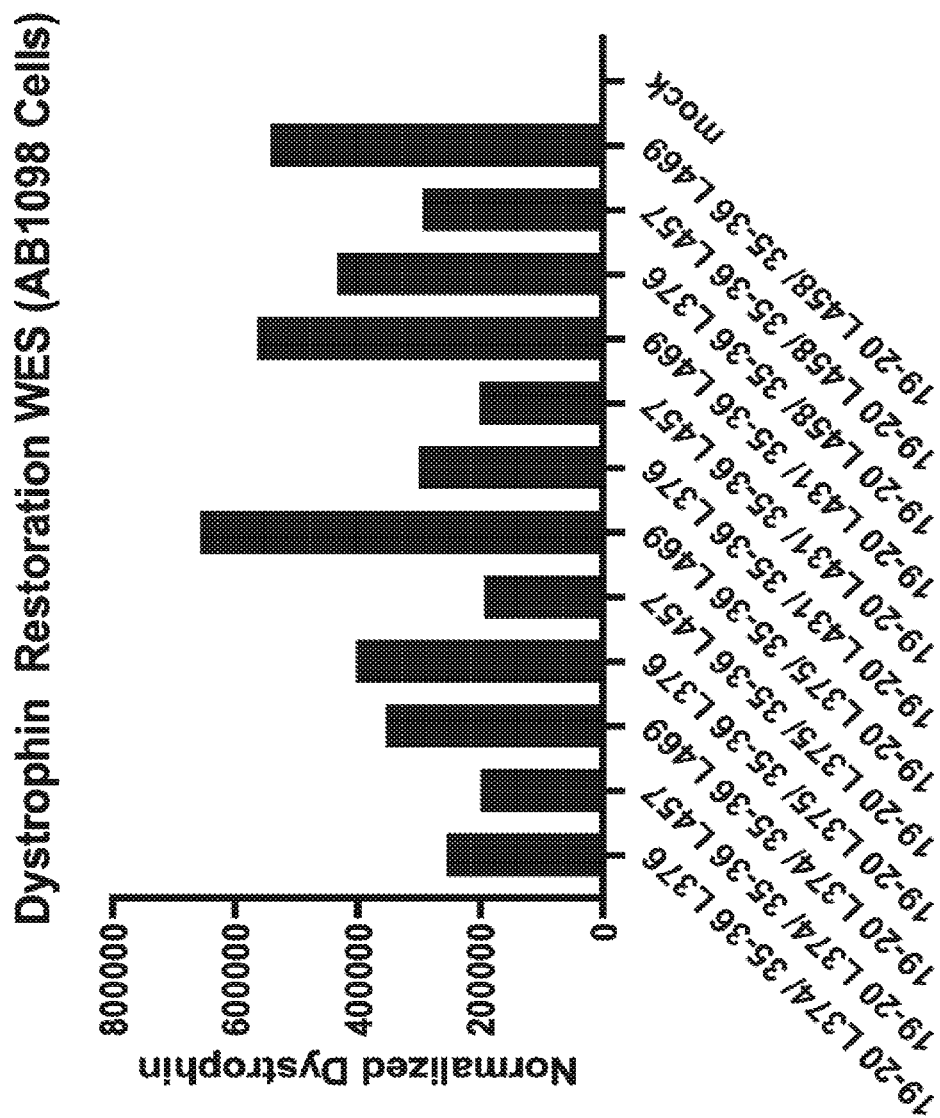
FIG. 23B provides a bar graph showing the shortened modified dystrophin protein levels by WES analysis normalized to the vinculin loading control for each of the pairs of indicated engineered DMD 19-20 and DMD 35-36 meganucleases.
Figure 24A:
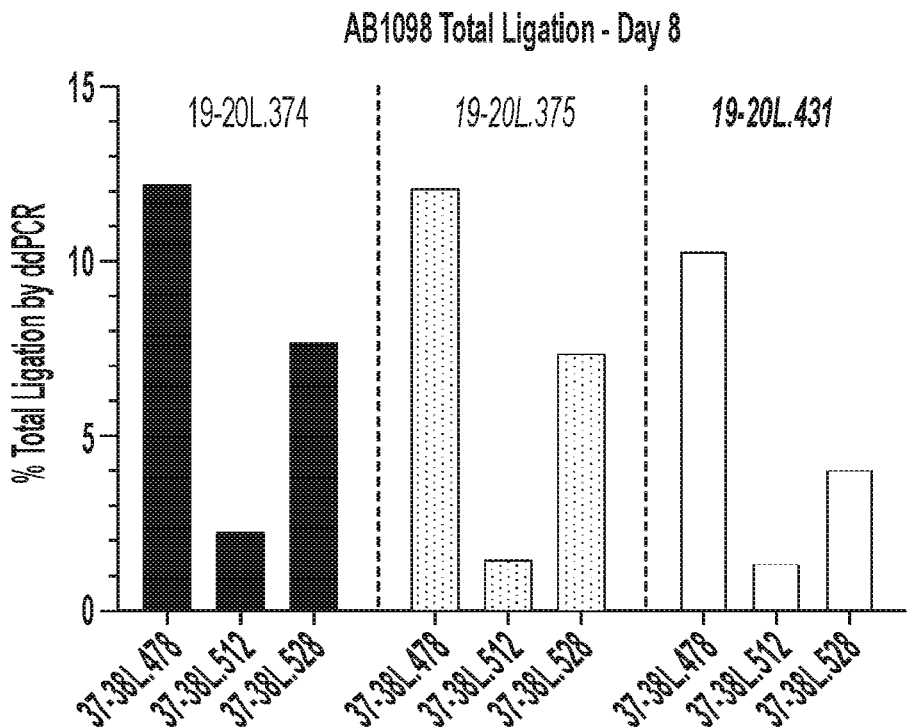
FIGS. 24A-24B.
Figure 24B:
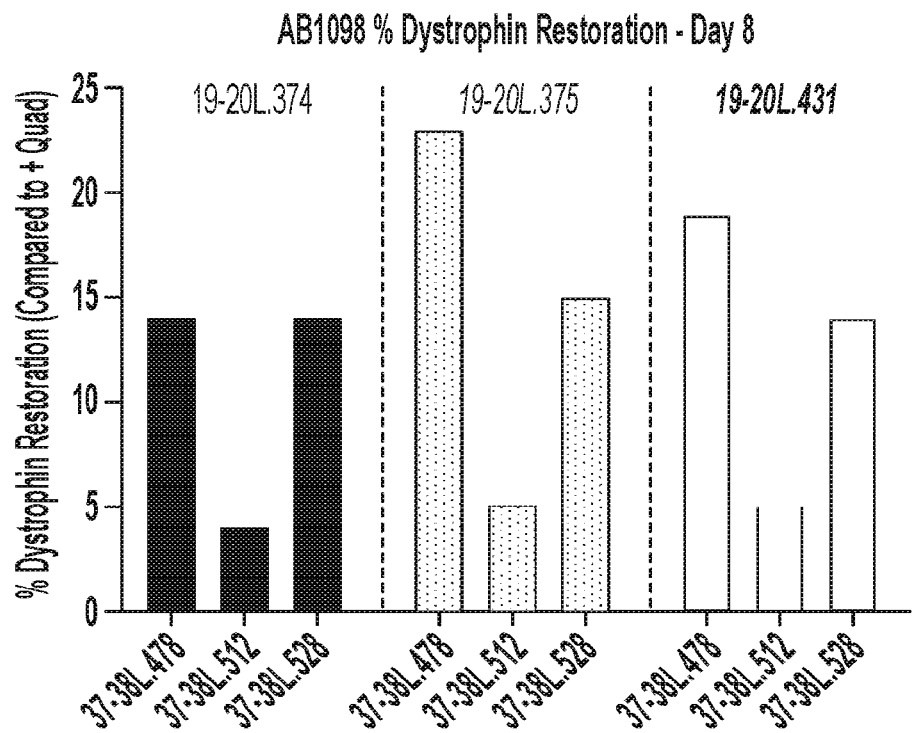
Figure 25A:
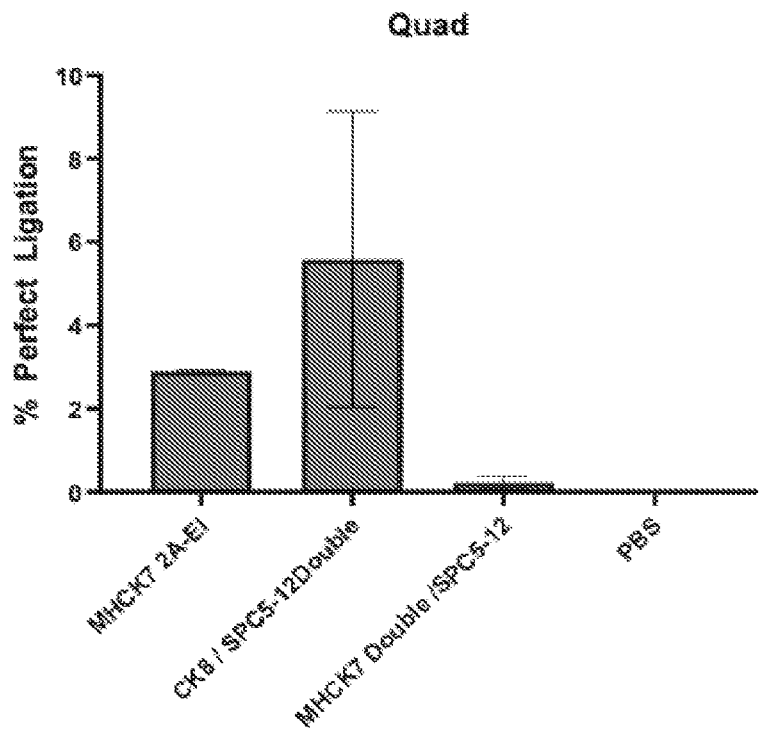
FIGS. 25A-25E provides bar graphs showing the percentage (%) of perfect ligation of genomic DNA adjacent to exons 45-55 in muscle tissues following cleavage of the DMD 19-20 and DMD 37-38 recognition sequences by the pair of DMD 19-20x.13 and DMD 37-38x.15 engineered meganucleases utilizing different muscle-specific promoter combinations.
Figure 25B:
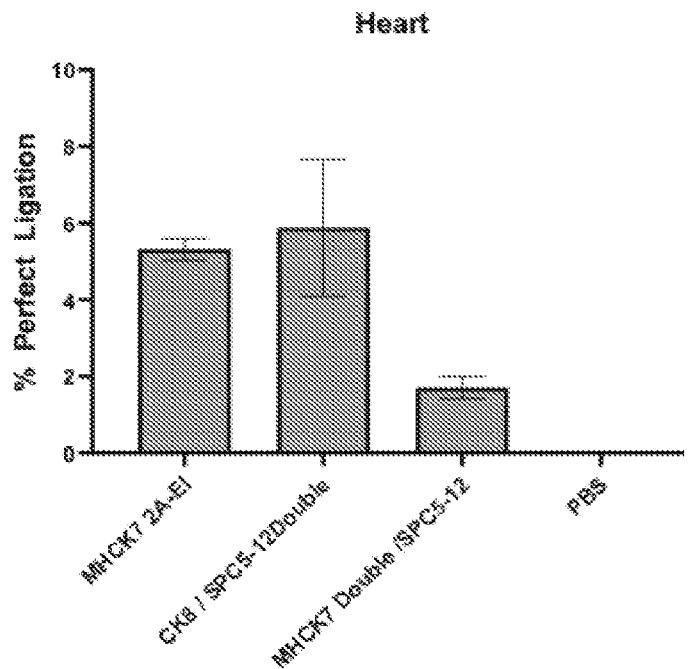
Figure 25C:
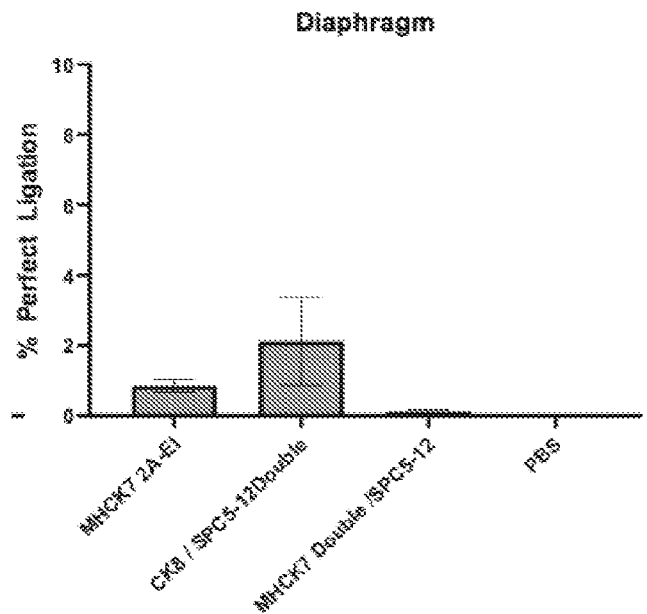
Figure 25D:
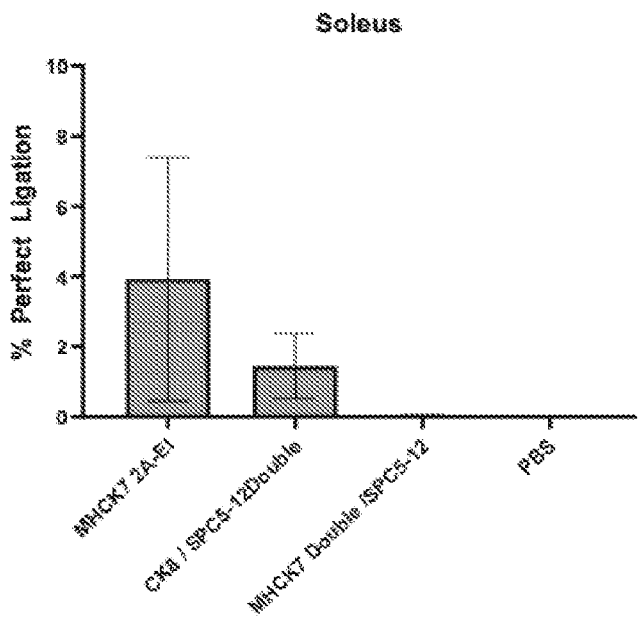
Figure 25E:
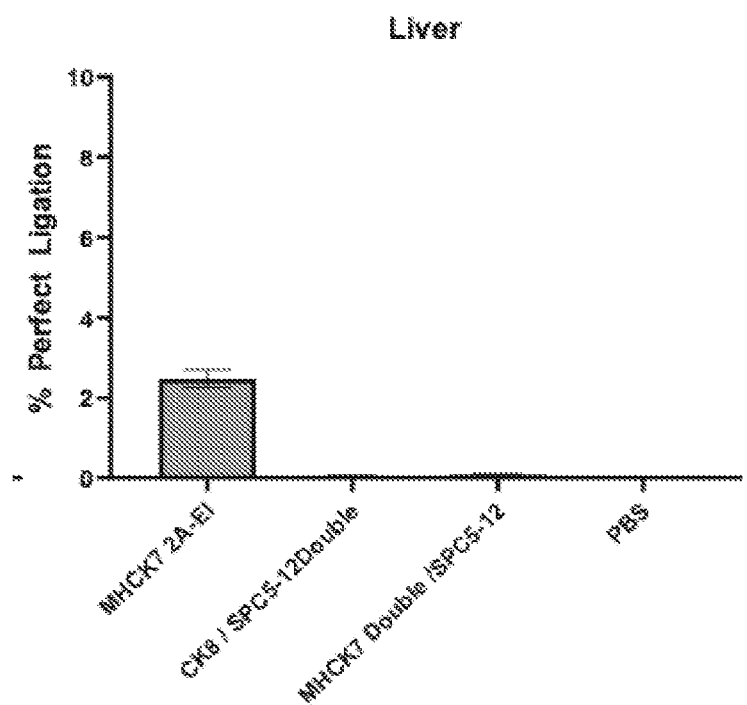
Figure 26A:
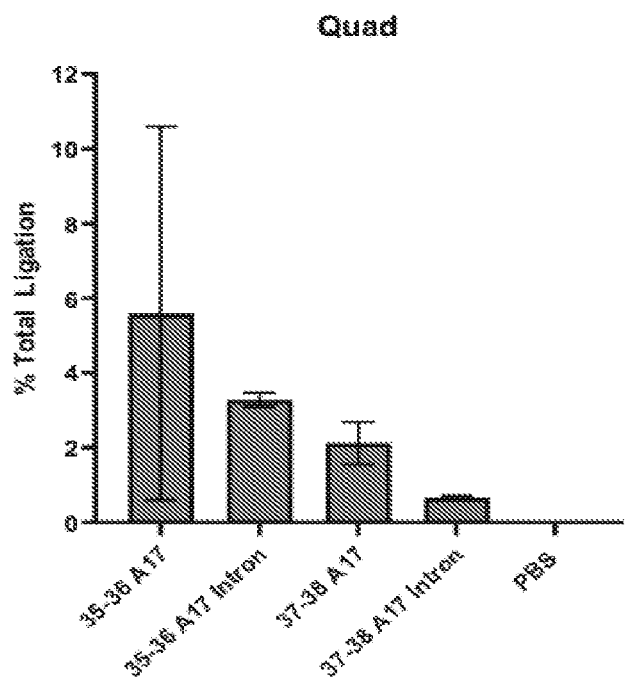
FIGS. 26A-26E provides bar graphs showing the percentage (%) of total ligation of genomic DNA adjacent to exons 45-55 in muscle tissues following cleavage of the DMD 19-20 and DMD 35-36 recognition sequences by the pair of DMD 19-20L.329 and DMD 37-38L.219 engineered meganucleases.
Figure 26B:
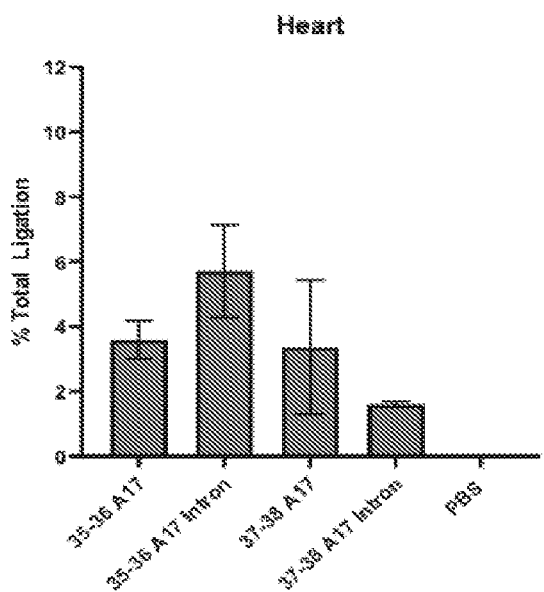
Figure 26C:
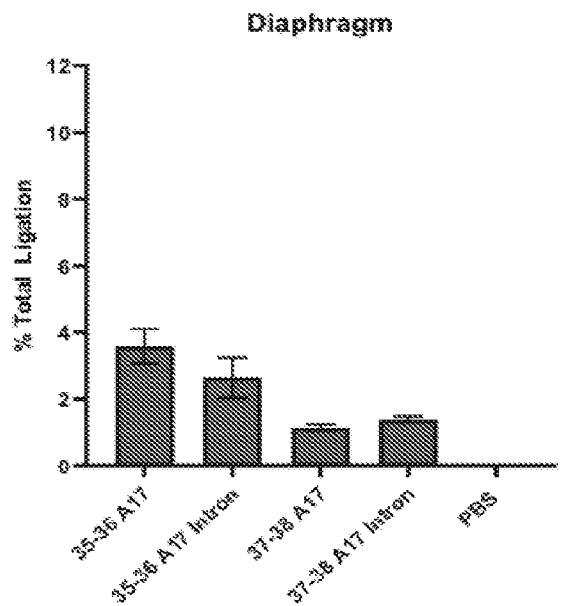
Figure 26D:
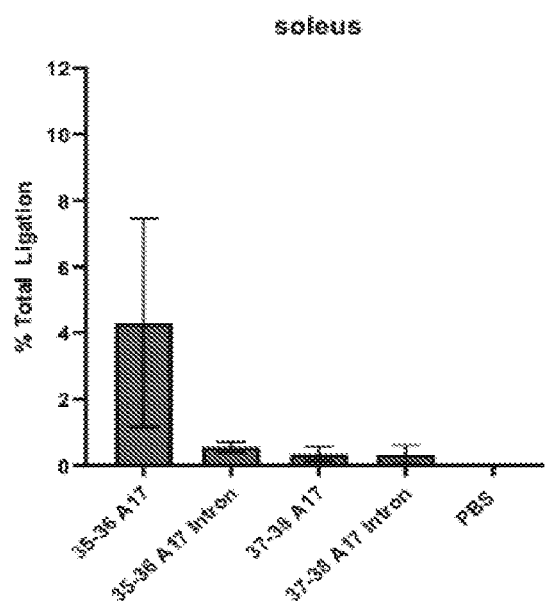
Figure 26E:
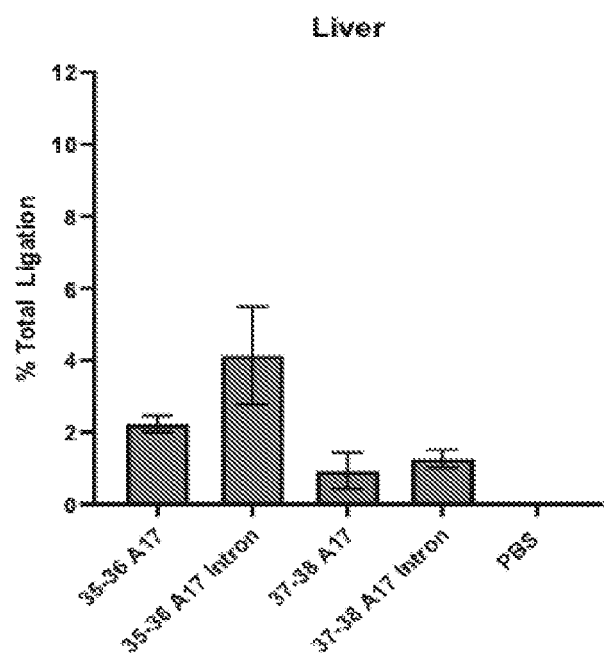
Figure 27A:
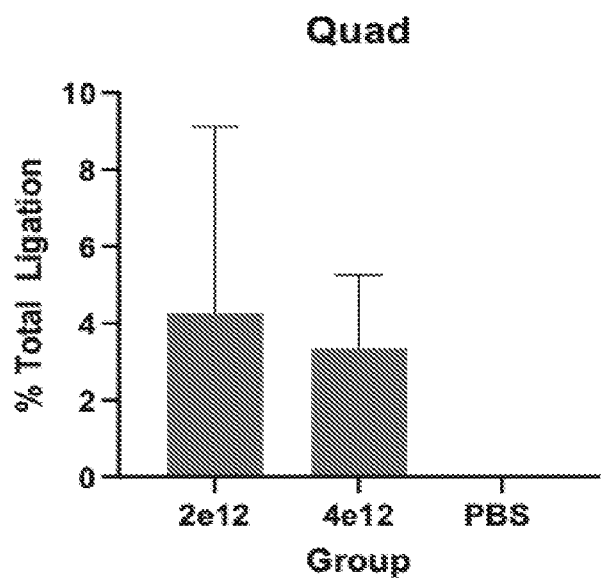
FIGS. 27A-27E provides bar graphs showing the percentage (%) of total ligation of genomic DNA adjacent to exons 45-55 in muscle tissues following cleavage of the DMD 19-20 and DMD 35-36 recognition sequence by the pair of DMD 19-20x.13 and DMD 37-38x.15 engineered meganucleases at two different dosage levels indicated by the total AAV amount ($2\times10^{12}$ or $4\times10^{12}$).
Figure 27B:
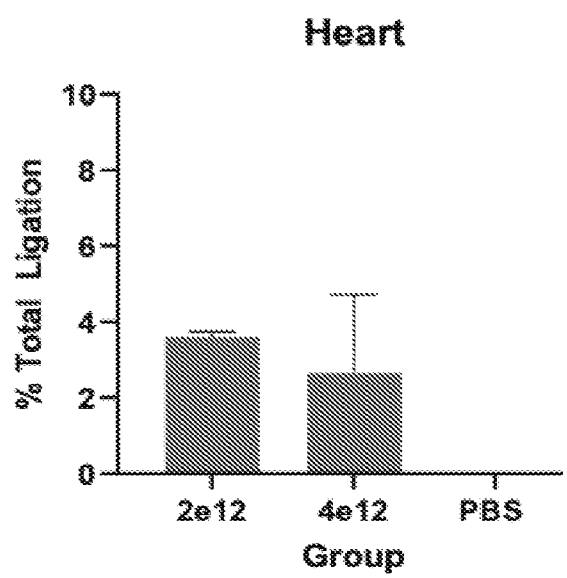
Figure 27C:
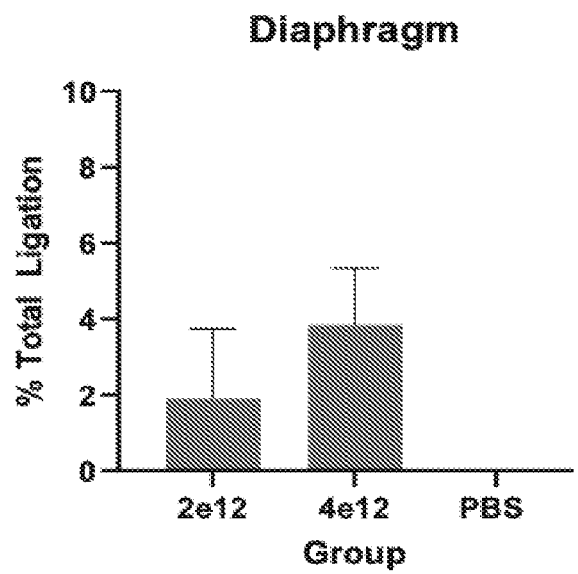
Figure 27D:
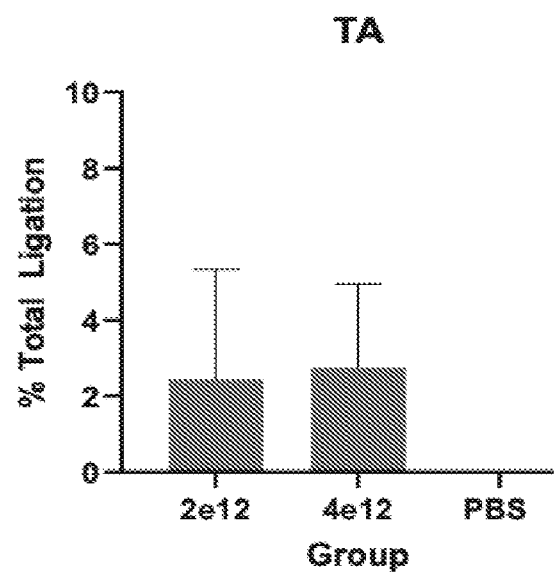
Figure 27E:
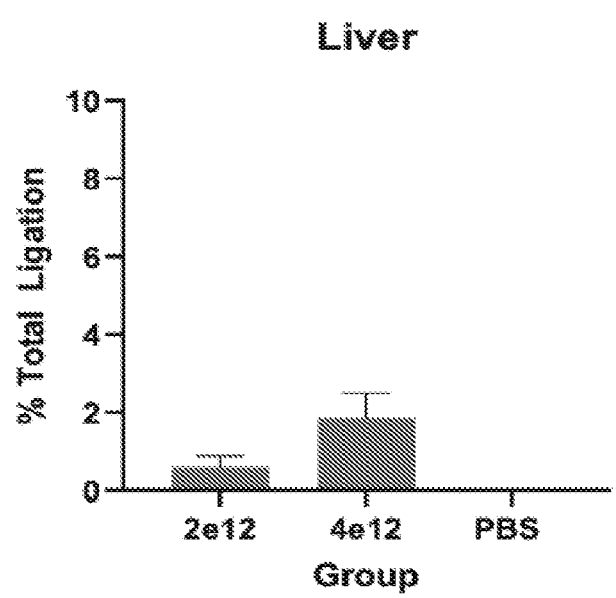

Varying levels of large deletion/total ligation were seen with different pairings of the DMD 19-20 and DMD 35-36 or DMD 19-20 and DMD 37-38 engineered meganucleases in this DMD patient cell line (FIG. 22 and FIG. 24A). Total ligations ranged from 8% to 22.7% with the DMD 19-20 and DMD 35-36 pairing (FIG. 22) and from a little over 1% to 12% with the DMD 19-20 and DMD 37-38 pairing (FIG. 24A). Expression of the shortened modified dystrophin protein, lacking the amino acids encoded by exons 45-55, was measured by WES. The WES system converted the chromatic data generated into a more traditional Western Blot figure and duplicated the read out. No dystrophin was detected in Mock untreated AB1098 cells. Shortened modified dystrophin was detected for each of the DMD 19-20 and DMD 35-36 engineered meganuclease pairs (FIG. 23A). Shortened modified dystrophin restoration was normalized to a loading control Vinculin Protein and the amount of protein restoration was calculated relative to loading (FIG. 23B). Similarly, shortened modified dystrophin was detected for cells treated with the pairing of DMD 19-20 and DMD 37-38 engineered meganucleases compared to the relative expression level of an equal load (500 ng) of lysate from hDMD mouse quadriceps muscle based on a standard curve generated from that tissue (FIG. 24B). No dystrophin was measured in mock, whereas shortened modified dystrophin was detected in each of the meganuclease pairs.

3. Conclusions

These experiments report the large deletion of exons 45 to 55 in a cell line isolated from a patient missing exons 48 to 50 in the dystrophin gene. This cell line does not express detectable levels of dystrophin and is a good in vitro model for the DMD disease. The WES protein data (FIG. 23A) and quantification in FIGS. 23B and 24B show restored expression of a shortened modified dystrophin protein with no protein expression in untreated mock cells to a detectable level across all engineered meganuclease dose ranges. This protein quantification is further confirmation and an in vitro proof of concept of using dual engineered meganucleases for the purpose of treating DMD patients by excising exons 45-55 and converting the dystrophin gene to a Beckers dystrophin phenotype.

Example 11

Editing of Dystrophin Gene In Vivo in hDMD Mouse Study (TD066)

1. Methods

An in vivo study in hDMD mice was conducted to investigate in vivo editing and human dystrophin protein restoration induced by delivery of the pair of DMD 19-20x.13 and DMD 37-38x.15 meganucleases. Mice were injected by retro orbital systemic injection with three different constructs encapsulated with AAV9 ($1\times10^{14}$ VG/kg). The first AAV was comprised of a viral genome that includes, from 5' to 3', the A17-120 enhancer, the muscle-specific promoter MHCK7, a SV40 intron sequence, the coding sequence for the DMD 19-20x.13 nuclease, a furin GSG P2A cleavage sequence, a coding sequences for the DMD37-38x.15 nuclease, a WPRE element, and an SV40 poly adenylation signal. Additionally, two AAV9 Constructs were investigated using a two-cassette approach where each nuclease is driven off a separate muscle specific promoter. Each viral genome comprised of either a CK8 or MHCK7 muscle specific promoter at the 5' end just after the ITR, then a HBA2 5'UTR, the coding sequence for the DMD 19-20x.13 nuclease, a WPRE element, an SV40 poly adenylation signal, then the muscle specific promoter SPc5-12, an XBG 5' UTR sequence, the coding sequence for the DMD 37-38x.15 nuclease, an XBG 3' UTR sequence and a BgH poly adenylation signal. At 14 days post-injection, mice were sacrificed and tissue sections from skeletal muscle (quadricep), heart, diaphragm, soleus, and liver were collected for molecular and histological analysis. The ddPCR assay of example 10 used a forward primer 5' of the 19-20 binding site, a reverse primer 3' to the 35-36 site and probe specific to sequence 51 base pairs 5' to the ligated 19-20/35-36 site. The perfect ligation assay in this example used a probe sequence specific to a perfect ligation of the 19-20 and 35-36 binding sites with a comparable forward and reverse primer pair (a forward primer 5' of the 19-20 binding site, a reverse primer 3' to the 35-36 site; Table 16).

TABLE 16

Primers used in ddPCR assay for perfect ligation determination

| Primer Name | Primer Sequence | SEQ ID NO. |
|---|---|---|
| 49 DMD 19-20 F1 | GGGTGGGTTGCTTTACCTCT | SEQ ID NO: 190 |
| 40-DMD 37-38 R | TCTGGATATCCTCTTCTGGG | SEQ ID NO: 191 |
| 89 DMD 1938 Probe | ATCAGAAGGATTATGTATAGGAATA | SEQ ID NO: 192 |
| P2 Reference | AGGACAAAAGAGGACGGTCTGCCCTGG | SEQ ID NO: 136 |
| Reference F2 | TAAGACCCAGCTTCACGGAG | SEQ ID NO: 137 |
| Reference R2 | TATGATCGCCTGTTCCTCCA | SEQ ID NO: 138 |

2. Results

The single promoter MHCK7 P2A AAV had successful perfect ligation events across all tissues; averaging 2.8% in the quadricep, 5.3% in the heart, 0.85% in the diaphragm, 3.9% in the soleus & 2.4% in the liver. The CK8/SPc5-12 double promoter AAV had successful perfect ligation in all tissues except the liver, averaging 5.5% in the quadricep, 5.9% in the heart, 2% in the diaphragm, 1.45% in the soleus & 0.3% in the liver. The MHCK7/SPC512 double promoter AAV had minimal perfect ligation events averaging 0.2% in the quadricep, 1.7% in the heart, 0.04% in the diaphragm, 1.45% in the soleus & 0.08% in the liver (FIG. 25A-25E).

3. Conclusions

Here we report in vivo excision of the hot spot region (exons 45-55) in a humanized DMD mouse model. The double promoter CK8+SPc5-12 combination appears to have low off-organ editing in the liver & higher editing in quad, diaphragm, and heart.

Example 12

Editing of Dystrophin Gene In Vivo in hDMD Mouse Study (TD069)

1. Methods

An in vivo study in hDMD mice was conducted to investigate in vivo editing and human modified dystrophin protein restoration induced by delivery of the pair of DMD 19-20L.329 and DMD 37-38L.219 meganucleases. Mice were injected by retro orbital systemic injection with four different constructs encapsulated with AAV9 ($1\times10^{14}$ VG/kg). The first set of AAVs varied the 3' downstream nuclease but kept all elements equal between the two. These were comprised of viral genomes that includes, from 5' to 3', the A 17-120 enhancer, the muscle-specific promoter CK8, an SV40 intron sequence, the coding sequence for the DMD 19-20L.329 nuclease, a furin GSG P2A cleavage sequence, a coding sequence for the DMD35-36L.349 or DMD37-38L.219 nucleases, a WPRE element, and an SV40 poly adenylation signal. The next set of AAVs varied the 3' downstream nuclease but kept all elements equal between the two. There were comprised of viral genomes that includes, from 5' to 3', the A17-120 enhancer, the muscle-specific promoter CK8, the coding sequence for the DMD 19-20L.329 nuclease, a furin GSG P2A cleavage sequence, a coding sequence for the DMD35-36L.349 or DMD37-38L.219 nucleases, a WPRE element, and an SV40 poly adenylation signal. At 14 days post-injection, mice were sacrificed and tissue sections from skeletal muscle (quadricep), heart, diaphragm, soleus, and liver were collected for molecular and histological analysis. ddPCR was conducted as described in Example 10.

2. Results

The AAV containing A17-120 CK8 SV40 intron DMD19-20L.329 P2A DMD35-36L.349 had successful total ligation events across all tissues; averaging 3.3% in the quadricep, 5.7% in the heart, 2.6% in the diaphragm, 0.6% in the soleus & 4.1% in the liver. The AAV containing A17-120 CK8 SV40 intron DMD19-20L.329 P2A DMD37-38L.219 had minimal total ligation events across all tissues; averaging 0.7% in the quadricep, 1.6% in the heart, 1.4% in the diaphragm, 0.3% in the soleus & 1.3% in the liver. The AAV containing A17-120 CK8 DMD19-20L.329 P2A DMD35-36L.349 had successful total ligation events across all tissues; averaging 5.6% in the quadricep, 3.6% in the heart, 3.6% in the diaphragm, 4.3% in the soleus & 2.2% in the liver. The AAV containing A17-120 CK8 DMD19-20L.329 P2A DMD37-38L.219 had minimal total ligation events across all tissues; averaging 2.1% in the quadricep, 3.4% in the heart, 1.2% in the diaphragm, 0.35% in the soleus & 0.93% in the liver (FIG. 26A-26E).

3. Conclusions

Here we report excision of exons 45-55 with the DMD 19-20 & DMD 35-36 meganucleases used in Example 11 as well as with the paring the DMD 19-20 nuclease with a different downstream nuclease at the DMD 37-38 target site. In this experiment, the paired DMD 19-20 meganuclease and DMD 35-36 meganuclease had higher levels of editing than the DMD19-20 and DMD 37-38 paired meganucleases. The addition of the SV40 intron downstream of the promoter increased editing minimally in target tissues and increased editing in the liver.

Example 13

Editing of Dystrophin Gene In Vivo in hDMDdel52/C57 Mouse Study (TD075)

1. Methods

An in vivo study in hDMDdel52/mdx (hDMD mouse) mice was conducted to investigate in vivo editing and shortened modified human dystrophin protein restoration induced by delivery of the pair of DMD 19-20x.13 and DMD 37-38x.15 meganucleases. Mice were injected by retro orbital systemic injection with one construct encapsulated with AAV9 at two doses, $1\times10^{14}$ VG/kg or $2\times10^{14}$ VG/kg. The AAV was comprised of a viral genome that includes, from 5' to 3', the muscle-specific promoter CK8, an SV40 intron sequence, the coding sequence for the DMD 19-20x.13 meganuclease, a furin GSG P2A cleavage sequence, a coding sequence for the DMD 37-38x.15 meganuclease, a WPRE element, and an SV40 poly adenylation signal. At 14 days post-injection, mice were sacrificed and tissue sections from skeletal muscle (quadricep), heart, diaphragm, TA, and liver were collected for molecular, protein, and histological analysis. ddPCR was conducted as described in Example 10. Dystrophin protein expression was assessed in the quadriceps, heart, and diaphragm of the nuclease-treated animals using the Wes™ system (Protein-Simple) as described in Example 10. Dystrophin expression was normalized to the house keeping protein vinculin and measured against a standard curve of dystrophin protein isolated from a hDMD mouse that expresses full-length dystrophin. Tissue sections from the nuclease-treated mice were also subjected to IHC analyses to visualize dystrophin and meganuclease protein expression.

2. Results

Figure 28A:
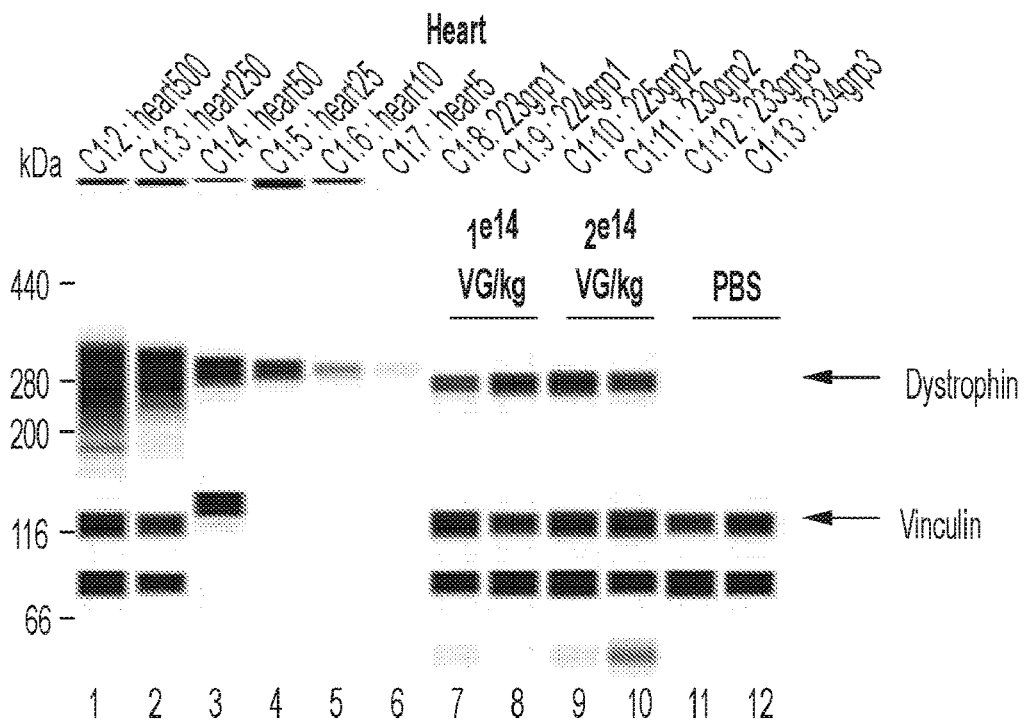
FIGS. 28A-28C provides a WES protein intensity read out for shortened modified dystrophin protein levels lacking exons 45-55 of the dystrophin gene after treatment with the DMD 19-20x.13 and DMD 37-38x.15 meganucleases. Lanes 1-6 of FIGS. 28A-28C represent a standard curve of protein band intensity of full length human dystrophin from a mouse that expresses human dystrophin; lanes 7-8 represent the protein band intensity of shortened modified dystrophin from mice treated with the combination of the DMD 19-20x.13 and DMD 37-38x.15 meganucleases at $1\times10^4$ VG/kg; lanes 9-10 represent the protein band intensity of shortened modified dystrophin from mice treated with the combination of the DMD 19-20x.13 and DMD 37-38x.15 meganucleases at $2\times10^{14}$ VG/kg; lanes 11-12 represent mice treated with PBS and without a meganuclease.
Figure 28B:
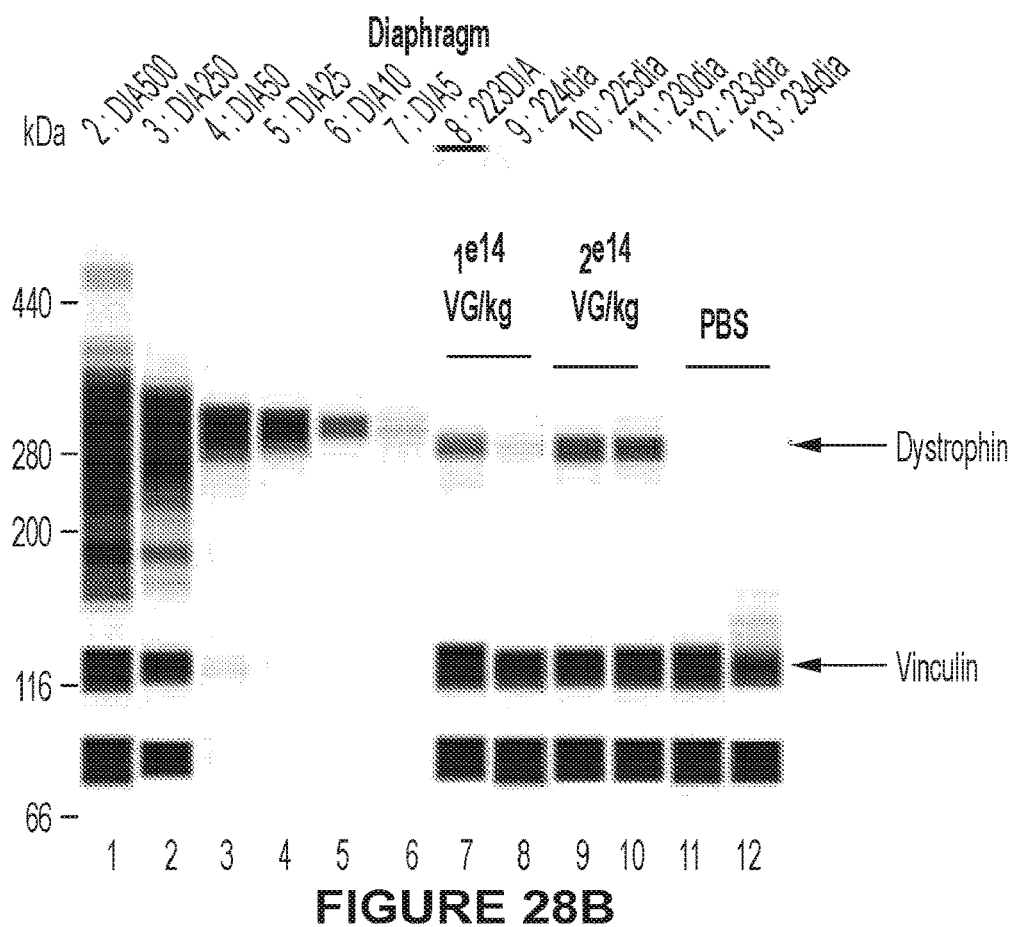
Figure 28C:
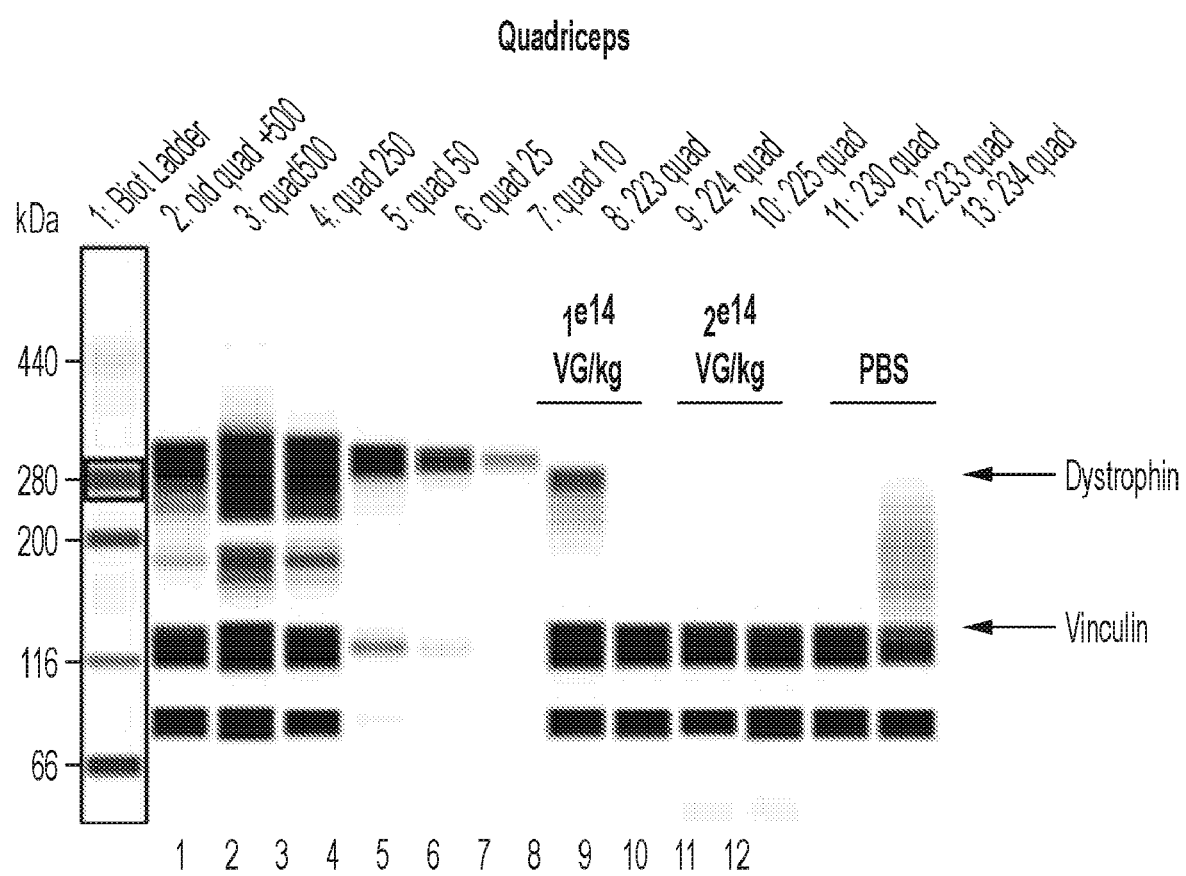

The AAV at the dose of $1\times10^{14}$ VG/kg ($1\times10^{12}$ total AAV) containing CK8, SV40 intron, and DMD19-20x.13 P2A DMD37-38x.15 had successful total ligation events across all tissues; averaging 4.3% in the quadricep, 3.6% in the heart, 1.9% in the diaphragm, 2.5% in the TA, and 0.6% in the liver. The AAV at the dose of $2\times10^{14}$ VG/kg ($4\times10^{12}$ total AAV) containing CK8, SV40 intron, and DMD19-20x.13 P2A DMD37-38x.15 had successful total ligation events across all tissues; averaging 3.4% in the quadricep, 2.7% in the heart, 3.9% in the diaphragm, 2.8% in the TA & 1.9% in the liver (FIGS. 27A-27E). Dystrophin restoration was quantified by comparing dystrophin protein from the corresponding tissues in hDMD mice from a protein standard by a standard curve from WES protein analysis. As shown in FIGS. 28A-28C lanes 1-6 represent the standard curve; lanes 7-8 represent muscle tissue from the hDMD mouse treated with $1\times10^{14}$ VG/kg of the DMD19-20x.13 and DMD37-38x.15 meganucleases; lanes 9-10 represent muscle treated with $2\times10^{14}$ VG/kg of the DMD19-20x.13 and DMD37-38x.15 meganucleases, and lanes 11-12 represent mice treated with PBS. Based on the standard curve, treated mice were found to average 6.5% dystrophin in the heart, 1.5% dystrophin (low dose) or 3% dystrophin (high dose) in the diaphragm, and 4.5% dystrophin in the quadricep (FIG. 28A-28C).

3. Conclusions

Here we report in vivo excision of the hot spot region (exons 45-55) in a humanized DMD mouse model with deletions in the human dystrophin gene. This genotype is an example of what could be found in a disease model or patient. No significant difference in editing was seen with the two dose levels. This mouse model does not make human dystrophin as seen in lanes 11 and 12 of FIGS. 28A-28C. Here, we report proof of concept of shortened modified human dystrophin restoration in an in vivo model that does not make human dystrophin due to mutations.

Example 14

Editing of Dystrophin Gene In Vivo in hDMDdel52/MDX Mouse Study (TD073)

1. Methods

An in vivo study in hDMDdel52/mdx (hDMD) mice was conducted to investigate in vivo editing and shortened modified human dystrophin protein restoration induced by delivery of the DMD 19-20L.329 and DMD 35-36L.349 pair of meganucleases. Mice were injected by retro orbital systemic injection with three different constructs encapsulated with AAV9 (1×10$^{14}$VG/kg). The first AAV was comprised of a viral genome that includes, from 5' to 3', the A17-120 enhancer, the muscle-specific promoter CK8, the coding sequence for the DMD 19-20L.329 meganuclease, a furin GSG P2A cleavage sequence, a coding sequence for the DMD35-36L.349 meganuclease, a WPRE element, and an SV40 poly adenylation signal. The second AAV was comprised of a viral genome that includes, from 5' to 3', the A17-120 enhancer, the muscle-specific promoter MHCK7, the coding sequence for the DMD 19-20L.329 nuclease, a furin GSG P2A cleavage sequence, a coding sequence for the DMD35-36L.349 nuclease, a WPRE element, and an SV40 poly adenylation signal. The third AAV was comprised of a viral genome that includes, from 5' to 3', the muscle-specific promoter CK8, the coding sequence for the DMD 19-20L.329 nuclease, a WPRE element, an SV40 poly adenylation signal, the muscle specific promoter SPc5-12, a coding sequence for the DMD35-36L.349 nuclease, a WPRE element, and a BgH poly adenylation signal. At 14 days post-injection, mice were sacrificed and tissue sections from skeletal muscle (quadricep), heart, diaphragm, and liver were collected for molecular, protein, and histological analysis. The ddPCR assay was conducted as described in Example 10. Dystrophin protein expression was assessed in the quadriceps, heart, and diaphragm of the nuclease-treated animals using the Wes™ system (ProteinSimple) as described in Example 10. Dystrophin expression was normalized to the house keeping protein vinculin and measured against a standard curve of dystrophin protein isolated from a hDMD mouse that expresses full-length dystrophin.

Quadricep tissue sections from the nuclease-treated mice were also subjected to IHC analyses to visualize dystrophin and meganuclease protein expression. Briefly, quadricep tissues were dewaxed and treated with HEIR (Heat-Induced Epitope Retrieval) with ER1 for 40 min on the BOND RX. Slides were blocked in 10% NGS PBST (PBS with 0.1% Tween20) with MoM (Mouse on Mouse Blocking reagent, VECTOR) blocking reagent for 1 h at room temp then incubated with Rabbit monoclonal anti-meganuclease antibody (PBI, Rab54) at a dilution of 1:1500 and Mouse Monoclonal anti-Pax7 antibody (DSHB, Supernatant, 1:5) in PBST with 2% NGS at 4 C overnight in a humid chamber. The next day samples were incubated with Secondary antibodies (Goat-anti-mouse IgG1 Alexa647 (Invitrogen)), goat-anti-rabbit Alexa555 (Invitrogen)., 1:500) for 1 hr at room temperature followed by DAPI nuclear counterstained for 5 min. Excess BOND RX wash buffer was removed, coverslips were mounted using VectaShield Vibrance Antifade Mounting Medium. Imaging was performed on Zeiss Apotome 2.0

Figure 34:
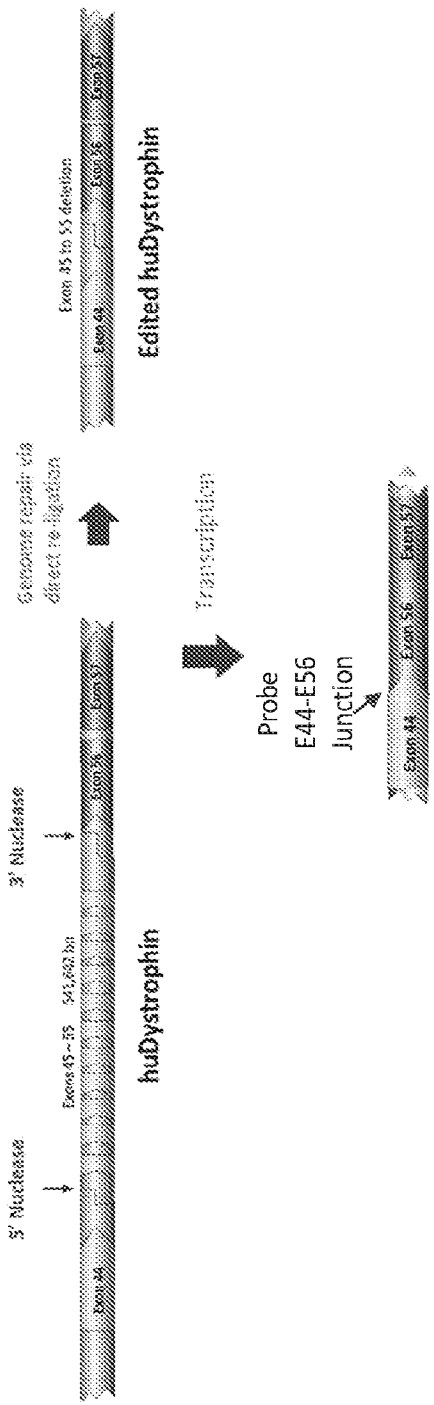
FIG. 34 provides a schematic of the BaseScope assay used to detect mRNA expression of a modified dystrophin transcript where exons 45-55 of the human dystrophin gene have been deleted following expression of two nucleases. The first nuclease binds and cleaves a recognition sequence located in the intron immediately 5' of exon 45, and the second nuclease binds and cleaves a recognition sequence located in the intron immediately 3' of exon 55. As shown the nucleases that bind and cleave recognition sequences located in these introns result in a double strand break that is then repaired by direct religation of the genome. Following transcription and splicing, an mRNA is produced with exon 44 and exon 56 spliced together. A probe designed to recognize this exon 44 to exon 56 junction (denoted as E44-E56 junction) is then used to detect this modified human dystrophin transcript in muscle tissue sections.

BaseScope analysis for co-expression of Pax7 RNA and the dystrophin spliced message of exons 44 and 56 was performed on quadriceps tissue sections. This technique utilizes a detectable RNA probe that is approximately 50 base pairs spanning the exon 44 and exon 56 junction (obtained from Advanced Cell Diagnostics (ACD), Newark, CA), which is created after genome repair via direct re-ligation (FIG. 34). Slides were dewaxed and incubated with RNAscope hydrogen peroxide solution for 10 min at room temperature followed by target retrieval in RNAscope 1× Target Retrieval Reagent in a steamer for 15 min at 95° C. and Protease TV treatment for 30 minutes at room temperature. The probes for the dystrophin exon44-56 junction and Pax7 were added and incubated in a HybEZ oven for 2 hours at 40° C. then stored overnight in 5×SSC. Signal was enhanced using the BaseScope Duplex Assay (ACD) per the manufacturer's protocol followed by hematoxylin staining and imaging of slides on a Leica GT450 digital scanner.

2. Results

Figure 29:
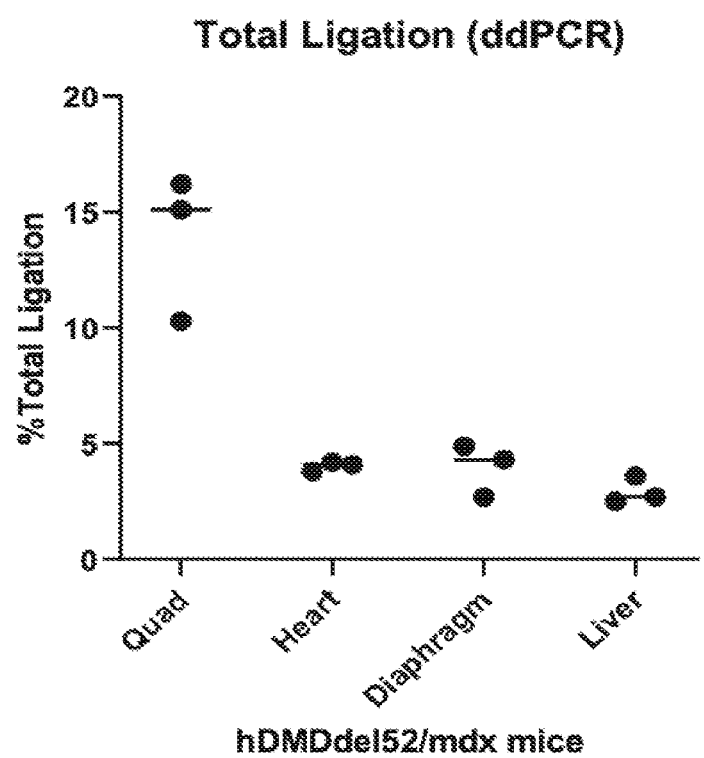
FIG. 29 provides a graph showing the percentage (%) of total ligation of genomic DNA adjacent to exons 45-55 in the quadricep, heart, and diaphragm muscle tissues following cleavage of the DMD 19-20 and DMD 35-36 recognitions sequence by the pair of DMD 19-20L.329 and DMD 35-36L.349 engineered meganucleases.
Figure 30A:
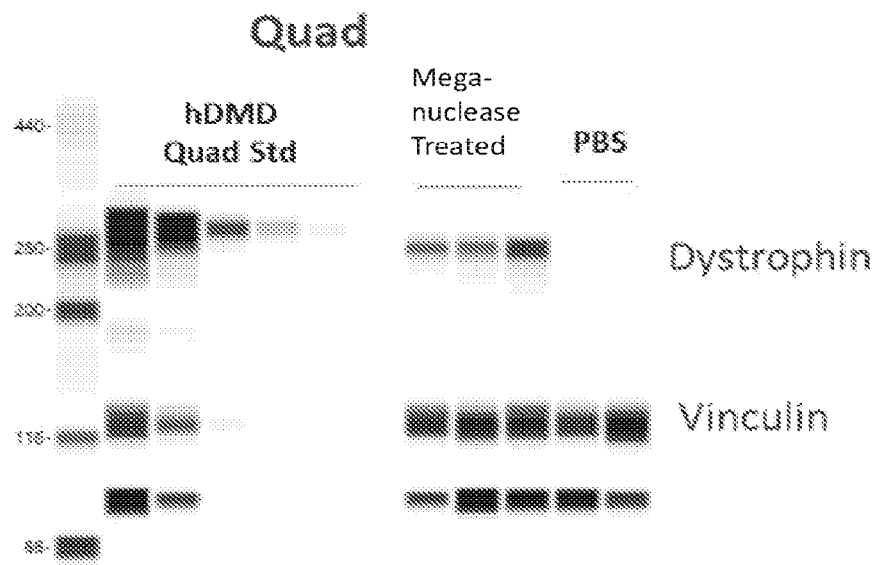
FIGS. 30A-30C provides a WES protein intensity read out for shortened modified dystrophin protein levels lacking exons 45-55 of the dystrophin gene after treatment with the DMD 19-20L.329 and DMD 35-36L.349 meganucleases utilizing different muscle specific promoters. Lane 1 of FIGS. 30A-30C represent the ladder; lanes 2-6 represent band intensity of full-length human dystrophin from a mouse that expresses human dystrophin; lane 7 represents band intensity of shortened modified dystrophin in mice treated with the combination of the DMD 19-20L.329 and DMD 35-36L.349 meganucleases at $1\times10^{14}$ VG/kg under the control of the CK8 muscle-specific promoter; lane 8 represents band intensity of shortened modified dystrophin in mice treated with the combination of the DMD 19-20L.329 and DMD 35-36L.349 meganucleases at $1\times10^{14}$ VG/kg under the control of the MHCK7 muscle-specific promoter; lane 9 represents band intensity of shortened modified dystrophin in mice treated with the combination of the DMD 19-20L.329 and DMD 35-36L.349 meganucleases at $1\times10^{14}$ VG/kg where the DMD 19-20L.329 meganuclease is under the control of the CK8 muscle-specific promoter and the DMD 35-36L.349 meganuclease is under the control of the SPc5-12 muscle specific promoter; lanes 10-11 represent mice treated with PBS.
Figure 30B:
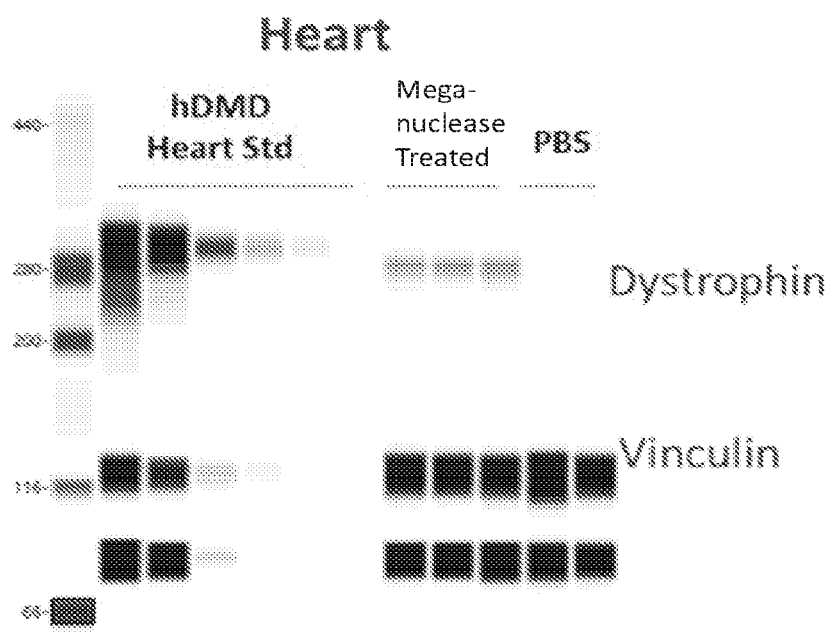
Figure 30C:
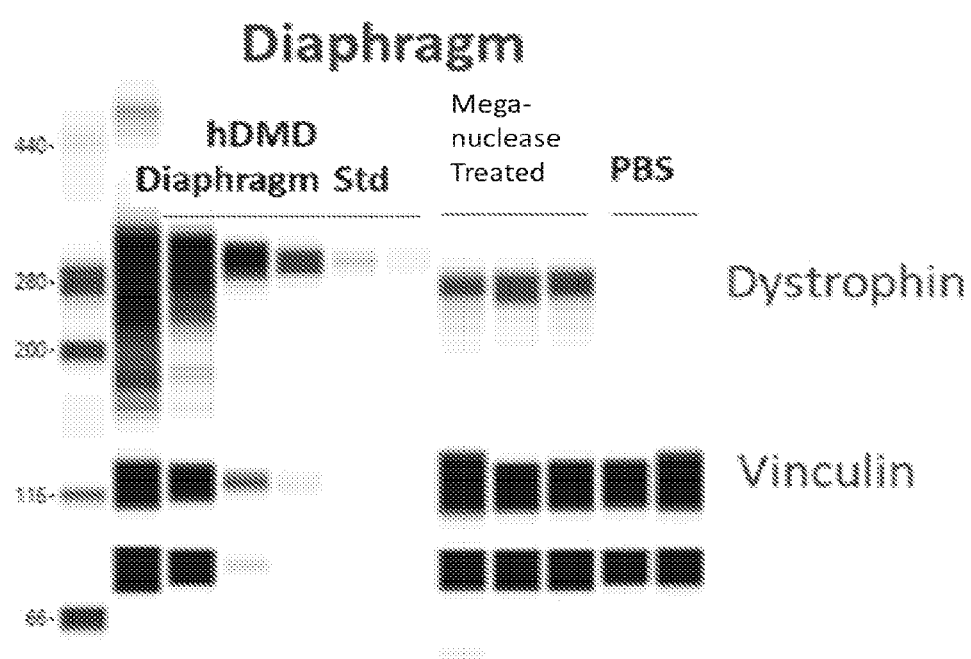
Figure 31:
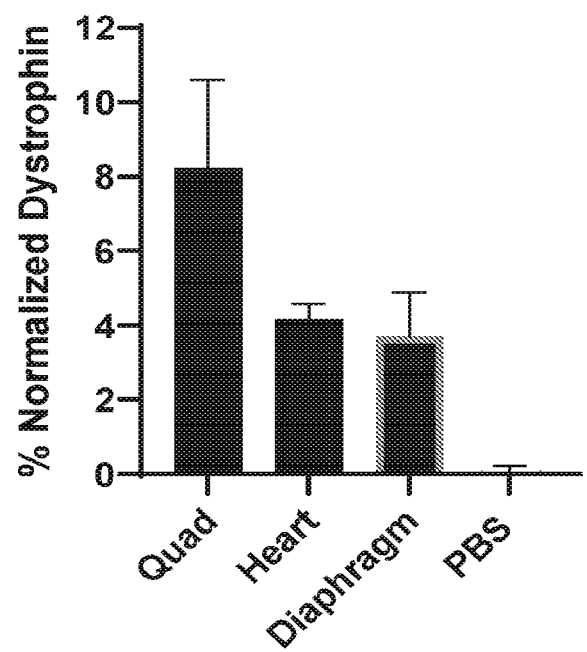
FIG. 31 provides a bar graph showing the modified shortened dystrophin protein levels by WES analysis normalized to the vinculin loading control for mice treated with the DMD 19-20L.329 and DMD 35-36L.349 meganucleases or PBS in the quadricep (quad), heart, and diaphragm tissue.
Figure 32:
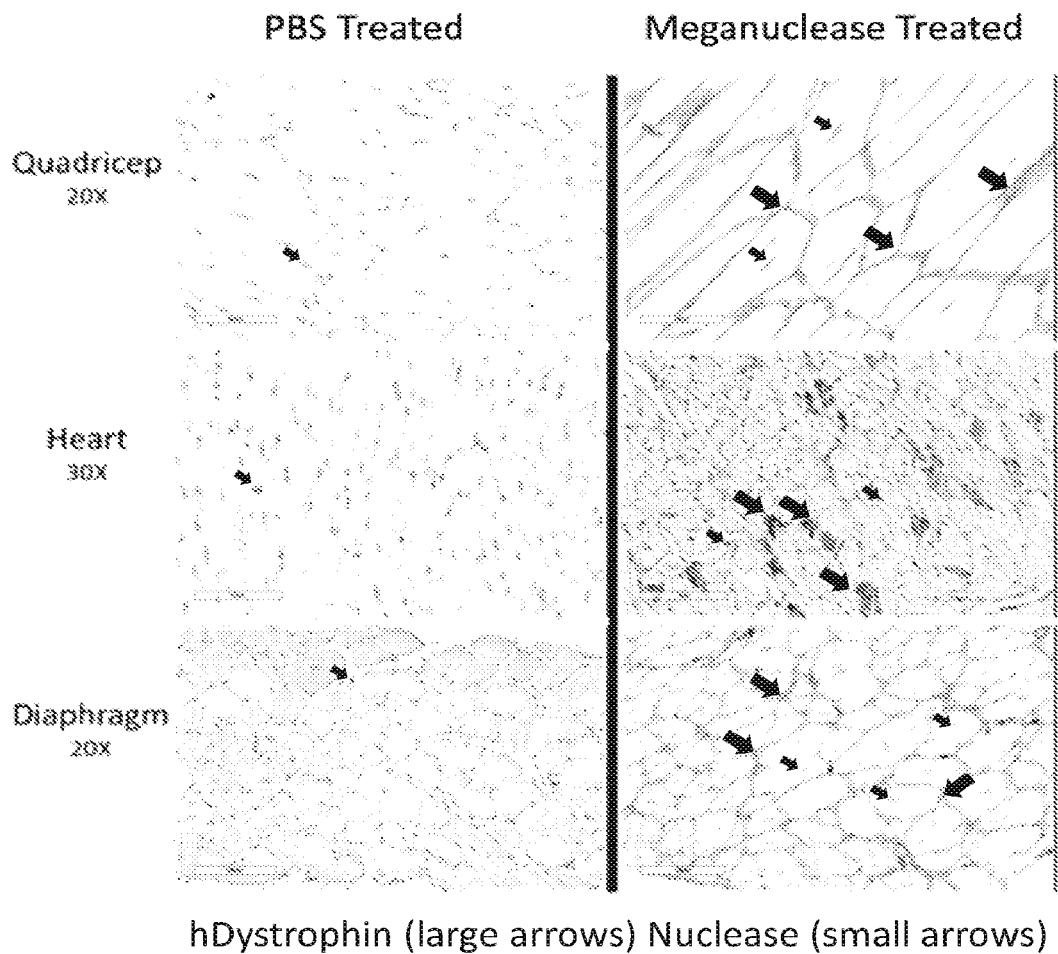
FIG. 32 provides immunohistochemistry imaging of the quadricep (quad), heart, and diaphragm muscle tissue from mice treated with the combination of the DMD 19-20L.329 and DMD 35-36L.349 meganucleases or PBS. Dark staining represents human dystrophin detection, which is only seen in mice treated with the combination of the meganucleases.
Figure 33A:
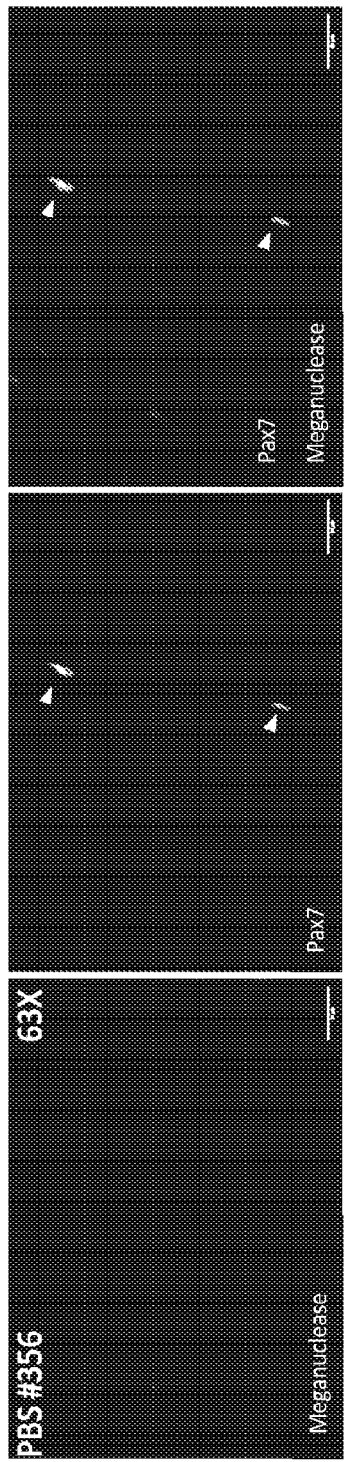
FIGS. 33A and 33B provides fluorescent immunohistochemistry imaging of murine quadricep tissue following treatment with either PBS or the DMD 19-20L.329 and DMD 35-36L.349 pair of meganucleases delivered using an AAV9 capsid to hDMDdel52/mdx (hDMD) mice.
Figure 33B:
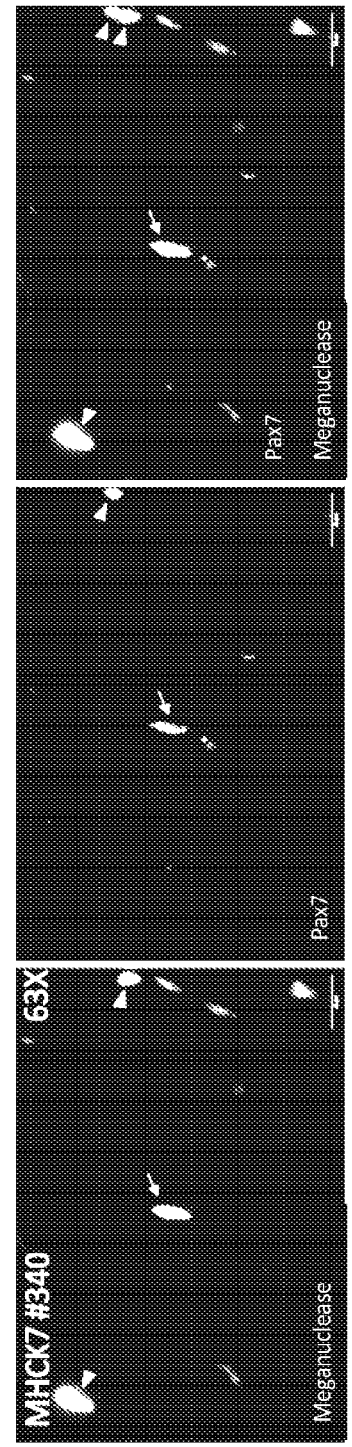
Figure 35A:
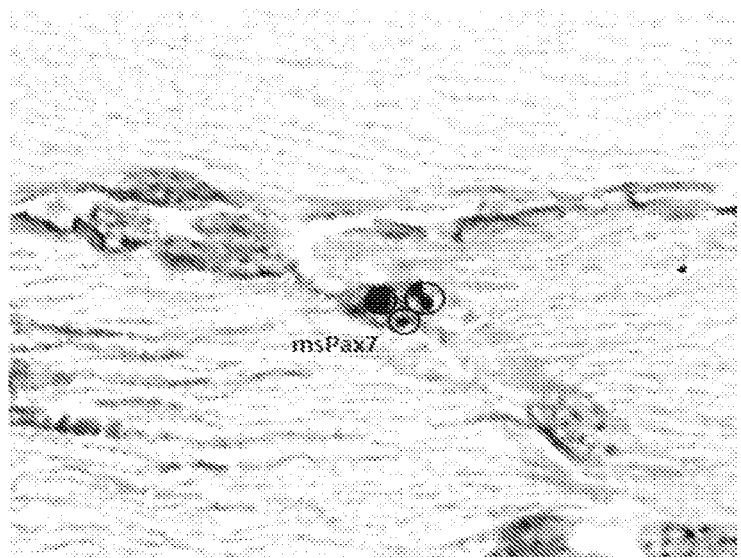
FIGS. 35A and 35B provides the BaseScope staining of murine quadricep tissue from hDMDdel52/mdx (hDMD) mice that were treated with either PBS or the DMD 19-20L.329 and DMD 35-36L.349 pair of meganucleases.
Figure 35B:
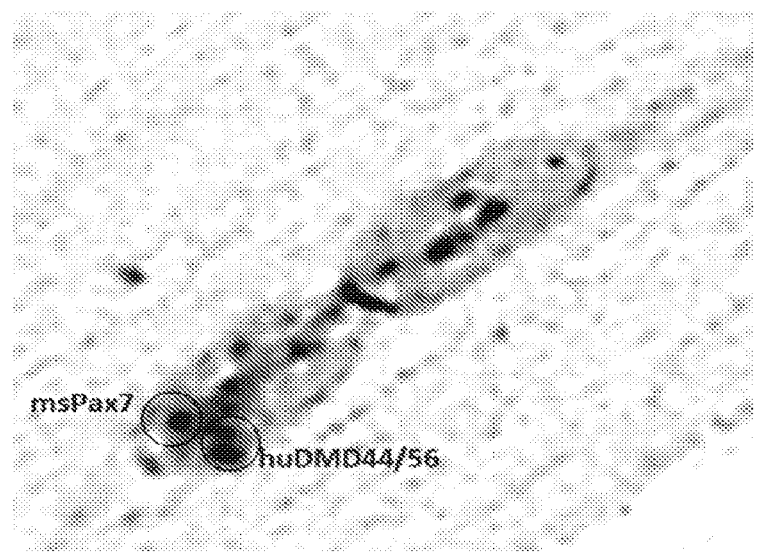

Total ligation averaged 15% in the quadricep and ~4% in the heart and diaphragm, relative to the reference site (FIG. 29). Shortened modified dystrophin restoration was quantified by comparing dystrophin protein from the corresponding tissues in hDMD mice using a standard curve (FIG. 30A-30C). Treated mice were found to average 8.2% in the quadricep, 4.2% in the heart, and 2.8% in the diaphragm (FIG. 31). In hDMD mice treated with PBS, no human dystrophin or meganuclease expression was detected in quadricep tissue. Notably, in hDMD mice exposed to DMD19-20L.329 and DMD35-36L.349, the expression of shortened modified human dystrophin was restored, and meganuclease protein staining was present in adjacent tissue sections (FIG. 32). Immunofluorescence staining of quadricep tissue sections show minimal background staining for nuclease in PBS treated animals and clear Pax7 staining of satellite cells (white arrow heads) (FIG. 33A). In nuclease treated animals, there is co-staining of a population of Pax7 positive cells indicating expression of the nuclease in satellite cells (FIG. 33B). BaseScope analysis showed co-expression of Pax7 and the spliced RNA product (exon 44-56) in treated animals (FIG. 35B) compared with Pax7 alone in PBS animals (FIG. 35A).

3. Conclusions

This study demonstrated in vivo proof of concept for excision of exons 45 to 55 & dystrophin protein restoration in a DMD disease model.

Example 15

Restoration of Dystrophin Protein Expression in DMD Patient Cell Lines

1. Methods

Previously we reported dystrophin protein restoration in a DMD patient cell line, AB1098, missing exons 48-50 as well as dystrophin expression. Here we report similar results with improved DMD 19-20L.329 and DMD 35-36L.349 meganucleases in an additional KM1328 DMD patient cell line. The DMD patient myoblast cell line was obtained from the Center for Research in Myology (Sorbonne University). This cell line was immortalized from the spinal muscle of a patient with a deletion of exon 52, which causes it to be dystrophin protein deficient due to the deleted exons. Cells were electroporated, cultivated and harvested as written in Example 10 previously. The meganuclease mRNA dose was 20 ng, 80 ng and 160 ng of DMD 19-20L.329 and DMD 35-36L.349 meganucleases. For comparison, AB1098 patient cells were transfected with 80 ng of DMD 19-20L.329 and DMD 35-36L.349 meganucleases. Protein was extracted, quantified and analyzed using the WES system as written in Example 10 previously. Primary antibody used for detection of dystrophin was 1:50 mandyS106. Primary antibody vs vinculin (Abcam) was used (1:100) as a loading control.

2. Results

Figure 36:
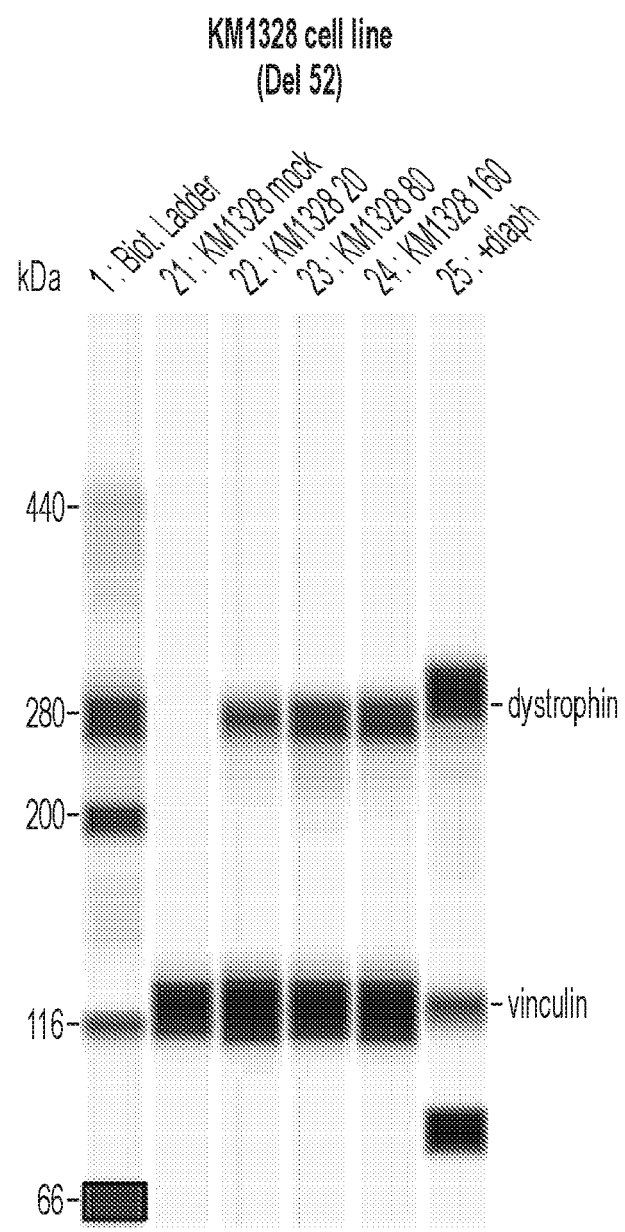
FIG. 36 provides a WES protein intensity read out for shortened modified dystrophin protein levels lacking exons 45-55 of the dystrophin gene after electroporation of the KM1328 patient cell line that normally lacks dystrophin expression with increasing doses of the DMD 19-20L.329 and DMD 35-36L.349 meganucleases at 20 ng, 80 ng, and 160 ng of mRNA encoding the meganucleases. Lane 1 represents the ladder, lane 2 represents the mock control; lanes 3-5 represents the band intensity of shortened modified dystrophin in cells treated with 20 ng, 80 ng, and 160 ng of meganuclease mRNA; lane 6 represents the band intensity of full length human dystrophin.

Expression of the shortened modified dystrophin protein, lacking the amino acids encoded by exons 45-55, was measured by WES automated western blot analysis. A dose-dependent increase in the amount of modified dystrophin was seen. The shortened modified dystrophin protein band can be visualized in lanes 3-5 of FIG. 36 and lane 3 of FIG. 37. The protein band for full length dystrophin for comparison can be visualized in lane 6 of FIG. 36 and lane 1 of FIG. 37. No dystrophin was detected in mock untreated KM1328 cells, with increasing intensity of bands for dystrophin across the dose range (FIG. 36).

Figure 37:
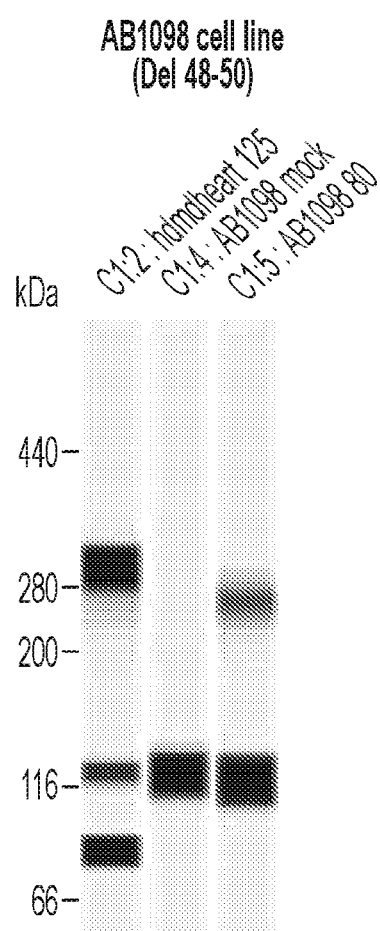
FIG. 37 provides a WES protein intensity read out for shortened modified dystrophin protein levels lacking exons 45-55 of the dystrophin gene after electroporation of the AB1098 patient cell line that normally lacks dystrophin with the DMD 19-20L.329 and DMD 35-36L.349 meganucleases at 80 ng of mRNA encoding the meganucleases. Lane 1 represents the band intensity of full length human dystrophin; lane 2 represents the mock control; lane 3 represents the band intensity of shortened modified dystrophin in cells treated with 80 ng of meganuclease mRNA.

A dose-dependent increase in the large deletion/perfect ligation was seen with increasing amounts of mRNA encoding the DMD 19-20L.329 and DMD 35-36L.349 engineered meganucleases in KM1328 cells. This ligation resulted in increased detection of shortened modified dystrophin at increasing doses of the pair of meganucleases (FIG. 36). Similarly, expression of the shortened modified dystrophin was observed with the 80 ng dose of the pair of meganucleases in AB1098 cells (FIG. 37).

3. Conclusions

These experiments report the large deletion of exons 45 to 55 in a cell line isolated from multiple DMD cell lines with deletions in the dystrophin gene. These cell lines do not express detectable levels of dystrophin and are a good in vitro model for the DMD disease. The WES protein data in FIG. 36 and FIG. 37 show restored expression of a shortened modified dystrophin protein with no protein expression in untreated mock cells to a detectable level across all engineered meganuclease dose ranges. This is further confirmation and in vitro proof of concept of using dual engineered meganucleases for the purpose of treating DMD patients by excising exons 45-55 and converting the dystrophin gene to a Beckers dystrophin phenotype.

Example 16

Editing of Dystrophin Gene In Vivo in PAX 7 Expressing Muscle Cells in a hDMDdel52/MDX Mouse Study Using AAVrh74

1. Methods

This in vivo study was an evaluation of an AAV comprised of a viral genome that includes, from 5' to 3', the A17-120 enhancer, the muscle-specific promoter MHCK7, the coding sequence for the DMD 19-20L.329 nuclease, a furin GSG P2A cleavage sequence, a coding sequence for the DMD35-36L.349 nuclease, a WPRE element, and an SV40 poly adenylation signal. The AAVrh74 containing the DMD 19-20L.329 and DMDL.349 meganucleases was compared to PBS delivered by retro orbital systemic injection with $1\times10^{14}$, $3\times10^{13}$, $1\times10^{13}$ or $5\times10^{12}$ VG/kg in hDMDdel52/mdx (hDMD) mice. At 28 days post-injection, mice were sacrificed and tissue sections from skeletal muscle (quadricep), heart, diaphragm, and liver were collected for molecular, protein, and histological analysis. Digital droplet PCR was conducted as described in Example 10. Dystrophin protein expression was assessed in the quadriceps, heart, and diaphragm of the nuclease-treated hDMDdel52/mdx animals using the Wes™ system (ProteinSimple) as described in Example 10. Dystrophin expression was normalized to the house keeping protein vinculin and measured against a standard curve of dystrophin protein isolated from a hDMD mouse that expresses full-length dystrophin. Tissue sections from the nuclease-treated mice were also subjected to fluorescent immunohistochemistry analyses to visualize dystrophin and meganuclease protein expression as outlined in Example 14.

2. Results

Figure 38A:
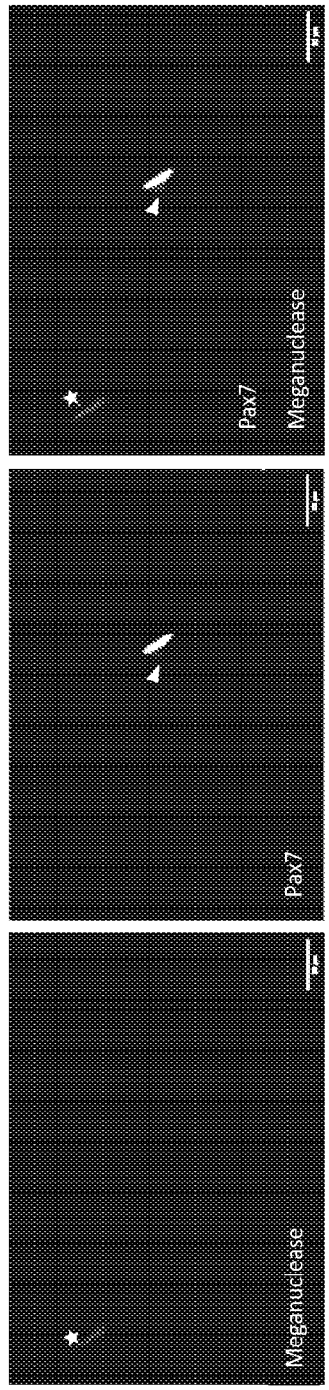
FIGS. 38A-38D provides fluorescent immunohistochemistry imaging of murine quadricep tissue following treatment with either PBS or the DMD 19-20L.329 and DMD 35-36L.349 pair of meganucleases delivered using an AAVrH74 capsid to hDMDdel52/mdx (hDMD) mice.
Figure 38B:
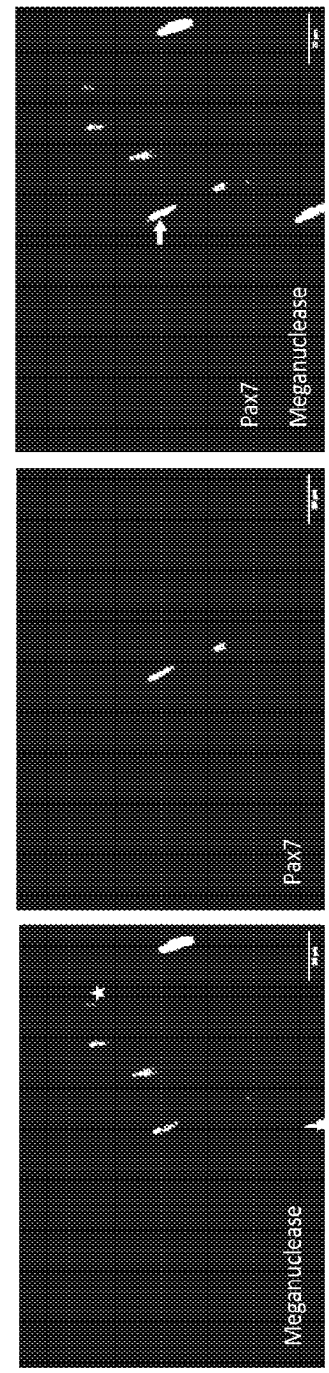
Figure 38C:
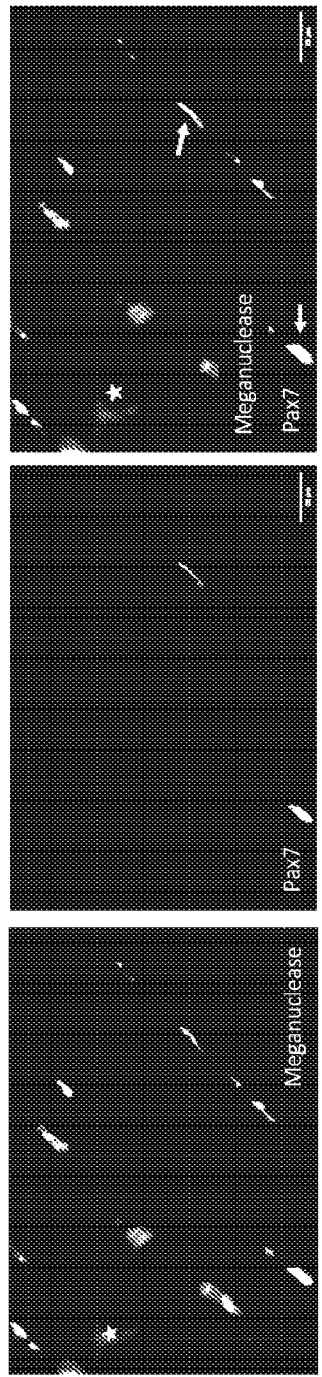
Figure 38D:
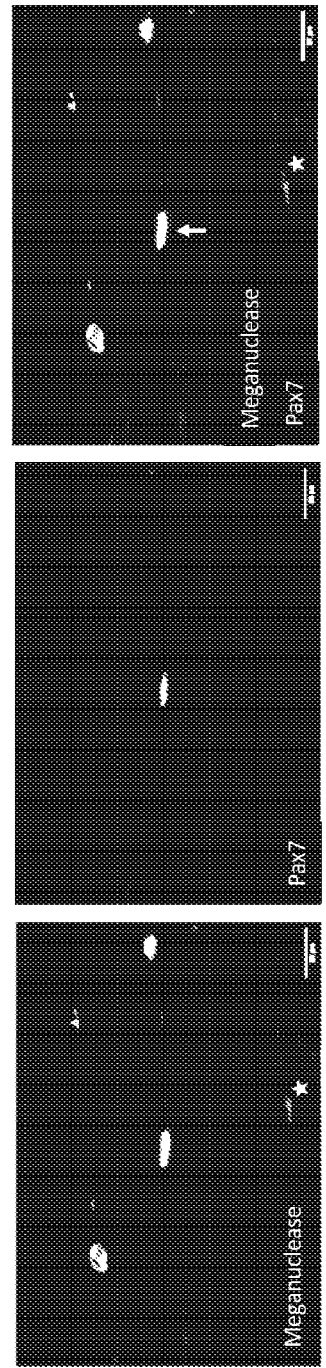

Immunofluorescence staining of quadriceps tissue sections shows minimal background staining for nuclease in PBS treated animals and clear Pax7 staining of satellite cells (white arrow heads) (FIG. 38A). In nuclease treated animals, there is co-staining of a population of Pax7 positive cells indicating expression of the nuclease in satellite cells (FIG. 38B). This study revealed expression of nuclease in Pax7 positive cells across all doses tested: $1\times10^{14}$ VG/kg (FIG. 38B), $3\times10^3$ VG/kg (FIG. 38C), and $1\times10^3$ VG/kg (FIG. 38D).

3. Conclusions

This study provides further proof of concept for editing the satellite cell population in the quadriceps muscle using an AAVrh74 encapsidating the dual meganucleases. The study showed coexpression of Pax7, a known satellite marker with expression of the engineered meganuclease indicating that the meganuclease is expressed in this target population and could therefore potentially edit these cells as previously shown in Example 14 with the same construct using the AAV9 capsid.

---

The invention claimed is:

1. A polynucleotide comprising a nucleic acid sequence encoding an engineered meganuclease that binds and cleaves a nucleic acid at a site that comprises a recognition sequence consisting of the nucleic acid sequence of SEQ ID NO: 10 in a dystrophin gene, wherein said engineered meganuclease comprises the amino acid sequence of SEQ ID NO: 51.

2. The polynucleotide of claim 1, wherein said polynucleotide comprises a promoter operably linked to said nucleic acid sequence encoding said engineered meganuclease.

3. The polynucleotide of claim 2, wherein said promoter is a muscle cell-specific promoter.

4. The polynucleotide of claim 1, wherein said polynucleotide is an mRNA.

5. A recombinant DNA construct comprising a polynucleotide comprising a nucleic acid sequence encoding an engineered meganuclease that binds and cleaves a nucleic acid at a site that comprises a recognition sequence consisting of the nucleic acid sequence of SEQ ID NO: 10 in a dystrophin gene, wherein said engineered meganuclease comprises the amino acid sequence of SEQ ID NO: 51.

6. The recombinant DNA construct of claim 5, wherein said polynucleotide comprises a promoter operably linked to said nucleic acid sequence encoding said engineered meganuclease.

7. The recombinant DNA construct of claim 6, wherein said promoter is a muscle cell-specific promoter.

8. A recombinant virus comprising a polynucleotide comprising a nucleic acid sequence encoding an engineered meganuclease that binds and cleaves a nucleic acid at a site that comprises a recognition sequence consisting of the nucleic acid sequence of SEQ ID NO: 10 in a dystrophin gene, wherein said engineered meganuclease comprises the amino acid sequence of SEQ ID NO: 51.

9. The recombinant virus of claim 8, wherein said recombinant virus is a recombinant AAV.

10. The recombinant virus of claim 9, wherein said recombinant AAV has a capsid protein comprising the amino acid sequence of SEQ ID NO: 182 or a capsid comprising the amino acid sequence of SEQ ID NO: 183.

11. The recombinant virus of claim 8, wherein said polynucleotide comprises a promoter operably linked to said nucleic acid sequence encoding said engineered meganuclease.

12. The recombinant virus of claim 11, wherein said promoter is a muscle cell-specific promoter.

13. The recombinant virus of claim 9, wherein said polynucleotide comprises a promoter operably linked to said nucleic acid sequence encoding said engineered meganuclease.

14. The recombinant virus of claim 13, wherein said promoter is a muscle cell-specific promoter.

15. The recombinant virus of claim 10, wherein said polynucleotide comprises a promoter operably linked to said nucleic acid sequence encoding said engineered meganuclease.

16. The recombinant virus of claim 15, wherein said promoter is a muscle cell-specific promoter.

* * * * *